US008981061B2

(12) United States Patent
Colonna et al.

(10) Patent No.: US 8,981,061 B2
(45) Date of Patent: Mar. 17, 2015

(54) RECEPTOR TREM (TRIGGERING RECEPTOR EXPRESSED ON MYELOID CELLS) AND USES THEREOF

(71) Applicant: Novo Nordisk A/S, Bagsvaerd (DK)

(72) Inventors: Marco Colonna, St. Louis, MO (US); Axel Bouchon, Wuppertal (DE); Rune Salbo, Hvidovre (DK); Charlotte Wiberg, Bjaerred (SE); Vibeke W. Stennicke, Kokkedal (DK); Anette Henriksen, Alleroed (DK); Mette D. Andersen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/690,828

(22) Filed: Nov. 30, 2012

(65) Prior Publication Data

US 2013/0150559 A1 Jun. 13, 2013

Related U.S. Application Data

(63) Continuation-in-part of application No. 13/560,612, filed on Jul. 27, 2012, now abandoned, which is a continuation of application No. 12/687,038, filed on Jan. 13, 2010, now abandoned, which is a continuation of application No. 11/188,281, filed on Jul. 25, 2005, now abandoned, which is a continuation of application No. 10/103,423, filed on Mar. 20, 2002, now abandoned.

(60) Provisional application No. 60/277,238, filed on Mar. 20, 2001.

(51) Int. Cl.

| | |
|---|---|
| ***C07K 16/00*** | (2006.01) |
| ***C12P 21/08*** | (2006.01) |
| ***C07K 16/28*** | (2006.01) |
| ***C07K 14/705*** | (2006.01) |

(52) U.S. Cl.
CPC ........... *C07K 16/28* (2013.01); *C07K 14/70503* (2013.01)
USPC .................. 530/387.9; 530/397.1; 530/388.1; 530/388.22

(58) Field of Classification Search
CPC .......................... C07K 16/28; A61K 2039/505
See application file for complete search history.

(56) References Cited

U.S. PATENT DOCUMENTS

| | | | |
|---|---|---|---|
| 4,444,887 | A | 4/1984 | Hoffmann |
| 4,522,811 | A | 6/1985 | Eppstein et al. |
| 4,676,980 | A | 6/1987 | Segal et al. |
| 4,683,195 | A | 7/1987 | Mullis et al. |
| 4,683,202 | A | 7/1987 | Mullis |
| 4,716,111 | A | 12/1987 | Osband et al. |
| 4,736,866 | A | 4/1988 | Leder et al. |
| 4,741,900 | A | 5/1988 | Alvarez et al. |
| 4,816,397 | A | 3/1989 | Boss et al. |
| 4,816,567 | A | 3/1989 | Cabilly et al. |
| 4,870,009 | A | 9/1989 | Evans et al. |
| 4,873,191 | A | 10/1989 | Wagner et al. |
| 4,873,316 | A | 10/1989 | Meade et al. |
| 4,946,778 | A | 8/1990 | Ladner et al. |
| 4,980,286 | A | 12/1990 | Morgan et al. |
| 4,987,071 | A | 1/1991 | Cech et al. |
| 5,116,742 | A | 5/1992 | Cech et al. |
| 5,223,409 | A | 6/1993 | Ladner et al. |
| 5,225,539 | A | 7/1993 | Winter |
| 5,258,498 | A | 11/1993 | Huston et al. |
| 5,272,057 | A | 12/1993 | Smulson et al. |
| 5,272,071 | A | 12/1993 | Chappel |
| 5,283,317 | A | 2/1994 | Saifer et al. |
| 5,328,470 | A | 7/1994 | Nabel et al. |
| 5,403,484 | A | 4/1995 | Ladner et al. |
| 5,413,923 | A | 5/1995 | Kucherlapati et al. |

(Continued)

FOREIGN PATENT DOCUMENTS

| | | |
|---|---|---|
| CA | 2342376 A1 | 9/2002 |
| EP | 239400 A2 | 9/1987 |

(Continued)

OTHER PUBLICATIONS

Riedemann et al., "Novel strategies for the treatment of sepsis," Nature Medicine, May 2003, vol. 9, No. 5, pp. 517-524.
Stone, Richard, "Search for Sepsis Drugs Goes on Despite Past Failures." Science, Apr. 15, 1994, vol. 264, pp. 365-367.
Thoma-Uszynski et al., "Induction of Direct Antimicrobial Activity Through Mammalian Toll-Like Receptors," Science, Feb. 23, 2001, vol. 291, pp. 1544-1547.
Tsuji et al., "Simultaneous Onset of Accute Inflammatory Response, Sepsis-Like Symptoms and Intestinal Mucosal Injury After Cancer Chemotherapy," Int. J. Cancer, 2003, vol. 107, pp. 303-308.

(Continued)

*Primary Examiner* — Daniel C Gamett
(74) *Attorney, Agent, or Firm* — Nonna G. Akopyan; Reza Green; Richard W. Bork

(57) ABSTRACT

Novel activating receptors of the lg super-family expressed on human myeloid cells, called TREM(s) (triggering receptor expressed on myeloid cells) are provided. Specifically, two (2) members of TREMs, TREM-1 and TREM-2 are disclosed. TREM-1 is a transmembrane glycoprotein expressed selectively on blood neutrophils and a subset of monocytes but not on lymphocytes and other cell types and is upregulated by bacterial and fungal products. Use of TREM-1 in treatment and diagnosis of various inflammatory diseases is also provided. TREM-2 is also a transmembrane glycoprotein expressed selectively on mast cells and peripheral dendritic cells (DCs) but not on granulocytes or monocytes. DC stimulation via TREM-2 leads to DC maturation and resistance to apoptosis, and induces strong upregulation of CCR7 and subsequent chemotaxis toward macrophage inflammatory protein 3-β. TREM-2 has utility in modulating host immune responses in various immune disorders, including autoimmune diseases and allergic disorders.

2 Claims, 60 Drawing Sheets

(56) References Cited

U.S. PATENT DOCUMENTS

| | | | |
|---|---|---|---|
| 5,420,526 | A | 5/1995 | Fensch |
| 5,424,286 | A | 6/1995 | Eng |
| 5,427,908 | A | 6/1995 | Dower et al. |
| 5,436,146 | A | 7/1995 | Shenk et al. |
| 5,459,039 | A | 10/1995 | Modrich et al. |
| 5,474,981 | A | 12/1995 | Leder et al. |
| 5,498,531 | A | 3/1996 | Jarrell |
| 5,516,637 | A | 5/1996 | Huang et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,658,727 | A | 8/1997 | Barbas et al. |
| 5,661,016 | A | 8/1997 | Lonberg et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,807,715 | A | 9/1998 | Morrison et al. |
| 5,814,318 | A | 9/1998 | Lonberg et al. |
| 5,821,047 | A | 10/1998 | Garrard et al. |
| 5,885,793 | A | 3/1999 | Griffiths et al. |
| 5,916,771 | A | 6/1999 | Hori et al. |
| 5,939,598 | A | 8/1999 | Kucherlapati et al. |
| 5,969,108 | A | 10/1999 | McCafferty et al. |
| 6,420,526 | B1 | 7/2002 | Ruben et al. |
| 6,504,010 | B1 | 1/2003 | Wang et al. |
| 6,509,448 | B2 | 1/2003 | Wang et al. |
| 6,858,204 | B2 | 2/2005 | Henderson et al. |
| 6,878,687 | B1 | 4/2005 | Ruben et al. |
| 8,013,116 | B2 | 9/2011 | Faure et al. |
| 2002/0128444 | A1 | 9/2002 | Gingras et al. |
| 2002/0172952 | A1 | 11/2002 | Henderson et al. |
| 2002/0197669 | A1 | 12/2002 | Bangur et al. |
| 2003/0049618 | A1 | 3/2003 | Ruben et al. |
| 2003/0054363 | A1 | 3/2003 | Henderson et al. |
| 2003/0077282 | A1 | 4/2003 | Bigler et al. |
| 2003/0134283 | A1 | 7/2003 | Peterson et al. |
| 2003/0165875 | A1 | 9/2003 | Colonna et al. |
| 2003/0166068 | A1 | 9/2003 | Ashida et al. |
| 2003/0170255 | A1 | 9/2003 | Watanabe et al. |
| 2003/0175858 | A1 | 9/2003 | Ruben et al. |
| 2003/0211510 | A1 | 11/2003 | Henderson et al. |
| 2004/0236092 | A1 | 11/2004 | Dziarski et al. |
| 2005/0255114 | A1 | 11/2005 | Labat et al. |
| 2006/0183125 | A1 | 8/2006 | Mariani et al. |
| 2009/0092582 | A1 | 4/2009 | Bogin et al. |
| 2010/0310560 | A1 | 12/2010 | Colonna et al. |

FOREIGN PATENT DOCUMENTS

| | | | |
|---|---|---|---|
| EP | 264166 | A1 | 4/1988 |
| EP | 439098 | A2 | 7/1991 |
| EP | 519596 | A1 | 12/1992 |
| EP | 592106 | A1 | 4/1994 |
| EP | 1022286 | A1 | 7/2000 |
| EP | 1498424 | A2 | 1/2005 |
| WO | 88/09810 | A1 | 12/1988 |
| WO | 89/10134 | A1 | 11/1989 |
| WO | 90/02809 | A1 | 3/1990 |
| WO | 90/11354 | A1 | 10/1990 |
| WO | 91/01140 | A1 | 2/1991 |
| WO | 91/06667 | A1 | 5/1991 |
| WO | 91/09967 | A1 | 7/1991 |
| WO | 91/10737 | A1 | 7/1991 |
| WO | 91/10741 | A1 | 7/1991 |
| WO | 92/00968 | A1 | 1/1992 |
| WO | 92/01047 | A1 | 1/1992 |
| WO | 92/06180 | A1 | 4/1992 |
| WO | 92/18619 | A1 | 10/1992 |
| WO | 92/20316 | A2 | 11/1992 |
| WO | 92/22324 | A1 | 12/1992 |
| WO | 92/22635 | A1 | 12/1992 |
| WO | 93/04169 | A1 | 3/1993 |
| WO | 93/11236 | A1 | 6/1993 |
| WO | 93/14188 | A1 | 7/1993 |
| WO | 93/20221 | A1 | 10/1993 |
| WO | 93/21232 | A1 | 10/1993 |
| WO | 94/08598 | A1 | 4/1994 |
| WO | 94/10300 | A1 | 5/1994 |
| WO | 9412649 | A2 | 6/1994 |
| WO | 94/16101 | A2 | 7/1994 |
| WO | 95/15982 | A2 | 6/1995 |
| WO | 95/20401 | A1 | 8/1995 |
| WO | 96/33735 | A1 | 10/1996 |
| WO | 96/34096 | A1 | 10/1996 |
| WO | 97/07668 | A1 | 3/1997 |
| WO | 97/07669 | A1 | 3/1997 |
| WO | 98/08871 | | 3/1998 |
| WO | 98/16654 | A1 | 4/1998 |
| WO | 98/24893 | A2 | 6/1998 |
| WO | 98/39446 | A2 | 9/1998 |
| WO | 98/39448 | A2 | 9/1998 |
| WO | 98/46645 | A2 | 10/1998 |
| WO | 98/50433 | A2 | 11/1998 |
| WO | 9902686 | A1 | 1/1999 |
| WO | 00/00610 | A2 | 1/2000 |
| WO | 01/53312 | A1 | 7/2001 |
| WO | 01/90304 | A2 | 11/2001 |
| WO | 02/058721 | A1 | 8/2002 |
| WO | 03/011213 | A2 | 2/2003 |
| WO | 03/025138 | A2 | 3/2003 |
| WO | 03/030835 | A2 | 4/2003 |
| WO | 03029401 | A2 | 4/2003 |
| WO | 03/037267 | A2 | 5/2003 |
| WO | 03/060071 | A2 | 7/2003 |
| WO | 03/061712 | A1 | 7/2003 |
| WO | 03/080667 | A2 | 10/2003 |
| WO | 2004/020591 | A2 | 3/2004 |
| WO | 2004/081233 | A1 | 9/2004 |
| WO | 2004081233 | A1 | 9/2004 |
| WO | 2005005601 | A2 | 1/2005 |
| WO | 2005/048823 | A2 | 6/2005 |
| WO | 2005/071408 | A1 | 8/2005 |
| WO | 2005/091944 | | 10/2005 |
| WO | 2005/113606 | A2 | 12/2005 |
| WO | 2006/028595 | A2 | 3/2006 |
| WO | 2006/028714 | A1 | 3/2006 |
| WO | 2006/056492 | A1 | 6/2006 |
| WO | 2006/065582 | A2 | 6/2006 |
| WO | 2006/078463 | A2 | 7/2006 |
| WO | 2006/097537 | A2 | 9/2006 |
| WO | 2006/135886 | A2 | 12/2006 |
| WO | 2006135886 | A2 | 12/2006 |
| WO | 2006138275 | A2 | 12/2006 |
| WO | 2007/146968 | A2 | 12/2007 |
| WO | 2008049113 | A2 | 4/2008 |
| WO | 2008/088849 | A2 | 7/2008 |
| WO | 2008088849 | A2 | 7/2008 |
| WO | 2008/121563 | A2 | 10/2008 |
| WO | 2009/018386 | A1 | 2/2009 |
| WO | 2009/020802 | A2 | 2/2009 |
| WO | 2009/030771 | A1 | 3/2009 |
| WO | 2009/117033 | A2 | 9/2009 |
| WO | 2009/126380 | A2 | 10/2009 |
| WO | 2009/141359 | A1 | 11/2009 |
| WO | 2010/006060 | A2 | 1/2010 |
| WO | 2010/042747 | A2 | 4/2010 |
| WO | 2010/044952 | A2 | 4/2010 |
| WO | 2010/065439 | A1 | 6/2010 |
| WO | 2010/084169 | A2 | 7/2010 |
| WO | 2010/132370 | A2 | 11/2010 |
| WO | 2010/142665 | A1 | 12/2010 |
| WO | 2010141469 | A2 | 12/2010 |
| WO | 2011/005481 | A1 | 1/2011 |
| WO | 2011/028952 | A1 | 3/2011 |
| WO | 2011/047097 | A2 | 4/2011 |
| WO | 2011055968 | A2 | 5/2011 |

(56) References Cited

FOREIGN PATENT DOCUMENTS

| | | |
|---|---|---|
| WO | 2011/069104 A2 | 6/2011 |
| WO | 2011/091078 A2 | 7/2011 |
| WO | 2011/137362 | 11/2011 |
| WO | 2012/064733 | 5/2012 |
| WO | 2012/088290 | 6/2012 |
| WO | 2012/088302 | 6/2012 |
| WO | 2012/109624 | 8/2012 |

OTHER PUBLICATIONS

Urban et al., "NF-κB contacts DNA by a heterodimer of the p50 and p65 subunit," The EMBO Journal, 1991, vol. 10, No. 7, pp. 1817-1825.

Van Zee et al., "Tumor necrosis factor soluble receptors circulate during experimental and clinical inflammation and can protect against excessive tumor necrosis factor a in vitro and in vivo," Proc. Natl. Acad. Sci. USA, Jun. 1992, vol. 89, pp. 4845-4849.

Vincent et al., "Clinical Trials of Immunomodulatory Therapies in Severe Sepsis and Septic Shock," Clin. Infect. Dis., Apr. 15 2002, vol. 34, pp. 1084-1093.

Warren, H. Sha, M.D., "Strategies for the Treatment of Sepsis," The New England Journal of Medicine, Mar. 27, 1997, vol. 336, No. 13, pp. 952-953.

Wasmuth et al., "Patient with acute on chromic liver failure display 'sepsis-like' immune paralysis," Journal of Hepatology, 2005, vol. 42, pp. 195-201.

Coskun et al., Endocrinology, "Fibroblast Growth Factor 21 Corrects Obesity in Mice", 2008, vol. 149, No. 12, pp. 6018-6027.

Erickson et al., Journal of Lipid Research, "Nonalcoholic Fatty Liver Disease", 2008, vol. -, No. -, pp. S412-S416.

Grundy et al., Circulation, "Definition of Metabolic Syndrome: Report of the National Heart, Lung, and Blood Institute/American Heart Association Conference on Scientific Issues Related to Definition", 2004, vol. 109, No. -, pp. 433-438.

Kharitonenkov et al., Endocrinology, "The Metabolic State of Diabetic Monkeys is Regulated by Fibroblast Growth Factor-21", 2007, vol. 148, No. 2, pp. 774-781.

Kharitonenkov et al., Journal of Clinical Investigation, "FGF-21 As a Novel Metabolic Regulator", 2005, vol. 115, No. -, pp. 1627-1635.

Knudsen, L.B., Journal of Medicinal Chemistry, "Glucagon-Like Peptide-1: The Basis of a New Class of Treatment for Type 2 Diabetes", 2004, vol. 47, No. 17, pp. 4128-4134.

Micanovic et al., Journal of Cellular Physiology, "Different Roles of N- and C-Termini in the Functional Activity of FGF21", 2009, vol. 219, No. 2, pp. 227-234.

Nauck, M.A et al., Regulatory Peptides, "Glucagon-Like Peptide 1 and Its Derivatives in the Treatment of Diabetes", 2005, vol. 128, No. 2, pp. 135-148.

Xu et al., Diabetes, "Fibroblast Growth Factor 21 Reverses Hepatic Steatosis, Increases Energy Expenditure, and Improves Insulin Sensitivity in Diet-Induced Obese Mice", 2009, vol. 58, No. 1, pp. 250-259.

Yie et al., FEBS Letters, "FGF21 N- and C-Termini Play Different Roles in Receptor Interaction and Activation", 2009, vol. 583, No. 1, pp. 19-24.

Zwaveling et al., "High plasma tumor necrosis factor (TNF)-a concentrations and a sepsis-like syndrome in patients undergoing hyperthermic isolated limb perfusion with recombinant TNF-a, interferson-g, and melphalan," Crit Care Med, 1996, vol. 24, No. 5, pp. 765-770.

Database EMBL, Sequence from Patent WO200283856-A2, Sep. 17, 2003 "Human G-protein coupled receptor phosphorylation site peptide SEQ ID 131", retrieved from EBI Database accession No. ABJ38803.

Database EMBL, Sequence information from JP2000116377-A, Oct. 10, 2000 "N-terminus of porcine trypsin", retrieved from EBI Database accession No. AAB03087.

Wheeler et al., "Treating Patients with Severe Sepsis" NEJM 1999, 340: 207-214.

Attwood. "The Babel of Bioinformatics" Science 2000; 290: 471-473.

The Merck Manuals Online Medical Library (online). Whitehouse Station, NJ: Merck Research Laboratories, 2006-2007. (Retrieved on Nov. 19, 2007). Retrieved from the internet: < URL: http://www.merck.com/mmpe/print/sec06/ch068/ch068a.html >.

Standen et al. "Septic Shock" N. Engl. J. Med. 2000, 343: 447-448.

Redl et at, "Animal Models as the Basis of Pharmacologic Intervention in Trauma and Sepsis Patients," World J. Surg. 1996, 20: 487-492.

Mori et al., "A novel amino acid substitution at the receptor-binding site on the hemagglutinin of H3N2 influenza A viruses isolated from 6 cases with acute encephalopathy during the 1997-1998 season in Tokyo," Archives of Birology 1999, 144: 147-155.

Gencic et al., "Conservative amino acid substitution in the myelin proteolipid protein of jimpymsd mice," The Journ. of Neuroscience 1990, 10: 117-124.

Schenk et al., "Trem-1—Expressing Intestinal Macrophages Crucially Amplify Chronic Inflammation in Experimental Colitis and Inflammatory Bowel Diseases," The Journ. of Clinical Investigation, 2007, vol. 117, No. 10, pp. 3097-3106.

Abravaya et al., "Detection of point mutations with a modified ligase chain reaction (Gap-LCR)" Nucleic Acids Res., (1995), 23:675-682.

Aderem et al., "Toll-0like receptors in the induction of the innate immune response." Nature, 406:782-7.

Alexander et al., "A recombinant human receptor antagonist to interleukin 1 improves survival after lethal endotoxemia in mice", J. Exp. Med., 173:1029-32, 1991.

Ames et al., "Conversion of murine Fabs isolated from a combinatorial phage display library to full length immunoglobulins", J. Immunol. Methods, vol. 184(2), (1995), pp. 177-186.

Amman et al., "Tightly regulated tac promoter vectors useful for the expression of unfused and fused proteins in *Escherichia coli*", Gene, (1988), 69:301-315.

Appelmelk et al., "Use of mucin and hemoglobin in experimental murine Gram-negative bacteremia enhances the immunoprotective action of antibodies reactive with the lipopolysaccharide core region", Antonie Van Leeuwenhoek, (1986), 52:537-42.

Arnon et al., "Monoclonal Antibodies for Immunotargeting of Drugs in Cancer Therapy", in Monoclonal Antibodies and Cancer Therapy, Reisfeld et al., eds., Alan R. Liss, Inc., (1985), pp. 243-56.

Baker et al., "NK cell activation: distinct stimulatory pathways counterbalancing inhibitory signals", Hum Immunol., 61:18-27. 2000.

Bakker et al., "DAP12-deficient mice fail to develop autoimmunity due to impaired antigen priming." Immunity 13:345-53. 2000.

Bakker et al., "Myeloid DAP12-associating lectin (MDL)-1 is a cell surface receptor involved in the activation of myeloid cells, "Proc. Natl. Acad. Sci. USA 96:9792, 1999.

Baldwin et al., "Analysis Results, and Future Prospective of the Therapeutic Use of the Radiolabeled Antibody in Cancer Therapy", in Monoclonal Antibodies for Cancer Detection and Therapy, eds. Adacemic Press, (1985, pp. 303-16.

Banerji et al., "A lymphocyte-specific cellular enhancer is located downstream of the joining region in immunoglobulin heavy chain genes", Cell, (1983), 33:729-740.

Barany,"Genetic disease detection and DNA amplification using cloned thermostable ligase", Proc. Natl. Acad. Sci. USA, (1991), 88:189.

Baldari et al., "A novel leader peptide which allows efficient secretion of a fragment of human interleukin 1b in *Saccharomyces cerevisiae*," EMBO J., (1987), 6:229-234.

Bartel et al., Bio Techniques, (1993), 14:920-924.

Bartel et al., "Isolation of new ribozymes from a large pool of random sequences",Science, (1993), 261:1411-1418.

Bauer et. al., "Activation of NK cells and T cells by NKG2D, a receptor for stress-inducible MICA", Science, 285:727-9, 1999.

Benda et al., "Differentiated Rat Glial Cell Strain in Tissue Culture," Science, (1968), 161:370-371.

Better et al., "*Escherichia coli* secretion of an active chimeric antibody fragment," Science, (1988), 240:1041-1043.

Beutler et al., "Passive immunization against cachectin/tumor necrosis factor protects mice from lethal effect of endotoxin", Science, 229:869-71, 1985.

(56) References Cited

OTHER PUBLICATIONS

Beutler, B., "Endotoxin, toll-like receptor 4, and the afferent limb of innate immunity", Curr. Opin. Microbiol., vol. 3 (1), (2000), pp. 23-28.
Boesen et al., "Circumvention of chemotherapy-induced myelosuppression by transfer of the mdr1 gene," Biotherapy, (1994), 6:291-302.
Bolin et al., "Survey of cell lines in the American Type Culture Collection for bovine viral diarrhea virus", J. Virol. Methods, (1994), 48: 211-221.
Bone, "The pathogenesis of sepsis," Ann. Intern. Med. 115:457-69, 1991.
Bordelon-Riser et al., "Necessity for two human chromosomes for human chorionic gonadotropin production in human-mouse hybrids", Somatic Cell Genetics, (1979), 5:597-613.
Bork & Bairoch, "Go hunting in sequence databases but watch out for the traps", Trends in Genetics, (1996)vol. 12(10), pp. 425-427.
Bork, "Powers and Pitfalls in Sequence Analysis: The 70% Hurdle", Genome Research, (2000), 10:398-400.
Bouchon et al., "Cutting edge: inflammatory responses can be triggered by TREM-1, a novel receptor expressed on neutroophils and monocytes", J. Immunol., vol. 164 (10). May 15, 2000), pp. 4991-4995.
Bouchon et al., "TREM-1 amplifies inflammation and is a crucial mediator of septic shock", Nature, vol. 410(6832), (Apr. 26, 2001), pp. 1103-1107.
Bout et al., "Lung Gene Therapy: In Vivo Adenovirus-Mediated Gene Transfer to Rhesus Monkey Airway Epithelium", Human Gene Therapy, (1994), 5:3-10.
Bradley, Teratocarcinomas and Embryonic Stem Cells: A Practical Approach, Robertson, ed., IRL, Oxford, (1987), pp. 113-152.
Bradley, "Modifying the mammalian genome by gene targeting", Current Opinion in Bio Technology, (1991), 2:823-829.
Brenner, "Errors in genome annotation", Trends in Genetics, vol. 15(4), (Apr. 1999), pp. 132-133.
Brinkman et al., "Phage display of disulfide-stabilized Fv fragments", J. Immunol. Methods, (1995), 182:41-50.
Burton et al., "Human Antibodies from Combinatorial Libraries ", Advances in Immunology, (1994), 57:191-280.
Byrne & Ruddle, "Multiplex gene regulation: a two-tiered approach to transgene regulation in transgenic mice", Proc. Natl. Acad. Sci. USA, (1989), 86:5473-5477.
Calame et al., "Transcriptional controlling elements in the immunoglobulin and T cell receptor loci", Adv. Immunol., vol. 43, (1988), pp. 235-275.
Calandra et al., J. Immunol., (2000), 145:3762-6.
Calandra et al., "Protection from septic shock by neutralization of macrophage migration inhibitory factor," Nat. Med., 6:164-70, 2000.
Campes & Tilghman, "Postnatal repression of the alpha-fetoprotein gene is enhancer independent", Genes Dev., (1989), 3:537-546.
Cantoni et al., "NKp44, atriggering receptor involved in tumor cell lysis by activated human natural killer cells, is a novel member of the immunoglobulin superfamily," J. Exp. Med. 189(5), (1999), pp. 787-796.
Carrell et al., "A Novel Procedure for the Synthesis of Libraries Containing Small Organic Molecules" Angew. Chem. Int. Ed. Engl., (1994), 33:2059 & 2061.
Cella et al., "Anovel inhibitory receptor (ILT3) expressed on monocytes, macrophages, and dendritic cells involved in antigen processing", J. Exp. Med., vol. 185(10), (1997), pp. 1743-1751.
Chen et al., "Gene therapy for brain tumors: regression of experimental gliomas by adenovirus-mediated gene transfer in vivo.", Proc. Natl. Acad. Sci. USA, (1994), 91:3054-3057.
Cho et al., "An unnatural biopolymer", Science, (1993), 261:1303.
Chomel et al., "*Bartonella henselae* Prevalence in Domestic Cats in California: Risk Factors and Association between Bacteremia and Antibody Titers.", Journal of Clinical Microbiology, vol. 33(9), (Sep. 1995), pp. 2445-2450.
Cohen et al., "[42] Receptor-mediated transport of DNA into eukaryotic cells", Meth. Enzymol., (1993), 217:618-644.
Clowes et al., "Long-term biological response of injured rat carotid artery seeded with smooth muscle cells expressing retrovirally introduced human genes.", J. Clin. Invest., (1994), 93:644-651.
Cohen et al., "Emerging Technologies for Sequencing Antisense Oligonucleotides: Capillary Electrophoresis and Mass Spectrometry," Adv. Chromatogr., (1996), 36:127-162.
Colberre-Garapin et al., "A new dominant hybrid selective marker for higher eukaryotic cells", J. Mol. Biol., (1981) 150:1.
Hoffman et al., "Phylogenetic perspectives in innate immunity", Science, vol. 284(5418), 1999, pp. 1313-1318.
Houghten, Bio Techniques, (1992), 13:412-421.
Hsu et al., "Detection of DNA point mutations with DNA mismatch repair enzymes", Carcinogenesis, (1994), 15:1657-1662.
Huston et al., "Protein engineering of single-chain Fv analogs and fusion proteins", Methods in Enzymology, (1991), 203-46-88.
Hyrup et al., "Peptide Nucleic Acids (PNA): Synthesis, properties and potential applications", Bioorganic & Medicinal Chemistry, 1996, 4(1): 5-23.
Inoue et al., "Synthesis and hybridization studies on two complementary nona(2'-O-methyl)ribonucleotides" Nucleic Acids Res., (1987), 15: 6131-6148.
Inoue et al., "Sequence-dependent hydrolysis of RNA using modified oligonucleotide splints and RNase H", FEBS Lett., (1987), 215: 327-330.
Iwabuchi et al., Oncogene, (1993), 8: 1693-1696.
Jespers et al., Bio Technology, (1988), 12: 899-903.
Jobling & Holmes, "Analysis of structure and function of the B Subunit of cholera toxin by the use of site-directd mutagenesis", Molecular Microbiology, vol. 5(7), pp. 1755-1767.
Katsuura et al., "CD48 expression on leukocytes in infectious diseases: flow cytometric analysis of surface antigen", Acta Paediatr Jpn., vol. 40(6), 1998, pp. 580-585.
Kaufman et al., EMBO J., (1987), 6: 187-195.
Keen et al., "Rapid detection of single base mismatches as heteroduplexes on Hydrolink gels", Trends Genet, (1991), 7:5.
Kessel & Gruss, "Murine developmental control genes", Science, (1990), 249: 374-379.
Kettleborough et al., "Isolation of tumor cell-specific single-chain Fv from immunized mice using phage-antibody libraries and the reconstruction of whole antibodies from these antibody fragments", Eur. J. Immunol., vol. 24(4), 1994, pp. 852-958.
Kiem et al., Retrovirus-Mediated Gene Transduction into Canine Peripheral Blood Repopulating Cells, Blood, (1994), 83: 1467-1473.
Knappik et al., Biotechniques, (1994), 17(4): 754-761.
Kohler, "Immunoglobulin chain loss in hybridoma lines", Proc. Natl. Acad.Sci. USA, (1980), 77: (4) 2197.
Koller & Smithies, "Inactivating the beta 2-microglobulin locus in mouse embryonic stem cells by homologous recombination", Proc. Natl. Acad. Sci. USA (1989), 86: 8932-8935.
Kozal et al., "Extensive polymorphisms observed in HIV?1 clade B protease gene using high?density oligonucleotide arrays", Nature Medicine, (1996), 2: 753-759.
Kozarsky & Wilson, "Gene therapy: adenovirus vectors", Current Opinion in Genetics and Development, (1993), 3: 499-503.
Krol et al., "Modulation of Eukaryotic Gene Expression by Complementary RNA or DNA Sequences" Bio/Techniques, (1988), 6: 958-976.
Kruse et al., "Characterization of a continuous human glioma cell line DBTRG-05MG: growth kinetics, karyotype, receptor expression, and tumor suppressor gene analyses", In Vitro Cell. Dev. Biol., (1992), 28A: 609-614.
Kubagawa et al., "Biochemical nature and cellular distribution of the paird immunoglobulin-like receptors, PIR-B." J. Exp. Med 189:309, 1999.
Kunkel et al., "Rapid and efficient site-specific mutagenesis without phenotypic selection", Methods Enzymol., (1987), 154: 367-82.
Kurjan & Herskowitz, "Structure of a yeast pheromone gene (MF?): A putative ?-factor precursor contains four tandem copies of mature ?-factor", Cell (1982), 30: 933-943.
Kwoh et al., "Transcription-based amplification system and detection of amplified human immunodeficiency virus type 1 with a bead-based sandwich hybridization format", Proc. Natl. Acad. Sci. USA, (1989), 86: 1173-1177.

(56) References Cited

OTHER PUBLICATIONS

Lakso et. al., "Targeted oncogene activation by site-specific recombination in transgenic mice", Proc. Natl. Acad. Sci. USA, (1992) 89: 6232-6236.
Lam, Nature, "A new type of synthetic peptide library for identifying ligand-binding activity", (1991), 354: 82-84.
Lam, "Mini-review. Application of combinatorial library methods in cancer research and drug discovery", Anticancer Drug Des., (1997), 12: 145.
Landegran et al., "A ligase-mediated gene detection technique", Science, (1988), 241: 1077-1080.
Lane et al., "CD40 ligand-independent B cell activation revealed by CD40 ligand-deficient T cell clones: evidence for distinct activation requirements for antibody formation and B cell proliferation", Eur. J. Immunol., (1995), 6: 1788.
Lanier et al., "NK cell receptors," Annu. Rev. Immunol., 16: 359 (1998).
Lanier, LL, "Immunoreceptor DAP12 bearing a tyrosine-based activation motif is involved in activating NK cells", Nature, vol. 391 (6668), (1998), pp. 703-707.
LeMaitre et al., "Specific antiviral activity of a poly(L-lysine)-conjugated oligodeoxyribonucleotide sequence complementary to vesicular stomatitis virus N protein mRNA initiation site", Proc. Natl. Acad. Sci. USA, (1987), 84: 648-652.
Letsinger et al., "Cholesteryl-conjugated oligonucleotides: synthesis, properties, and activity as inhibitors of replication of human immunodeficiency virus in cell culture", Proc. Natl. Acad. Sci. USA, (1989), 86: 6553-6556.
Li et al., "Targeted mutation of the DNA methyltransferase gene results in embryonic lethality," Cell, (1992), 69: 915.
Lizardi et al., "Exponential amplification of recombinant-RNA hybridization probes," Nature Biotechnology, (1988), 6: 1197-1202.
Loeffler & Behr, "Gene transfer into primary and established mammalian cell lines with lipopolyamine-coated DNA," Meth. Enzymol., (1993), 217: 599-618.
Lonberg et al., "Human antibodies from transgenic mice", Int. Rev. Immunol., vol. 13(1), (1995) pp. 65-93.
Lowy et al., "Isolation of transforming DNA: Cloning the hamster aprt gene," Cell, (1980), 22: 817.
Lucklow & Summers, "High level expression of nonfused foreign genes with *Autographa californica* nuclear polyhedrosis virus expression vectors," Virology, (1989), 170: 31-39.
Madura et al., "N-recognin/Ubc2 interactions in the N-end rule pathway," J. Biol. Chem., (1993), 17: 5973-88.
Mag et al., "Synthesis and selective cleavage of oligodeoxyribonucleotides containing non-chiral intemucieotlde phosphoramidate linkages," Nucleic Acids Res., (1989), 17: 5973-88.
Maher, "DNA Triple-Helix Formation: An Approach to Artificial Gene Repressors?," Bioassays, (1992), 14(12): 807-15.
Malaviya et al., "Mast cell modulation of neutorphil influx and bacterial clearance at sites of infection thrugh TNF-alpha", Nature, 381, (1996), pp. 77-80.
Mastrangeli et al., "Diversity of airway epithelial cell targets for in vivo recombinant adenovirus-mediated gene transfer," J. Clin. Invest., (1993), 91: 225-234.
Maxam & Gilbert, "A new method for sequencing DNA," Proc. Natl. Acad. Sci. USA, (1977), 74: 560.
McNamara et al., "Interleukin-1 receptor antibody (IL-1rab) protection and treatment against lethal endotoxemia in mice", J. Surg. Res., 54, (1993), 316-21.
Medzhitov et al., "Innate immunity", N. Engl. J. Med., vol. 343, (2000), pp. 338-344.
Zon, "Oligonucleotide Analogues as Potential Chemotherapeutic Agents," Pharm. Res., (1988), 5: 539-549.
Zuckermann et al., "Discovery of Nanomolar Ligands for 7-Transmembrane G-Protein-Coupled Receptors from a Diverse N-(Substituted)glycine Peptoid Library," J. Med.Chem., (1994), 37: 2678.
Basic Methods in Molecular Biology, Elsevier Science Publishing Co., New York, (1986), pp. 75-78 and 84-87.
Current Protocols in Molecular Biology, John Wiley & Sons, New York, (1989), Supp 24, 6.3.1-6.3.6.
NCBL Sequence Viewer Accession No. D78812 (Jul. 20, 2006).
NCBL Sequence Viewer Accession No. AI337247 (Mar. 18, 1999).
NCBL Sequence Viewer Accession No. AW139572 (Oct. 30, 1999).
NCBL Sequence Viewer Accession No. AW274906 (Jan. 3, 2000).
NCBL Sequence Viewer Accession No. AW139573 (Oct. 30, 1999).
NCBL Sequence Viewer Accession No. AW394041 (Feb. 4, 2000).
NCBL Sequence Viewer Accession No. AI621023 (Dec. 14, 1999).
NCBL Sequence Viewer Accession No. AI186456 (Oct. 28, 1998).
NCBL Sequence Viewer Accession No. AI968134 (Aug. 25, 1999).
NCBL Sequence Viewer Accession No. AI394092 (Mar. 30, 1999).
NCBL Sequence Viewer Accession No. AI681036 (Dec. 16, 1999).
NCBL Sequence Viewer Accession No. AI962750 (Mar. 8, 2000).
NCBL Sequence Viewer Accession No. AA494171 (Aug. 19, 1997).
NCBL Sequence Viewer Accession No. AA099288 (May 11, 1997).
NCBL Sequence Viewer Accession No. AW139363 (Oct. 30, 1999).
NCBL Sequence Viewer Accession No. AW135801 (Oct. 29, 1999).
NCBL Sequence Viewer Accession No. AA101983 (May 11, 1997).
NCBL Sequence Viewer Accession No. AF196329 (May 24, 2000).
NCBL Sequence Viewer Accession No. AF213457 (May 23, 2000).
NCBL Sequence Viewer Accession No. N41388 (Jan. 24, 1996).
Sharif and Knapp, "From expression to signaling: Roles of TREM-1 and TREM-2 in innate immunity and bacterial infection," Immunobiology, vol. 213, No. 9-10, pp. 701-713 (2008).
Turnbull et al., "Cutting Edge: TREM-2 Attenuates Macrophage Activation," J. Immunol., vol. 177, pp. 3520-3524 (2006).
Adrie et al., "Postresuscitation disease after cardiac arrest: a sepsis-like syndrom?", Current Opinion in Critical Care, Jun. 2004, vol. 10, pp. 208-212.
Begum et al., "*Mycobacterium bovis* BCG Cell Wall-Specific Differentially Expressed Genes Identified by Differential Display and cDNA Subtraction in Human Macrophages," Infection and Immunity, Feb. 2004, pp. 937-948.
Beleharski et al., "ARole for Triggering Receptor Expressed on Myeloid Cells-1 in Host Defense During the Early-Induced and Adaptive Phases of the Immune Response," The Journal of Immunology, 2003, vol. 170, pp. 3812-3818.
Bone et al., "Definitions for Sepsis and Organ Failure and Guidelines for the Use of Innovative Therapies in Sepsis," Jun. 1992, vol. 101, pp. 1644-1655.
Cohen, Jonathan, "TERM-1 in sepsis," The Lancet, Sep. 8, 2001, vol. 358, pp. 776-778.
Cohen, Jonathan, "The immunopathogenesis of sepsis," Nature, Dec. 19/26, 2002, vol. 420, pp. 885-891.
Collart et al., "Regulation of Tumor Necrosis Factor Alpha Transcription in Macrophages: Involvement of Four kB-Like Motifs and Constitutive and Inducible Forms of NF-kB," Molecular and Cellular Biology, Apr. 1990, vol. 10, No. 4, pp. 1498-1506.
Colonna et al., TREM-1 (Triggering Receptor Expressed on Myeloid Cells): A New Player in Acute inflammatory Responses, Journal of Infectious Diseases, 2003, 187, suppl. 2: pp. S397-S401.
Colonna et al., "TREMS in the Immune System and Beyond." Nature Reviews Immunology, Jun. 2003, vol. 3, No. 6, pp. 445-453 (printed as pp. 1-9).
Dinarello et al., "Proinflammatory and Ant-inflammatory Cytokines as Mediators in the Pathogenesis of Septic Shock," Chest, Dec. 1997, vol. 112, No. 6, pp. 321S-329S.
Echtenacher et al., "Tumor Necrosis Factor-Dependen Adhesions as a Major Protective Mechanism Early in Septic Peritonitis in Mice." Infection and Immunity, Jun. 2001, vol. 69, No. 6, pp. 3550-3555.
Echtenacher et al., "Requirement of Endogenous Tumor Necrosis Factor/Cachectin for Recovery from Experimental Peritonitis." Journal of Immunology, Dec. 1, 1990, vol. 145, No. 11, pp. 3762-3766.
Fisher et al., Treatment of Septic Shock with the Tumor Necrosis Factor Receptor: Fc Fusion Protein.: The New England Journal of Medicine, 1996, vol. 334, No. 26, pp. 1697-1702.
Gibot et al., "A Soluble Form of the Triggering Receptor Expressed on Myeloid Cells-1 Modulates the Inflammatory Response in Murine Sepsis," The Journal of Experimental Medicine, Dec. 6, 2004, Vo. 200 No. 11 pp. 1419-1426.

(56) References Cited

OTHER PUBLICATIONS

Griffin et al., "Abnormal Hear Rate Characteristics Preceding Neonatal Sepsis and Sepsis-Like Illness," Pediatric Research, 2003, vol. 53, No. 6, pp. 920-926.
Hiscott et al., "Characterization of a Functional NF-kB Site in the Human Interleukin 1b Promoter: Evidence for a Positive Autoregulatory Loop," Molecular and Cellular Biology, Oct. 1993, vol. 13 No. 10, pp. 6231-6240.
Hotchkiss et al., "The Pathophysiology and Treatment of Sepsis," The New England Journal of Medicine, Jan. 9, 2003, pp. 138-150.
Keane et al., "Tuberculosis Associated with infliximab, a Tumor Necrosis Factor a-Neutralizing Agent," The New England Journal of Medicine, Oct. 11, 2001, vol. 345, No. 15, pp. 1098-1104.
Kelker et al., "Crystal Structure of Human Triggering Receptor Expressed on Myeloid Cells 1 (TREM-1) at 1.47 A," J. Mol. Biol. 2004, vol. 342, pp. 1237-1248.
Lantz et al., "Characterization In Vitro of a Human Tumor Necrosis Factor-binding Protein: A Soluble Form of a Tumor Necrosis Factor Receptor," J. Clin. Invest., Nov. 1990, vol. 89, pp. 1396-1402.
Lolis et al., "Therapeutic Approaches to Innate Immunity:Severe Sepsis and Septic Shock," Nature Reviews Drug Discovery, Aug. 2003, vol. 2, pp. 635-645.
NCBI Reference Sequences (RefSeq) NP_061113 (2 pgs).
NCBI Reference Sequences (RefSeq) NP_067381 (2 pgs).
Radaev et. al., "Crystal Structure of the Human Myeloid Cell Activation Receptor TREM-1," Structure, Dec. 2003, vol. 11, pp. 1527-1535.
Saleeba et al., "Chemical cleavage of mismatch to detect mutations," Methods Enzymol., (1992), 217: 286-295.
Sallusto et al., "Efficient peresentation of soluble antigen by cultured human dendritic cells is maintained by granulocyte/macrophage colony-stimulation factor plus interleukin 4 and downregulated by tumor necrosis factor alpha", J. Exp. Med., 1994, vol. 179(4), pp. 1109-1118.
Salmons & Gunzberg, "Targeting of Retroviral Vectors for Gene Therapy," Human Gene Therapy, (1993), 4: 129-141.
Sambrook et al., Molecular Cloning, A Laboratory Manual, 2nd Edition, Cold Spring Harbor Laboratory, Cold Spring Harbor, NY, (1990), Chapters 16 & 17.
Sanger, "DNA sequencing with chain-terminating inhibitors," Proc. Natl. Acad. Sci. USA, (1977), 74: 5463.
Santerre et al., "Expression of prokaryotic genes for hygromycin B and G418 resistance as dominant-selection markers in mouse L cells," Gene, (1984), 30: 147.
Sawai et al., "Direct Production of the Fab Fragment Derived From the Sperm Immobillizing Antibody Using Polymerase Chain Reaction and cDNA Expression Vectors," AJRI, (1995), 34:26-34.
Schultz et al., "Expression and secretion in yeast of a 400-kda envelope glycoprotein derived from epstein-barr virus," Gene, (1987), 54: 113-123.
Scott & Smith, "Searching for peptide ligands with an epitope library," Science, (1990), 249: 386-390.
Seed, "An LFA-3 cDNA encodes a phospholipid-linked membrane protein homologous to its receptor CD2," Nature, (1987), 329: 840.
Shu et al., "Secretion of a single-gene-encoded immunoglobulin from myeloma cells", Proc. Natl. Acad. Sci. USA, vol. 90(17), (1993), pp. 7995-7999.
Skerra et al., "Assembly of a functional immunoglobulin Fv fragment in *Escherichia coli*", Science, vol. 240(4855), (1988), pp. 1038-1041.
Skolnick & Fetrow, "From gene to protein structure and function: novel applications of computational approaches in the genomic era", Trends in Biotech, vol. 18(1), (2000) pp. 34-39.
Smith et al., "Production of human beta interferon in insect cells infected with a baculovirus expression vector," Mol. Cell Biol., (1983), 3: 2156-2165.
Smith & Johnson, "Single-step purification of polypeptides expressed in *Escherichia coli* as fusions with glutathione S-transferase," Gene, (1988), 67: 31-40.
Smith & Zhang, "The challenges of genome sequence annotation or 'The devil is in the details'", Nature Biotechnology, vol. 15 (Nov. 1997), pp. 1222-1223.
Springer et al., "Traffic signals for lymphocyte recirculation and leukocyte emigration: The multistep paradigm," Cell, 76: 301, 1994.
Stemple & Anderson, "Isolation of a stem cell for neurons and glia from the mammalian neural crest," Cell, (1992), 71:973-985.
Studnicka et al., "Human-engineered monoclonal antibodies retain full specific binding activity by preserving non-CDR complementarity-modulating residues," Protein Engineering, (1994), 7(6):805-814.
Sugimoto et al., "Determination of cell surface membrane antigens common to both human neuroblastoma and leukemia-lymphoma cell lines by a panel of 38 monoclonal antibodies", J. Natl. Cancer Inst., vol. 73(1), (1984), pp. 51-57.
Szybalska & Szybalski, "Genetics of human cell lines, IV. DNA-mediated heritable transformation of a biochemical trait," Proc. Natl. Acad. Sci. USA, (1962), 48: 2026.
Thomas & Capecchi, "Site-directed mutagenesis by gene targeting in mouse embryo-derived stem cells," Cell, (1987), 51: 503.
Thorpe et al., "The Preparation and Cytotoxic Properties of Antibody-Toxin Conjugates," Immunol. Rev., (1982), 62: 119-58.
Thorpe, Antibody Carriers of Cytotoxic Agents in Cencer Therapy: A Review, in Monoclonal Antibodies 84: Biological and Clinical Applications, Pinchera et al., eds., (1985), pp. 475-506.
Tolstoshev, "Gene Therapy, Concepts, Current Trials and Future Directions," Ann. Rev. Pharmacol. Toxicol., (1993), 32: 573-596.
Tomasello et al., "Combined natural killer cell and dendritic cell functional deficiency in KASRAP/DAP12 loss-of-function mutant mice", Immunity 13: 355-64, 2000.
Tomic et al., "A rapid and simple method for introducing specific mutations into any position of DNA leaving all other positions unaltered," Nucleic Acids Res., (1990), 18(6): 1656.
Tracey et al., "Shock and tissue injury induced by recombinant human cachectin." Science 234-470-4 1986.
Traunecker et al., "Myeloma based expression system for production of large mammalian proteins," Trends Biotechnol., vol. 9, (1991), pp. 109-113.
Trowbridge et al., "Establishment and characterization of ferret cells in culture," In Vitro, (1982), 18: 952-960.
Ulevitch et al., "Recognition of Gram-negative bacteria and endotoxin by the innate immune system," Curr. Opin. Immunol, vol. 11, (1999), pp. 19-22.
Upender et al., "Megaprimer Method for In Vitro Mutagenesis Using Parallel Templates," Biotechniques, (1995), 18(1): 29-30, 32.
Van Keuren et al., "Regional assignment of human liver-type 6-phosphofructokinase to chromosome 21q22.3 by using somatic cell hybrids and a monoclonal anti-L antibody," Hum. Genet., (1986), 74:34-40.
Wada et al., "Codon usage tabulated from the GenBank genetic sequence data," Nucleic Acid Res., (1992), 20: 2111-2118.
Wakayama et al., "Mice cloned from embryonic stem cells," Proc. Natl. Acad. Sci. USA, (1999), 96: 14984-14989.
Walsh et al., "Gene Therapy for Human Hemoglobinopathies," Proc. Soc. Exp. Biol. Med., (1993), 204: 289-300.
Wang et al., "A packaging cell line for propagation of recombinant adenovirus vectors containing two lethal gene-region deletions," Gene Therapy, (1995), 2: 775-783.
Wang et al., "HMG-1 as a late mediator of endotoxin lethality in mice", Science, vol. 285, (1999), pp. 248-251.
Weintraub et al., "Anti-sense RNA as a molecular tool for genetic analysis," Reviews—Trends in Genetics, (1986), vol. 1(1), pp. 22-25.
Wells, "Additivity of Mutational Effects in Proteins", Biochemistry, vol. 29(37), (Sep. 18, 1990), pp. 8509-8517.
Wigler et al., "Transfer of purified herpes virus thymidine kinase gene to cultured mouse cells," Cell, (1977), 11: 223.
Wigler et al., "Transformation of mammalian cells with an amplifiable dominant-acting gene," Natl. Acad. Sci. USA, (1980), 77: 3567.
Wilmut et al., "Viable offspring derived from fetal and adult mammalian cells," Nature, (1997), 385: 810-813.
Wilson et al., "The structure of an antigenic determinant in a protein", Cell, vol. 37(3), (1984), pp. 767-778.

(56) References Cited

OTHER PUBLICATIONS

Winoto & Baltimore, "A novel, inducible and T cell-specific enhancer located a the 3' end of the T cell receptor a locus," EMBO J., (1989), 8: 729-733.
Wu & Wu, "Receptor-mediated in vitro gene transformation by a soluble DNA carrier system," J. Biol. Chem., (1987), 262: 4429-4432.
Wu & Wu, "Delivery systems for gene therapy," Biotherapy, (1991), 3: 87-95.
Yamashita, "Inhibitory and stimulatory functions of paired Ig-like receptor (PIR family in RBL-2H3 Cells," J. Immunol. 161, (1998), pp. 4042-4047.
Zervos et al., "Mxi1, a protein that specifically interacts with Max to bind Myc-Max recognition sites," Cell, (1993), 72: 223-232.
Zijlstra et al., "Germ-line transmission of a disrupted b2-microglobulin gene produced by homologous recombination in embryonic stem cells," Nature, (1989), 342: 435-438.
Michael et al., Biotechniques, (1994), 16(3): 410-412.
Miller et al., "Use of retroviral vectors for gene transfer and expression," Meth. Enzymol., (1993), 217: 581-599.
Morgan & Anderson, "Human Gene Therapy," Ann. Rev. Biochem., (1993), 62: 191-217.
Morrison et al., "Endotoxins and disease mechanisms." Annu. Rev. Med. 38: 417-32, 1987.
Morrison, "Transfectomas provide novel chimeric antibodies," Science, (1985), 229: 1202.
Mulligan, "The basic science of gene therapy," Science, (1993), 260: 926-932.
Mulligan & Berg, "Selection for animal cells that express the *Escherichia coli* gene coding for xanthine-guanine phosphoribosyltransferase," Proc. Natl. Acad. Sci. USA, (1981), 78: 2072.
Mullinax et al., Bio Techniques, (1992), 12(6): 864-869.
Myers et al., "Detection of single base substitutions in total genomic DNA," Nature, (1985), 313: 495.
Myers et al., "Detection of single base substitutions by ribonuclease cleavage at mismatches in RNA:DNA duplexes," Science, (1985), 230: 1242.
Nakajima et al., "Human myeloid cells express and activating ILT receptor (ILTI) that associates with Fc receptor y-chain," J. Immunol. 162: 5. (1999), pp. 5-8.
Nakajima et al., "2B4: an NK cell activating receptor with unique specificity and signal transduction mechanism", Humm Immunol., vol. 61, (2000), pp. 39-43.
Nakazawa et al., "UV and skin cancer: specific p53 gene mutation in normal skin as a biologically relevant exposure measurement," Proc Natl. Acad. Sci. USA, (1994), 91: 360-364.
Naramura et al., "Mechanisms of cellular cytotoxicity mediated by a recombinant antibody-IL2 fusion protein against human melanoma cells," Immunol. Lett., (1994), 39: 91-99.
Nathan & Ding, "TREM-1: A new regulator of innate immunity in sepsis syndrome", Nature Medicine, vol. 7(5), May, 2001), pp. 530-532.
Nederman et al., "An in vitro bioassay for quantitation of human interferons by measurements of antiproliferative activity on a continuous human lymphoma cell line." Biologicals, vol. 18(1), (1990), pp. 29-34.
NGO et al., "The Protein Folding Problem and Tertiary Structure Prediction, Chapter 14: Computational Complexity Protein Structure Prediction, and the Levinthal Paradox", (Mar. 2, 1995), pp. 492-495.
Nicoletti et al., "A rapid and simple method for measuring thymocyte apoptosis by propidium iodide staining and flow cytometry," J. Immunol. Methods, (1991), 139: 271-279.
O'Gorman et al., "Recombinase-mediated gene activation and site-specific integration in mammalian cells," Science, (1991), 251: 1351-1355.
O'Hare et al., "Transformation of mouse fibroblasts to methotrexate resistance by a recombinant plasmid expressing a prokaryotic dihydrofolate reductase," Proc. Natl. Acad. Sci. USA, (1981), 78: 1527.
Ohlsson et al., "Interleukin-1 receptor antagonist reduces mortality from endotoxin shock", Nature, vol. 348, (1990), pp. 550-552.
Oi et al., "Chimeric Antibodies," Bio Techniques, (1986), 4: 214-221.
Oishi et al., "Inhibition of Neutrophil Apoptosis by Antioxidants in Culture Medium," Scand. J. Immunol., (1997), 45: 21-27.
Oliveira et al., "Fungal infections in marrow transplant recipients under antifungal prophylaxis with fluconazole", Brazilian Journal of Medical and Biological Research, vol. 35(7), (Jul. 2002), pp. 789-798.
Olopade et al., "Molecular Analysis of Deletions of the Short Arm of Chromosome 9 in Human Gliomas," Cancer Res., (1992), 52: 2523-2529.
Orita et al., "Detection of polymorphisms of human DNA by gel electrophoresis as single-strand conformation polymorphisms," Proc. Natl. Acad. Sci. USA, (1989), 86: 2766.
Owerbach et al., "Genetics of the large, external, transformation-sensitive (LETS) protein: assignment of a gene coding for expression of LETS to human chromosome 8," Proc. Natl. Acad. Sci. USA, (1978), 75: 5640-5644.
Padlan, "A possible procedure for reducing the immunogenicity of antibody variable domains while preserving their ligand-binding properties," Molecular Immunology, (1991), 28(4/5): 489-498.
Pajunen et al. "Assignment of the gene coding for both the beta-subunit of prolyl 4-hydroxylase and the enzyme isomerase somerase to human chromosome region 17p11—qter," Cytogenet. Cell Genet., ( 1988), 47: 37-41 (Abstract).
Perry-O'Keefe et al., "Peptide nucleic acid pre-gel hybridization: An alternative to Southern?hybridization," Proc. Natl. Acad. Sci. USA, (1996), 93: 14670-675.
Persic et al., "An integrated vector system for the eukaryotic expression of antibodies or their fragments after selection from phage display libraries", Gene, vol. 187(1), (1997), pp. 9-18.
Peschon et al., "TNF receptor-deficient mice reveal divergent roles for p55 and p75 in several models of inflammation", J. Immunol., vol. 160, (1998), pp. 943-952.
Petersen et al., A PNA-DNA linker synthesis of N-((4,4?-dimethoxytrityloxy)ethyl)-N-(thymin-1-ylacetyl)glycine, Bioorganic Med. Chem. Lett., (1995), 5: 1119-1124.
Pfeffer et al., "Mice deficient for the 55 kd tumor necrosis factor receptor are resistant to endotoxic shock, yet succumb to *L. monocytogenes* infection", Cell, vol. 73, (1993) pp. 457-467.
Pinkert et al., "An albumin enhancer located 10 kb upstream functions along with its promoter to direct efficient, liver-specific expression in transgenic mice," Genes Dev., (1987), 1: 268-277.
Pittelkow & Scott, "New Techniques for the In Vitro Culture of Human Skin Keratinocytes and Perspectives on Their Use for Grafting of Patients With Extensive Burns," Mayo Clinic Proc., (1986), 61: 771.
Prosser, "Detecting single-base mutations," Tibtech, (1993), 11: 238-246.
Proudfoot, "Transcriptional interference and termination between duplicated globin gene constructs suggests a novel mechanism for gene regulation," Nature, (1986), 322: 562.
Queen & Baltimore, "Immunoglobulin gene transcription is activated by downstream sequence elements," Cell, (1983), 33: 741-748.
Radany et al., "Directed establishment of rat brain cell lines with the phenotypic characteristics of type 1 astrocytes," Proc. Natl. Acad. Sci. USA, (1992) 89: 6467-6471.
Rheinwald, "Chapter 15 Serial Cultivation of Normal Human Epidermal Keratinocytes," Meth. Cell Bio., (1980), 21A:229.
Riechmann et al., "Reshaping human antibodies for therapy," Nature, (1988), 332: 323.
Roguska et al., "Humanization of murine monoclonal antibodies through variable domain resurfacing," Proc. Natl. Acad. Sci. USA, (1994), 91: 969-973.
Rosenbaum & Reissner, "Temperature-gradient gel electrophoresis: Thermodynamic analysis of nucleic acids and proteins in purified form and in cellular extracts," Biophys. Chem., (1987), 26:235-246.
Rosenberg et al., "Inflammation," In Fundamental Immunology, 4th Ed. W. E. Paul, ed., p. 1051, 1999.
Rosenfeld et al., "Adenovirus-mediated transfer of a recombinant alpha 1-antitrypsin gene to the lung epithelium in vivo," Science, (1991), 252: 431-434.

(56) References Cited

OTHER PUBLICATIONS

Rosenfeld et al., "In vivo transfer of the human cystic fibrosis transmembrane conductance regulator gene to the airway epithelium," Cell, (1992), 68:143-155.
Rothe et al., "Mice lacking the tumour necrosis factor rector receptor 1 are resistant to TNF-mediated toxicity but highly susceptible to infection by *Listeria monocytogenes*" Nature, vol. 364, (1993), pp. 798-802.
Saiki et al., "Analysis of enzymatically amplified b-globin and HLA-DQa DNA with allele-specific oligonucleotide probes," Nature, (1986), 324: 163.
Saiki et al., "Genetic analysis of amplified DNA with immobilized sequence-specific oligonucleotide probes," Proc. Natl. Acad. Sci. USA, (1989), 86:6230.
Bouchon et al, Journal of Immunology, "Cutting Edge: Inflammatory Responses Can Be Triggered by TERM-1, A Novel Receptor Expressed on Neutrophils and Monocytes", 2000, vol. 164, No. 10, pp. 4991-4995.
Bouchon et al, Nature, "TREM-1Amplifies Inflammation and is a Crucial Mediator of Septic Shock", 2001, vol. 410, No. , pp. 1103-1107.
J. Phua et al, European Respiratory Journal, "Soluble Triggering Receptor Expressed on Myeloid Cells-1 in Acute Respiratory Infections", 2006, vol. 28, No. , pp. 695-702.
Jun Kuai et al, Rheumatology, "TREM-1 Expression Is Increased in the Synovium of Rheumatoid Arthritis Patients and Induces the Expression of Pro-Inflammatory Cytokines", 2009, vol. 48, No. , pp. 1352-1358.
Mirjam Schenk, Journal of Clinical Investigation, "TREM-1—Expressing Intestinal Macrophages Crucially Amplify Chronic Inflammation in Experimental Colitis and Inflammatory Bowel Diseases", 2007, vol. 117, No. , pp. 3097-3106.
Yousuke Murakami et al, Arthritis and Rheumatism, "Intervention of an Inflammation Amplifier, Triggering Receptor Expressed on Myeloid Cells 1, for Treatment of Autoimmune Arthritis", 2009, vol. 60, No. 6, pp. 1615-1623.
Cotton et al., "Reactivity of cytosine and thymine in single-base-pair mismatches with hydroxylamine and osmium tetroxide and its application to the study of mutations", Proc. Natl. Acad. Sci. USA, (1988), 85:4397.
Cotton, "Current methods of mutation detection", Mutat. Res., (1993), 285:125-144.
Cox et al., "IL-10 enhances resolution of pulmonary inflammation in vivo by promoting apoptosis of neutrophils," Am. J. Physiol. Lung Cell Mol Physiol., (1996), 271:L566-L571.
Cronin et al., "Cystic fibrosis mutation detection by hybridization to light-generated DNA probe arrays" , Human Mutation, (1996), 7:244-255.
Cruikshank et al., J. Acquired Immune Deficiency Syndromes and Human Retrovirology, (1997) 14:193.
Cull et al., "Screening for receptor ligands using large libraries of peptides linked to the C terminus of the lac repressor.", Proc. Natl. Acad. Sci. USA, (1992), 89:1865-1869.
Cwirla et al., "Peptides on phage: a vast library of peptides for identifying ligands.", Proc. Natl. Acad. Sci. USA, (1990), 87:6378-6382.
Daws et al., "Cloning and Characterization of a Novel Mouse Myeloid DAP12-Associated Receptor Family," Eur. J. Immunol. 2001, 31:783-791.
Devlin, "Random peptide libraries: a source of specific protein binding molecules",Science, (1990), 249:404-406.
Dewitt et al., "Diversomers: an approach to nonpeptide, nonoligomeric chemical diversity", Proc. Natl. Acad. Sci. USA, (1993), 90:6909.
Dietrich et al., "Signal-regulatory protein β1 is a DAP12-associated activation receptor expressed in myeloid cells." J. Immunol. 164:9, 2000.
Doerks et al., "Protein annotation: detective work for function prediction", Trends in Genetics, vol. 14(6), (Jun. 1998), pp. 248-250.
Downey et al., "Intracellular signaling in neutropohil priming and activation," Semin Cell Bio. 6:345-356, 1995.
Echtenacher et al., "Requirement of endogenous tumor necrosis factor/cachectin for recovery from experimental peritonitis," J. Immunol. 145:3762-6, 1990.
Echtenacher et al. "Critical protective role of mast cells in a model of acute septic peritonitis", Nature, (1996), 381:75-7.
Edlund et al., "Cell-specific expression of the rat insulin gene: evidence for role of two distinct 5' flanking elements", Science, (1985) 230:912-916.
Erb et al., "Recursive deconvolution of combinatorial chemical libraries",Proc. Natl. Acad. Sci. USA, (1994), 91:11422.
Eskandari et al., "Anti-tumor necrosis factor antibody therapy fails to prevent lethality after cecal ligation and puncture of endotoxemia", J. Immunol., (1992), 148:2724-30.
Facchetti et al., "Suppurative Granulomatous Lymphadenitis; Immunohistochemical Evidence for a B-cell-Associated Granuloma," Am. J. Surg. Pathol., (1992), 16: 955-61.
Felici, "Selection of antibody ligands from a large library of oligopeptides expressed on a multivalent exposition vector", J. Mol. Biol., (1991), 222:301-310.
Fell et al., "Genetic construction and characterization of a fusion protein consisting of a chimeric F(ab') with specificity for carcinomas and human IL-2.", J. Immunol., (1991), 146:2446-2452.
Finn et al., Synthesis and Properties of DNA-PNA Chimeric Oligomers Nucleic Acids Res., (1996), 24(17): 3357-63.
Fodor, "Multiplexed biochemical assays with biological chips", Nature, (1993), 364:555-556.
Forster et al., "CCR7 coordinates the primary immune response by establishing functional microenvironments in secondary lymphoid organ," Cell 99:23-33, 1999.
Gallop et al., "Applications of Combinatorial Technologies to Drug Discovery. 1. Background and Peptide Combinatorial Libraries", J. Med. Chem., (1994), 37:1233.
Gasparini et al., "Restriction site generating-polymerase chain reaction (RG-PCR) for the probeless detection of hidden genetic variation: application to the study of some common cystic fibrosis mutations", Mol. Cell Probes, (1992), 6:1.
Gaultier et al.,"a-DNA IV: a-anomeric and b-anomeric tetrathymidylates covalently linked to intercalating oxazolopyridocarbazole. Synthesis, physicochemical properties and poly (rA) binding" Nucleic Acids Res., (1987), 15:6625-6641.
Gelrud et al., "Interaction of Tumor Necrosis Factor-a and Granulocyte Colony-Stimulation Factor on Neutrophil Apoptosis, Receptor Expression, and Bactericidal Function" Proc. Assoc. Am. Physicians, (1996), 108:455-456.
Gentz et al., "Bioassay for trans-activation using purified human immunodeficiency virus tat-encoded protein: trans-activation requires mRNA synthesis", Proc. Natl. Acad. Sci. USA, (1989), 86:821-824.
Gibbs et al., "Detection of single DNA base differences by competitive oligonucleotide priming" Nucleic Acids Res., (1989), 17:2437-2448.
Gibot et al., "Plasma Level of Trigering Receptor Expressed on Myeloid Cells-1: Its Diagnostic Accuracy in Patients with Suspected Sepsis," (2004), pp. 9-16.
Gibot et al., "Soluble Triggering Receptor Expressed on Myeloid Cells and the Diagnosis of Pneumonia," The New England Journal of Medicine, (2004), pp. 451-458.
Gillies et al., "High-level expression of chimeric antibodies using adapted cDNA variable region cassettes", J. Immunol. Methods, (1989), 125:191-202.
Gillies et al., "Antibody-targeted interleukin 2 stimulates T-cell killing of autologous tumor cells", Proc. Natl. Acad. Sci. USA., (1992), 89:1428-1432.
Gingras et al., "TREM-1, MDL-1, and DAP12 Expression is Associated with a Mature Stage of Myeloid Development," Molecular Immunology 38 (2001) pp. 817-824.
Glauser et al., "Septic shock: pathogenesis," Lancet 338:732-6, 1991.
Goldspiel et al., "Human Gene Therapy," Clinical Pharmacy, (1993), 12:488-505.
Gon et al. Microbiol. Immunol., (1996) 40:463-465.

(56) References Cited

OTHER PUBLICATIONS

Griffin et al., "DNA sequencing", Appl. Biochem. Biotechnol., (1993), 38:147-159.
Grossman & Wilson, "Retroviruses: delivery vehicle to the liver", Curr. Opin. in Genetics and Devel., (1993), 3:110-114.
Guatelli et al., "Isothermal, in vitro amplification of nucleic acids by a multienzyme reaction modeled after retroviral replication", Proc. Natl. Acad. Sci. USA, (1990), 87:1874-1878.
Haapala et al., "Isolation from cats of an endogenous type C virus with a novel envelope glycoprotein.", J. Virol., (1985), 53:827-833.
Hammerling et al., Moloclonal Antibodies and T-Cell Hybridomas, Elsevier, New York, (1981) pp. 563-681.
Haselhoff et al., "Simple RNA enzymes with new and highly specific endoribonuclease activities", Nature, (1988), 334: 585-591.
Hayashi, "PCR-SSCP: A method for detection of mutations", Genet. Anal. Tech. Appl., (1992), 9:73-79.
He et al., "Expression of O6-Methylguanine-DNA Methyltransferase in Six Human Medulloblastoma Cell Lines", Cancer Res., (1992), 52:1144-1148.
Hebert et al., "Sequential morphologic events during apoptosis of human neutrophils. Modulation by lipoxygenase-derived eicosanoids.", J. Immunol., (1996), 157:3105-3115.
Helene, "The anti-gene strategy: control of gene expression by triplex-forming-oligonucleotides" Anticancer Drung Des., (1991), 6(6):569-84.
Helene, "Control of Gene Expression by Triple Helix-Forming Oligonucleotides. The Antigene Strategy", Ann. N.Y. Acad. Sci., (1992), 660:27-36.
Hellstrom et al., "Antibodies for Drug Delivery" in Controlled Drug Delivery, 2nd edition, Robinson et al., eds., Marcel Dekker, Inc., (1987), pp. 623-653.
Proudfoot, "Transcriptional interference and termination between duplicated ; ; globin gene constructs suggests a novel mechanism for gene regulation," Nature, (1986), 322: 562.
NCBI Reference Sequences (RefSeq) NP_067381 (2 pgs), Jan. 13, 2003.
Arts Rob J W et al. "Trem-1 interaction with the LPS/TLR4 receptor complex" European Cytokine Network. 2011. vol. 22(1). p. 11-14.
R&D Systems: "Human TREM-1 Antibody." Internet Citation. Retrieved Nov. 27, 2012. http://www.rndsystems.com/Products/MAB1278.
Eleanor Molloy. "Triggering Receptor Expressed on Myeloid Cells (TREM) Family and the Application of its Antagonists." Recent Patents on Anti-Infective Drug Discovery. vol. 4(1). 2009. pp. 51-56.
Nagihan Bostanci et al. "Involvement of the TREM-1/DAP12 pathway in the innate immune responses to" Molecular Immunology. vol. 49(1) pp. 387-394, (2001).
Tessarz et al. "The TREM-1-DAP12 pathway." Immunology Letters, 2011, vol. 116(2) pp. 111-116.
Mohamadzadeh et al. "Activation of triggering receptor expressed on myeloid cells-1 on human neutrophils by Marburg and ebola viruses." Journal od Virology. 2006. vol. 80(14). pp. 7235-7244.
MacCallum Robert M.,Antibody-antigen Interactions: Contact Analysis and Binding Site Topography, Journal :Journal of Molecular Biology, Year 1996, vol. 262, pp. 732-745.
Pascalis Roberto De et al.,Grafting of Abbreviated Complementarity-Determining Regions Containing Specificity-Determining Residues Essential for Ligand Contact to Engineer a Less Immunogenic Humanized Monoclonal Antibody, Journal: The Journal of Immunology, Year 2002, vol. 169, pp. 3076-3084.
Casset Florence et al ,A peptide mimetic of an anti-CD4 monoclonal antibody by rational design, Journal:Biochemical and Biophysical Research Communications, Year 2003, vol. 307, pp. 198-205.
Chen Y et al.Selection and Analysis of an Optimized Anti-VEGF Antibody: Crystal Structure of an Affinity-matured Fab in Complex with Antigen, Journal :Journal of molecular Biology, Year 1999, vol. 293, pp. 865-881.
Wu herren et al .,Humanization of a Murine Monoclonal Antibody by Simultaneous optimization of Framework and CDR Residues, Journal:Journal of Molecular Biology, Year 1999, vol. 294, pp. 151-162.
Rudikoff Stuart et al.,Single amino acid substitution altering antigen-binding specificity, Journal :PNAS USA, Year 1982, vol. 79, pp. 1979-1983.
Dziarski Roman et al.The peptidoglycan recognition proteins (PGRPs), Journal :Genome BiologyYear 2006, vol. 7 pp. 232.1-232.13.
Gimano D Amatngalim et al: Cathelicidin Peptide LL-37 Modulates TREM-1 Expression and Inflammatory Responses to Microbial Compounds,Journal : Inflammation, Year,Sep. 2, 2010 , vol. 34, No. 5 pp. 412-425.
Julien Royet et al: "Peptidoglycan recognition proteins: modulators of the microbiome and inflammation",Journal: Nature Reviews Immunology,Year :Dec. 2011 pp. 837-851.
LS Bio/LifeSpan BioSciences, Inc., Pglyrp1 / pgrp antibody (ls-c579) http://www.lsbio.com/Antibodies/PGLYRP1-PGRP-Antibody-LS-C579/2801.
LS Bio/LifeSpan BioSciences, Inc.,Pglyrp1 / pgrp antibody (ls-c578) http://www.lsbio.com/Antibodies/PGLYRP1-PGRP-Antibody-LS-0578/2800.
LS Bio/LifeSpan BioSciences, Inc,Pglyrp1 / pgrp antibody (ls-c38137) http://www.lsbio.com/Antibodies/PGLYRP1-PGRP-Antibody-LS-C38137/37645.
Ghosh Amit et al.,A Novel Antimicrobial Peptidoglycan Recognition Protein in the Cornea, Journal:Invest. Ophthalmol. Vis. Sci. Year Sep. 2009 vol. 50 No. 9 pp. 4185-4191.
Dziarski Roman et al. , Mammalian peptidoglycan recognition proteins (PGRPs) in innate immunity, Journal Innate Immunity, Year 2010, vol. 16 No. 3, pp. 168-174.
LS Bio/LifeSpan BioSciences, Inc.,Pglyrp1 / pgrp antibody (ls-b4940), http://www.lsbio.com/Antibodies/PGLYRP1-PGRP-Antibody-LS-B4940/128350.
ABCAM,Anti-PGRPS antibody [188C424] (ab13903), http://www.abcam.com/PGRPS-antibody-188C424-ab13903.html Accessed on Jun. 12, 2014.
Kang Daiwu et al.,A peptidoglycan recognition protein in innate immunity conserved from insects to humans, Journal :Proc. Natl. Acad. Sci. USA, Year 1998, vol. 95, pp. 10078-10082.
Haselmayer Phillipp et al. TREM-1 ligand expression on platelets enhances neutrophil activation, Journal : Blood, Year 2007 vol. 110,pp. 1029-1035.
Dziarski Roman et al, Peptidoglycan recognition in innate immunity, Journal :Innate Immunity, Year Oct. 2005 vol. 11 No. 5 pp. 304-310.
Pant S.D. et al,Bovine PGLYRP1 polymorphisms and their association with resistance to *Mycobacterium avium* ssp. *paratuberculosis*, Journal Animal Genetics, Year Aug. 20, 2010,vol. 42, pp. 354-360.
Steiner Hakan , Peptidoglycan recognition proteins:On and off switches for innate immunity, Journal :Immunological Reviews ,Year 2004, vol. 198 pp. 83-96.
Larin Sergey S et al. Immunotherapy with autologous tumor cells engineered to secrete Tag7/PGRP, an innate immunity recognition molecule, Journal :The Journal of Gene Medicine Year 2004;vol. 6 pp. 798-808.
Kang Daiwu et al,.A peptidoglycan recognition protein in innate immunity conserved from insects to humans, Journal: Proc. Natl. Acad. Sci. USA, Year Aug. 1998, vol. 95, pp. 10078-10082.
Guan Rongjin et al, Crystal Structure of Human Peptidoglycan Recognition Protein S (PGRP-S) at 1.70 A Resolution, Journal :Journal of Molecular Biology.Year 2005, vol. 347,pp. 683-691.
A. Osanai et al.,Mouse Peptidoglycan Recognition Protein PGLYRP-1 Plays a Role in the Host Innate Immune Response against *Listeria monocytogenes* Infection, Journal: Infection and Immunity,Year Dec. 6, 2010 vol. 79, No. 2, pp. 858-866, XP055060881.
Arts Rob J W et al: "TREM-1 interaction with the LPS/TLR4 receptor complex.", Journal :European Cytokine Network,Year Mar. 2011, vol. 22, No. 1.pp. 11-14.

(56) References Cited

OTHER PUBLICATIONS

S. Gibot et al. Modulation of the Triggering Receptor Expressed on the Myeloid Cell Type 1 Pathway in Murine Septic Shock,Journal: Infection and Immunity,Year May 1, 2006 vol. 74, No. 5,pp. 2823-2830.

Ramanathan B et al: Cloning of porcine triggering receptor expressed on myeloid cells-1 (TREM-1) and its induction by lipopolysaccharide, peptidoglycan, and *Salmonella entérica* serovar Typhimurium, Dev Comp Immunol. 2005;29(1):1-7.

Thekla Poukoulidou et al. TREM-1 expression on neutrophils and monocytes of septic patients: relation to the underlying infection and the implicated pathogen,Journal : BMC Infectious Diseases, Year Nov. 4, 2011 vol. 11, No. 1, p. 309(1-8).

Dziarski R, Peptidoglycan recognition proteins (PGRPs), Journal :Molecular Immunology, Year 2004, vol. 40 pp. 877-886.

Saha et al., PGLYRP-2 and Nod2 Are Both Required for Peptidoglycan-Induced Arthritis and Local Inflammation, Journal :Cell Host & Microbe, Year 2009,vol. 5 pp. 137-150.

Saha et al.Peptidoglycan Recognition Proteins Protect Mice from Experimental Colitis by Promoting Normal Gut Flora and Preventing Induction of Interferon-y, Journal : Cell Host and Microbe, Year 2010, vol. 8, pp. 147-162.

ABCAM, Atlas Antibodies,PGRP Antibodies, United States Biological,List of Anti-PGRP Abs,http://www.antibodyresource.com/search/Antibodies/ffb4623f-177d-13a0-16e2-1105223fb311/PGRP.(Accessed Aug. 1, 2014).

ABCAM, Atlas Antibodies,United States Biological ,O75594 Antibodies, List of Anti-PGRP Abs, http://www.antibodyresource.com/search/Antibodies/125bfebf-0922-1605-34f6-8213e473b271/O75594 (Accessed Aug. 1, 2014).

ABCAM, Atlas Antibodies, United States Biological,Cytokine tag7 Antibodies,List of Anti-PGRP Abs,http://www.antibodyresource.com/search/Antibodies/f7a31750-abb9-1c85-b872-c3a2e796189c/Cytokine-tag7.(Accessed Aug. 1, 2014).

ABCAM, Atlas Antibodies, United States Biological,Peptidoglycan recognition protein 1 Antibodies,List of Anti-PGRP Abs, http://www.antibodyresource.com/search/Antibodies/1208015d-1757-26ad-1f04-6c9171376236/Peptidoglycan-recognition-protein-1(Accessed Aug. 1, 2014).

ABCAM, Atlas Antibodies, United States Biological,Peptidoglycan recognition protein 1 Antibodies,List of Anti-PGRP Abs, http://www.antibodyresource.com/search/Antibodies/ede383a0-138e-c073-17f0-f9db1294bc02/Peptidoglycan-recognition-protein-1(Accessed Aug. 1, 2014).

ABCAM, Atlas Antibodies, United States Biological Peptidoglycan recognition protein short Antibodies, List of Anti-PGRP Abs http://www.antibodyresource.com/search/Antibodies/3a8d5b63-12d8-12d6-1b99-11fb615758f5/Peptidoglycan-recognition-protein-short(Accessed Aug. 1, 2014).

ABCAM, Atlas Antibodies, United States Biological,TNFSF3L Antibodies,List of Anti-PGRP Abs http://www.antibodyresource.com/search/Antibodies/f33a5126-45cd-5220-878c-0fd9aa63ba35/TNFSF3L (Accessed Aug. 1, 2014).

ABCAM, Atlas Antibodies, United States Biological,Tag7 Antibodies,List of Anti-PGRP Abs http://www.antibodyresource.com/search/Antibodies/04107f68-8402-51df-bb36-4dd2bf8e16d1/Tag7(Accessed Aug. 1, 2014).

TREM-1 mrklrlwgll wmlfvsELRA ATKLTEEKYE LKEGQTLDVK CDYTLEKFAS 50

SQKAWQIIRD GEMPKTLACT ERPSKNSHPV QVGRIILEDY HDHGLLRVRM 100

VNLQVEDSGL YQCVIYQPPK EPHMLFDRIR LVVTKGFSGT PGSNENSTQN 150

VYKIPPTTTK ALCPLYTSPR TVTQAPPKST ADVSTPDSEIN LTNVTDIIR 200

VPVFNIVILL ACGFLSKSLV FSVLFAVTLR SFVP 234

TREM-2 meplrlllil fvlELSGAHN TTVFQGVAGQ SLQVSCPYDS MKHWGRRKAW 50

CRQLGEKGPC QRVVSTHNLW LLSFLRRWNG STAITDDTLG GTLTITLRNL 100

QPHDAGLYQC QSLHGSEADT LRKVLVEVLA DPLDHRDAGD LWFPGESESF 150

EDAHVEHSIS RSLLEGEIPF PPTSILLLLA CIFLIKILAA SALWAAAWHG 200

QKPGTHPPSE LDCGHDPGYQ LQTLPGLRDT 230

FIG. 1

```
  1 ctactactac taaattcgcg gccggtcgac gctggtgcac aggaaggatg aggaagacca
 61 ggctctgggg gctgctgtgg atgctctttg tctcagaact ccgagctgca actaaattaa
121 ctgaggaaaa gtatgaactg aaagaggggc agaccctgga tgtgaaatgt gactacacgc
181 tagagaagtt tgccagcagc cagaaagctt ggcagataat aagggacgga gagatgccca
241 agaccctggc atgcacagag aggccttcaa agaattccca tccagtccaa gtggggagga
301 tcatactaga agactaccat gatcatggtt tactgcgcgt ccgaatggtc aaccttcaag
361 tggaagattc tggactgtat cagtgtgtga tctaccagcc tcccaaggag cctcacatgc
421 tgttcgatcg catccgcttg gtggtgacca agggtttttc agggacccct ggctccaatg
481 agaattctac ccagaatgtg tataagattc ctcctaccac cactaaggcc ttgtgcccac
541 tctataccag ccccagaact gtgacccaag ctccacccaa gtcaactgcc gatgtctcca
601 ctcctgactc tgaaatcaac cttacaaatg tgacagatat catcagggtt ccggtgttca
661 acattgtcat tctcctggct ggtggattcc tgagtaagag cctggtcttc tctgtcctgt
721 ttgctgtcac gctgaggtca tttgtaccct aggcccacga acccacgaga atgtcctctg
781 acttccagcc acatccatct ggcagttgtg ccaagggagg agggaggagg taaaaggcag
841 ggagttaata acatgaatta aatctgtaat caccagctat ttct
```

FIG.2

```
   1 tgacatgcct gatcctctct tttctgcagt tcaagggaaa gacgagatct tgcacaaggc
  61 actctgcttc tgcccttggc tggggaaggg tggcatggag cctctccggc tgctcatctt
 121 actctttgtc acagagctgt ccggagccca caacaccaca gtgttccagg gcgtggcggg
 181 ccagtccctg caggtgtctt gcccctatga ctccatgaag cactggggga ggcgcaaggc
 241 ctggtgccgc cagctgggag agaagggccc atgccagcgt gtggtcagca cgcacaactt
 301 gtggctgctg tccttcctga ggaggtggaa tgggagcaca gccatcacag acgataccct
 361 gggtggcact ctcaccatta cgctgcggaa tctacaaccc catgatgcgg gtctctacca
 421 gtgccagagc ctccatggca gtgaggctga caccctcagg aaggtcctgg tggaggtgct
 481 ggcagacccc ctggatcacc gggatgctgg agatctctgg ttccccgggg agtctgagag
 541 cttcgaggat gcccatgtgg agcacagcat ctccaggagc ctcttggaag gagaaatccc
 601 cttcccaccc acttccatcc ttctcctcct ggcctgcatc tttctcatca agattctagc
 661 agccagcgcc ctctgggctg cagcctggca tggacagaag ccagggacac atccacccag
 721 tgaactggac tgtggccatg acccagggta tcagctccaa actctgccag ggctgagaga
 781 cacgtgaagg aagatgatgg gaggaaaagc ccaggagaag tcccaccagg gaccagccca
 841 gcctgcatac ttgccacttg gccaccagga ctccttgttc tgctctggca agagactact
 901 ctgcctgaac actgcttctc ctggaccctg gaagcaggga ctggttgagg gagtggggag
 961 gtggtaagaa cacctgacaa cttctgaata ttggacattt taaacactta caaataaatc
1021 caagactgtc atatttaaaa a
```

FIG.3

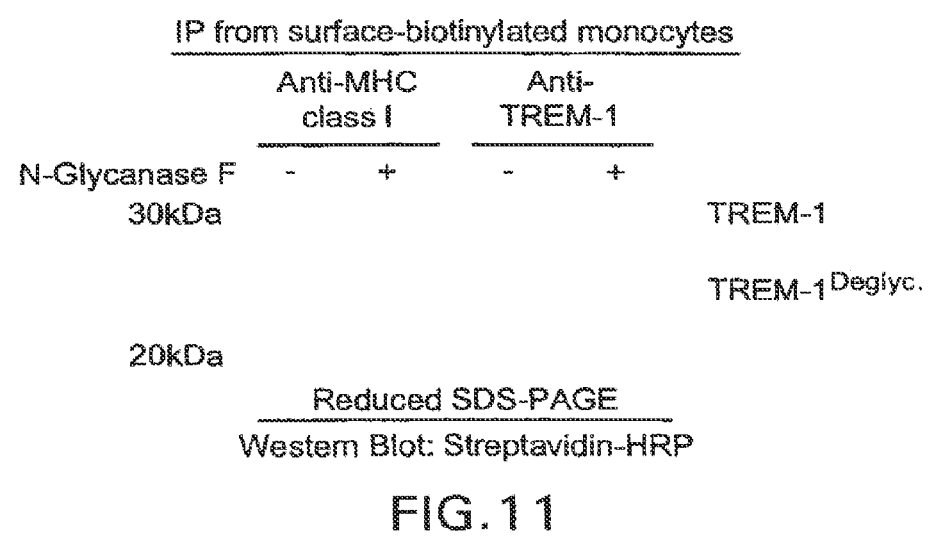

IP from surface-biotinylated monocytes

Anti-MHC class I

Anti-TREM-1

N-Glycanase F - + - +

30kDa

TREM-1

TREM-1 Deglyc.

20kDa

Reduced SDS-PAGE

Western Blot: Streptavidin-HRP

FIG. 11

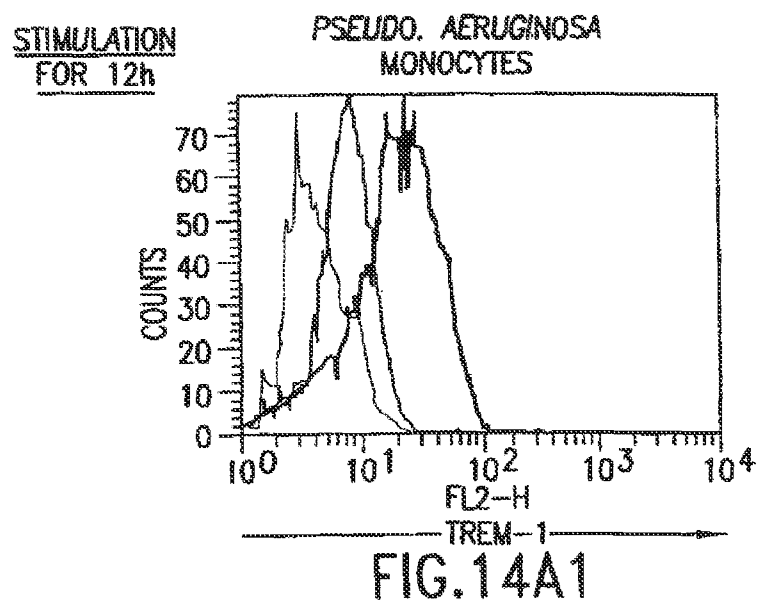
FIG. 14A1
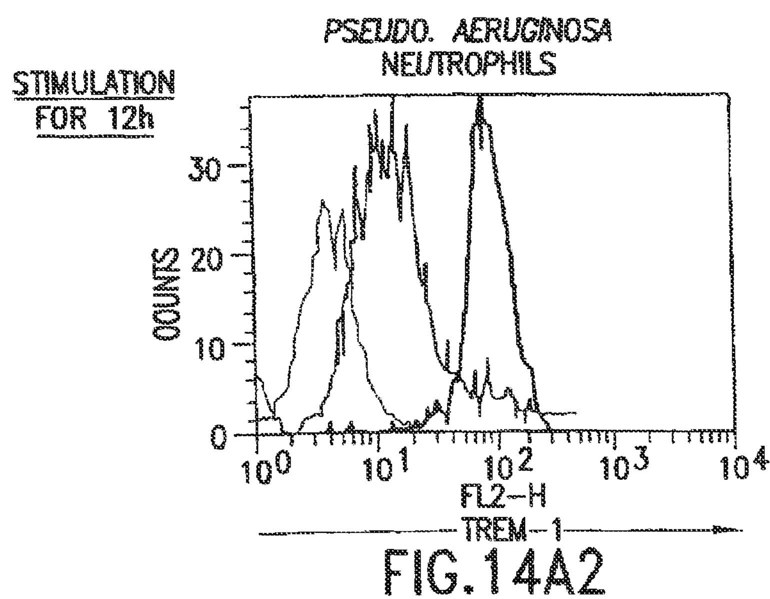
FIG. 14A2

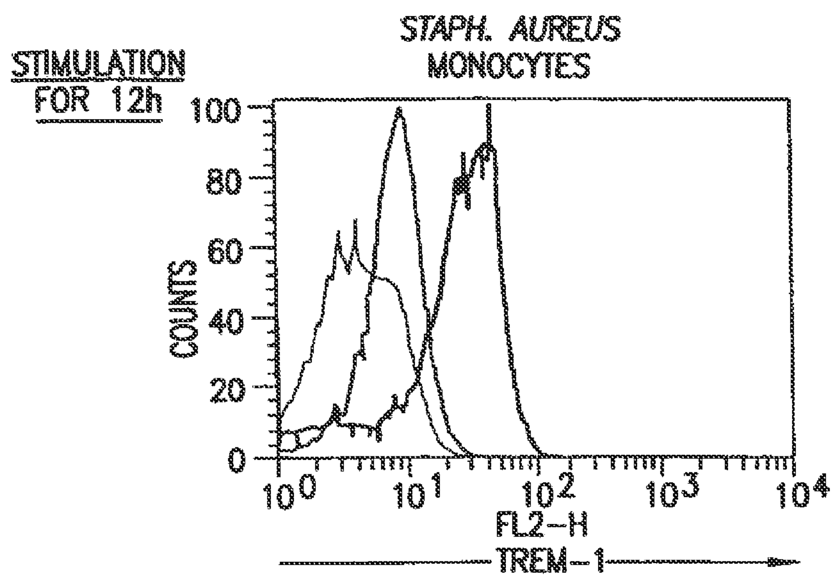
FIG.14A3
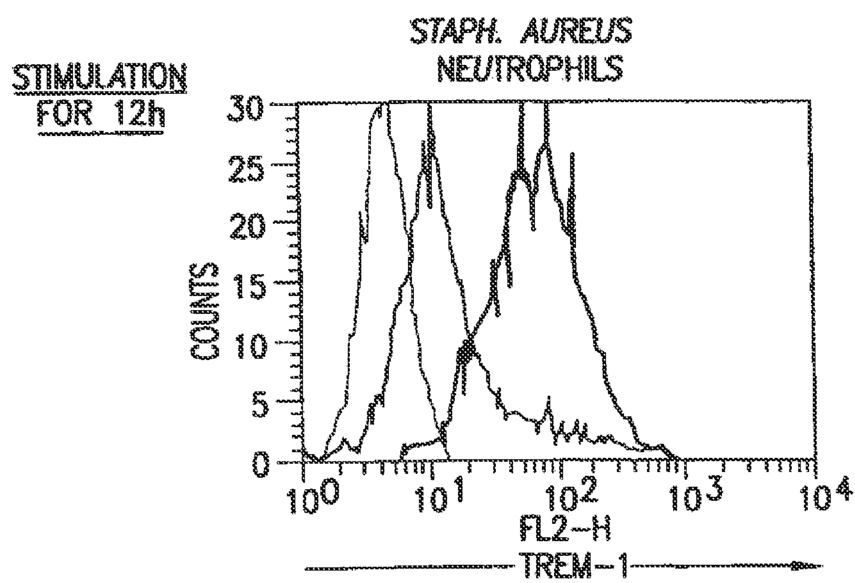
FIG.14A4

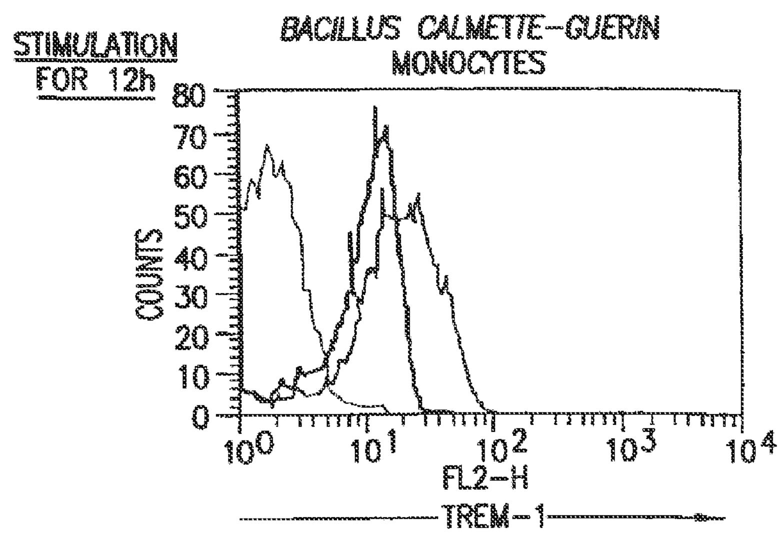
FIG.14A5
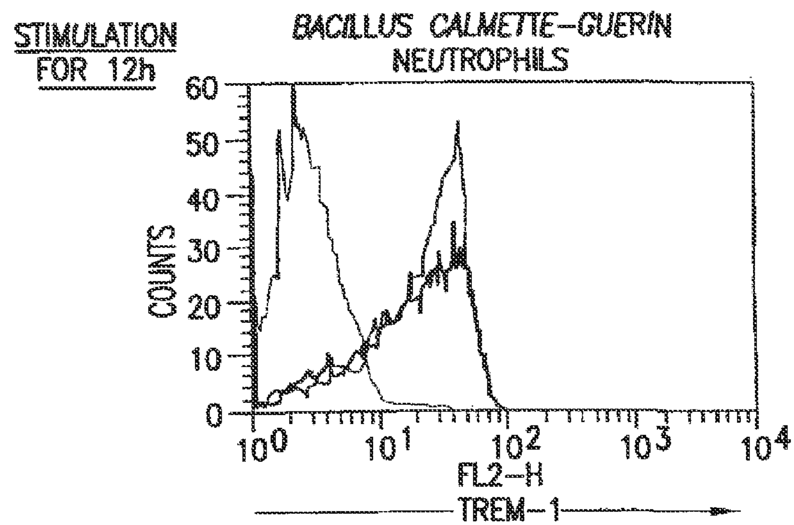
FIG.14A6

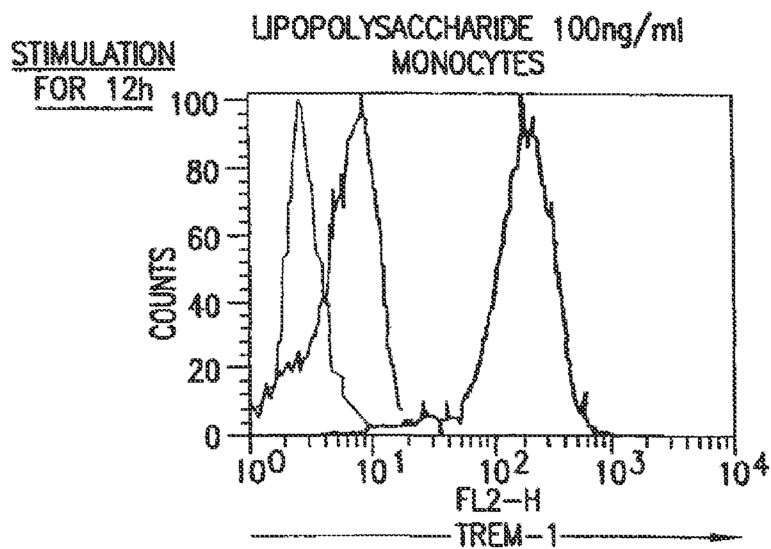
FIG.14B1
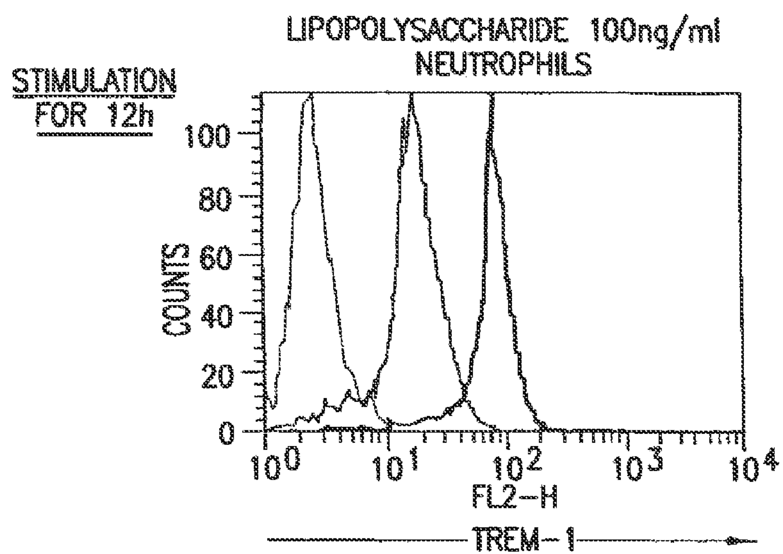
FIG.14B2

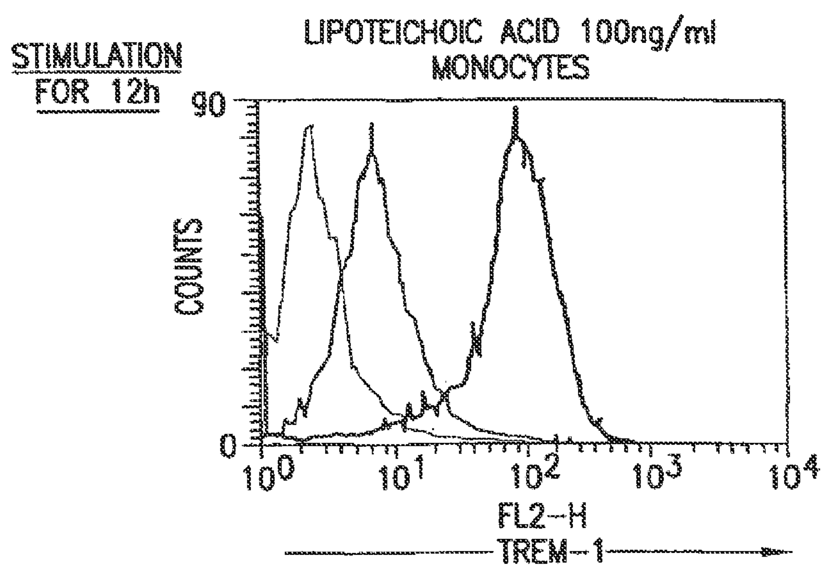
FIG.14B3
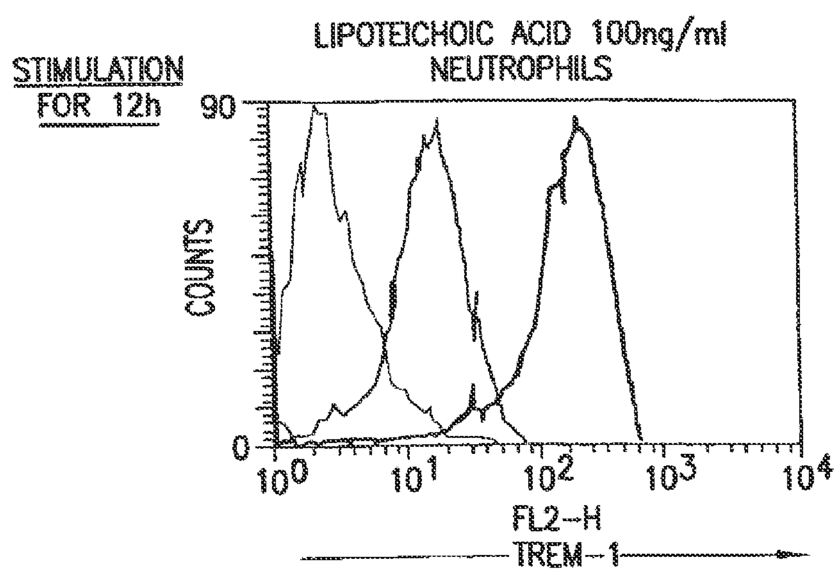
FIG.14B4

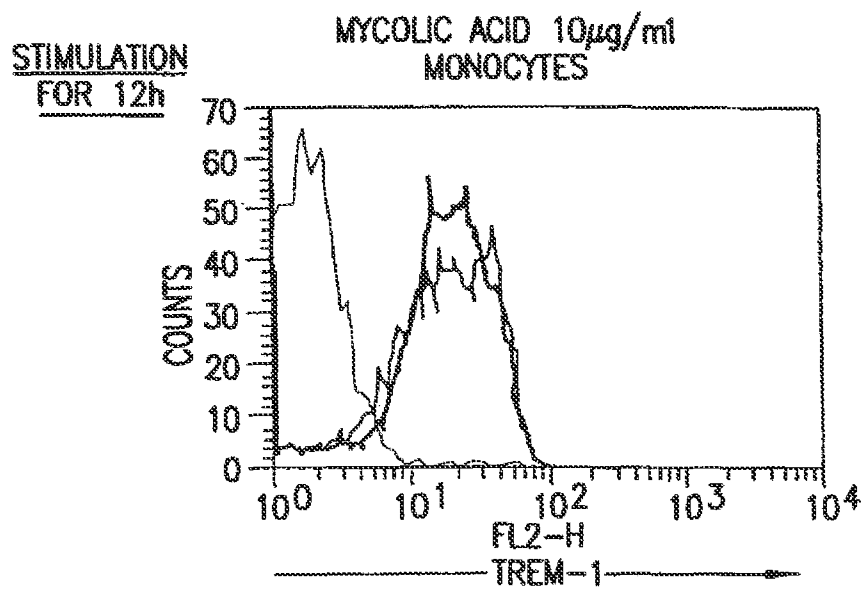
FIG.14B5
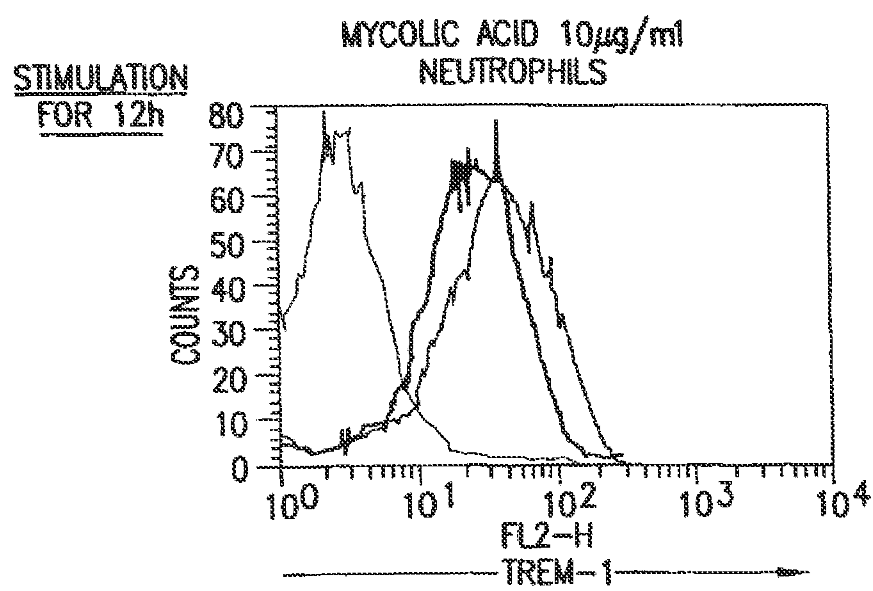
FIG.14B6

Anti-TREM-1 mAb

Control IgG1,κ

Anti-TREM-1 mAb

Control IgG1,κ

Anti-TREM-1 mAb

Control IgG1,κ

Anti-TREM-1 mAb

Control IgG1,κ

Anti-CD15 mAb
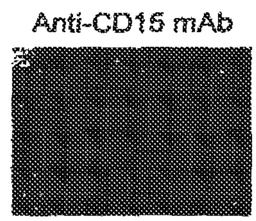
FIG.18A
Anti-TREM-1 mAb
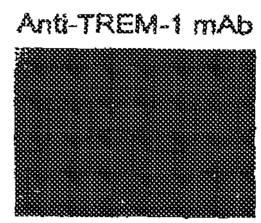
FIG.18B
Anti-CD15 mAb
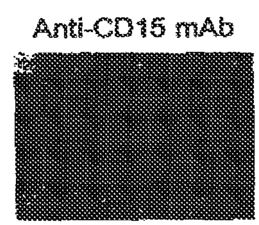
FIG.18C
Anti-TREM-1 mAb
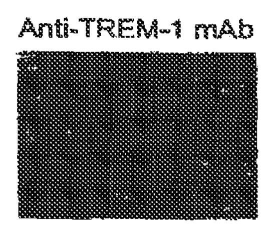
FIG.18D
Anti-CD15 mAb
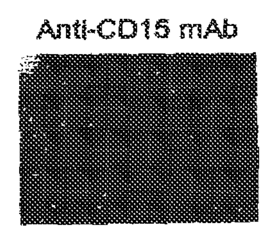
FIG.18E
Anti-TREM-1 mAb
FIG.18F FIG. 40A
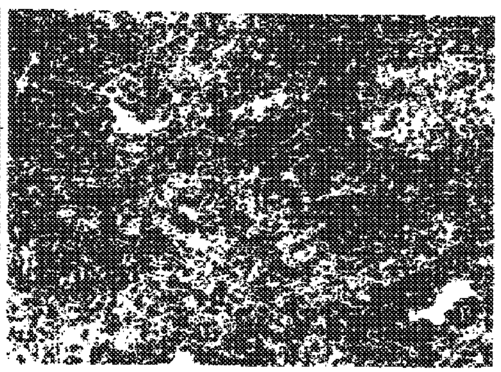
FIG. 40B
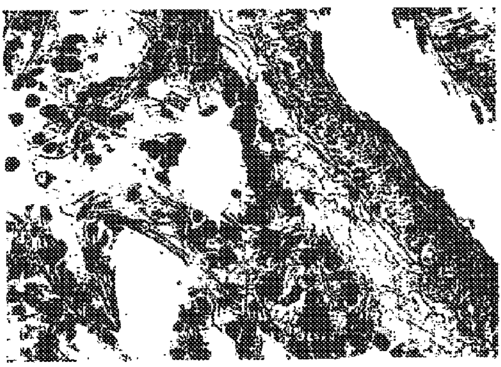
FIG. 40C
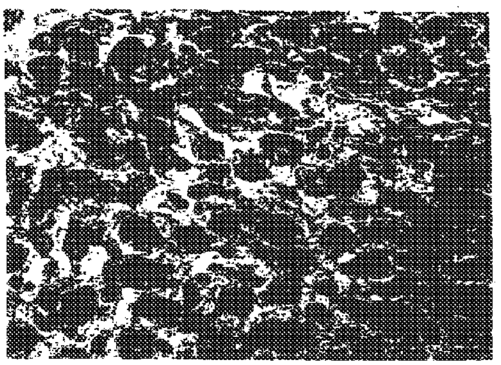
FIG. 40D

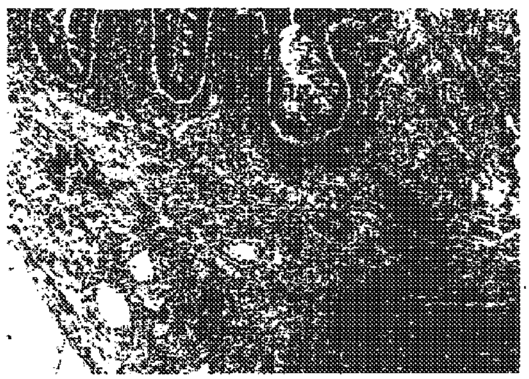
FIG. 40E
FIG. 40F
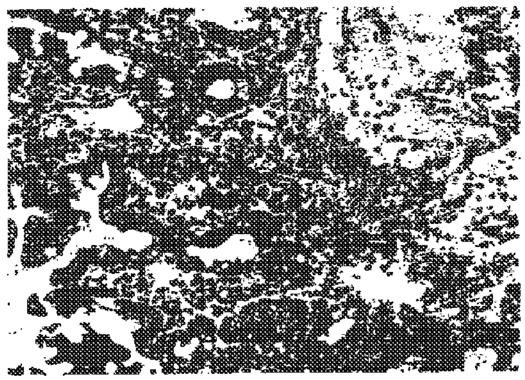
FIG. 40G
FIG. 40H

SEQUENCE LISTING

<160> NUMBER OF SEQ ID NOS: 37

<210> SEQ ID NO 1
<211> LENGTH: 884
<212> TYPE: DNA
<213> ORGANISM: Homo sapiens

<400> SEQUENCE: 1

```
ctactactac taaattcgcg gccggtcgac gctggtgcac aggaaggatg aggaagacca      60
ggctctgggg gctgctgtgg atgctctttg tctcagaact ccgagctgca actaaattaa     120
ctgaggaaaa gtatgaactg aaagaggggc agaccctgga tgtgaaatgt gactacacgc     180
tagagaagtt tgccagcagc cagaaagctt ggcagataat aagggacgga gagatgccca     240
agaccctggc atgcacagag aggccttcaa agaattccca tccagtccaa gtggggagga     300
tcatactaga agactaccat gatcatggtt tactgcgcgt ccgaatggtc aaccttcaag     360
tggaagattc tggactgtat cagtgtgtga tctaccagcc tcccaaggag cctcacatgc     420
tgttcgatcg catccgcttg gtggtgacca agggtttttc agggacccct ggctccaatg     480
agaattctac ccagaatgtg tataagattc ctcctaccac cactaaggcc ttgtgcccac     540
tctataccag ccccagaact gtgacccaag ctccacccaa gtcaactgcc gatgtctcca     600
ctcctgactc tgaaatcaac cttacaaatg tgacagatat catcagggtt ccggtgttca     660
acattgtcat tctcctggct ggtggattcc tgagtaagag cctggtcttc tctgtcctgt     720
ttgctgtcac gctgaggtca tttgtaccct aggcccacga acccacgaga atgtcctctg     780
acttccagcc acatccatct ggcagttgtg ccaagggagg agggaggagg taaaaggcag     840
ggagttaata acatgaatta aatctgtaat caccagctat ttct                      884
```

<210> SEQ ID NO 2
<211> LENGTH: 1041
<212> TYPE: DNA
<213> ORGANISM: Homo sapiens

<400> SEQUENCE: 2

```
tgacatgcct gatcctctct tttctgcagt tcaagggaaa gacgagatct tgcacaaggc      60
actctgcttc tgcccttggc tggggaaggg tggcatggag cctctccggc tgctcatctt     120
actctttgtc acagagctgt ccggagccca caacaccaca gtgttccagg gcgtggcggg     180
ccagtccctg caggtgtctt gcccctatga ctccatgaag cactggggga ggcgcaaggc     240
ctggtgccgc cagctgggag agaagggccc atgccagcgt gtggtcagca cgcacaactt     300
gtggctgctg tccttcctga ggaggtggaa tgggagcaca gccatcacag acgataccct     360
gggtggcact ctcaccatta cgctgcggaa tctacaaccc catgatgcgg gtctctacca     420
gtgccagagc ctccatggca gtgaggctga caccctcagg aaggtcctgg tggaggtgct     480
ggcagacccc ctggatcacc gggatgctgg agatctctgg ttccccgggg agtctgagag     540
cttcgaggat gcccatgtgg agcacagcat ctccaggagc cctcttggaag gagaaatccc     600
cttcccaccc acttccatcc ttctcctcct ggcctgcatc tttctcatca agattctagc     660
agccagcgcc ctctgggctg cagcctggca tggacagaag ccagggacac atccacccag     720
tgaactggac tgtggccatg acccaggta tcagctccaa actctgccag ggctgagaga     780
cacgtgaagg aagatgatgg gaggaaaagc ccaggagaag tcccaccagg gaccagccca     840
gcctgcatac ttgccacttg gccaccagga ctccttgttc tgctctggca agagactact     900
ctgcctgaac actgcttctc ctggaccctg gaagcaggga ctggttgagg gagtggggag     960
```

```
gtggtaagaa cacctgacaa cttctgaata ttggacattt taaacactta caaataaatc   1020

caagactgtc atatttaaaa a                                             1041


<210> SEQ ID NO 3
<211> LENGTH: 234
<212> TYPE: PRT
<213> ORGANISM: Homo sapiens

<400> SEQUENCE: 3

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230


<210> SEQ ID NO 4
<211> LENGTH: 230
<212> TYPE: PRT
<213> ORGANISM: Homo sapiens

<400> SEQUENCE: 4

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
```

```
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230


<210> SEQ ID NO 5
<211> LENGTH: 16
<212> TYPE: PRT
<213> ORGANISM: Homo sapiens

<400> SEQUENCE: 5

Met Arg Lys Thr Arg Leu Trp Gly Leu Leu Trp Met Leu Phe Val Ser
1               5                   10                  15


<210> SEQ ID NO 6
<211> LENGTH: 218
<212> TYPE: PRT
<213> ORGANISM: Homo sapiens

<400> SEQUENCE: 6

Glu Leu Arg Ala Ala Thr Lys Leu Thr Glu Glu Lys Tyr Glu Leu Lys
1               5                   10                  15

Glu Gly Gln Thr Leu Asp Val Lys Cys Asp Tyr Thr Leu Glu Lys Phe
            20                  25                  30

Ala Ser Ser Gln Lys Ala Trp Gln Ile Ile Arg Asp Gly Glu Met Pro
        35                  40                  45

Lys Thr Leu Ala Cys Thr Glu Arg Pro Ser Lys Asn Ser His Pro Val
    50                  55                  60

Gln Val Gly Arg Ile Ile Leu Glu Asp Tyr His Asp His Gly Leu Leu
65                  70                  75                  80

Arg Val Arg Met Val Asn Leu Gln Val Glu Asp Ser Gly Leu Tyr Gln
                85                  90                  95

Cys Val Ile Tyr Gln Pro Pro Lys Glu Pro His Met Leu Phe Asp Arg
            100                 105                 110

Ile Arg Leu Val Val Thr Lys Gly Phe Ser Gly Thr Pro Gly Ser Asn
        115                 120                 125

Glu Asn Ser Thr Gln Asn Val Tyr Lys Ile Pro Pro Thr Thr Thr Lys
    130                 135                 140

Ala Leu Cys Pro Leu Tyr Thr Ser Pro Arg Thr Val Thr Gln Ala Pro
```

```
145                 150                 155                 160

Pro Lys Ser Thr Ala Asp Val Ser Thr Pro Asp Ser Glu Ile Asn Leu
                165                 170                 175

Thr Asn Val Thr Asp Ile Ile Arg Val Pro Val Phe Asn Ile Val Ile
            180                 185                 190

Leu Leu Ala Gly Gly Phe Leu Ser Lys Ser Leu Val Phe Ser Val Leu
        195                 200                 205

Phe Ala Val Thr Leu Arg Ser Phe Val Pro
    210                 215


<210> SEQ ID NO 7
<211> LENGTH: 4
<212> TYPE: PRT
<213> ORGANISM: Homo sapiens

<400> SEQUENCE: 7

Asn Ser Thr Gln
1


<210> SEQ ID NO 8
<211> LENGTH: 4
<212> TYPE: PRT
<213> ORGANISM: Homo sapiens

<400> SEQUENCE: 8

Asn Leu Thr Asn
1


<210> SEQ ID NO 9
<211> LENGTH: 4
<212> TYPE: PRT
<213> ORGANISM: Homo sapiens

<400> SEQUENCE: 9

Asn Val Thr Asp
1


<210> SEQ ID NO 10
<211> LENGTH: 29
<212> TYPE: PRT
<213> ORGANISM: Homo sapiens

<400> SEQUENCE: 10

Val Pro Val Phe Asn Ile Val Ile Leu Leu Ala Gly Gly Phe Leu Ser
1               5                   10                  15

Lys Ser Leu Val Phe Ser Val Leu Phe Ala Val Thr Leu
            20                  25


<210> SEQ ID NO 11
<211> LENGTH: 5
<212> TYPE: PRT
<213> ORGANISM: Homo sapiens

<400> SEQUENCE: 11

Arg Ser Phe Val Pro
1               5


<210> SEQ ID NO 12
<211> LENGTH: 13
<212> TYPE: PRT
<213> ORGANISM: Homo sapiens

<400> SEQUENCE: 12
```

```
Met Glu Pro Leu Arg Leu Leu Ile Leu Leu Phe Val Thr
1               5                   10


<210> SEQ ID NO 13
<211> LENGTH: 134
<212> TYPE: PRT
<213> ORGANISM: Homo sapiens

<400> SEQUENCE: 13

Glu Leu Ser Gly Ala His Asn Thr Thr Val Phe Gln Gly Val Ala Gly
1               5                   10                  15

Gln Ser Leu Gln Val Ser Cys Pro Tyr Asp Ser Met Lys His Trp Gly
            20                  25                  30

Arg Arg Lys Ala Trp Cys Arg Gln Leu Gly Glu Lys Gly Pro Cys Gln
        35                  40                  45

Arg Val Val Ser Thr His Asn Leu Trp Leu Leu Ser Phe Leu Arg Arg
    50                  55                  60

Trp Asn Gly Ser Thr Ala Ile Thr Asp Asp Thr Leu Gly Gly Thr Leu
65                  70                  75                  80

Thr Ile Thr Leu Arg Asn Leu Gln Pro His Asp Ala Gly Leu Tyr Gln
                85                  90                  95

Cys Gln Ser Leu His Gly Ser Glu Ala Asp Thr Leu Arg Lys Val Leu
            100                 105                 110

Val Glu Val Leu Ala Asp Pro Leu Asp His Arg Asp Ala Gly Asp Leu
        115                 120                 125

Trp Phe Pro Gly Glu Ser
    130


<210> SEQ ID NO 14
<211> LENGTH: 4
<212> TYPE: PRT
<213> ORGANISM: Homo sapiens

<400> SEQUENCE: 14

Asn Thr Thr Val
1


<210> SEQ ID NO 15
<211> LENGTH: 53
<212> TYPE: PRT
<213> ORGANISM: Homo sapiens

<400> SEQUENCE: 15

Glu Ser Phe Glu Asp Ala His Val Glu His Ser Ile Ser Arg Ser Leu
1               5                   10                  15

Leu Glu Gly Glu Ile Pro Phe Pro Pro Thr Ser Ile Leu Leu Leu Leu
            20                  25                  30

Ala Cys Ile Phe Leu Ile Lys Ile Leu Ala Ala Ser Ala Leu Trp Ala
        35                  40                  45

Ala Ala Trp His Gly
    50


<210> SEQ ID NO 16
<211> LENGTH: 30
<212> TYPE: PRT
<213> ORGANISM: Homo sapiens

<400> SEQUENCE: 16

Gln Lys Pro Gly Thr His Pro Pro Ser Glu Leu Asp Cys Gly His Asp
```

```
1               5                   10                  15

Pro Gly Tyr Gln Leu Gln Thr Leu Pro Gly Leu Arg Asp Thr
            20                  25                  30


<210> SEQ ID NO 17
<211> LENGTH: 218
<212> TYPE: PRT
<213> ORGANISM: Homo sapiens

<400> SEQUENCE: 17

Glu Leu Arg Ala Ala Thr Lys Leu Thr Glu Glu Lys Tyr Glu Leu Lys
1               5                   10                  15

Glu Gly Gln Thr Leu Asp Val Lys Cys Asp Tyr Thr Leu Glu Lys Phe
            20                  25                  30

Ala Ser Ser Gln Lys Ala Trp Gln Ile Ile Arg Asp Gly Glu Met Pro
        35                  40                  45

Lys Thr Leu Ala Cys Thr Glu Arg Pro Ser Lys Asn Ser His Pro Val
    50                  55                  60

Gln Val Gly Arg Ile Ile Leu Glu Asp Tyr His Asp His Gly Leu Leu
65                  70                  75                  80

Arg Val Arg Met Val Asn Leu Gln Val Glu Asp Ser Gly Leu Tyr Gln
                85                  90                  95

Cys Val Ile Tyr Gln Pro Pro Lys Glu Pro His Met Leu Phe Asp Arg
            100                 105                 110

Ile Arg Leu Val Val Thr Lys Gly Phe Ser Gly Thr Pro Gly Ser Asn
        115                 120                 125

Glu Asn Ser Thr Gln Asn Val Tyr Lys Ile Pro Pro Thr Thr Thr Lys
    130                 135                 140

Ala Leu Cys Pro Leu Tyr Thr Ser Pro Arg Thr Val Thr Gln Ala Pro
145                 150                 155                 160

Pro Lys Ser Thr Ala Asp Val Ser Thr Pro Asp Ser Glu Ile Asn Leu
                165                 170                 175

Thr Asn Val Thr Asp Ile Ile Arg Val Pro Val Phe Asn Ile Val Ile
            180                 185                 190

Leu Leu Ala Gly Gly Phe Leu Ser Lys Ser Leu Val Phe Ser Val Leu
        195                 200                 205

Phe Ala Val Thr Leu Arg Ser Phe Val Pro
    210                 215


<210> SEQ ID NO 18
<211> LENGTH: 217
<212> TYPE: PRT
<213> ORGANISM: Homo sapiens

<400> SEQUENCE: 18

Glu Leu Ser Gly Ala His Asn Thr Thr Val Phe Gln Gly Val Ala Gly
1               5                   10                  15

Gln Ser Leu Gln Val Ser Cys Pro Tyr Asp Ser Met Lys His Trp Gly
            20                  25                  30

Arg Arg Lys Ala Trp Cys Arg Gln Leu Gly Glu Lys Gly Pro Cys Gln
        35                  40                  45

Arg Val Val Ser Thr His Asn Leu Trp Leu Leu Ser Phe Leu Arg Arg
    50                  55                  60

Trp Asn Gly Ser Thr Ala Ile Thr Asp Asp Thr Leu Gly Gly Thr Leu
65                  70                  75                  80

Thr Ile Thr Leu Arg Asn Leu Gln Pro His Asp Ala Gly Leu Tyr Gln
```

```
                85                  90                  95

Cys Gln Ser Leu His Gly Ser Glu Ala Asp Thr Leu Arg Lys Val Leu
            100                 105                 110

Val Glu Val Leu Ala Asp Pro Leu Asp His Arg Asp Ala Gly Asp Leu
        115                 120                 125

Trp Phe Pro Gly Glu Ser Glu Ser Phe Glu Asp Ala His Val Glu His
    130                 135                 140

Ser Ile Ser Arg Ser Leu Leu Glu Gly Glu Ile Pro Phe Pro Pro Thr
145                 150                 155                 160

Ser Ile Leu Leu Leu Leu Ala Cys Ile Phe Leu Ile Lys Ile Leu Ala
                165                 170                 175

Ala Ser Ala Leu Trp Ala Ala Ala Trp His Gly Gln Lys Pro Gly Thr
            180                 185                 190

His Pro Pro Ser Glu Leu Asp Cys Gly His Asp Pro Gly Tyr Gln Leu
        195                 200                 205

Gln Thr Leu Pro Gly Leu Arg Asp Thr
    210                 215


<210> SEQ ID NO 19
<211> LENGTH: 48
<212> TYPE: DNA
<213> ORGANISM: Homo sapiens

<400> SEQUENCE: 19

atgaggaaga ccaggctctg gggctgctg tggatgctct ttgtctca                 48


<210> SEQ ID NO 20
<211> LENGTH: 565
<212> TYPE: DNA
<213> ORGANISM: Homo sapiens

<400> SEQUENCE: 20

gaactccgag ctgcaactaa attaactgag gaaaagtatg aactgaaaga ggggcagacc     60

ctggatgtga aatgtgacta cacgctagag aagtttgcca gcagccagaa agcttggcag    120

ataataaggg acggagagat gcccaagacc ctggcatgca cagagaggcc ttcaaagaat    180

tcccatccag tccaagtggg gaggatcata ctagaagact accatgatca tggtttactg    240

cgcgtccgaa tggtcaacct tcaagtggaa gattctggac tgtatcagtg tgtgatctac    300

cagcctccca aggagcctca catgctgttc gatcgcatcc gcttggtggt gaccaagggt    360

ttttcaggga cccctggctc caatgagaat tctacccaga atgtgtataa gattcctcct    420

accaccacta aggccttgtg cccactctat accagcccca gaactgtgac ccaagctcca    480

cccaagtcaa ctgccgatgt ctccactcct gactctgaaa tcaaccttac aaatgtgaca    540

gatatcatca gggttccggt gttca                                          565


<210> SEQ ID NO 21
<211> LENGTH: 81
<212> TYPE: DNA
<213> ORGANISM: Homo sapiens

<400> SEQUENCE: 21

gtgttcaaca ttgtcattct cctggctggt ggattcctga gtaagagcct ggtcttctct     60

gtcctgtttg ctgtcacgct g                                               81


<210> SEQ ID NO 22
<211> LENGTH: 20
```

<212> TYPE: DNA
<213> ORGANISM: Homo sapiens

<400> SEQUENCE: 22
gtcatttgta ccctaggccc 20

<210> SEQ ID NO 23
<211> LENGTH: 39
<212> TYPE: DNA
<213> ORGANISM: Homo sapiens

<400> SEQUENCE: 23
atggagcctc tccggctgct catcttactc tttgtcaca 39

<210> SEQ ID NO 24
<211> LENGTH: 402
<212> TYPE: DNA
<213> ORGANISM: Homo sapiens

<400> SEQUENCE: 24
gagctgtccg gagcccacaa caccacagtg ttccagggcg tggcgggcca gtccctgcag 60
gtgtcttgcc cctatgactc catgaagcac tgggggaggc gcaaggcctg gtgccgccag 120
ctgggagaga agggcccatg ccagcgtgtg gtcagcacgc acaacttgtg gctgctgtcc 180
ttcctgagga ggtggaatgg gagcacagcc atcacagacg ataccctggg tggcactctc 240
accattacgc tgcggaatct acaaccccat gatgcgggtc tctaccagtg ccagagcctc 300
catggcagtg aggctgacac cctcaggaag gtcctggtgg aggtgctggc agaccccctg 360
gatcaccggg atgctggaga tctctggttc cccggggagt ct 402

<210> SEQ ID NO 25
<211> LENGTH: 159
<212> TYPE: DNA
<213> ORGANISM: Homo sapiens

<400> SEQUENCE: 25
gagagcttcg aggatgccca tgtggagcac agcatctcca ggagcctctt ggaaggagaa 60
atccccttcc cacccacttc catccttctc ctcctggcct gcatctttct catcaagatt 120
ctagcagcca gcgccctctg ggctgcagcc tggcatgga 159

<210> SEQ ID NO 26
<211> LENGTH: 90
<212> TYPE: DNA
<213> ORGANISM: Homo sapiens

<400> SEQUENCE: 26
cagaagccag ggacacatcc acccagtgaa ctggactgtg gccatgaccc agggtatcag 60
ctccaaactc tgccagggct gagagacacg 90

<210> SEQ ID NO 27
<211> LENGTH: 657
<212> TYPE: DNA
<213> ORGANISM: Homo sapiens

<400> SEQUENCE: 27
gaactccgag ctgcaactaa attaactgag gaaaagtatg aactgaaaga ggggcagacc 60
ctggatgtga aatgtgacta cacgctagag aagtttgcca gcagccagaa agcttggcag 120
ataataaggg acggagagat gcccaagacc ctggcatgca cagagaggcc ttcaaagaat 180

```
tcccatccag tccaagtggg gaggatcata ctagaagact accatgatca tggtttactg    240

cgcgtccgaa tggtcaacct tcaagtggaa gattctggac tgtatcagtg tgtgatctac    300

cagcctccca aggagcctca catgctgttc gatcgcatcc gcttggtggt gaccaagggt    360

ttttcaggga cccctggctc caatgagaat tctacccaga atgtgtataa gattcctcct    420

accaccacta aggccttgtg cccactctat accagcccca gaactgtgac ccaagctcca    480

cccaagtcaa ctgccgatgt ctccactcct gactctgaaa tcaaccttac aaatgtgaca    540

gatatcatca gggttccggt gttcaacatt gtcattctcc tggctggtgg attcctgagt    600

aagagcctgg tcttctctgt cctgtttgct gtcacgctga ggtcatttgt accctag       657
```

<210> SEQ ID NO 28
<211> LENGTH: 651
<212> TYPE: DNA
<213> ORGANISM: Homo sapiens

<400> SEQUENCE: 28

```
gagctgtccg gagcccacaa caccacagtg ttccagggcg tggcgggcca gtccctgcag     60

gtgtcttgcc cctatgactc catgaagcac tgggggaggc gcaaggcctg gtgccgccag    120

ctgggagaga agggcccatg ccagcgtgtg gtcagcacgc acaacttgtg gctgctgtcc    180

ttcctgagga ggtggaatgg gagcacagcc atcacagacg ataccctggg tggcactctc    240

accattacgc tgcggaatct acaaccccat gatgcgggtc tctaccagtg ccagagcctc    300

catggcagtg aggctgacac cctcaggaag gtcctggtgg aggtgctggc agaccccctg    360

gatcaccggg atgctggaga tctctggttc cccggggagt ctgagagctt cgaggatgcc    420

catgtggagc acagcatctc caggagcctc ttggaaggag aaatcccctt cccacccact    480

tccatccttc tcctcctggc ctgcatcttt ctcatcaaga ttctagcagc cagcgccctc    540

tgggctgcag cctggcatgg acagaagcca gggacacatc cacccagtga actggactgt    600

ggccatgacc cagggtatca gctccaaact ctgccagggc tgagagacac g             651
```

<210> SEQ ID NO 29
<211> LENGTH: 30
<212> TYPE: DNA
<213> ORGANISM: Homo sapiens

<400> SEQUENCE: 29

```
tagtaggaat tcaggatgag gaaggctggg                                      30
```

<210> SEQ ID NO 30
<211> LENGTH: 42
<212> TYPE: DNA
<213> ORGANISM: Homo sapiens

<400> SEQUENCE: 30

```
tagtagaagc ttatacttac cgtcagcatc tgtcccattt at                        42
```

<210> SEQ ID NO 31
<211> LENGTH: 20
<212> TYPE: DNA
<213> ORGANISM: Homo sapiens

<400> SEQUENCE: 31

```
gctggtgcac aggaaggatg                                                 20
```

<210> SEQ ID NO 32
<211> LENGTH: 21

```
<212> TYPE: DNA
<213> ORGANISM: Homo sapiens

<400> SEQUENCE: 32

ggctggaagt cagaggacat t                                           21


<210> SEQ ID NO 33
<211> LENGTH: 20
<212> TYPE: DNA
<213> ORGANISM: Homo sapiens

<400> SEQUENCE: 33

tgatcctctc ttttctgcag                                             20


<210> SEQ ID NO 34
<211> LENGTH: 21
<212> TYPE: DNA
<213> ORGANISM: Homo sapiens

<400> SEQUENCE: 34

gtgtttaaaa tgtccaatat t                                           21


<210> SEQ ID NO 35
<211> LENGTH: 37
<212> TYPE: DNA
<213> ORGANISM: Homo sapiens

<400> SEQUENCE: 35

tagtaggaat tcactctgct tctgcccttg gctgggg                          37


<210> SEQ ID NO 36
<211> LENGTH: 48
<212> TYPE: DNA
<213> ORGANISM: Homo sapiens

<400> SEQUENCE: 36

tagtagaagc ttatacttac cgggtgggaa agggatttct ccttccaa              48


<210> SEQ ID NO 37
<211> LENGTH: 29
<212> TYPE: DNA
<213> ORGANISM: Homo sapiens

<400> SEQUENCE: 37

acctgcaggc atgcgtcgac atacttacc                                   29
```

RECEPTOR TREM (TRIGGERING RECEPTOR EXPRESSED ON MYELOID CELLS) AND USES THEREOF

CROSS-REFERENCE TO RELATED PATENT APPLICATIONS

This application is a continuation-in-part of U.S. patent application Ser. No. 13/560,612, filed Jul. 27, 2012, which is a continuation of U.S. patent application Ser. No. 12/687,038, filed Jan. 13, 2010, now abandoned, which is a continuation of U.S. patent application Ser. No. 11/188,281, filed Jul. 25, 2005, now abandoned, which is a continuation of U.S. patent application Ser. No. 10/103,423, filed Mar. 20, 2002, now abandoned, which claims priority to U.S. Provisional Patent Application No. 60/277,238, filed Mar. 20, 2001, all of which are incorporated herein by reference in their entirety.

1. INTRODUCTION

This invention relates generally to new activating receptors of the Ig super-family expressed on human myeloid cells, called TREM (triggering receptor expressed on myeloid cells) which are involved in immune and inflammatory responses. Specifically, this invention relates to two (2) members of TREMs: TREM-1 and TREM-2.

2. BACKGROUND OF THE INVENTION

Inflammatory responses to bacterial and fungal infections are primarily mediated by neutrophils and monocytes (Medzhitov, R. & Janeway, C, Jr., 2000, N. Engl. J. Med. 343:338-44; Hoffmann, J. A., Kafatos, F. C, Janeway, C. A. & Ezekowitz, R. A., 1999, Science 284:1313-8). These cells express pattern recognition receptors (PRR) which recognize conserved molecular structures shared by groups of microorganisms (Aderem, A. & Ulevitch, R. J., 2000, Nature 406: 782-7; Beutler, B., 2000, Curr. Opin. Microbiol. 3:23-8). Engagement of PRRs by microbial products activate signaling pathways which control the expression of a variety of genes. These inducible genes encode proinflammatory chemokines and cytokines and their receptors, as well as adhesion molecules and enzymes that produce low molecular weight proinflammatory mediators and reactive oxygen species. The combined action of all these products presumably leads to elimination of the infectious agents and tissue repair. However, excessive secretion of pro-inflammatory mediators, together with overexpression of their receptors, cause excessive autocrine/paracrine activation of neutrophils and monocytes, leading to tissue damage and septic shock (Bone, R. C, 1991, Ann. Intern. Med 115:457-69; Beutler, B., Milsark, I. W. & Cerami, A. C, 1985, Science 229:869-71; Morrison, D. C. & Ryan, J. L., \9S7, Annu. Rev. Med 38:417-32; Tracey, K. J. et al., 1986, Science 234:470-74; Glauser, M. P., Zanetti, G., Baumgarmer, J. D. & Cohen, J., 1991, Lancet 338:732-36). Thus, the regulation of neutrophil and monocyte activation by stimulatory receptors and their ligands is crucial to the outcome of host inflammatory responses to infections.

Neutrophil- and monocyte/macrophage-mediated inflammatory responses can be stimulated through many receptors with different structures and specificities (Rosenberg, H. F., and J. I. Gallin, 1999, hiflammation. In Fundamental Immunology, 4^^ Ed., W. E. Paul, ed., Lippincott-Raven, Philadelphia p. 1051). These include G protein-1 inked seven transmembrane domain receptors specific for either fIVILP, lipid mediators, complement factors, or chemokines, the Fc and complement receptors, the CD 14 and Toll-like receptors for LPS, as well as the cytokine receptors for IFN-y and TNF-a (Ulevitch, R. J., and P. S. Tobias, 1999, Curr. Opin. Immunol. 11:19). In addition, engagement of these receptors can upregulate or "prime" the responsiveness of myeloid cells to other stimuli, potentiating the inflammatory response (Downey, G. P., T. Fukushima, L. Fialkow, and T. K. Waddell, 1995, Semin. Cell Biol. 6:345).

Neutrophils and macrophages express additional activating receptors, but their role in inflammation is unknown. These receptors belong either to the Ig superfamily (Ig-SF), such as Ig-like transcripts (ILT)/leukocyte Ig-like receptors (L[R)/monocyte/macrophage Iglike receptors (MIRs), paired Ig-like receptor (PIR-As), and signal regulatory protein βI (SIRPpI), or to the C-type lectin superfamily, such as myeloid DAP12-associating lectin-1 (MDL-I) (Nakajima, H., J. Samaridis, L. Angman, and M. Colonna, 1999, J. Immunol. 162:5; Yamashita, Y., M. Ono, and T. Takai, 1998, J. Immunol. 161:4042; Kubagawa, H., et al., 1999, J. Exp. Med 189:309; Dietrich, J., M. Celia, M. Seiffert, H.-J. Bühring, and M. Colonna, 2000, J. Immunol. 164:9; Bakker, A. B., E. Baker, G. R. Sutherland, J. H. Phillips, and L. L. Lanier, 1999, Proc. Natl. Acad. Sci. USA 96:9792). Typically, all of these receptors bear some homology with activating NK cell receptors (Lanier, L. L., 1998, Annu. Rev. Immunol. 16:359). In particular, they contain a short intracellular domain that lacks docking motifs for signaling mediators and a transmembrane domain with a positively charged amino acid residue. This residue allows pairing with transmembrane adapter proteins, which contain a negatively charged amino acid in the transmembrane domain and a cytoplasmic immunoreceptor tyrosine-based activation motif (ITAM). Specifically, ILT/LIR/MIR and PIRs are coupled with the y-chain of the Fc receptors (FcRy) (Nakajima, H., supra; Yamashita, Y., supra; Kubagawa, H., swpra), whereas SIRPβI and MDL-I pair with DAP12 (Dietrich, J., supra; Bakker, A. B., supra). Upon ITAM phosphorylation, these adapters recruit protein tyrosine kinases, which initiate a cascade of phosphorylation events that ultimately lead to cell activation.

DAPI2-deficient mice exhibit a dramatic accumulation of dendritic cells (DCs) in muco-cutaneous epithelia, associated with an impaired hapten-specific contact sensitivity (Bakker, A. B., et al., 2000, Immunity 13:345-53; Tomasello, E., et al., 2000, Immunity 13:355-64). Furthermore, recent evidence suggests that the interaction between CCR7 (CC family chemokine receptor no. 7) and ELC (Epstein-Barr virus-induced molecule I ligand chemokine) triggers DC trafficking to the lymph nodes. In particular, skin DCs from CCR7 −/− mice, as well as in DAP12 −/− mice, are severely impaired in migrating to the draining LNs following activation (Foster, R., et al., 1999, Cell 99:23-33). However, the DAP12-associated receptor responsible for these phenotypes is yet unknown.

The recent discovery of a new DAPI 2-associated receptor on NK cells, called NKp44 (Cantoni, C, et al., 1999, J. Exp. Med. 189:787), suggested the possible existence of yet unknown DAPI 2-associated receptors also on other cells involved in innate responses.

The present inventors have identified new immunoglobulin-super-family (Ig-SF) receptors designated as TREMs (triggering receptor expressed on myeloid cells), that are involved in the regulation of a variety of cellular responses, especially immune and inflammatory responses as well as trafficking of DCs.

3. SUMMARY OF THE INVENTION

The present invention is based upon the inventors' identification of two cDNA molecules which encode triggering receptors expressed on myeloid cells (TREM-1: SEQ ID NO: 1; and TREM-2: SEQ ID NO:2). These molecules, expressed on human myeloid cells, are novel transmembrane proteins of the immunoglobulin superfamily (Ig-SF).

TREM-1 is a transmembrane glycoprotein having the amino acid sequence of SEQ ID NO:3 that is selectively expressed on blood neutrophils and a subset of monocytes but not on lymphocytes and other cell types and is up-regulated by bacterial LPS. TREM-1 has utility in the regulation of acute inflammations.

The TREM-2 is a transmembrane glycoprotein having the amino acid sequence of SEQ ID NO:4 which is selectively expressed on mast cells and dendritic cells (DCs), but not on granulocytes or monocytes. Stimulation of DCs via TREM-2 leads to maturation of DCs, renders them resistant against apoptosis, and induces strong upregulation of CCR7 and subsequent Chemotaxis towards ELC/MIP3-β (macrophage inflammatory protein 3-β). TREM-2 has utility in the regulation of immune response and dendritic cell function.

Thus, the members of TREM (TREM or TREMs) may be useful in regulating a variety of cellular processes, especially immune and inflammatory responses, as well asdendritic cell functions, and therefore have a great potential for therapeutic as well asdiagnostic uses.

Accordingly, this invention provides isolated or recombinantly prepared TREMs, or fragments, homologues, derivatives, or variants thereof, as defined herein, which are herein collectively referred to as "peptides of the invention" or "proteins of the invention." Furthermore, this invention provides nucleic acid molecules encoding the polypeptide of the invention, which are herein collectively referred to as "nucleic acids of the invention" and include cDNA, genomic DNA, and RNA.

Accordingly, this invention provides isolated nucleic acid molecules which comprise or consist of a nucleotide sequence that Is about 30%, 35%, 40%, 45%, 50%, 55%, 60%, 65%, 70%, 75%, 80%, 85%, 90%, 95%, or 98% identical to the nucleotide sequence of SEQ ID NO: 1, 2, or a complement thereof. In specific embodiments, such nucleic acid molecules exclude nucleotide sequences of accession nos. D78812, A037247, AW139572, AW274906, AW139573, AI394041, AI621023, AI186456, AI968134, AI394092, AI681036, AI962750, AA49417I, AA099288, AW139363, AW135801, AA101983, and N41388.

This invention further provides isolated nucleic acid molecules which comprise or consist of about 25, 30, 35, 40, 45, 100, 150, 200, 250, 300, 350, 400, 450, 500, 550, 600, 650, 700, 750, 800, 850, or more contiguous nucleotides of the nucleotide sequence of SEQ ID NO:I, or a complement thereof. In specific embodiments, such nucleic acid molecules exclude nucleotide sequences of accession nos. D78812, AI337247, AW139572, AW274906, AW139573, AI394041, AI621023, AH 86456, AI968134, AI394092, AI681036, AI962750, AA494171, AA099288, AW139363, AW135801, and AA101983.

This invention further provides isolated nucleic acid molecules which comprise or consist of about 25, 30, 35, 40, 45, 100, 150, 200, 250, 300, 350, 400, 450, 500, 550, 600, 650, 700, 750, 800, 850, 900, 950, 1000, or more contiguous nucleotides of the nucleotide sequence of SEQ ID N0:2, or a complement thereof. In specific embodiments, such nucleic acid molecules exclude the nucleotide sequence of accession no. N41388.

The invention provides isolated polypeptides or proteins which are encoded by a nucleic acid molecule consisting of or comprising a nucleotide sequence that is at least about 30%, 35%, 40%, 45%, 50%, 55%, 60%, 65%, 70%, 75%, 80%, 85%, 90%, 95%, or 98% identical to the nucleotide sequence of SEQ ED NO: I or a complement thereof, or SEQ ID NO:2 or a complement thereof. In specific embodiments, such polypeptides or proteins exclude polypeptides or proteins encoded by nucleotide sequences of accession nos. D78812, AI337247, AW139572, AW274906, AW139573, AI394041, AI621023, AI186456, AI968134, AI394092, AI681036, AI962750, AA494171, AA099288, AW139363, AW135801, AA101983, and N41388.

The invention provides isolated polypeptides or proteins which are encoded by a nucleic acid molecule consisting of or comprising a nucleotide sequence that is at least about 25, 30, 35, 40, 45, 100, 150, 200, 250, 300, 350, 400, 450, 500, 550, 600, 650, 700, 750, 800, 850, or more contiguous nucleotides of the nucleotide sequence of SEQ ID NO: I or a complement thereof. In specific embodiments, such polypeptides or proteins exclude polypeptides or proteins encoded by nucleotide sequences of accession nos. D78812, AI337247, AW139572, AW274906, AW139573, AI394041, AI621023, AI186456, AI968134, AI394092, AI681036, AI962750, AA494171, AA099288, AW139363, AW135801, and AA101983.

The invention provides isolated polypeptides or proteins which are encoded by a nucleic acid molecule comprising a nucleotide sequence that is at least about 25, 30, 35, 40, 45, 100, 150, 200, 250, 300, 350, 400, 450, 500, 550, 600, 650, 700, 750, 800, 850, 900, 950, 1000 or more contiguous nucleotides of the nucleotide sequence of SEQ ID NO:2 or a complement thereof. In specific embodiments, such polypeptides or proteins exclude a polypeptide encoded by the nucleotide sequence of accession no. N41388. The invention provides isolated nucleic acid molecules comprising a nucleotide sequence encoding a protein having an amino acid sequence that is at least about 40%, 45%, 50%, 55%, 60%, 65%, 70%, 75%, 80%, 85%, 90%, 95%, or 98% identical to the amino acid sequence of SEQ ID NO:3 or 4, or fragments, homologues, derivatives, or variants of said protein, or complement of said nucleic acid molecules. In specific embodiments, such nucleic acid molecules exclude nucleotide sequences of accession nos. D78812, AI337247, AW139572, AW274906, AW139573, AB94041, AI621023, AI186456, AI968134, AI394092, AI681036, AI962750, AA494171, AA099288, AW139363, AW135801, AA10I983, and N41388.

The invention provides isolated nucleic acid molecules comprising a nucleotide sequence encoding a protein having an amino acid sequence that comprises or consists of at least about 10, 15, 20, 25, 30, 50, 75, 100, 125, 150, 175, 200, 225, 230 or more contiguous amino acids of SEQ ID NO:3, or fragments, homologues, derivatives, or variants of said protein, or complements of said nucleic acid molecules. In specific embodiments, such nucleic acid molecules exclude nucleotide sequences of accession nos. D78812, AI337247, AW139572, AW274906, AW139573, AI394041, AI621023, AI186456, AI968134, A1394092, A1681036, AI962750, AA494171, AA099288, AW139363, AW135801, and AA101983.

The invention provides isolated nucleic acid molecules comprising a nucleotide sequence encoding a protein having an amino acid sequence that comprises or consists of at least about 10, 15, 20, 25, 30, 50, 75, 100, 125, 150, 175, 200, 225, or more contiguous amino acids of SEQ ID NO:4, or fragments, homologues, derivatives, or variants of said protein, or complements of said nucleic acid molecules. In specific embodiments, such nucleic acid molecules exclude the nucleotide sequence of accession no. N41388.

Furthermore, the invention provides isolated polypeptides or proteins comprising an amino acid sequence that is at least about 40%, 45%, 50%, 55%, 60%, 65%, 70%, 75%, 80%, 85%, 90%, 95%, or 98%) identical to the amino acid sequence of SEQ ID NO:3 or 4, or fragments, homologues, derivatives, or variants thereof. In specific embodiments, such polypeptides or proteins exclude polypeptides or proteins encoded by nucleotide sequences of accession nos. D78812, AI337247, AW139572, AW274906, AW139573, AI394041, AI62I023, AI186456, AI968134, AI394092, AI681036, AI962750, AA494I71, AA099288, AW139363, AW135801, AA101983, and N41388.

The invention provides isolated polypeptides or proteins comprising an amino acid sequence that comprises or consists of at least about 10, 15, 20, 25, 30, 50, 75, 100, 125, 150, 175, 200, 225, 230 or more contiguous amino acids of SEQ ID NO:3, or fragments, homologues, derivatives, or variants thereof. In specific embodiments, such polypeptides or proteins exclude polypeptides or proteins encoded by nucleotide sequences of accession nos. D78812, AI337247, AW139572, AW274906, AW13'9573, AI394041, AI621023, A1186456, AI968134, AI394092, AI681036, AI962750, AA494171, AA099288, AW139363, AW135801, and AA10I983.

The invention provides isolated polypeptides or proteins comprising an amino acid sequence that comprises or consists of at least about 10, 15, 20, 25, 30, 50, 75, 100, 125, 150, 175, 200, 225, or more contiguous amino acids of SEQ ID NO: 4, or fragments, homologues, derivatives, or variants thereof. In specific embodiments, such polypeptides or proteins exclude a polypeptide encoded by the nucleotide sequence of accession no. N41388. In preferred embodiments, such fragments, homologues, derivatives or variants of TREM-1 or TREM-2 have a biological activity of a TREM-1 or TREM-2 full-length protein, such as antigenicity, immunogenicity, triggering of proinflammatory chemokines and cytokines, mobilization of cytosolic Ca^^, protein tyrosine-phosphorylation, mediator release, and other activities readily assayable.

In one embodiment, this invention provides isolated nucleic acid molecules which hybridize under stringent or moderately stringent conditions, as defined herein, to a nucleic acid having the sequence of SEQ ID NO: 1 or 2, or a complement thereof.

Furthermore, this invention also provides nucleic acid molecules which are suitable for use as primers or hybridization probes for the detection of nucleic acids encoding a polypeptide of the invention.

In one embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. Further, the invention also provides host cells containing such a vector or engineered to contain and/or express a nucleic acid molecule of the invention and host cells containing a nucleotide sequence of the invention operably linked to a heterologous promoter. The invention also provides methods for preparing a polypeptide of the invention by a recombinant DNA technology in which the host cells containing a recombinant expression vector encoding a polypeptide of the invention or a nucleotide sequence encoding a polypeptide of the invention operably linked to a heterologous promoter, are cultured, and the polypeptide of the invention produced and isolated.

The invention further provides antibodies that specifically bind a polypeptide of the invention. Such antibodies include, but are not limited to: polyclonal, monoclonal, bispecific, multi-specific, human, humanized, chimeric antibodies, single chain antibodies. Fab fragments, F(ab')2 fragments, disulfide-linked Fvs, and fragments containing either a VL or VH domain or even a complementary determining region (CDR) that specifically binds to a polypeptide of the invention.

In one embodiment, the invention provides methods for detecting the presence, activity or expression of a polypeptide of the invention in a biological material, such as cells, blood, saliva, urine, and so forth. The increased or decreased activity or expression of the polypeptide in a sample relative to a control sample can be determined by contacting the biological material with an agent which can detect directly or indirectly the presence, activity or expression of the polypeptide of the invention.

In another embodiment, an agent modulates the expression of a polypeptide of the invention by modulating transcription, splicing, or translation of an mRNA encoding a polypeptide of the invention. In one embodiment, such an agent is a nucleic acid molecule having a nucleotide sequence that is antisense to all or a portion of the coding strand of an mRNA encoding a polypeptide of the invention.

The invention also provides methods for modulating the activity of a polypeptide of the invention comprising contacting a cell with an agent that modulates (e.g., inhibits or stimulates) the activity or expression of a polypeptide of the invention such that activity or expression in the cell is modulated. In one embodiment, such a modulating agent is an antibody that is specific for a polypeptide of the invention. In another embodiment, the agent is a fragment of a polypeptide of the invention or a nucleic acid molecule encoding such a polypeptide fragment.

In another aspect, the present invention provides methods for identifying a compound or ligand that binds to or modulates the activity of a polypeptide of the invention. Such a method comprises measuring a biological activity of the polypeptide in the presence or absence of a test compound and identifying test compounds that alter (increase or decrease) the biological activity of the polypeptide. In another aspect, the invention provides a method for identifying a compound that modulates the expression of a polypeptide or nucleic acid of the invention by measuring the expression of the polypeptide or nucleic acid in the presence or absence of the compound.

In one embodiment, the invention provides a fusion protein comprising a bioactive molecule and one or more domains of a polypeptide of the invention or fragment thereof. In particular, the present invention provides fusion proteins comprising a bioactive molecule recombinantly fused or chemically conjugated (including both covalent and non-covalent conjugations) to one or more domains of a polypeptide of the invention or fragments thereof.

The present invention also provides methods for treating a subject having a disorder which is characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, such a modulator is a polypeptide of the present invention or fragments thereof. In another embodiment, such a modulator is a nucleic acid of the invention {e.g., gene therapy). In another embodiment, the modulator may be an antibody which is specific to a polypeptide of the invention.

Furthermore, the invention provides a pharmaceutical composition comprising a polypeptide or nucleic acid molecule of the present invention or an antibody or fragments thereof specific to a polypeptide of the invention.

The invention further provides a kit containing a polypeptide, nucleic acid molecule of the present invention, or an antibody or fragments thereof specific to a polypeptide of the invention.

3.1 DEFINITIONS

The term "immunoglobulin superfamily" or "Ig-SF" refers to a group of cell membrane proteins having a common structure similar to an immunoglobulin constant region (CI-type and C2-type) or variable region (V-type). The prototype of V-type domains are the variable domains of immunoglobulins and T-cell receptors. V-type immunoglobulin domains are larger than CI and C2 domains. Some proteins carry many such domains and others few.

The term "triggering receptor expressed on myeloid cells" or "TREM" refers to a group of activating receptors which are selectively expressed on different types of myeloid cells, such as mast cells, monocytes, macrophages, dendritic cells (DCs), and neutrophils, and may have a predominant role in immune and inflammatory responses. TREMs are primarily transmembrane glycoproteins with an Ig-type fold in their extracellular domain and, hence, belong to the Ig-SF. These receptors contain a short intracellular domain, but lack docking motifs for signaling mediators and require adapter proteins, such as DAP 12, for cell activation.

The term "myeloid cells" as used herein refers to a series of bone marrow-derived cell lineages including granulocytes (neutrophils, eosinophils, and basophils), monocytes, macrophages, and mast cells. Furthermore, peripheral blood dendritic cells of myeloid origin, and dendritic cells and macrophages derived in vitro from monocytes in the presence of appropriate culture conditions, are also included.

The term "homologue," especially "TREM homologue" as used herein refers to any member of a series of peptides or nucleic acid molecules having a common biological activity, including antigenicity/immunogenicity and inflammation regulatory activity, and/or structural domain and having sufficient amino acid or nucleotide sequence identity as defined herein. TREM homologues can be from either the same or different species of animals.

The term "variant" as used herein refers either to a naturally occurring allelic variation of a given peptide or a recombinantly prepared variation of a given peptide or protein in which one or more amino acid residues have been modified by amino acid substitution, addition, or deletion.

The term "derivative" as used herein refers to a variation of given peptide or protein that are otherwise modified, i.e., by covalent attachment of any type of molecule, preferably having bioactivity, to the peptide or protein, including non-naturally occurring amino acids.

An "isolated" or "purified" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%), 5%, 2.5%, or 1%), (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10% i, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment of the invention, nucleic acid molecules encoding polypeptides/proteins of the invention are isolated or purified. The term "isolated" nucleic acid molecule does not include a nucleic acid that is a member of a library that has not been purified away from other library clones containing other nucleic acid molecules.

Other abbreviations used herein are: SIRPβI, signal regulatory protein βI; HA, hemagglutinin; TNP, 2,4,6-trinitrophenyl; MCP, monocyte chemoattractant protein; PLC-y, phospholipase C-y; DC, dendritic cell; MPO, myeloperoxidase; ITAM, immuno receptor tyrosine-based activation motif; ERK, extracellular signal-related kinase; mAb, monoclonal antibody.

The names of amino acids referred to herein are abbreviated either with three-letter or one-letter symbols.

4. DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows the predicted amino acid sequences of TREM-1 (SEQ ID N0:3) (top) and TREM-2 (SEQ YD NO:4) (bottom), respectively. The signal peptide is indicated in lower-case letters. The potential iV-glycosylation sites are indicated by asterisks. The cysteines potentially involved in generating the intrachain disulfide bridge of the Ig-SF V-type fold are marked in bold and are shown in the context of their flanking consensus sequences (boxed). The predicted transmembrane domain is underlined, and the charged lysine residue is also marked in bold and boxed.

FIG. 2 shows the mRNA sequence of TREM-1 (SEQ ID NO: 1).

FIG. 3 shows the mRNA sequence of TREM-2 (SEQ ID NO:2).

Figure 4A:
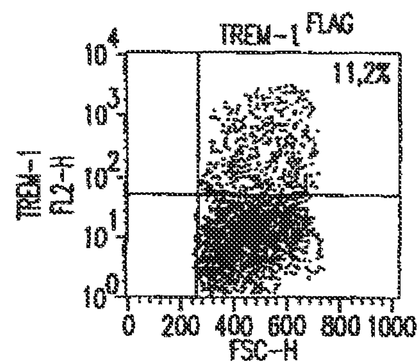
Figure 4B:
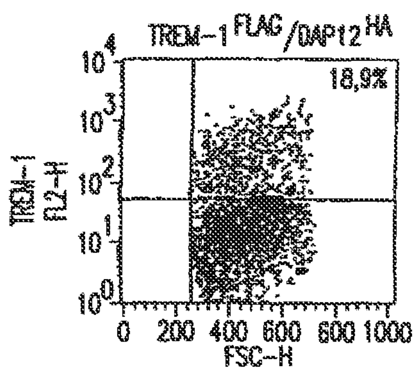
Figure 4C:
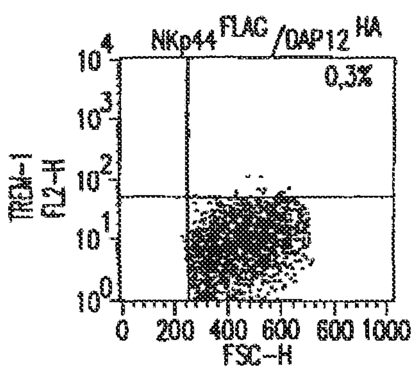

FIGS. 4A-4C show the result of FACS analysis for cell surface expression of transfected cDNAs, i.e., TREM-I^^^o (FIG. 4A), TREM-1 ^'^'^^/DAP12^^ (FIG. 4B), or NKp44^^'^^/DAP12"^ (FIG. 4C), in COS-7 cells. Cells were analyzed by FACS with mAb 21C7 (anti-TREM-1, IgGI). The percentage of TREM-1 positive cells (upper right quadrant) is indicated. Expression of TREM-1 NKp44"^^^, and DAP 12"^ was confirmed using anti-FLAG and anti-HA mAbs (data not shown). Cells stained with a control Ab were contained within the lower right quadrant.

Figure 5A:
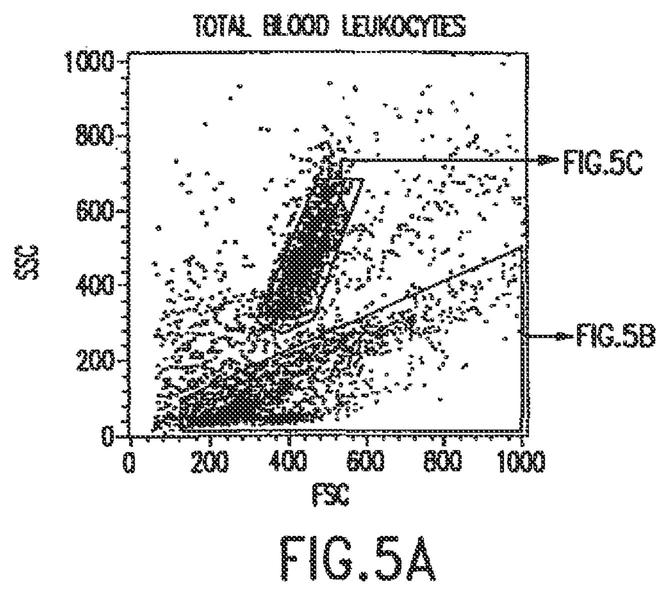
Figure 5B:
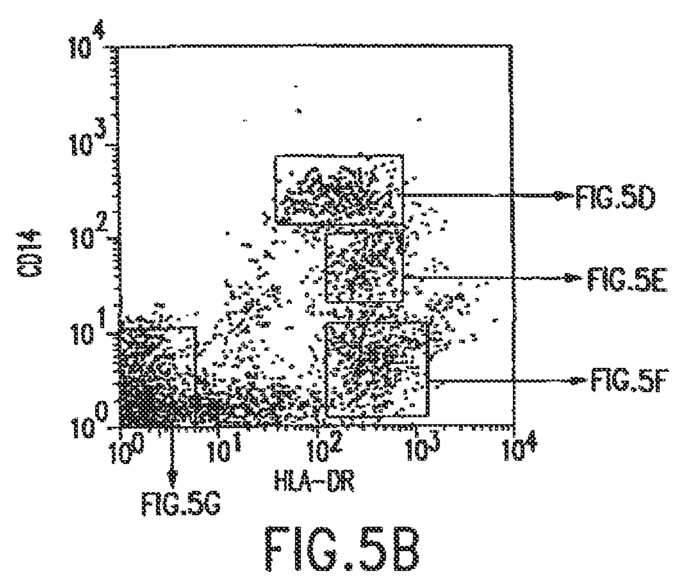
Figure 5C:
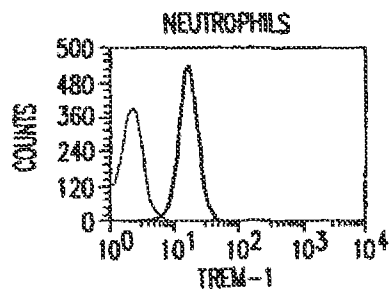

FIGS. 5A-5G show the result of three-color FACS analysis of whole blood leukocytes using mAbs 21C7 (anti-TREM-I, IgGI; (FIG. 5A)), 3C10 (anti-CD14, IgG2b; (FIG. 5B)), and L243 (anti-HLA-DR, IgG2a) followed by isotype-specific FITC/PE/biotinconjugated secondary Abs and further APC-labeled streptavidin. High side scatter cells correspond to TREM-P neutrophils (FIG. 5C). Low side scatter cells include CD14'^'^VHLA-DR^ cells (monocytes; (FIG. 5D)), CDM^'^/HLA-DR^ (monocytes; (FIG. 5E)), CDH'/HLA DR^ cells (which include B cells and DCs; (FIG. 5F)), and CD14"/IU.ADR' cells (mostly lymphocytes; (FIG. 5G)).

Figure 6A:
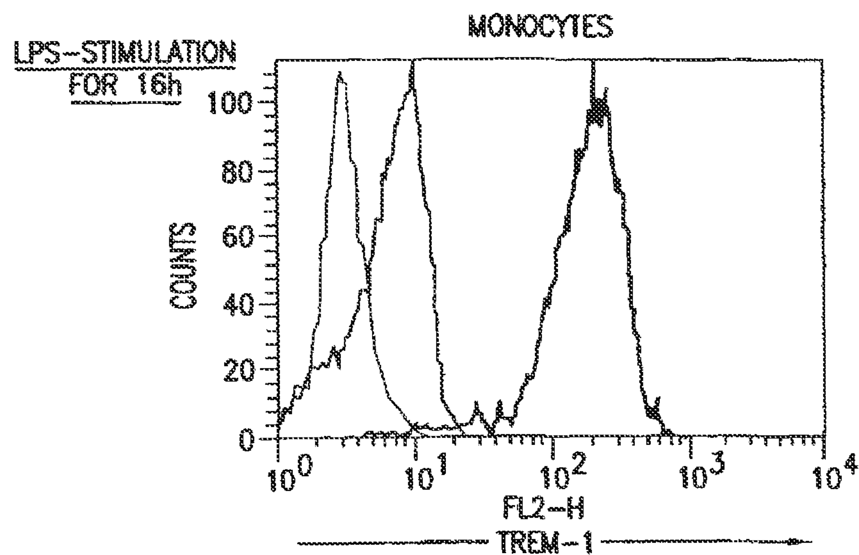
Figure 6B:
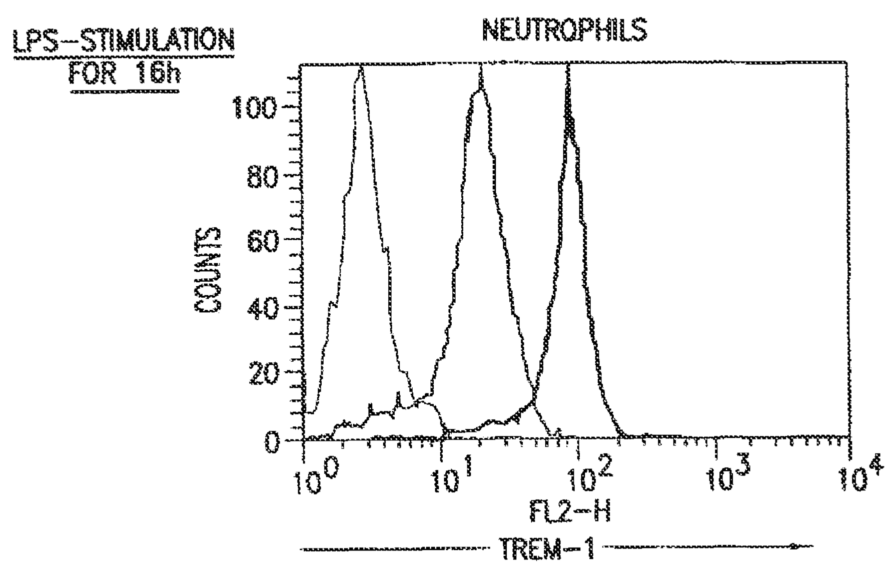

FIGS. 6A-6B show the result of three-color FACS analysis of monocytes (FIG. 6A) and neutrophils (FIG. 6B) which were stimulated with LPS (1 |.ig/ml) for 16 h and stained with either mAb 21C7 or mAb 1B7.11, which is a control IgGI (anti-2,4,6-trinitrophenyl (TNP)), followed by human immunoglobulin-adsorbed PE-conjugated goat anti-mouse IgG. LPS-treated monocytes or neutrophils are expressed with a solid bold line, whereas LPS-untreated cells are expressed with a solid line. The background staining with a control IgGI mAb is shown as a dashed line.

FIGS. 7A-7H show the TREM-I-mediated cytokine production and degranulation by neutrophils and monocytes that are reacted with mAb 21C7 or 1 FI I (anti-MHC class I) in the presence or absence of LPS (1 \ig/m\). Secretion of IL-8 (FIG. 7A) and MPO (FIG. 7B) by neutrophils and that of MCP-1 (FIG. 7D), IL-8 (FIG. 7E), and TNF-a (FIG. 7F) by monocytes was measured by ELISA and the results are shown in the upper panels. TREM-I-mediated degranulation of neutrophils (FIG. 7C) and secretion of TNF-a (FIG. 7G) and MCP-1 (FIG. 7H) by monocytes after priming these cells with LPS are shown in the lower panels.

Figure 8A:
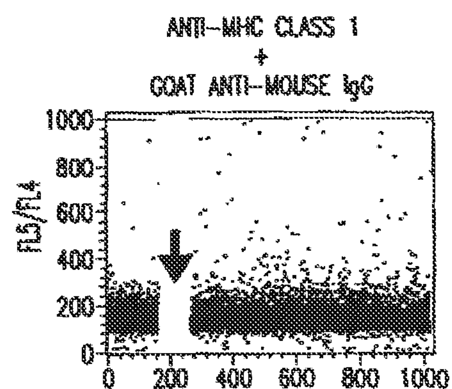
Figure 8B:
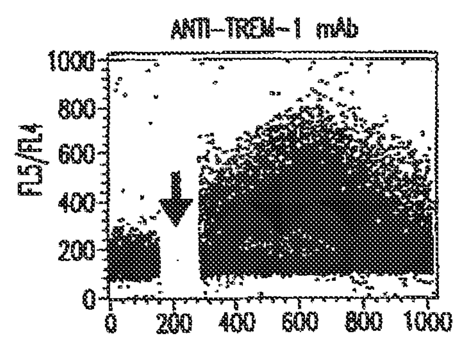
Figure 8C:
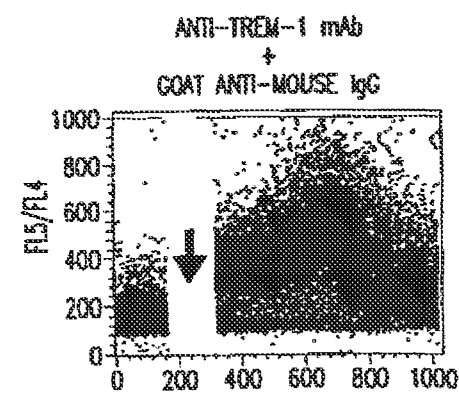

FIGS. 8A-8C show the result of intracellular calcium measurements in monocytes treated with anti-TREM-I alone (FIG. 8B) or in combination with a cross-linking Ab (FIG. 8C). Intracellular calcium was also measured for monocytes which were treated with a control IgGI mAb (anti-MHC class I) and a cross-linking Ab (FIG. 8A). Addition of Abs is indicated by an arrow.

Figure 9:
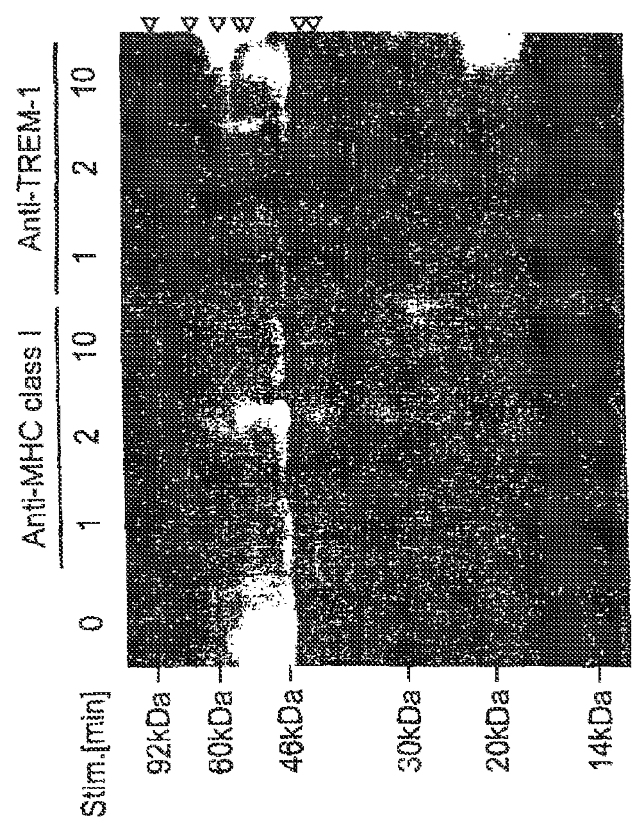

FIG. 9 shows the anti-phosphotyrosine blot of cell lysates from monocytes stimulated with anti-TREM-I or control IgG 1 mAbs in the presence of a cross-linking Ab for the indicated time periods.

Figures 10A, 10B, 10C, 10D:
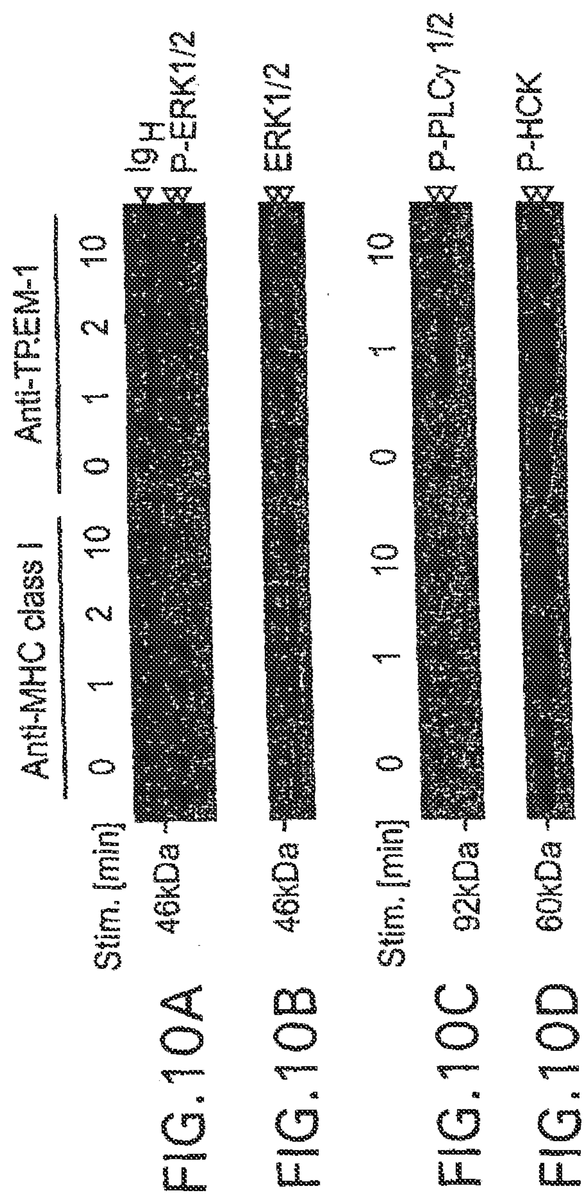

FIGS. 10A-10B show the result of Western blot in which the lysates of monocytes stimulated with anti-TREM-I or a control antibody (anti-MHC class 1 mAb) were immunoblotted with anti-phospho-ERKI/2 (FIG. IOA) and anti-ERKI/2 (FIG. IOB) mAbs. Phosphorylated proteins are indicated by arrows in all panels. Molecular weight markers are also shown.

FIG. 10C-10D show the result of Western blot in which tyrosine phosphorylated proteins were precipitated from the lysate of monocytes stimulated with anti-TREM-I or a control antibody and immunoblotted with anti-phospholipase C-y (PLC-y) (FIG. 10C) or anti-Hck (FIG. 10D) Abs. Anti-Hck blotting was performed as a loading control because phosphorylation of Hck is similar in both stimulated and unstimulated monocytes. Phosphorylated proteins are indicated by arrows in all panels. Molecular weight markers are also shown.

FIG. 11 shows the result of Western blot analysis under reducing condition in which the surface-biotinylated monocyte lysates were immunoprecipitated with anti-TREM-I mAb or a control IgGI (anti-MHC class 1 mAb) and left untreated or treated with A^-glycanase F followed by Streptavidin-HRP blot. Deglycosylated TREM-1 is indicated as TREM-1°'^'^^

Figure 12:
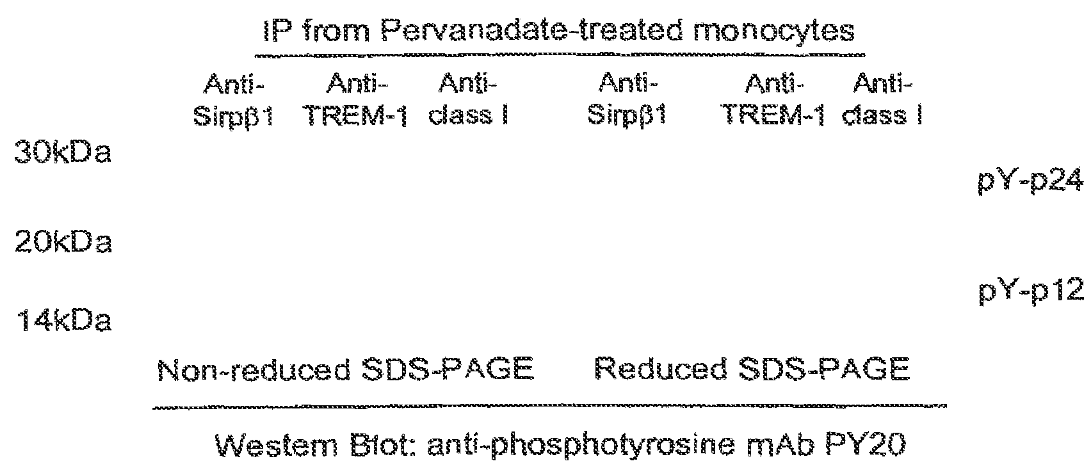

FIG. 12 shows the result of Western blot analysis in which pervanadate-treated monocytes were subjected to immunoprecipitation with anti-TREM-I mAb, anti-SiRP mAb as a positive control, or control IgGI (anti-MHC class I mAb). The precipitates were analyzed by anti-phosphotyrosine blot under reducing and nonreducing conditions.

Figure 13:
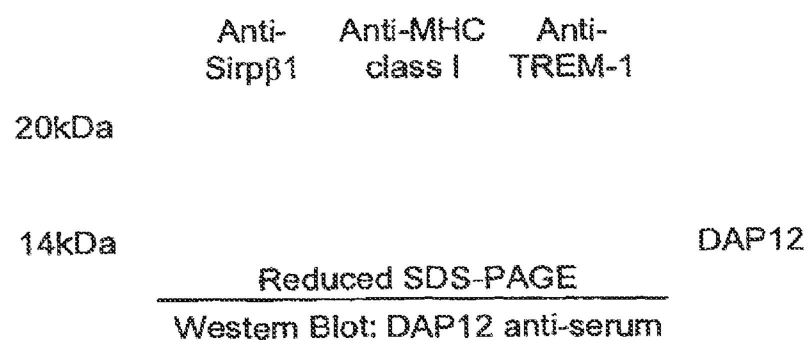

FIG. 13 shows the result of anti-DAP12 blot analysis of a TREM-1 immunoprecipitate from monocytes (reducing conditions). Control IgGI (anti-MHC class I mAb) and anti-SIRP mAb immunoprecipitates were included as negative and positive control, respectively. TREM-1 and DAP 12 are indicated by arrows. Molecular weight markers are also shown.

FIGS. 14A-14B show the result of three-color FACS analysis for TREM-1 expression on monocytes and neutrophils which were stimulated with heat-inactivated gramnegative (*Pseudomonas aeruginosa*; FIG. 14A(1) and FIG. 14A(2)) or gram-positive (*Staphylococcus aureus*; FIG. 14A(3) and FIG. 14A(4)) bacteria, or mycobacteria (Bacillus of Calmette-Guerin; FIG. 14A(5) and FIG. 14A(6)) as well as with their cell wall components Lipopolysaccharide (100 ng/ml; FIG. 14B(1) and FIG. 14B(2)), Lipoteichoic acid (100 ng/ml; FIG. 14B(3) and FIG. 143(4)), Mycotic acid (10 ^g/ml; FIG. 14B (5) and FIG. 14B(6)).

Figure 15A:
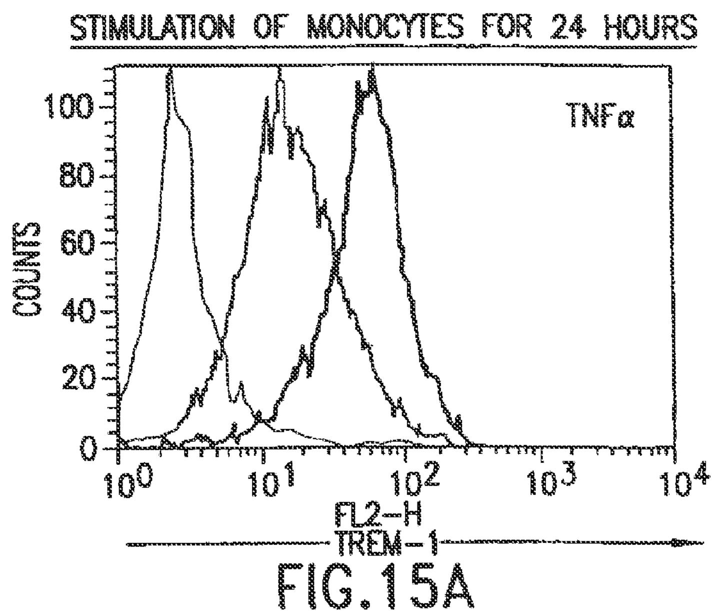
Figure 15B:
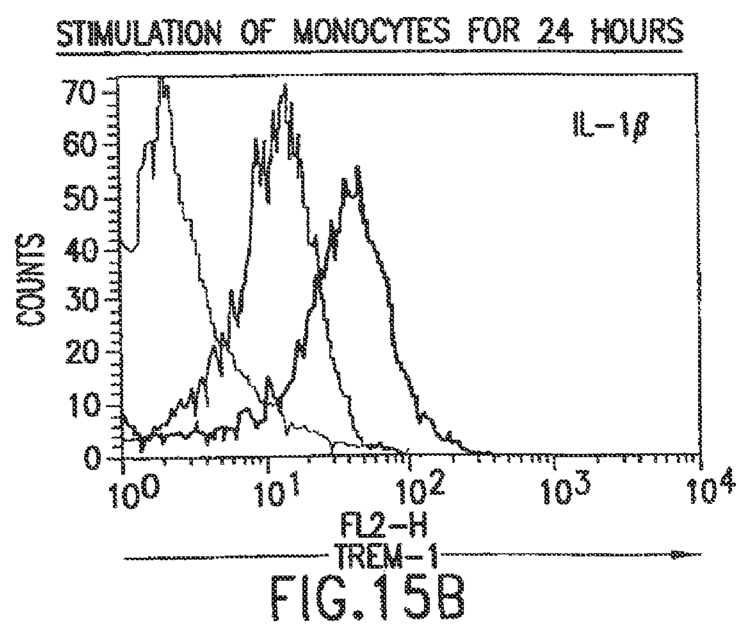
Figure 15C:
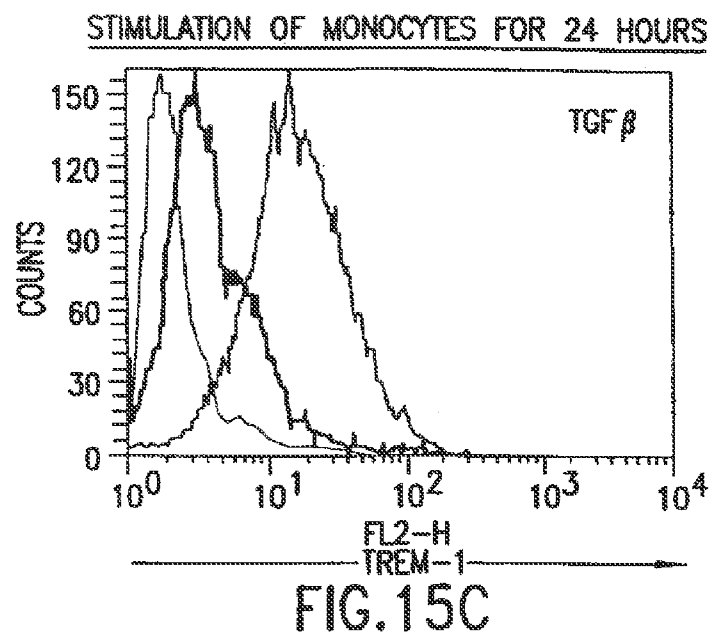
Figure 15D:
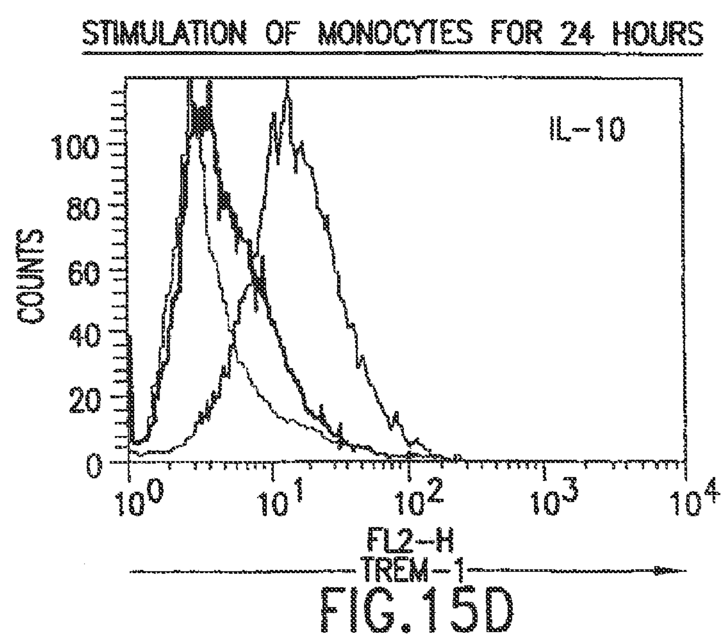

FIGS. 15A-15D show the result of three-color FACS analysis of monocytes which were stimulated with proinflammatory cytokines such as TNF-a (20 ng/ml; FIG. 15A), IL-Iβ (20 ng/ml; FIG. 15B), TGFβ (20 ng/ml; FIG. 15C), and IL-10 (20 ng/ml; FIG. 15D).

Figure 16A:
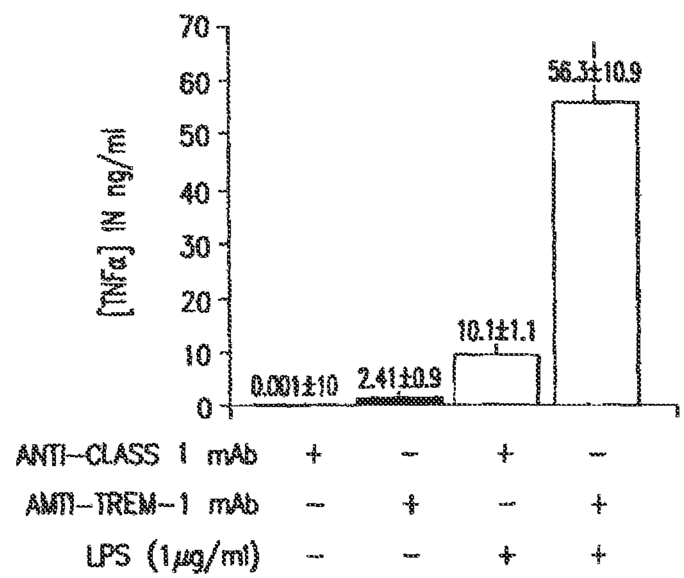
Figure 16B:
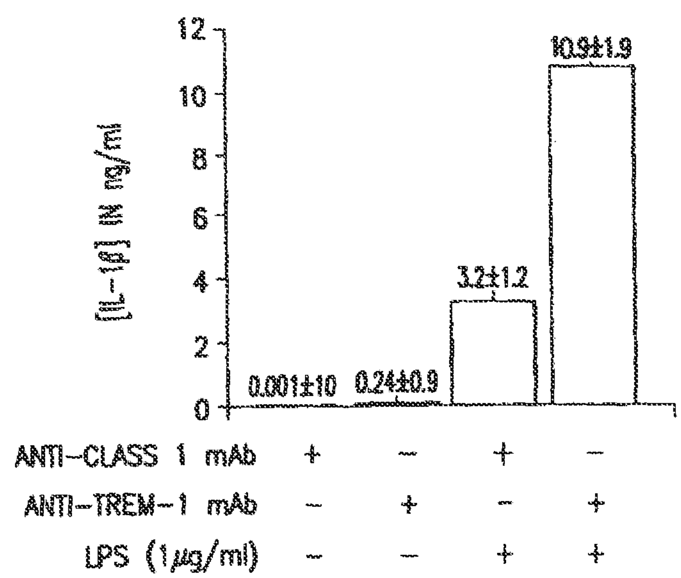

FIGS. 16A-16B show the effect of TREM-1 ligation on LPS-mediated release of TNF-a (FIG. 16A) and IL-Iβ (FIG. 16B) by monocytes which were measured by ELISA. All data points correspond to the mean±standard deviation of four independent experiments.

Figure 17A:
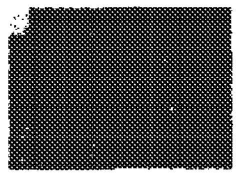
Figure 17B:
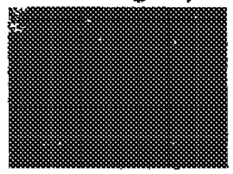
Figure 17C:
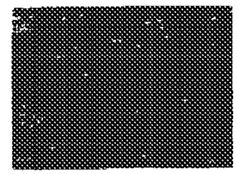
Figure 17D:
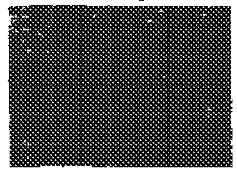
Figure 17E:
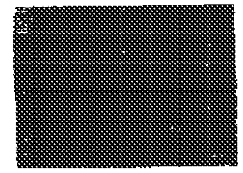
Figure 17F:
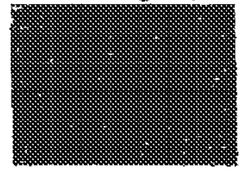

FIGS. 17A-17H show the result of immunohistochemical staining of acute inflammatory lesions caused by bacteria and fungi, using anti-TREM-I mAb (FIGS. 17A, 17C, 17E, 17G) and control IgG,K mAb (FIGS. 17B, 17D, 17F, 17H). FIGS. 17A, 17B: Acute cutaneous folliculitis caused by *Staphylococcus aureus*; FIGS. 17C, I 7D: impetigo caused by *Staphylococcus aureus*; FIGS. 17E, 17F: Cat scratch granuloma induced by *Bartonella henselae*; FIGS. I7G-17H: Granuloma caused by *Aspergillus fiimigatus*.

FIGS. 18A-18F show the result of immunohistochemical staining of tissues with non-pathogenic inflammations. FIGS. 18A-18B: Psoriasis; FIGS. 18C-18D: Ulcerative colitis; and FIGS. 18E-18F: Vasculitis caused by immune complexes. FIGS. 18A, 18C and 18E are stained by anti-CD 15 mAb (staining granulocytes), whereas FIGS. 18B, 18D, and 18F are stained by anti-TREM-I mAb.

Figure 19A:
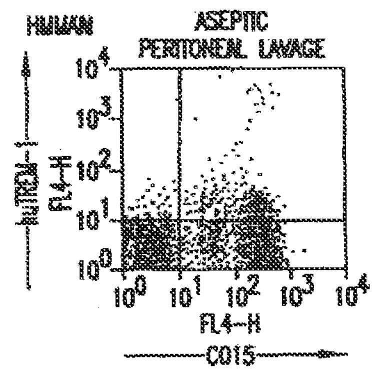
Figure 19B:
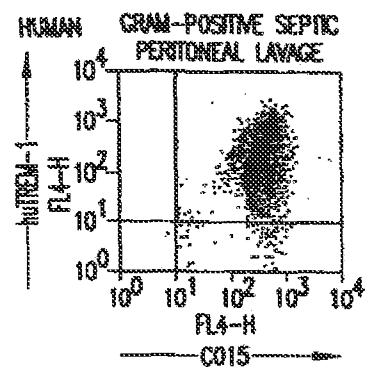
Figure 19C:
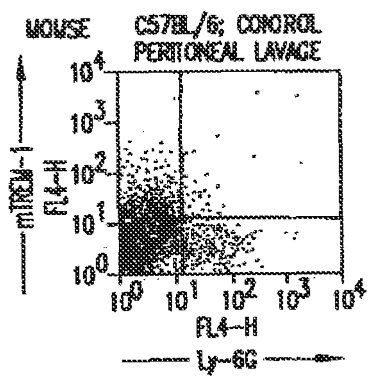

FIGS. 19A-19D show the results of flow cytometric analysis of peritoneal lavage cells from patients with aseptic SIRS due to aseptic cholecystitis (FIG. 19A) or polymicrobial gram-positive sepsis caused by bowel perforation (FIG. 19B). CDI5^'^ cells correspond to neutrophils. Four-color analysis of peritoneal leukocytes from LPS-treated C57BL/6 mice (FIG. 19D) compared to control animals (FIG. 19C). Ly-6G^'^/TREM-I^'^^ cells correspond to murine neutrophils. The Ly-6G'*""-"'^^""/TREM-I'^'^" cells are CDI ib/Mac-I"^ (data not shown) and therefore correspond to peritoneal macrophages. Staining with isotype-matched control mAbs were set to the indicated lower quadrants.

Figure 20:
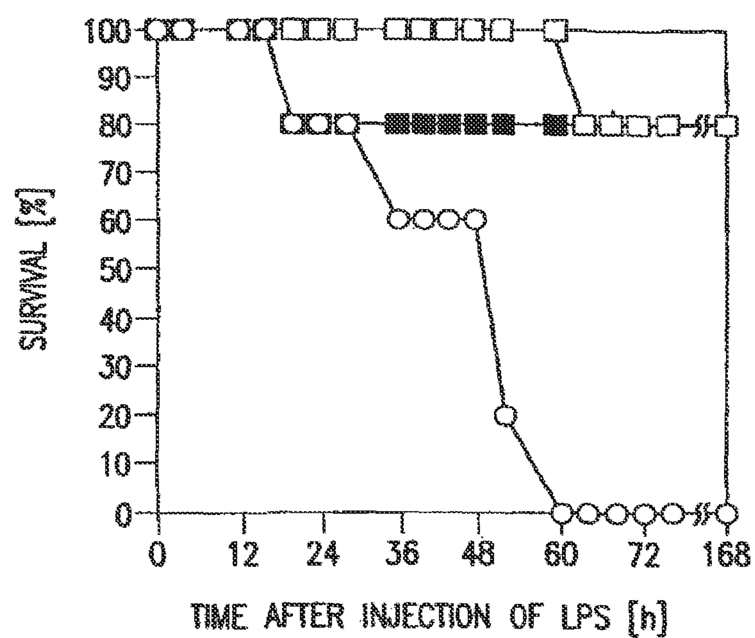

FIG. 20 shows the comparison of prophylactic effects between huTREM-1 and mTREM-1 in mice with LPS-induced septic shock. Mice (5 mice per group) were treated with either human IgGI,K (500 (xg/mouse, i.p.; open circles), purified human or mouse TREM-1-IgGI (500 |xg/mouse, i.p.; closed and open squares, respectively). One hour later, all mice received an LDioo of LPS (20 mg/kg, i.p.). One of four (4) representative experiments is shown.

Figure 21A:
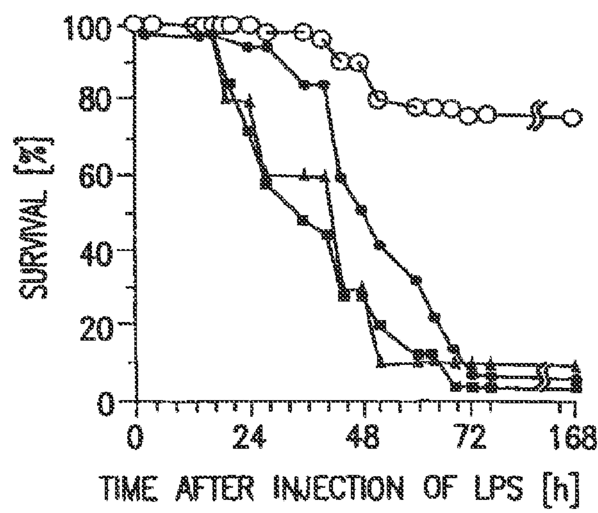

FIG. 21A shows the survival curve of C57BL/6 mice treated with control huIgGI (closed circles) or mTREM-1-IgGI (open circles) 1 hour prior to administration of LPS. Data points are from seven independent experiments, each of which included 5-10 animals per group. Survival was 76% (37 of 49) in mice treated with mTREM-I-IgGI and 6% (3 of 49) in mice treated with huIgGI (P=0.0002, two-tailed Fisher's exact test). In additional controls, mice received injections with purified human ILT3-IgGI (closed squares, n=25) or heat-inactivated mTREM-I-IgGI (closed triangles; n=10) before induction of endotoxemia.

Figure 21B:
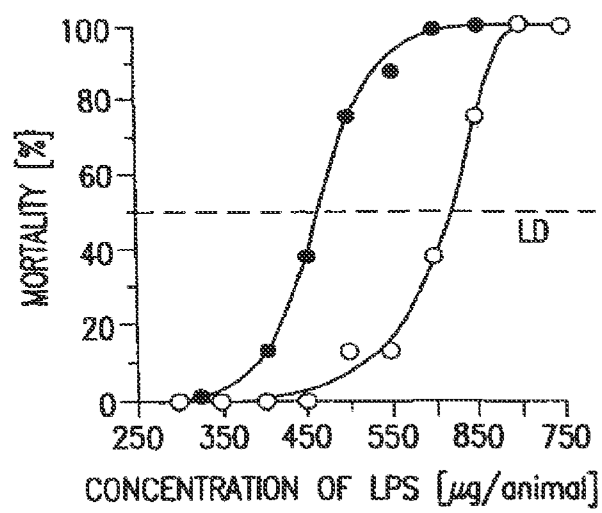

FIG. 21B shows the estimation of the LPS LD50 in mice treated with mTREMI-IgGI or huIgGI. Mice were randomly assigned to 20 groups each containing 10 animals. Ten groups received intraperitoneal injections of mTREM-1-IgG 1, whereas 10 groups were injected with huIgGI. One hour later, endotoxemia was induced by application of various quantities of LPS as indicated. Calculation of LD50 was accomplished as previously described j.LD5omTREM-i.igGi ^ ^ig, LDSO""^"^'=467 ^g; P<0.0001) (Beutler, B., et a i, 1985, Science 229:869-71).

Figure 21C:
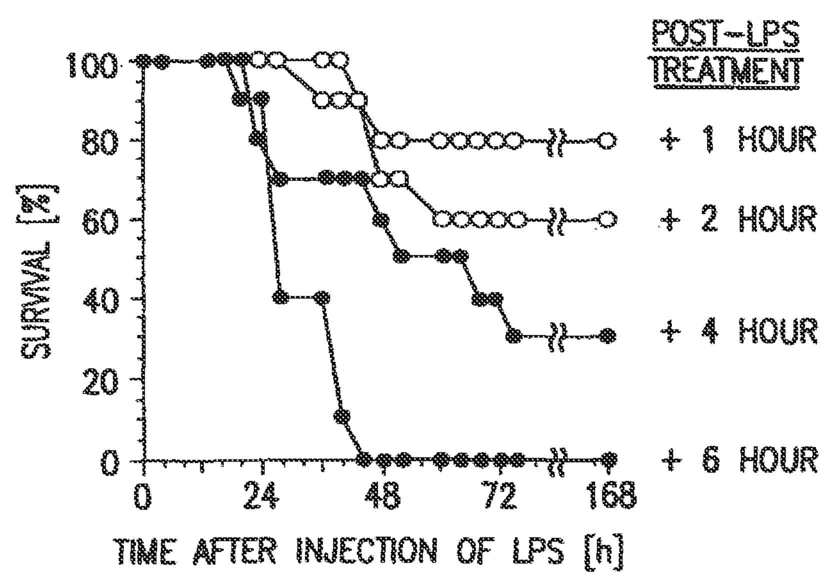

FIG. 21C shows the survival curve of mice with LPS-induced lethal peritonitis. Mice were injected with LPS one (white circles), two (light grey circles), four (dark grey circles) and six hours (black circles) prior to administration of mTREM-I-IgGI. Data points are from two independent experiments, which included 3-7 animals per group. Survival was 80% (P=0.0007, two-tailed Fishers exact test), 60% (P=0.0108, two-tailed Fishers exact test), 40% and 0%, respectively.

Figure 22A:
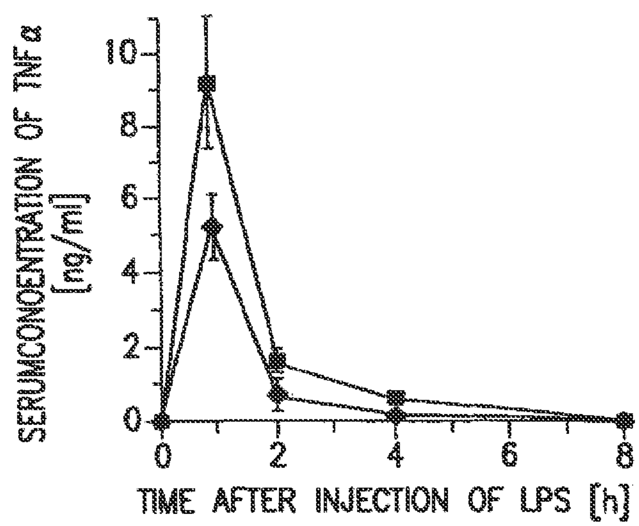
Figure 22B:
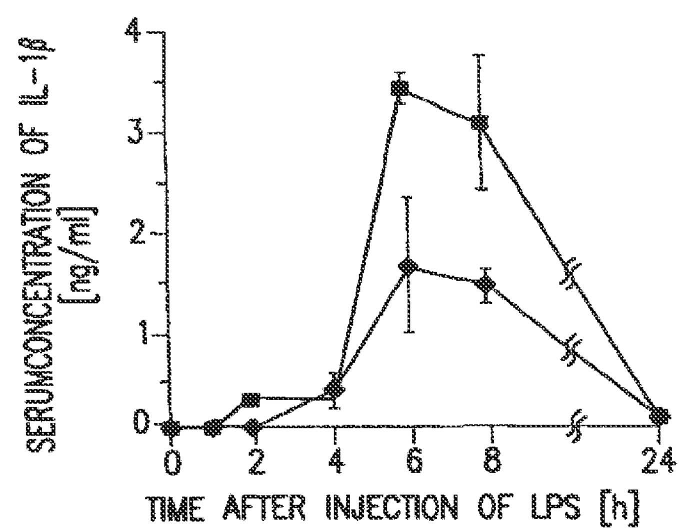

FIGS. 22A-22B show the serum levels of TNF-a (FIG. 22A) and IL-1β (FIG. 22B) during LPS-induced septic shock. Female, 6-8-week old C57BL/6 mice (6 mice per group) treated with either human IgGI,K (500 ^g/mouse, i.p.; closed squares) or mTREM-1-IgGI (500 p,g/mouse, i.p.; closed diamonds) prior to injection with an LDioo of LPS (20 mg/kg, i.p.). Serum levels of TNF-a and IL-Iβ at 1, 2, 4, 6, 8, and 24 hours after LPS administration, were determined by ELISA.

Figure 22C:
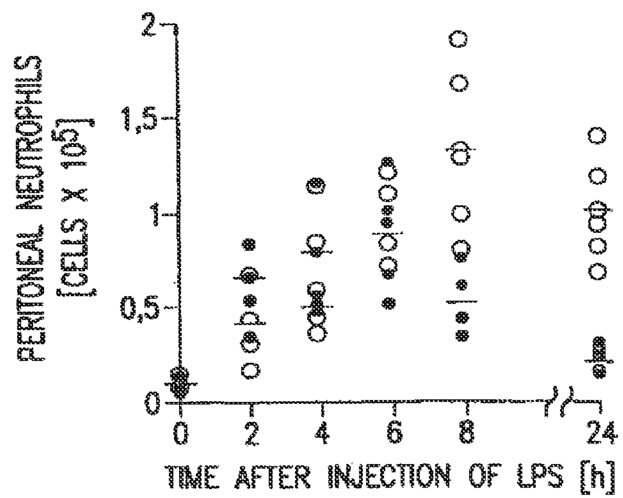
Figure 22D:
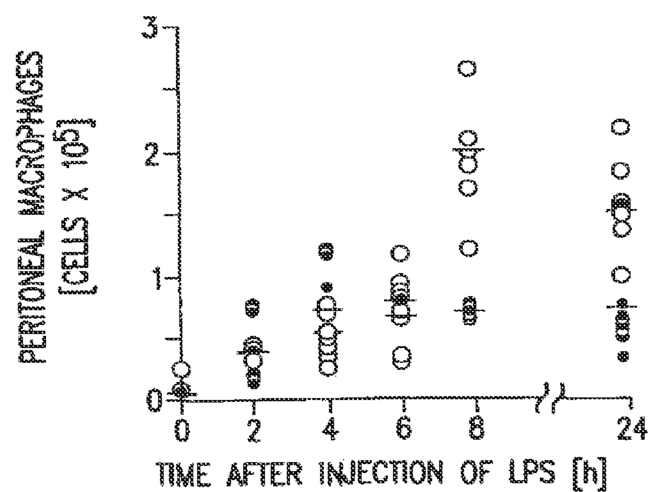

FIGS. 22C-22D show the analysis of peritoneal lavage cells during LPS induced septic shock. Mice were treated, as described for FIG. 19A, with human IgG I,K (500 jig/mouse, i.p.; open circle) or mTREM-1-IgGI (500 |ig/mouse, i.p.; closed circle), and peritoneal lavage cells were collected at 2, 4, 6, 8, and 24 hours after LPS administration. Neutrophils (FIG. 22C) and macrophages (FIG. 22D) were quantified on cytospin slides.

Figure 23A:
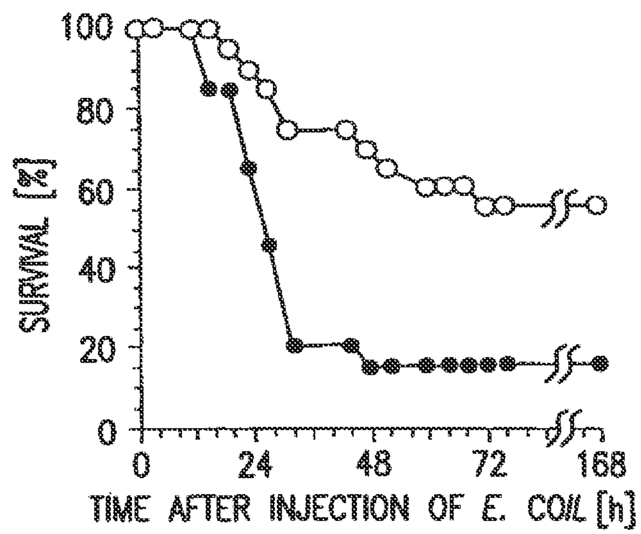

FIG. 23A shows the survival curve of C57BL/6 mice that were injected intraperitoneally with mTREM-I-IgGI (open circles) or huIgGI (closed circles) one hour before intraperitoneal administration of *E. coli*. Data points are from two independent experiments, which included 5-15 animals per group. Survival was 55% i (11 of 20) in mice treated with mTREM-1-IgGI and \5% (3 of 20) in mice treated with control huIgGI (P=0.0187, two-tailed Fisher's exact test).

Figure 23B:
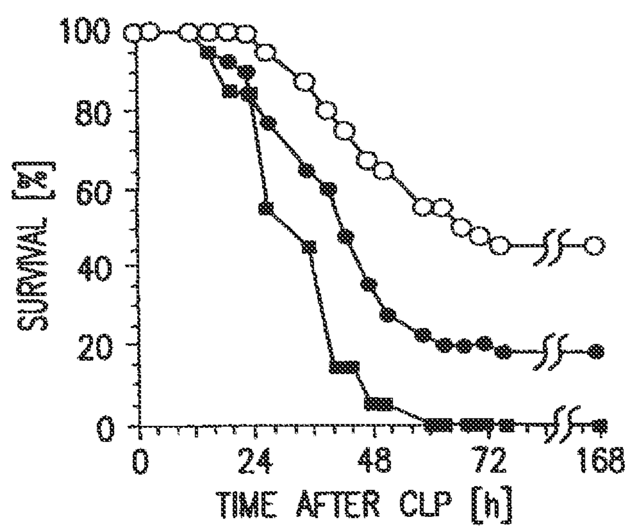

FIG. 23B shows the survival curve of C57BL/6 mice that were injected intraperitoneally with mTREM-1-IgGI (open circles), huIgGI (closed circles) or TNF-RI-IgGI (closed squares) immediately after cecal ligation and puncture (CLP). Data points are from four independent experiments, which included 5-10 animals per group. Survival was 45% (18 of 40) in mice treated with mTREM-1-IgGI, 17.5% (7 of 40) in mice treated with control huIgGI (P~0.015, two-tailed Fishers exact test) and 0% (0 of 20) in mice treated with TNF-RI-IgGI.

Figure 24A:
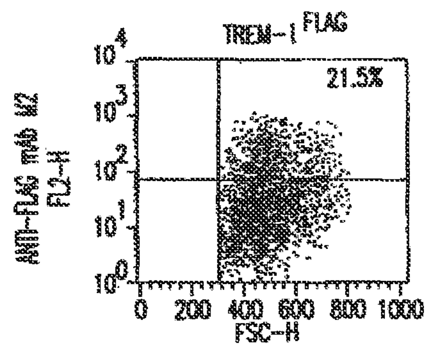
Figure 24B:
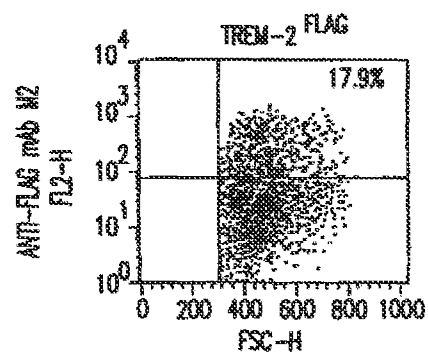
Figure 24C:
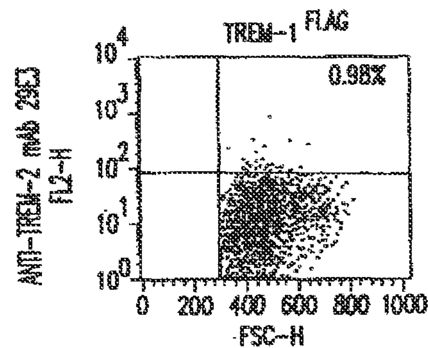
Figure 24D:
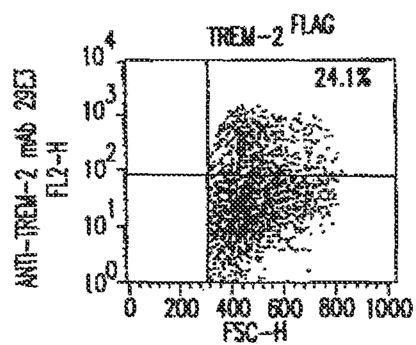
Figure 25A:
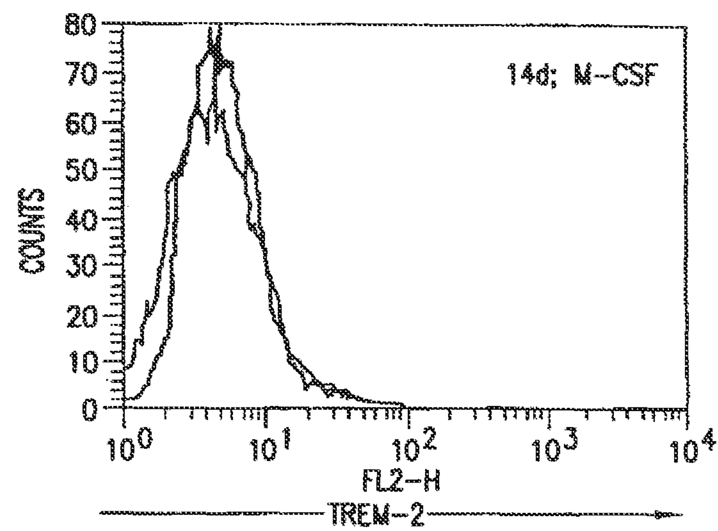
Figure 25B:
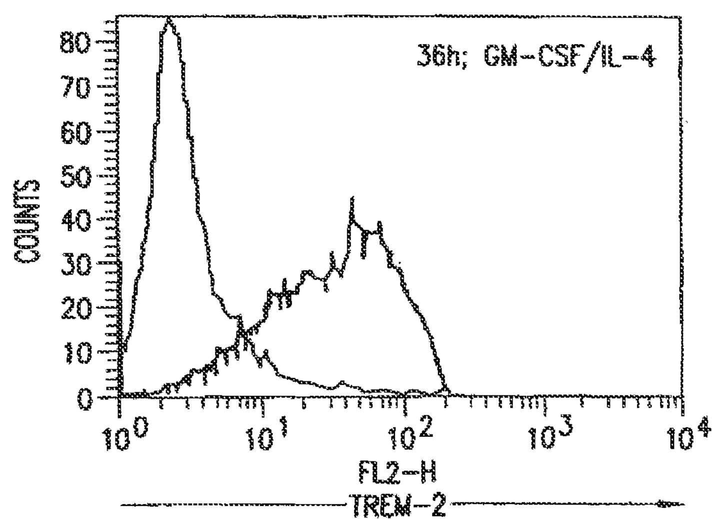
Figure 25C:
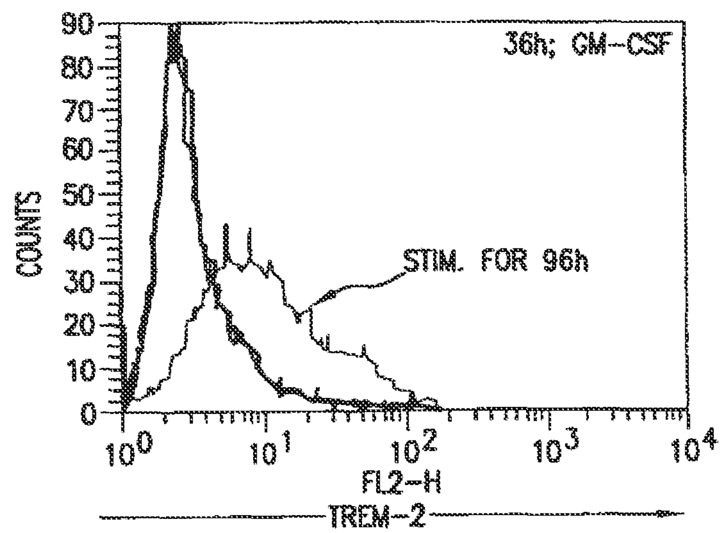
Figure 25D:
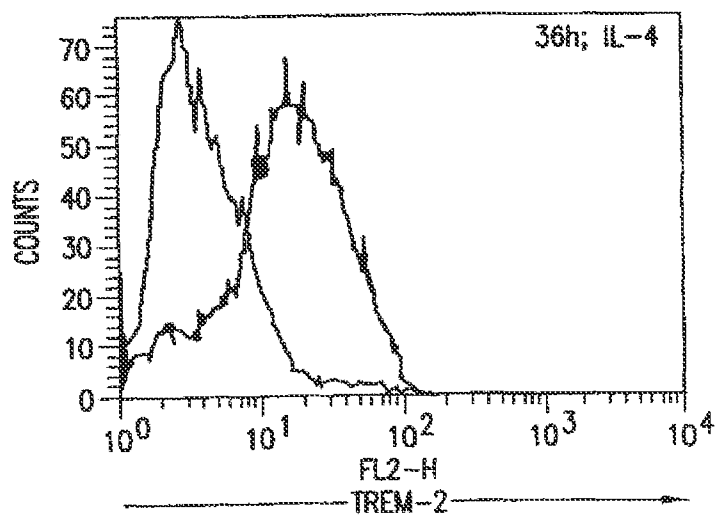

FIGS. 24A-24D show the result of FACS analysis demonstrating the specific binding of 29E3 mAb to TREM-2. The 293 cells expressing TREM-2^'-^*^ (FIGS. 24B, 24D) and those expressing TREM-I^^'^*^ (FIGS. 24A, 24C) were compared for staining with 29E3 mAb (FIGS. 24C, 24D). Expression of TREM-I"^^^ (FIG. 24A) and TREM-2'"-'^^ (FIG. 24B) was confirmed using anti-FLAG mAbs. The percentages of the cells stained with each mAb (upper right quadrant) are indicated. Staining with an isotype-matched control mAbs was set to the indicated lower quadrant.

FIGS. 25A-25D show the result of three-color FACS analysis for TREM-2 expression on monocytes (solid bold line) which were stimulated with M-CSF (FIG. 25A), GM-CSF (FIG. 25C), IL-4 (FIG. 25D), or GM-CSF+IL-4 (FIG. 25B) for 36 hours. Dashed profiles indicate background staining with a control IgGI mAb.

Figure 26A:
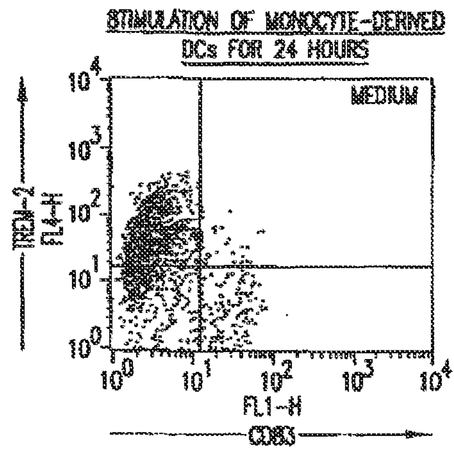
Figure 26B:
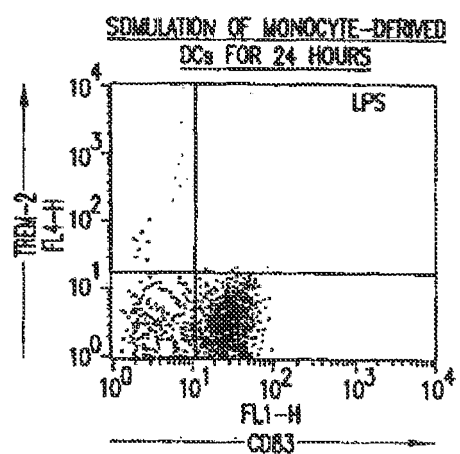
Figure 26C:
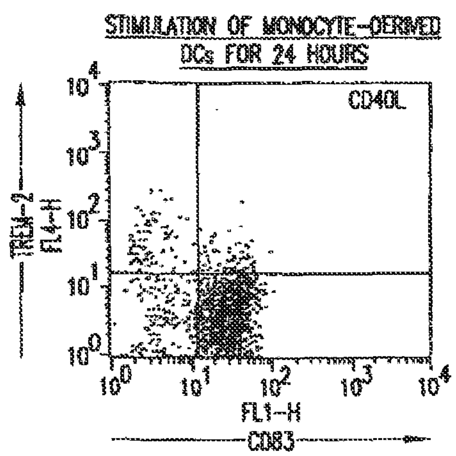
Figure 26D:
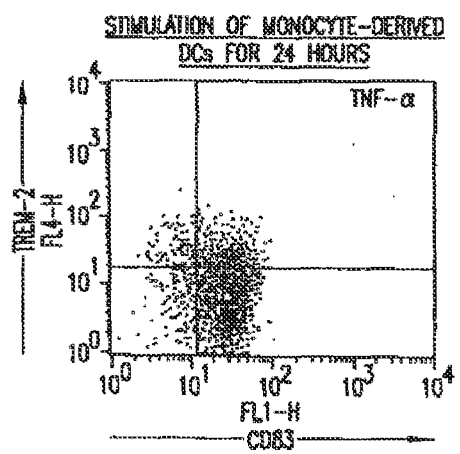

FIGS. 26A-26D show the three-color FACS analysis for TREM-2 and CD83 expression on monocyte-derived DCs that are stimulated with LPS (FIG. 26B), CD40L (FIG. 26C), TNF-a (FIG. 26D), or medium (unstimulated; FIG. 26A) for 36 hours. Staining with isotype-matched control mAb was set to the indicated lower quadrants.

Figure 27:
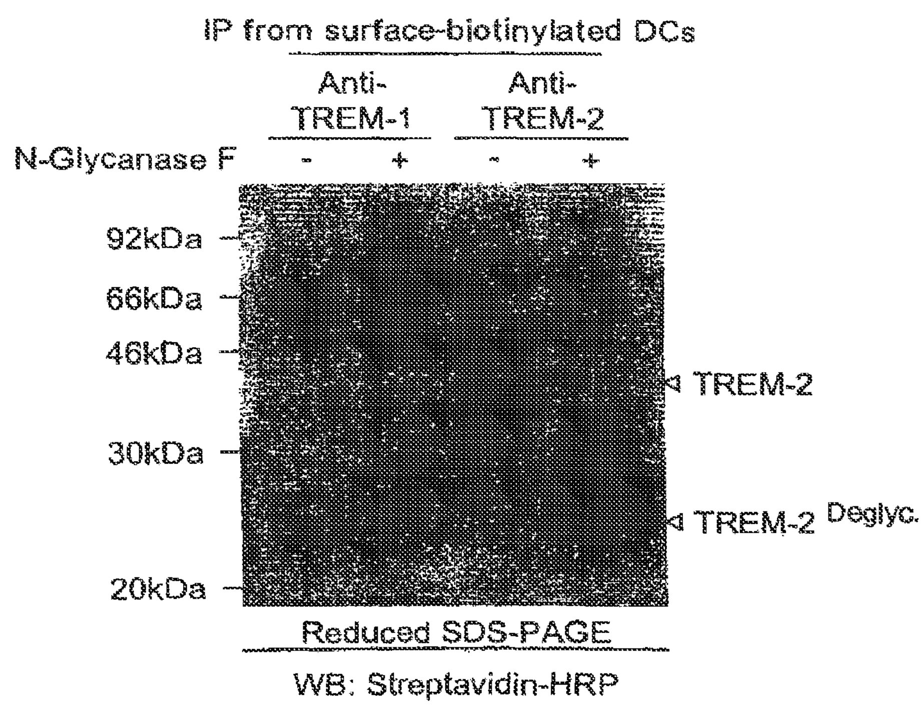

FIG. 27 shows the result of Western blot analysis under reducing condition in which the surface-biotinylated monocyte-derived DCs lysates were immunoprecipitated with anti-TREM-2 mAb 29E3 (right lanes) or a control IgGI (anti-TREM-I mAb21C7; left lanes). Immunoprecipitates were left untreated or treated with iV-glycanase F and analyzed by Western Blot analysis with Streptavidin-HRP. Deglycosylated TREM-2 is indicated as TREM-2°^^'*^ Molecular weight markers and specific protein bands are indicated.

Figure 28:
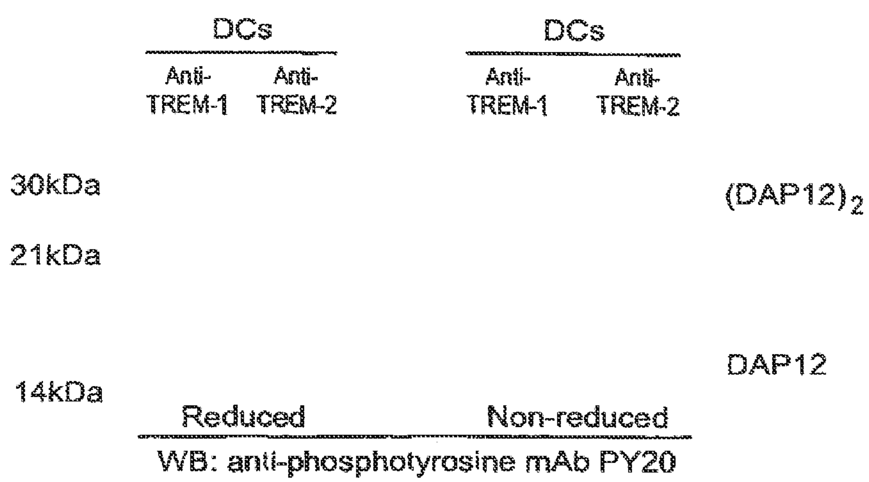

FIG. 28 shows the result of Western blot analysis in which pervanadate-treated monocyte-derived DCs were subjected to immunoprecipitation with anti-TREM-2 mAb 29E3, or control IgG 1 (anti-MHC class I mAb). The precipitates were analyzed by antiphosphotyrosine blot under reducing (left lanes) and nonreducing conditions (right lanes). Tyrosine phosphorylated proteins are marked by arrows. Molecular weight markers are indicated.

Figure 29:
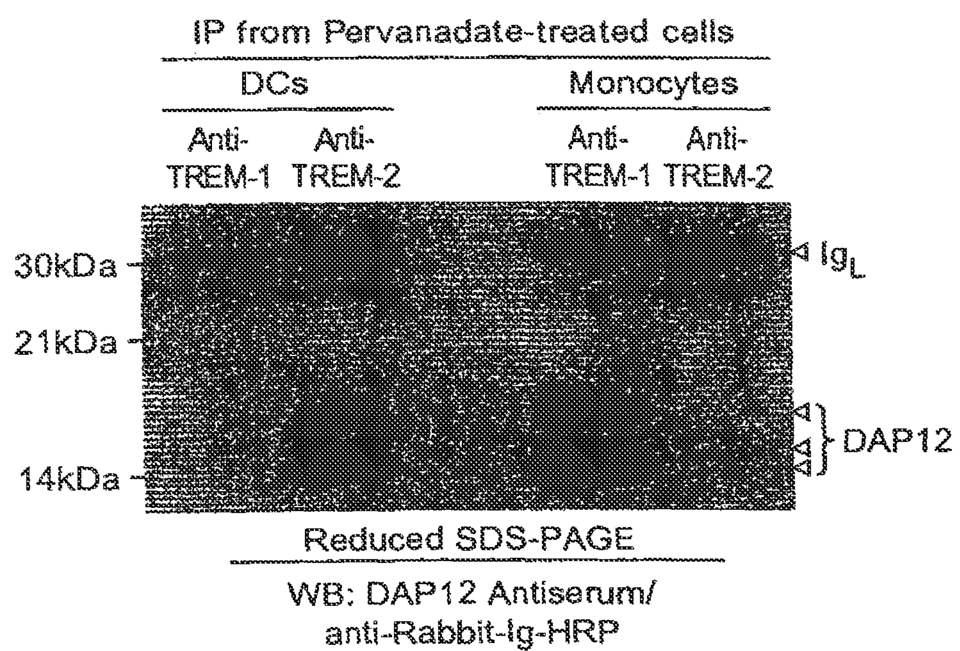

FIG. 29 shows the result of anti-DAP12 blot analysis, under reducing condition, of a TREM-2 immunoprecipitate from monocyte-derived DCs (left lanes) and monocytes (right lanes) after pervanadate stimulation. TREM-1 immunoprecipitates from monocytes and monocyte-derived DCs were included as positive and negative controls, respectively. Molecular weight markers and specific protein bands are indicated.

Figure 30:
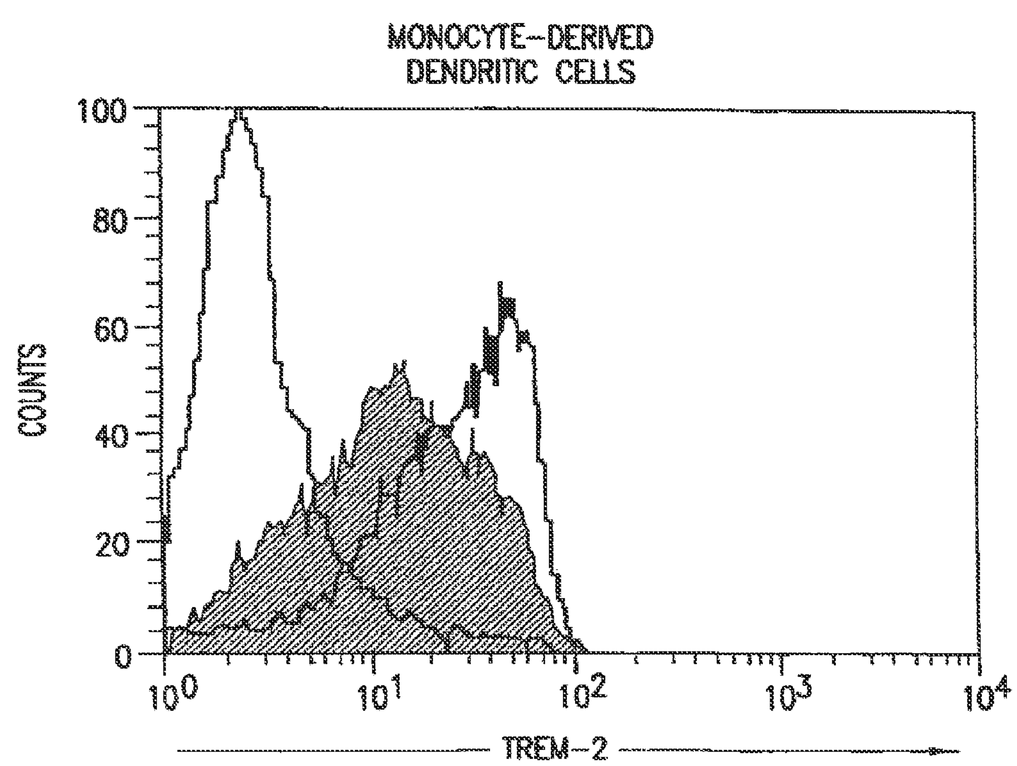

FIG. 30 shows the functional characterization of Fab and F(ab')2 fragments of anti-TREM-2 mAb 29E3^'°'^. Monocyte-derived DCs were analyzed by FACS for cell surface expression of TREM-2 using either F(ab')2 29E3^'"^'" (solid bold profile) or Fab 2c,£3Biotin profile) followed by Streptavidine-PE. TREM-1 is not detectable on monocyte-derived DCs with F(ab')2 9E2^'°"" (solid profile) or Fab 9E2^""" (dashed profile) followed by Streptavidine.

Figure 31A:
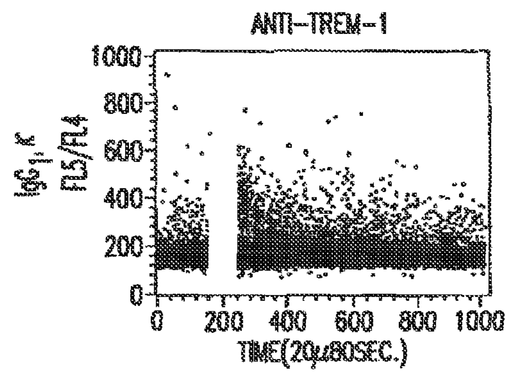
Figure 31B:
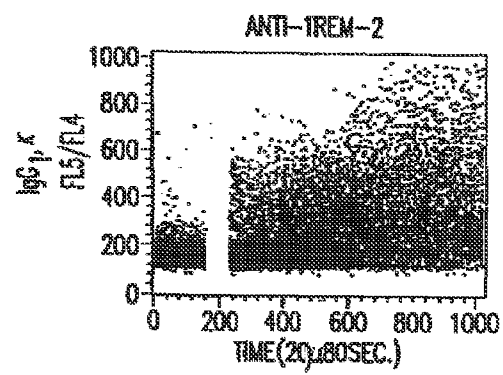
Figure 31C:
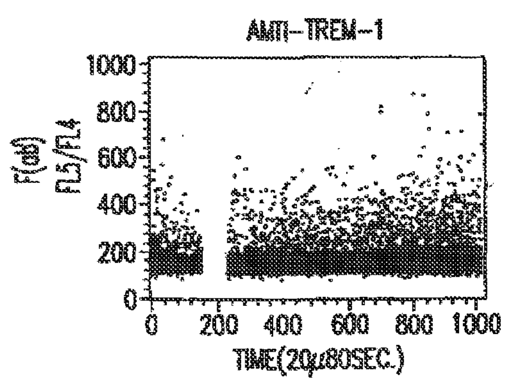
Figure 31D:
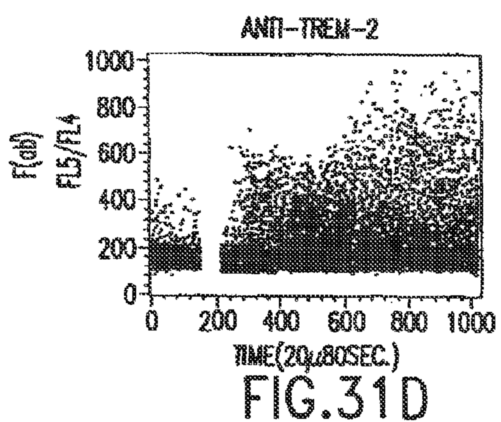

FIGS. 31A-31D show the result of intracellular calcium measurements in monocyte-derived DCs treated with anti-TREM-I mAb 21C7 (FIG. 3IA) or its F(ab')2 fragments (FIG. 31C), or anti-TREM-2 mAb 29E3 (FIG. 3 IB) or its F(ab')2 fragments (FIG. 31D). Monovalent engagement of TREM-2 by Fab 29E3^'"^^ is sufficient for induction of Ca^'^-flux only in the presence of cross-linking Streptavidine (data not shown).

Figure 32:
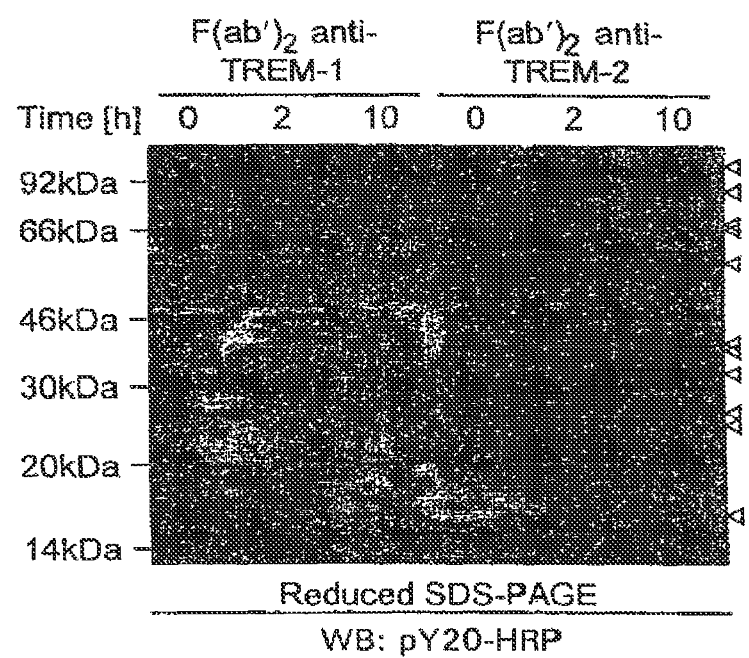

FIG. 32 shows the anti-phosphotyrosine blot of cell lysates from monocyte derived DCs stimulated with F(ab')2 29E3 (anti-TREM-2) or control F(ab')2 9E2 (anti-TREM-I) for the indicated time periods.

Figures 33A, 33B:
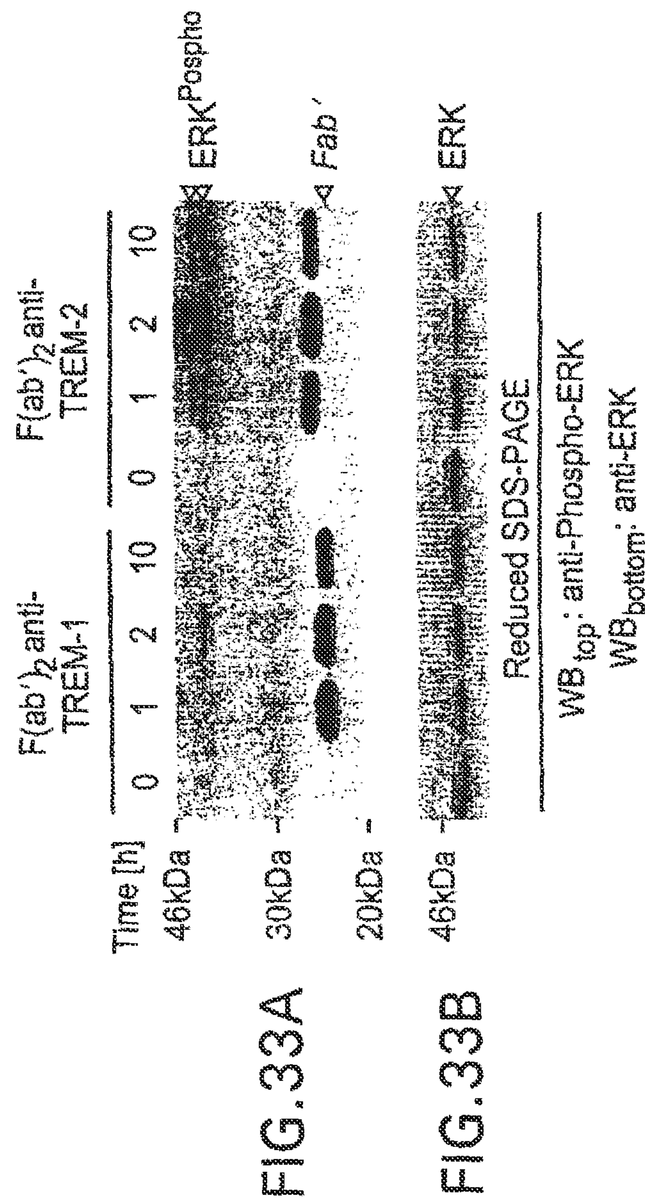

FIGS. 33A-33B show the result of Western blot in which the lysates of monocyte-derived DCs were stimulated as described for FIG. 32 and examined by Western Blot analysis for anti-phospho-Erk I and 2 (FIG. 33A) compared to anti-Erk I and 2 (FIG. 33B). Phosphorylated proteins are indicated by arrows. Molecular weight markers are shown.

Figure 34:
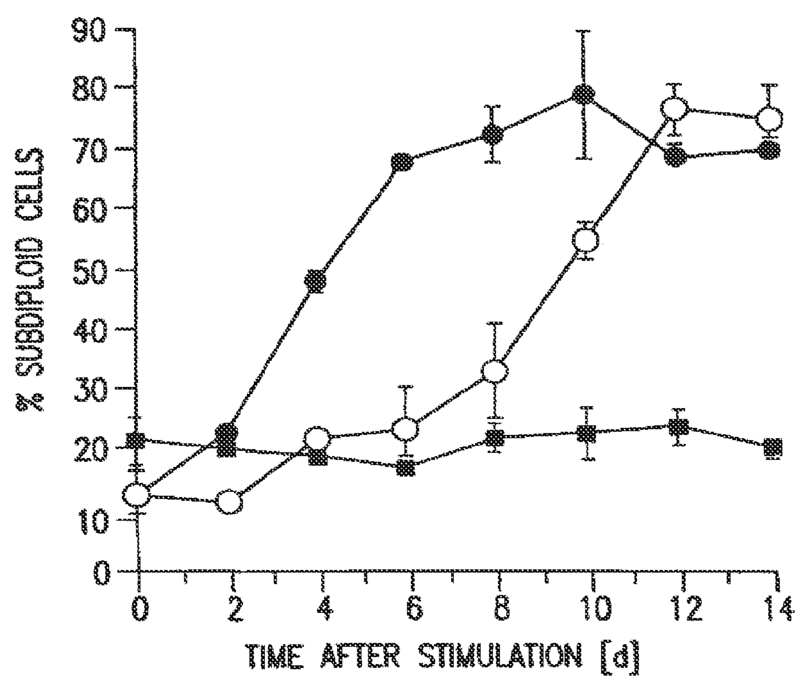

FIG. 34 shows the apoptotic cell death of monocyte-derived DCs that were stimulated with GM-CSF/IL-4 (closed squares), plastic-bound F(ab')2 29E3 (open circles) or control F(ab')2 (closed circles) for the indicated time periods. Apoptotic cell death was determined by measurement of DNA fragmentation.

Figure 35:
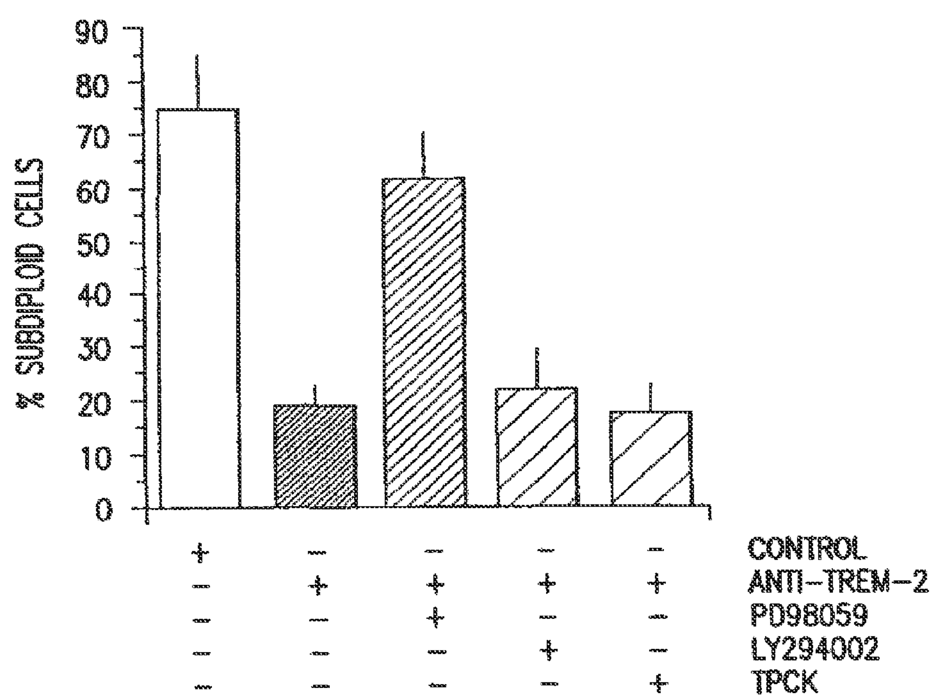
Figure 36A:
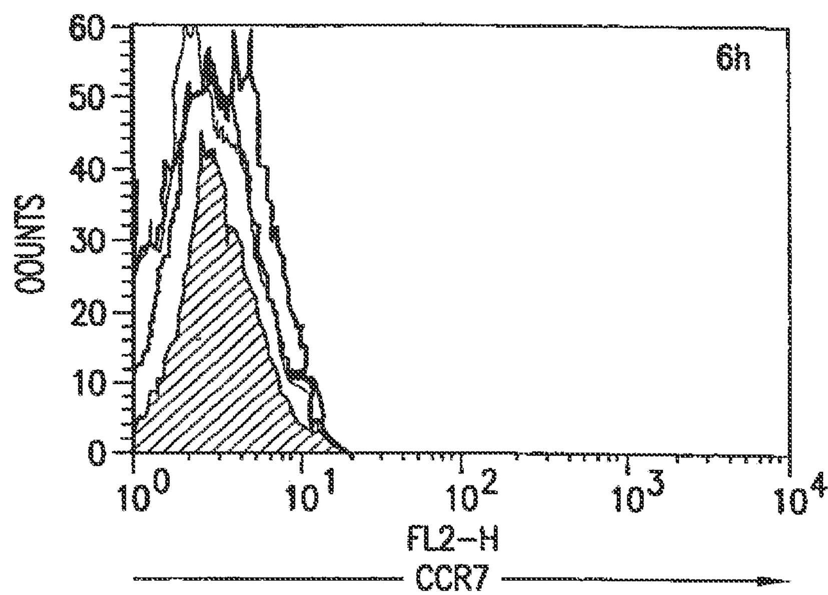
Figure 36B:
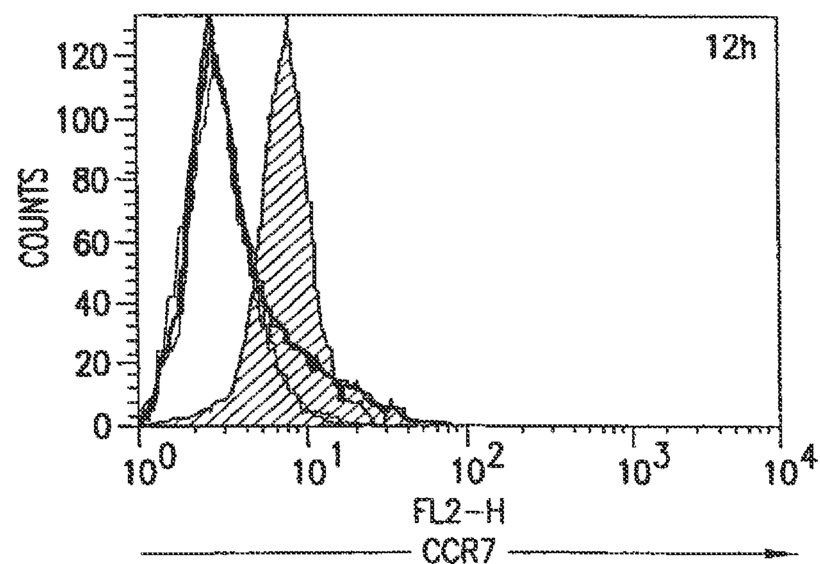
Figure 36C:
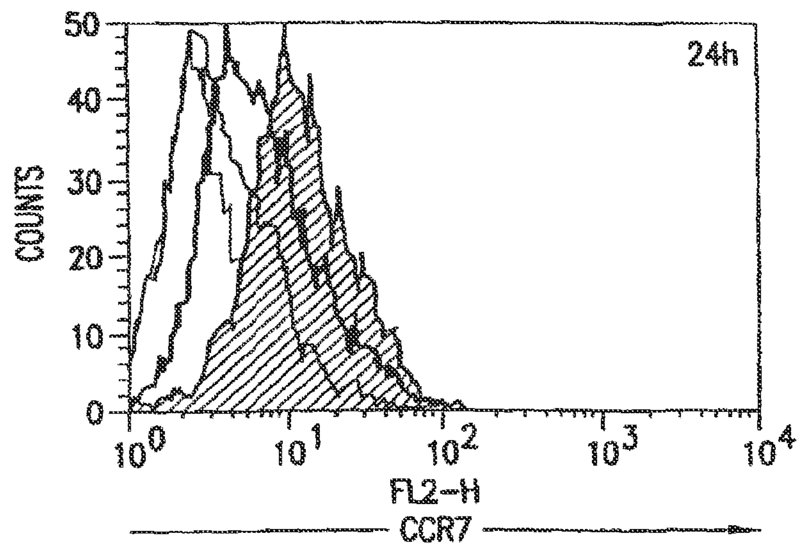
Figure 36D:
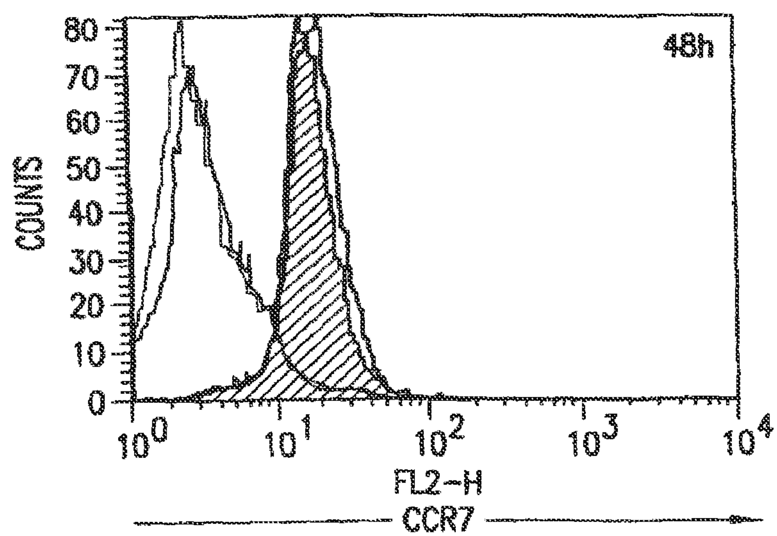

FIG. 35 shows the apoptotic cell death of monocyte-derived DCs that were stimulated as described for FIG. 34 in the presence or absence of PD98059 (Erk Inhibitor), LY294002 (PI 3 Kinase Inhibitor) or TPCK (Inhibitor of NFkB-activation). Apoptotic cell death was determined after 8 days by measurement of DNA fragmentation.

FIGS. 36A-36D show the FACS analysis of CCR7 expression on DCs that were stimulated with F(ab')2 control mAb (anti-TREM-i; solid line profiles), F(ab')2 anti-TREM-2 mAb (grey profiles), or LPS (solid bold profiles) for the indicated time periods. Dashed profiles indicate background staining with a control IgM mAb.

Figure 37:
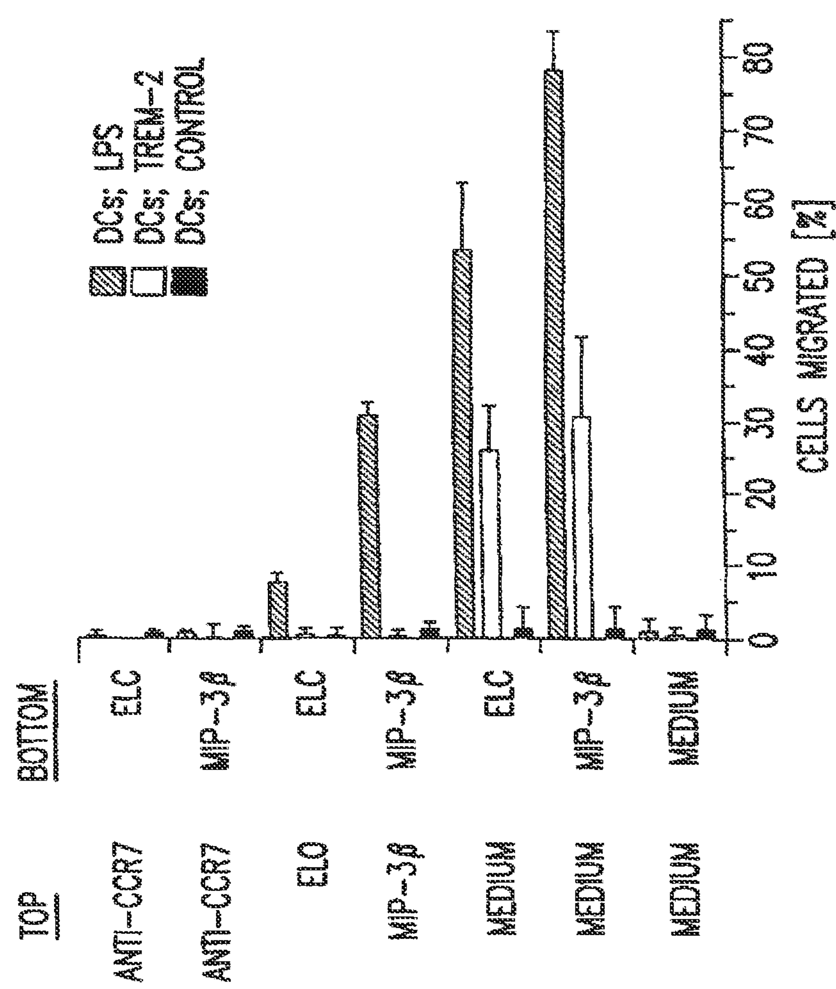

FIG. 37 shows the DC Chemotaxis induced by F(ab')2 anti-TREM-2 mAb. DCs stimulated for 24 hours with plastic-coated F(ab')2 control mAb (black bars), F(ab')2 anti-TREM-2 mAb (light-grey bars), or LPS (dark-grey bars) were used in transwell Chemotaxis assays to assess their chemotactic properties towards medium alone, medium supplemented with 100 ng/ml MIP-3β or ELC. In control experiments, Chemotaxis was inhibited by stimulating cells with MIP-3β, ELC or anti-CCR7 mAb 10 min prior to the onset of Chemotaxis.

Figure 38A:
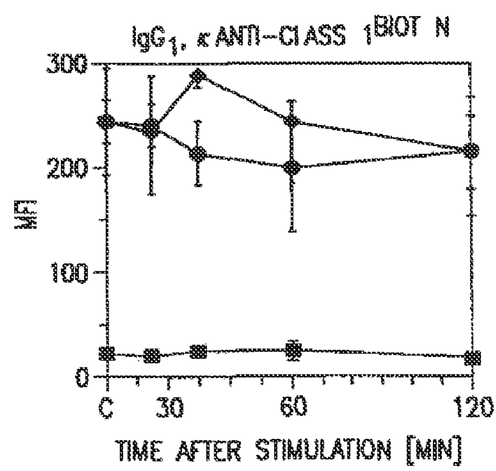
Figure 38B:
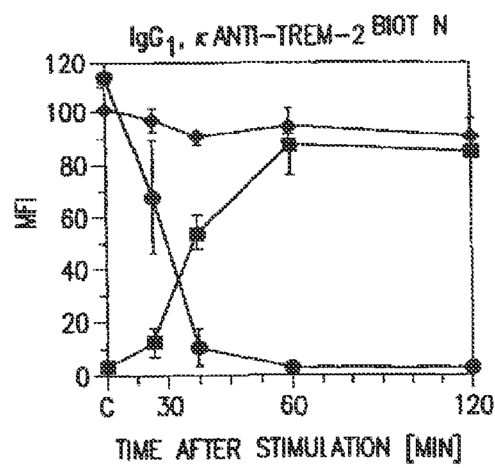
Figure 38C:
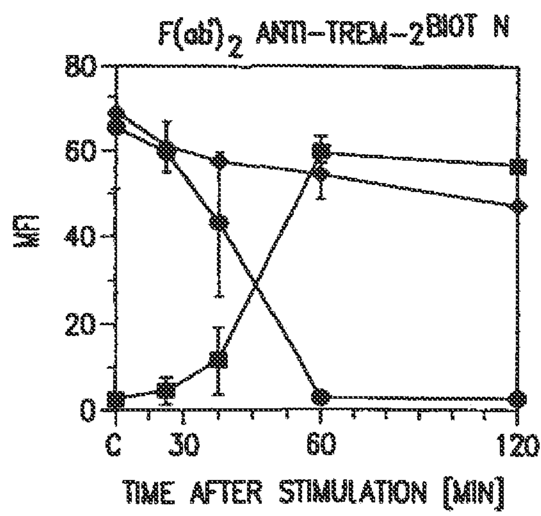
Figure 38D:
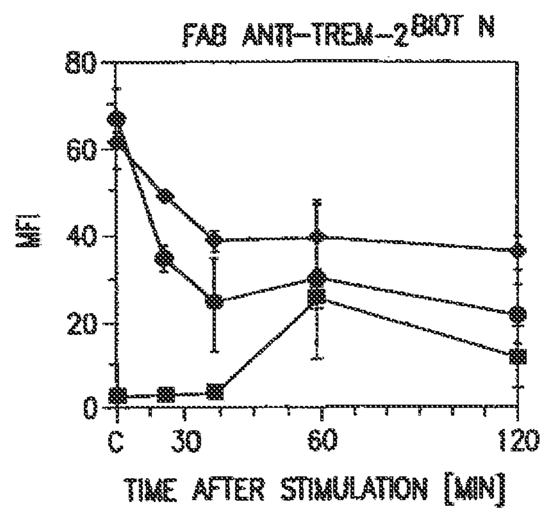

FIGS. 38A-38D show the internalization of TREM-2 on monocyte-derived DCs upon ligation. The DCs were incubated with either 1 FI 1^"""" (anti-MHC class I mAb; FIG. 38A), 29E3^*'^"" (anti-TREM-2 mAb; FIG. 38B), F(ab')2 29E3^'°^" (FIG. 38C), or Fab 29E3^'°^" (FIG. 38D). The cells were subsequently kept on ice, prepared for total (closed diamonds), extracellular (closed circles), or intracellular receptor (closed squares) staining with a second step Goat-anti mouse IgG-PE or Streptavidine-PE and analyzed by FACS. Numerical values indicate specific mean fluorescence intensity (MFI) after subtraction of the fluorescence detected with an isotype-matched control antibody. The data are representative of 3 independent experiments.

Figure 39A:
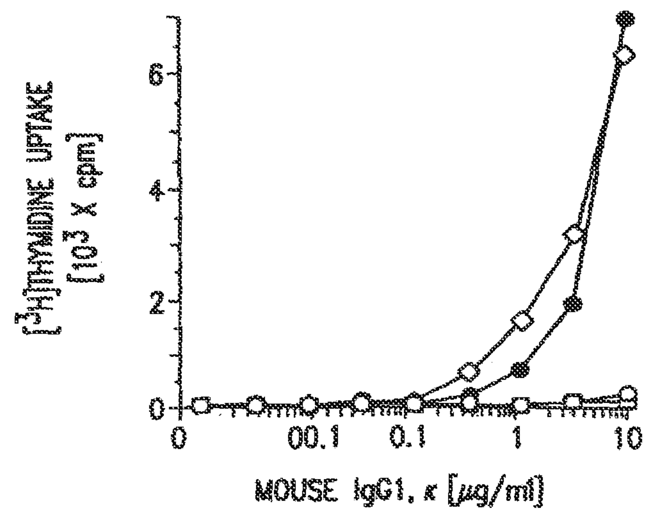
Figure 39B:
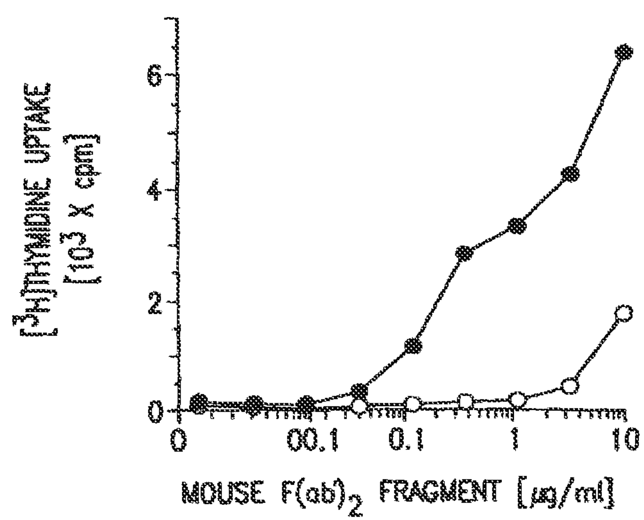

FIGS. 39A-39B show the result of antigen presentation assay using [.'HJthymidine uptake by mouse-IgGI specific T cell clone as an indicator. In FIG. 39A, DCs were stimulated with the indicated concentrations of anti-ILT3 mAb (open diamonds), anti-TREM-2 mAb (closed circles), control mAb (open circles), or anti-CDI Ib mAb (open squares), whereas, in FIG. 39B, DCs were stimulated with F(ab') 2 anti-TREM-2 (closed circles) or F(ab')2 control mAb (open circles). F(ab')2 anti-TREM-2 was presented to T-cells ~100-fold more efficiently than was F(ab')2 control mAb. The data are representative of 3 independent experiments.

FIGS. 40A-40H depict the expression of TREM-2 in mast cells of normal tissues and allergic nasal polyps. Expression of TREM-2 is shown for (FIG. 40A) skin; (FIG. 40B) lymph node; (FIG. 40C) lung; (FIG. 40D) placenta; (FIG. 40E) normal bronchi; (FIG. 40F) normal bronchi (at higher magnification); (FIG. 40G) small intestine; and (FIG. 40H) a nasal polyp caused by allergy. Anti-TREM-2 antibody was detected by the indirect immunoperoxidase technique. Samples were developed with ethyl-carbazole and counterstained with Meyers haematoxylin. In the nasal polyp, anti-TREM-2 antibody was detected with an indirect-immunoalkaline phosphatase technique. The samples were developed with fast red and counterstained with Meyers haematoxylin.

Figures 41A, 41B:
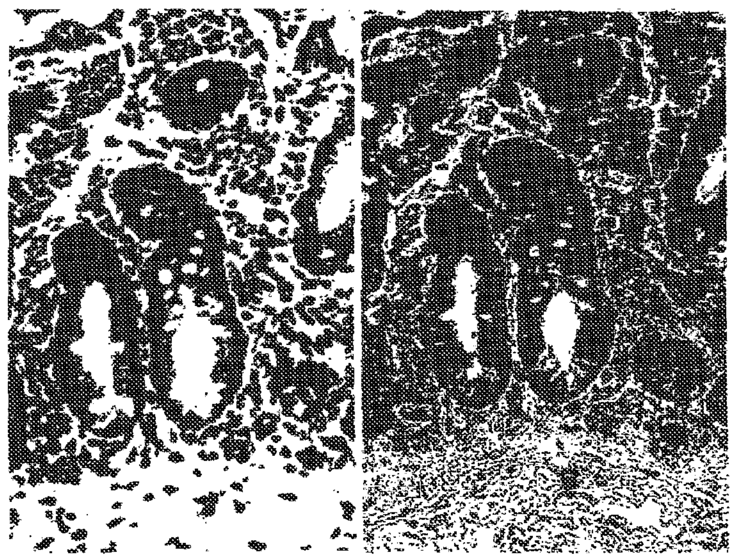
Figure 41C:
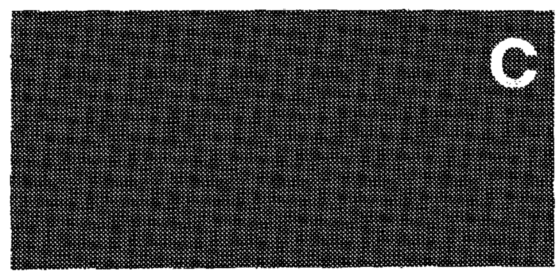
Figure 41D:
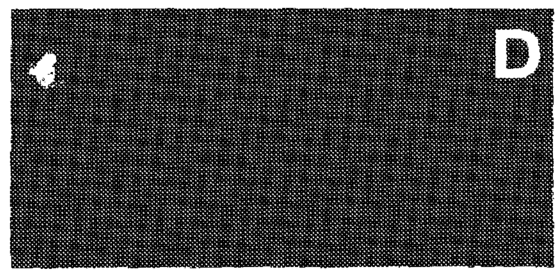
Figure 41E:
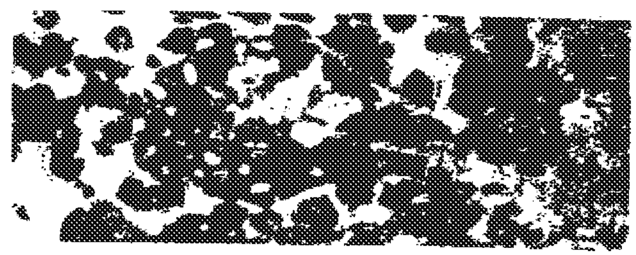
Figure 41F:
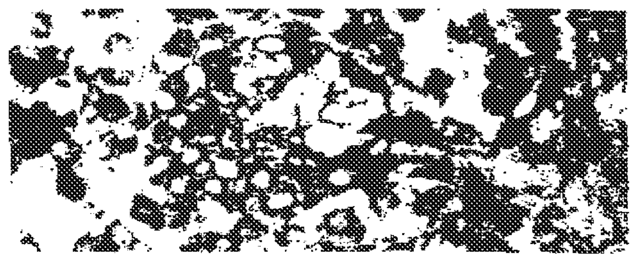

FIGS. 41A-41F indicate that TREM-2 is expressed m mast cells. Serial sections of intestinal mucosa were stained for (FIG. 41 A) TREM-2; and (FIG. 4 IB) ToJuidin blu, showing co-localization of TREM-2+ cells and metachromatic cells, respectively. The Metachromatic cells correspond with mast cells. Two-color immunofluorescence analysis was performed for (FIG. 41C, red) TREM-2 and (FIG. 41D, green) c-Kit of nasal mucosa. TREM-2 and c-Kit are found to co-localize, but TREM-2 is found on a subset of c-Kit positive mast cells. A section of intestinal mucosa was initially stained for TREM-2 (FIG. 41E), and then bleached using 50% ethanol before staining with the Giemsa technique (FIG. 41F). The results reveal that TREM-2+ and Giemsa metachromatic cells (mast cells) clearly co-localize.

Figure 42A:
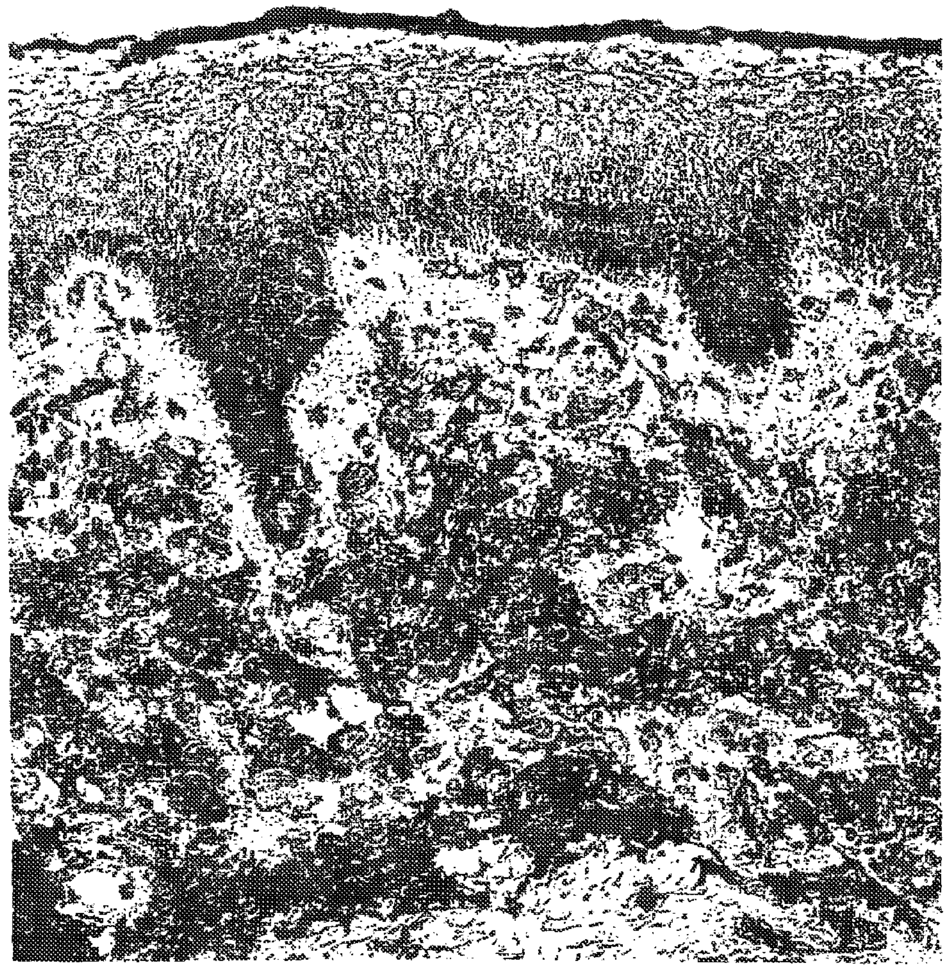
Figure 42B:
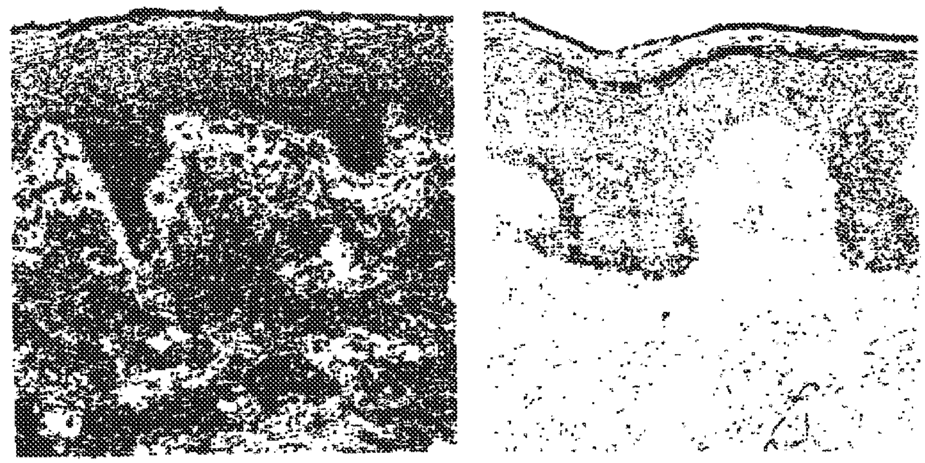

FIGS. 42A-42B depict the expression of TREM-2 in skin mastocytoma. In FIG. 42A, cutaneous mastocytoma is stained for TREM-2, and in FIG. 42B, TREM-2 staining of the cutaneous mastocytoma (from FIG. 42A) is compared with the staining obtained with a negative control antibody.

5. DETAILED DESCRIPTION OF THE INVENTION

This invention relates generally to new activating receptors of the Ig super-family expressed on human myeloid cells, called TREM (triggering receptor expressed on myeloid cells) which are involved in inflammatory responses. Specifically, this invention relates to TREM-1 and its homologue, TREM-2.

5.1 Human TREM-1 and TREM-2

A cDNA encoding TREM-1 was discovered by its homology to NKp44. The human TREM-1 cDNA is 884-nucleotide long (FIG. 2; SEQ ID NO:I) and the open reading frame of TREM-1 is nucleotides 48 to 752 of SEQ ID NO:I, which encodes a transmembrane protein comprising the 234 amino acid sequence shown in FIG. 1(*a*) (SEQ ID N0:3). Biochemical analysis of TREM-1 by immunoprecipitation and Western blot showed that TREM-1 is a glycoprotein of –30 kDa, which is reduced to 26 kDa after Λ^-deglycosylation.

TREM-1 is a novel Ig-SF cell surface molecule which activates neutrophils and monocytes through the transmembrane adapter protein DAP12. TREM-I induces secretion of inflammatory chemokines and cytokines, release of MPO, and up-regulation of adhesion molecules involved in extravasation. Cellular distribution and functional properties of TREM-I suggest that it has a role in acute inflammation, which is characterized by an exudate of neutrophils and monocytes. TREM-I-mediated pro-inflammatory responses are potentiated by priming of neutrophils and monocytes with LPS. Moreover, LPS, bacteria, and fungi up-regulate TREM-I expression. Thus, TREM-1 and bacterial products induce inflammatory responses via intersecting and mutually stimulating pathways. As discussed in the Examples below, the fusion protein between human IgGI constant region and the extracellular domain of mouse TREM-1 (mTREM-I) or that of human TREM-I (huTREMI) showed a remarkable protective effect against endotoxemia in mice, demonstrating its therapeutic utility in controlling acute inflammation caused by bacterial infections.

In addition to TREM-1, the present inventors also cloned a novel cDNA encoding a TREM-I-homologue, called TREM-2. The cDNA encoding human TREM-2 is 1041-nucleotides long (FIG. 3; SEQ ID NO:2) and the open reading frame of TREM-2 is nucleotides 95 to 787 of SEQ ID N0:2, which encode a transmembrane protein comprising the 230 amino acid sequence shown in FIG. 1B (SEQ ID NO:4). Stimulation of DCs via TREM-2 leads to maturation of DCs which is indicated by upregulation of CD40, CD86 and MHC class II. In addition, TREM-2 stimulation renders DCs resistant against apoptosis and induces strong upregulation of CCR7 and subsequent Chemotaxis towards ELC/MIP3-β (macrophage inflammatory protein 3-β). Thus, TREM-2 regulates DC functions in initiating immune responses by inducing CCR7 expression on peripheral DCs and directing them from the periphery to the draining lymph node. TREM-2 expression has also been identified in mast cells in vivo; these cells have been implicated as performing a vital function in the immune response, particularly in regard to allergic reactions. Findings suggest that the TREM receptors may regulate distinct immune and inflammatory responses, allowing myeloid cells to mount distinct types of responses to different antigens.

Both TREM-I and TREM-2 display some sequence homology with activating NK cell receptors, such as NKp44 (Cantoni, C., et. al. 1999, J. Exp. Med 189:787). All of these molecules display a single V-type Ig-like extracellular domain and associate with DAP 12 to induce activation. In addition, they are encoded by genes on human chromosome 6. Thus, this chromosome may contain a gene cluster encoding structurally related receptors that activate cell types involved in different innate responses.

As shown in FIGURE IA (SEQ ID NO:3), the deduced amino acid sequence of TREM-1 starts with a hydrophobic signal peptide at amino acid residues 1 to 16 of SEQ ID NO:3 (SEQ ID NO:5) followed by an extracellular region composed of a single Ig-SF domain, encompassing amino acid residues 17 to 200 of SEQ ID NO:3 (SEQ UD NO:6), which contain three potential 7V-glycosylation sites at amino acid residues 146 to 149 of SEQ ID N0:3 (Asn-Ser-Thr-Gln; SEQ ID N0:7), 190 to 193 of SEQ ID N0:3 (Asn-Leu-Thr-Asn; SEQ ID NO:8), and 193 to 196 of SEQ ID NO:3 (Asn-Val-Thr-Asp; SEQ ID NO:9), and the consensus sequences, Leu-Xaa-Val-Xaa-Cys-Xaa-Tyr (at positions 37-43 of SEQ ID N0:3; "Xaa" indicates any amino acid) and Asp-Xaa-Gly-Xaa-Tyr-Xaa-Cys (at positions 107-113 of SEQ ID NO:3), characteristic of the intrachain disulfide bridge of the Ig-SF V-type fold. The putative transmembrane domain starts from amino acid residues 201 to 229 of SEQ ID NO:3 (SEQ ID NO: 10) and contains a charged lysine residue at position 217. Its cytoplasmic tail consists of 5 amino acid residues (SEQ ID NO:I 1) and appears to contain no signaling motifs.

TREM-2 (FIG. IB; SEQ ID NO:4) starts with a signal peptide at amino acid residues 1 to 13 of SEQ ID NO:4 (SEQ ID NO: 12), followed by an extracellular region composed of a single Ig-SF domain, encompassing amino acid residues 14 to 167 of SEQ ID NO:4 (SEQ ID N0:13), which contains one potential A/-glycosylation site at amino acid residues 20 to 23 of SEQ ID NO:4 (Asn-Thr-Thr-Val; SEQ ID NO:I4), and the characteristic Ig-SF consensus sequences at positions 32-38 and 104-110 of SEQ ID NO:4. The putative transmembrane domain expands from amino acid residues 168 to 200 of SEQ ID NO:4 (SEQ ID NO: 15) and contains a charged lysine residue at position 186. Its cytoplasmic tail consists of amino acid residues 201 to 230 of SEQ ID NO:4 (SEQ ID NO:16).

A "signal sequence" or "signal peptide" as used herein refers to a peptide of at least about 10 to 40 amino acid residues which occurs at the N-terminus of secretory or membrane-bound proteins and contains at least about 50-75% hydrophobic amino acid residues such as alanine, leucine, isoleucine, phenylalanine, proline, tyrosine, tryptophan, or valine. A signal sequence serves to direct a protein containing such a sequence to a lipid bilayer. A signal sequence is usually cleaved during the maturation process of the protein. Thus, the invention also includes the domains and the mature protein resulting from cleavage of such a signal peptide.

Accordingly, a mature TREM comprises one or more of the following domains: (1) an extracellular domain which contains at least one Ig-SF domain; (2) a transmembrane domain; and (3) a cytoplasmic domain.

Thus, in one embodiment, a polypeptide of the invention comprises the amino acid sequence of SEQ ID N0:3 or 4. In another embodiment, a polypeptide of the invention is a mature polypeptide which does not contain a signal peptide and comprises amino acid residues 17 to 234 of SEQ ID NO:3 (SEQ ID NO:17) or amino acid residues 14 to 230 of SEQ ID NO:4 (SEQ ID NO: 18). In another aspect, a polypeptide of the invention comprises the amino acid sequence of SEQ ID NO:3 or 4 except that amino acid residues 1 to 16 of SEQ ID NO:3 or 1 to 13 of SEQ ID NO:4 are replaced by a heterologous signal peptide by genetic engineering.

Yet, in another embodiment, a polypeptide of the invention comprises an extracellular domain comprising amino acid residues 17 to 200 of SEQ ID NO:3 (SEQ ID NO:6) or amino acid residues 14 to 167 of SEQ ID NO:4 (SEQ ID NO: 13). In another embodiment, a polypeptide of the invention comprises a transmembrane domain comprising amino acid residues 201 to 229 of SEQ ID NO:3 (SEQ ID NO:10) or amino acid residues 168 to 200 of SEQ ID NO:4 (SEQ ID NO: 15).

Further, a polypeptide of the invention comprises a cytoplasmic domain comprising amino acid residues 230 to 234 of SEQ ID NO:3 (SEQ ID NO:I I) or amino acid residues 201 to 230 of SEQ ID NO:4 (SEQ ID NO: 16).

In preferred embodiments, a polypeptide of the invention comprises a fragment of SEQ ID NO:3 or 4 which exhibits at least one structural and/or functional feature of TREM-1 or TREM-2, wherein said functional feature includes a capability of eliciting a specific immune response, such as producing anti-TR£-I or anti-TREM-2 antibodies or ability to immunospecifically bind anti-TREM-I or anti-TREM-2 antibodies.

Included within the present invention is an isolated nucleic acid molecule that encodes a polypeptide of the invention having the amino acid sequence of SEQ ID NO:3, 4, 5, 6, 10, 11, 12, 13, 15, 16, 17, or 18, or a complement thereof. The nucleic acid molecules of the invention include the entire or a portion (of at least 5, 10, 15, 20, 25, 50, 75, 100, 150, 200, 250, 300, 350, 400, 450, 500, 550, 600, 650 or more contiguous nucleotides) of the nucleotide sequence of SEQ ID N0:1 or 2, e.g., SEQ ID NO:I, 2, 19, 20, 21, 22, 23, 24, 25, 26, 27, or 28, or a complement thereof, respectively, which corresponds to the nucleotide sequence encoding the amino acid sequence of SEQ ID NO:3, 4, 5, 6, 10, 11, 12, 13, 15, 16, 17, or 18, respectively. Furthermore, because of the genetic code degeneracy, the invention also includes nucleic acid molecules that are different from SEQ ID NO:I, 2, 19, 20, 21, 22, 23, 24, 25, 26, 27, or 28, but encode the amino acid sequence of SEQ ID NO:3, 4, 5, 6, 10, 11, 12, 13, 15, 16, 17, oris.

5.2 Homologues. Variants, and Derivatives of TREM-1 and TREM-2

In addition to the nucleic acid molecules and polypeptides described above, nucleic acid molecules or polypeptides of the invention also encompass those nucleic acid molecules and polypeptides having a common biological activity and/or structural domain and having sufficient nucleotide sequence or amino acid identity (homologues) as defined herein. These homologues can be from either the same or different species of animal, preferably from mammals, more preferably from rodents, such as mouse and rat, and most preferably from human. Preferably, they exhibit at least one structural and/or functional feature of TREM-1 or TREM-2, including antigenicity/immunogenicity.

Homologues of the TREM-1 and TREM-2 nucleic acid molecules (i.e., SEQ ID NO:I and SEQ ID NO: 2, respectively) can be isolated based on their close nucleotide sequence identity to the human nucleic acid molecules disclosed herein, by standard hybridization techniques under stringent or moderately stringent conditions, as defined herein below, using the human cDNA of the invention or a portion thereof as a hybridization probe.

Accordingly, the invention also includes an isolated nucleic acid molecule being at least 25, 50, 100, 200, 300, 400, 500, 600, 700, 800, 900, or 1000 contiguous nucleotides in length and hybridizing under stringent or moderately stringent conditions to the nucleic acid molecule comprising the nucleotide sequence of SEQ ID NO: 1, 2, 19, 20, 21, 22, 23, 24, 25, 26, 27, or 28, or a complement thereof.

The term "under stringent condition" refers to hybridization and washing conditions under which nucleotide sequences having at least 60%>>, preferably 65%, more preferably 70%, most preferably 75% identity to each other remain hybridized to each other. The term "moderately stringent condition" refers to hybridization and washing conditions under which nucleotide sequences having at least 40%, preferably 45%, more preferably 50%>, most preferably 55% o identity to each other remain hybridized to each other. Such hybridization conditions are described in, for example but not limited to, *Current Protocols in Molecular* Biology, 1989, John Wiley & Sons, New York, 6.3.1-6.3.6., and Basic Methods in Molecular Biology, 1986, Elsevier Science Publishing Co., Inc., New York, 1986, pp. 75-78, and 84-87, and are well known to those skilled in the art. A preferred, non-limiting example of stringent hybridization conditions is hybridization in 6× sodium chloride/sodium citrate (SSC) at about 45° C. followed by one or more washes in 0.2×SSC, 0.1% SDS at about 50-65"C. A preferred, non-limiting example of moderately stringent conditions is hybridization in 6×SSC at about 42° C. followed by one or more washes in 0.2×SSC, 0.1% SDS at about 45-55° C.

In another aspect, an isolated nucleic acid molecule of the invention encodes a variant of a polypeptide of the invention in which the amino acid sequences have been modified by genetic engineering in order to either enhance or reduce biological activities of the polypeptides, or change the local structures thereof without significantly altering the biological activities. hi one aspect, these variants can act as either agonists or as antagonists.

An agonist can retain substantially the same or a portion of the biological activities of the polypeptides of the invention and an antagonist can inhibit one or more of the activities of the polypeptides of the invention. Such modifications include amino acid substitution, deletion, and/or insertion. Amino acid modifications can be made by any method known in the art and various methods are available to and routine for those skilled in the art.

For example, mutagenesis may be performed in accordance with any of the techniques known in the art including, but not limited to, synthesizing an oligonucleotide having one or more modifications within the sequence of a given polypeptide to be modified. Site-specific mutagenesis can be conducted using specific oligonucleotide sequences which encode the nucleotide sequence containing the desired mutations in addition to a sufficient number of adjacent nucleotides in the polypeptide. Such oligonucleotides can serve as primers which can form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generate a library of mutants.

The technique of site-specific mutagenesis is well known in the art, as described in various publications (e.g., Kunkel et al., 1987, Methods Enzymoi, 154:367-82, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to-DNA polymerizing enzymes such as T7 DNA polymerase, in order to complete the synthesis of the mutation-bearing stand. Thus, a heteroduplex is formed wherein one strand encodes the original non-mutated sequence and the second stand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

alternatively, the use of PCR™ with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic ei a/., \9^1, Nucleic Acids Res., 18(6):1656, and Upender et al., 1995, Biotechniques, I8(I):29-30, 32, for PCR™-mediated mutagenesis procedures, which are hereby incorporated in their entireties. PCR™ employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, 1994, Biotechniques, 16(3):410-412, which is hereby incorporated by reference in its entirety).

Other methods known to those skilled in art of producing sequence variants of a given polypeptide or a fragment thereof (e.g., an extracellular-domain, transmembrane domain, and cytoplasmic-domain fragments) can be used. For example, recombinant vectors encoding the amino acid sequence of the polypeptide or a fragment thereof may be treated with mutagenic agents, such as hydroxylamine, to obtain sequence variants.

Preferably, the amino acid residues to be modified are surface exposed residues. Additionally, in making amino acid substitutions, preferably the amino acid residue to be substituted is a conservative amino acid substitution, for example, a polar residue is substituted with a polar residue, a hydrophilic residue with a hydrophilic residue, hydrophobic residue with a hydrophobic residue, a positively charged residue with a positively charged residue, or a negatively charged residue with a negatively charged residue. Moreover, preferably, the amino acid residue to be modified is not highly or completely conserved across species and/or is critical to maintain the biological activities of the protein.

Accordingly, included in the scope of the invention are nucleic acid molecules encoding a polypeptide of the invention that contains amino acid modifications that are not critical to activity. Thus, an isolated nucleic acid molecule of the invention includes a nucleotide sequence encoding a polypeptide having an amino acid sequence that is at least about 40%, 45%, 50%, 55%, 60%, 65%, 70%, 75%, 80%, 85%, 90%, 95%, or 98% identical to the amino acid sequence of SEQ ID NO:3, 4, 5, 6, 10, II, 12, 13, 15, 16, 17 or 18, and has one or more TREM-1 and/or TREM-2 biological activities.

Furthermore, the invention also encompasses derivatives of the polypeptides of the invention. For example, but not by way of limitation, derivatives may include peptides or proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. Additionally, the derivative may contain one or more non-classical amino acids.

In another aspect, the invention further includes antisense nucleic acid molecules which are complementary to an entire or partial sense nucleic acid encoding a polypeptide of the invention (e.g., a coding stand of cDNA or an mRNA). The antisense nucleic acid molecules can also be complementary to non-coding region of the nucleic acid which will not be translated. The antisense nucleic acid molecules of the invention can be administered to a subject so that they hybridize with cellular mRNA or genomic DNA which encodes a polypeptide of the invention. This blocks the transcription and/or translation of the target sequence and, thereby inhibits expression of the polypeptide. An antisense nucleic acid may be about 5, 10, 15, 20, 25, 30, 35, 40, 45, or 50 nucleotide long or longer and can be prepared by chemical synthesis and enzymatic ligation reactions using methods well known in the art. For, example, an antisense nucleic acid can be chemically synthesized using naturally occurring nucleotides or variously modified nucleotides designed to increase the biological stability of the molecules or to increase the physical stability of the duplex formed between the antisense and sense nucleic acids; for example, phosphorothioate derivatives and acridine substituted nucleotides can be used.

Examples of modified nucleotides which can be used to generate the antisense nucleic acid include 5-fluorouracil, 5-bromouracil, 5-chloro uracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uraci 1-5-oxyacetic acid methylester, urac i 1-5-oxy acetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an a-anomeric nucleic acid molecule. An a-anomeric nucleic acid molecule forms specific double-stranded hybrids with complementary RNA in which, contrary to the usual β-units, the strands mn parallel to each other (Gaultier et al., {9S7, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., i987, FEBS Lett 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes, such as hammerhead ribozymes (described in Haselhoff and Gerlach, 1988, Nature, 334:585-591) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA. For example, a derivative of a Tetrahymena L-19 ÍVS RNA can be constructed in which the nucleotide sequence of the active site is complementary to the nucleotide sequence to be cleaved (Cech et al., U.S. Pat. No. 4,987,071; and Cech et ai, U.S. Pat. No. 5,116,742). Alternatively, an mRNA encoding a polypeptide of the invention disclosed herein can be used to select a catalytic RNA having a specific ribonuclease activity from a pool of RNA molecules. See. e.g., Bartel and Szostak, 1993, Science, 261:1411-1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des., 6(6):569-84; Helene, 1992, Ann. N.Y. Acad. Sci., 660:27-36; and Maher, 1992, Bioassays, 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et ai, 1996, Bioorganic & Medicinal Chemistry, 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et a i, supra; Perry-O'Keefe et ai, 1996, Proc. Nati Acad. Sci USA 93: 14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., SI nucleases (Hymp, supra); or as probes or primers for DNA sequence and hybridization (Hymp, supra; Perry-O'Keefe et ai, supra).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hymp, supra). The synthesis of PNA-DNA chimeras can be performed as described in Hymp, supra, and Finn et a i, 1996, Nucleic Acids Res., 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et a i, 1989, Nucleic Acids Res. 17:5973-88). PNA monomers are then coupled in a stepwise manner to produce a chimeric molecule with a 5' PNA segment and a 3' DNA segment (Finn et a i, 1996, Nucleic Acids Res. 24(17):3357-63). Alternatively, chimeric molecules can be synthesized with a 5' DNA segment and a 3' PNA segment (Peterser et a i, 1975, Bioorganic Med. Chem. Lett. 5:1119-1124).

In other embodiments, the oligonucleotide may include other appended groups such as peptides (e.g., for targeting host cell receptors in vivo), or agents facilitating transport across the cell membrane (see, e.g., Letsinger et a i, 1989, Proc. Nati Acad. Sci USA 86:6553-6556; Lemaitte et al., 1987, Proc. Nati Acad. Sci USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et a/., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Recombinant Expression Vectors and Host Cells

The present invention also provides vectors, preferably expression vectors, containing a nucleic acid encoding a polypeptide of the invention or a portion thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a vkal vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain expression vectors, are capable of directing the expression of genes to which they are operably linked. In general, expression vectors of utility in recombinant DNA techniques are often in the form of plasmids (vectors). However, the invention also includes other forms of expression vectors, such as viral vectors (e.g., replication defective retroviruses, adenoviruses and adeno-associated viruses), which serve equivalent functions.

The recombinant expression vectors of the invention comprise a nucleic acid of the invention In a form suitable for expression of the nucleic acid in a host cell. In other words, the recombinant expression vectors include one or more regulatory sequences, preferably heterologous to the nucleic acid of the invention, which are selected on the basis of the host cells to be used for expression and are operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, 1990, Gene Expression Technology: Methods in Enzymology 185, Academic Press, San Diego, Calif. Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

A variety of host-vector systems may be utilized in the present invention to express the protein-coding sequence. These include but are not limited to bacteria transformed with bacteriophage, DNA, plasmid DNA, or cosmid DNA; microorganisms such as yeast containing yeast vectors; insect cell systems infected with vims (e.g., baculovirus); or mammalian cell systems infected with virus (e.g., vaccinia virus, adenovirus, etc.). The expression elements of vectors vary in their strengths and specificities. Depending on the host-vector system utilized, any one of a number of suitable transcription and translation elements may be used. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, Gene 67:31-40), pMAL (New England Biolabs, Beverly, Mass.) and pRIT5 (Pharmacia, Piscataway, N.J.) which fuse glutathione S-transferees (GST), maltose E binding protein, or protein A, respectively, to the target recombinant protein. Fusion proteins comprising a polypeptide of the invention are further discussed in section 5.4 below.

Examples of suitable inducible non-fusion *E. coli* expression vectors include pTrc (Amann et a i, 1988, Gene 69:301-315) and pET 1 id (Studier et a i, 1990, Gene Expression Technology: Methods in Enzymology, 185, Academic Press, San Diego, Calif., pp. 60-89). Target gene expression from the pTrc vector relies on host RNA polymerase transcription from a hybrid trp-lac fusion promoter. Target gene expression from the pET 1 Id vector relies on transcription from a T7 gnl 0-lac fusion promoter mediated by a coexpressed viral RNA polymerase (T7 gnl). This viral polymerase is supplied by host strains BL21 (DE3) or HMS174 (DE3) from a resident X prophage harboring a T7 gn I gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, 1990, Gene Expression Technology: Methods in Enzymology 185, Academic Press, San Diego, Calif., pp. 119-128). Another strategy is to alter the nucleic acid sequence of the nucleic acid to be inserted into an expression vector so that the individual codons for each amino acid are those preferentially utilized in *E. coli* (Wada et a i, 1992, Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec 1 (Baldari et a i, 1987, EMBO J. 6:229-234), pMFa (Kurjan and Herskowitz, 1982, Cell 30:933-943), pJRY88 (Schultz et a i, 1987, Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith ei a/., 1983, Mo/. Cell Bioi 3:2156-2165) and the pVL series (Lucklow and Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et a i, 1987, EMBO J. 6:187-195). When used in mammalian cells, the expression vector's control functions are often provided by viral regulatory elements. For example, commonly used promoters are derived from polyoma, adenovirus 2, cytomegalovirus and Simian Vims 40. For other suitable expression systems for both prokaryotic and eukaryotic cells see chapters 16 and 17 of Sambrook et a i, 1990, Molecular Cloning, A Laboratory Manual, 2d Ed., Cold Spring Harbor Laboratory, Cold Spring Harbor, N.Y.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkerteia/., 1987, Genes Dev., 1:268-277), lymphoid-specific promoters (Caíame and Eaton, 1988, Adv. Immunol. 43:235-275), in particular promoters of T cell receptors (Winoto and Baltimore, 1989, EMBO J. 8:729-733) and immunoglobulins (Banerji et a i, 1983, Cell 33:729-740; Queen and Baltimore, 1983, Cell 33:741-748), neuron-specific promoters (e.g., the neurofilament promoter; Byme and Ruddle, 1989, Proc. Nati Acad. Sci USA 86:5473-5477), pancreas-specific promoters (Edlund et a i, 1985, Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gmss, 1990, Science 249:374-379) and the G-fetoprotein promoter (Campes and Tilghman, 1989, Genes Dev. 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated vims in which antisense nucleic acids are produced under the control of a high efficiency regulatory region, the activity of which can be determined by the cell type into which the vector is introduced. For a discussion of the regulation of gene expression using antisense genes, see Weintraub et a i, 1986, Reviews—Trends in Genetics, Vol. 1(1).

Another aspect of the invention pertains to host cells into which a recombinant expression vector of the invention has been introduced. The terms "host cell" and "recombinant host cell" are used interchangeably herein, it is understood that such terms refer not only to the particular subject cell but to the progeny or potential progeny of such a cell. Because certain modifications may occur in succeeding generations due to either mutation or environmental influences, such progeny may not be identical to the parent cell, but are still included within the scope of the term as used herein.

A host cell can be any prokaryotic (e.g., *E. coli*) or eukaryotic cell (e.g., insect cells, yeast or mammalian cells). A host cell strain may be selected which modulates the expression of the inserted sequences, or modifies and processes the gene product in the specific fashion desired. Expression from certain promoters can be elevated in the presence of certain inducers; thus, expression of the genetically engineered polypeptide/protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, neuronal cell lines such as, for example, SK-N-AS, SK-N-FI, SK-N-DZ human neuroblastomas (Sugimoto et a i, 1984, y. Nati Cancer Inst. 73:51-57), SK-N-SH human neuroblastoma (1982, Biochim. Biophys. Acta 704:450-460), Daoy human cerebellar medulloblastoma (He et a i, 1992, Cancer Res. 52:1144-1148), DBTRG-05MG glioblastoma cells (Kmse eí a/., 1992,/<< Vitro Celi Dev. Bioi 28A:609-6I4), IMR-32 human neuroblastoma (1970, Cancer Res. 30:2110-2118), 1321N1 human astrocytoma (1977, Prac. ÍVí3//^ca<i. 5ci. 0X4 74:4816), MOG-G-CCM human astrocytoma (1984, Br. J. Cancer 49:269), U87MG human glioblastoma-astrocytoma (\96S, Acta Pathoi Microbioi Scand. 1968, 74:465-486), A172 human glioblastoma (Olopade et a i, 1992, Cancer Res. 52:2523-2529), C6 rat glioma cells (Bendae/a/., \96^, Science 161:370-371), Neuro-2a mouse neuroblastoma (1970, Proc. Nati Acad. Sei USA 65:129-136), NB41 A3 mouse neuroblastoma (1962, Proc. Nati Acad. Sei USA 48:1184-1190), SCP sheep choroid plexus (Bolin et a i, 1994, 7 Viroi Methods 48:211-221), G355-5, PG-4 Cat normal astrocyte (Haapala eidî/., 1985, 7 Viroi 53:827-833), Mpf ferret brain (Trowbridge et a i, 1982, In Vitro 18:952-960), and normal cell lines such as, for example, CTX TNA2 rat normal cortex brain (Radany et a i, 1992, Proc. Nati Acad. Sei USA 89:6467-6471), CRL7030 and Hs578Bst. Furthermore, different vector/host expression systems may effect processing reactions to different degrees.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-d extran-mediated transfection, lipofection, or electroporation. Suitable methods for transforming or transfecting host cells can be found in Sambrook, et a i, supra, and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker is generally introduced into the host cells along with the gene of interest A number of selection systems may be used, including but not limited to the herpes simplex vims thymidine kinase (Wigler, et a i, 1977, Cell 11:223), hypoxanthine-guanine phosphoribosyltransferase (Szybalska & Szybalski, 1962, Proc. Natl. Acad. Sei. USA 48:2026), and adenine phosphoribosyltransferase (Lowy, et ai, 1980, Cell 22:817) genes can be employed in tk', hgprt' or aprt" cells, respectively. Also, antimetabolite resistance can be used as the basis of selection for dhfr, which confers resistance to methotrexate (Wigler, et a i, 1980, Nati Acad Sei USA 77:3567; O'Hare, et a i, J981, Proc. Nati Acad. Sei USA 78:1527); gpt, which confers resistance to mycophenolic acid (Mulligan & Berg, 1981, Proc. Nati Acad. Sei USA 78:2072); neo, which confers resistance to the aminoglycoside G-418 (Colberre-Garapin, et a i, 1981, 7. Moi Biol. 150:1); and hygro, which confers resistance to hygromycin (Santerre, et a i, 1984, Gene 30:147) genes.

In another embodiment, the expression characteristics of an endogenous gene sequence (e.g., TREM-1 and TREM-2) within a cell, cell line or cloned microorganism may be modified by inserting a DNA regulatory element heterologous to the endogenous gene of interest into the genome of a cell, stable cell line or cloned microorganism such that the inserted regulatory element is operatively linked with the endogenous gene and controls, modulates or activates the endogenous gene. For example, endogenous TREM-1 and TREM-2 which are expressed only at very low levels in a cell or cell line, may be activated by inserting a regulatory element which is capable of promoting the expression of a normally expressed gene product in that cell or cell line. Alternatively, endogenous TREM-1 and TREM-2 genes which are normally "transcriptionally silent," i.e., TREM-1 and TREM-2 genes which are normally not expressed, may be activated by insertion of a promiscuous regulatory element that works across cell types.

A heterologous regulatory element may be inserted into a stable cell line or cloned microorganism, such that it is operatively linked with and activates expression of endogenous TREM-1 and TREM-2 genes, using techniques, such as targeted homologous recombination, which are well known to those skilled in the art, and described, for example, in Chappel, U.S. Pat. No. 5,272,071; PCT publication No. WO 91/06667 (published May 16, 1991).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of the invention, into which a recombinant expression vector encoding a polypeptide of the invention has been introduced, in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous sequences encoding a polypeptide of the invention have been altered. Such animals are useful for studying the function and/or activity of the polypeptide and for identifying and/or evaluating modulators of polypeptide activity. In addition to particular gene expression and/or polypeptide expression phenotypes, the transgenic animals of the invention can exhibit any of the phenotypes (e.g., processes, disorder symptoms and/or disorders associated with the gene expression). As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention or a homologue thereof into the male pronuclei of a fertilized oocyte, for example, by microinjection or retroviral infection, and allowing the oocyte to develop in a pseudopregnant female foster anhnal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, 1986, Manipulating the Mouse Embryo, Cold Spring Harbor Laboratory Press, Cold Spring Harbor, N.Y., and Wakayama et a i, 1999, Proc. Nati Acad. Sei. USA 96:14984-\ 4989. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, Cell 51:503, for a description of homologous recombination vectors). The vector is introduced into an embryonic stem cell line (e.g., by electroporation) and cells in which the introduced gene has homologously recombined with the endogenous gene are selected (see, e.g., Li, et a i, 1992, Cell 69:915). The selected cells are then injected into a blastocyst of an animal (e.g., a mouse) to form aggregation chimeras (see, e.g., Bradley in Teratoearcinomas and Embryonic Stem Cells: A Practical Approach, 1987, Robertson, ed., IRL, Oxford, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, 1991, Current Opinion in Bio/Technology 2:823-829, and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage PI. For a description of the creAoxP recombinase system, see, e.g., Lakso, et a i, 1992, Proc. Nati Acad. Sei USA 89:6232-6236. Another example of a recombinase system is the FLP recombinase system of *Saccharomyces cerevisiae* (O'Gorman, et a i, \99\, Science, 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et a i, 1997, Nature 385:810-813, and PCT Publication Nos. WO 97/07668 and WO 97/07669.

5.4 Fusion Proteins

The present invention further encompasses fusion proteins in which the polypeptides of the invention or fragments thereof, are recombinantly fused or chemically conjugated (including both covalent and non-covalent conjugations) to heterologous polypeptides (i.e., an unrelated polypeptide or portion thereof, preferably at least 10, at least 20, at least 30, at least 40, at least 50, at least 60, at least 70, at least 80, at least 90 or at least 100 amino acids of the polypeptide) to generate fusion proteins! The fusion does not necessarily need to be direct, but may occur through linker sequences.

In one example, a fusion protein in which a polypeptide of the invention or a fragment thereof can be fused to sequences derived from various types of immunoglobulins. For example, a polypeptide of the invention can be fused to a constant region (e.g., hinge, CH2, and CH3 domains) of human IgGI or IgM molecule, for example, as described in sections 6.3.1, 6.3.2, and 6.3.4 below, so as to make the fused polypeptides or fragments thereof more soluble and stable in vivo. Such fusion proteins can be used as an immunogen for the production of specific antibodies which recognize the polypeptides of the invention or fragments thereof. In another embodiment, such fusion proteins can be administered to a subject so as to inhibit interactions between a ligand and its receptors in vivo. Such inhibition of the interaction will block or suppress signal transduction which triggers certain cellular responses. One of the examples is described in section 6.10, in which the fusion protein between the extracellular portion of TREM-I and the constant domain of human IgGI (TREM-1-huIgGI) was administered to mice before and after the lipopolysaccharide (LPS) injection. The soluble fusion protein protected the mice from septicemia and increased the survival rate presumably by blocking the interactions between the cell surface TREM-1 and its ligand(s), thereby inhibiting inflammatory responses. Another example is described in section 6.18, in which a fusion protein comprising the extracellular portion of TREM-2 was administered to mice before and after colitis was induced using DSS. The soluble fusion protein protected the mice from inflammatory disease presumably by blocking the interactions between the cell surface TREM-2 and its ligand(s), thereby inhibiting inflammatory responses.

In one aspect, the fusion protein comprises a polypeptide of the invention which is fused to a heterologous signal sequence at its N-terminus. For example, the signal sequence naturally found in the polypeptide of the invention can be replaced by a signal sequence which is derived from a heterologous origin. Various signal sequences are commercially available. For example, the secretory sequences of melittin and human placental alkaline phosphatase (Stratagene; La Jolla, Calif.) are available as eukaryotic heterologous signal sequences. As examples of prokaryotic heterologous signal sequences, the phoA secretory signal (Sambrook, et ai, supra; and Current Protocols in Molecular Biology, 1992, Ausubel, et a i, eds., John Wiley & Sons) and the protein A secretory signal (Pharmacia Biotech; Piscataway, N. J.) can be listed. Another example is the gp67 secretory sequence of the baculovirus envelope protein (Current Protocols in Molecular Biology, 1992, Ausubel, et a i, eds., John Wiley & Sons).

In another embodiment, a polypeptide of the invention can be fused to tag sequences, e.g., a hexa-histidine peptide, such as the tag provided in a pQE vector (QIAGEN, Inc., 9259 Eton Avenue, Chatsworth, Calif., 91311), among others, many of which are commercially available. As described in Gentz, et a i, 1989, Proc. Natl. Acad. ScL USA 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson, et a i, 1984, Cell 37:767) and the "flag" tag (Knappik, et a i, 1994, Biotechniques 17(4):754-761). These tags are especially useful for purification of recombinantly produced polypeptides of the invention.

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (See, e.g. Current Protocols in Molecular Biology, 1992, Ausubel, et a i, eds., John Wiley & Sons).

The nucleotide sequence coding for a fusion protein can be inserted into an appropriate expression vector, i.e., a vector which contains the necessary elements for the transcription and translation of the inserted protein-coding sequence. Various host-vector systems and selection systems are available as described in section 5.3.

In a specific embodiment, the expression of a fusion protein is regulated by a constitutive promoter. In another embodiment, the expression of a fusion protein is regulated by an inducible promoter. In accordance with these embodiments, the promoter may be a tissue-specific promoter.

Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g., thymidine kinase activity, resistance to antibiotics, transformation phenotype, occlusion body formation in baculovims, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein) expressed by the recombinant. Such assays can be based, for example, on the physical or functional properties of the fusion protein in in vitro assay systems, e.g., binding with anti-fusion protein antibody.

For long-term, high-yield production of recombinant proteins, stable expression is preferred. For example, cell lines which stably express the fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the differentially expressed or pathway gene protein. Such engineered cell lines may be particularly useful in screening and evaluation of compounds that affect the endogenous activity of the differentially expressed or pathway gene protein.

Once a fusion protein of the invention has been produced by recombinant expression, it may be purified by any method known in the art for purification of a protein, for example, by chromatography (e.g., ion exchange, affinity, particularly by affinity for the specific antibody, and sizing column chromatography), centrifugation, differential solubility, or by any other standard technique for the purification of proteins.

5.5 Preparation of Antibodies

Antibodies which specifically recognize a polypeptide of the invention or fragments thereof can be used for various diagnostic and therapeutic purposes. For example, in one specific embodiment, an antibody which is specific for TREM-1 or TREM-2 can be used for various in vitro detection assays, including enzyme-linked immunosorbent assays (ELISA), radioimmunoassays, Western blot. Flow Cytometry analysis, immunohistochemical analysis, and so forth for the detection of TREM-1 or TREM-2 molecules or fragments thereof in biological samples, such as blood, serum, plasma, urine, saliva, tissues, cells, etc., as well as for in vivo detection of these molecules for diagnostic purposes. For example, anti-TREM-I antibody can be used in immunohistochemical analysis of pathological tissue specimens to differentiate local and systemic inflammations caused by different types of agents. Since TREM-1 is strongly expressed in the presence of certain bacterial and fungal products, such as LPS, detection of TREM-I in the inflamed tissue specimens would suggest a bacterial and/or fungal origin of the inflammation.

In another specific embodiment, an anti-TREM-I or anti-TREM-2 antibody which acts as an antagonist against TREM-I or TREM-2 (i.e., inhibiting TREM-I or TREM-2 activities), respectively, on myeloid cells may be used as a therapeutic agent for reducing systemic and/or local immune or inflammatory responses triggered by causative agents (e.g., bacteria and fungi). Such antibodies can block the binding of ligands to these receptors and, thereby, prevent subsequent signal transduction and inflammatory responses from occurring. Examples of immune responses include allergic reactions and parasitic resistance, while examples of local inflammations include pulmonitis, pleuritis, impetigo, abscesses, sinovitis, arthritis, etc. and systemic inflammations include meningitis, peritonitis, sepsis, etc. Thus, these antibodies are useful in modulating immune or inflammatory responses mediated by TREM-1 and/or TREM-2.

In another specific embodiment, anti-TREM-2 antibody may be used as an adjuvant to facilitate the migration of DCs from the periphery to the lymph nodes by cross-linking TREM-2 on DCs and upregulating CCR7 expression by DCs.

Other diagnostic, therapeutic, or prophylactic uses of antibodies specific for the polypeptides of the invention will be further discussed below.

Antibodies specific for the polypeptides of the invention may be generated by any suitable method known in the art. Polyclonal antibodies to an antigen-of-interest can be produced by various procedures well known in the art. For example, an antigen derived from the polypeptide of the invention can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to: Freund's (complete and incomplete) adjuvant, mineral gels such as aluminum hydroxide, surface active substances (such as lysolecithin, pluronic polyols, polyanions), peptides, oil emulsions, keyhole limpet hemocyanins, dinittophenol, and potentially useful adjuvants for humans, such as BCG (Bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow, et a i, 1988, Antibodies: A Laboratory Manual, 2d. ed. Cold Spring Harbor Laboratory Press; Hammerling, et a i, 1981, in: Monoclonal Antibodies and T-Cell Hybridomas, Elsevier, New York, pp. 563-681 (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Epitopes

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined through various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term epitope herein comprises both types of binding region in any particular region of TREM-1 that specifically binds to a TREM-1 antibody. TREM-1 may comprise a number of different epitopes, which may include, without limitation, conformational epitopes which consist of one or more non-contiguous amino acids located near each other in the mature TREM-1 conformation and post-translational epitopes which consist, either in whole or part, of molecular structures covalently attached to TREM-1, such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At an even less detailed level the epitope can be characterized by the amino acid residues that it comprises as defined by a specific criteria such as the distance between or solvent accessibility of atoms in the Ab:Ag complex. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as TREM-1 residues characterized by having a heavy atom (i.e. a non-hydrogen atom) within a distance of, e.g., 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue are shared by the epitopes.

Epitopes may also be defined indirectly, by means of comparing the binding kinetics of antibodies to wild type human TREM-1 with those of human TREM-1 variants that have alanine mutations in anticipated epitopes. Decreased affinity or abrogated binding of an antibody to variants of human TREM-1 in which an amino acid residue has been replaced with an alanine residue indicates that the mutated amino acid contributes to the interaction between said antibody and wild type human TREM-1. This approach provides a negative identification of the epitope. The method is compromised in effectively defining the epitope by the fact that protein misfolding or unfolding would give similar results as abrogation of interaction. The analysis can be complemented by comparative gain of function mutational analyses of an orthologous target protein, if a cross-reactive antibody exists. The comparison will define the epitope differences between the antibody that does not cross-react with TREM-1 and the cross-reactive antibody.

The effect of the same mutations on any given cross-reactive antibody makes it possible to discriminate between possible protein misfolding (abrogated binding to both antibodies) and loss of interaction in human TREM-1 (binding to one of the antibodies and abrogated binding to the other antibody), whilst unambiguously providing information on the epitope differences between the antibody that does not cross-react and the cross reactive antibody on an amino acid level.

An antibody according to the invention may be capable of specifically binding a polypeptide comprising amino acids D38-F48 and T70-L96 of wild type human TREM-1 (SEQ ID NO: 3).

An antibody according to the invention may be capable of specifically binding a polypeptide comprising amino acids D38-F48 and T70-R84 of wild type human TREM-1 (SEQ ID NO: 3).

An antibody according to the invention may have an epitope comprising one, two or all of the amino acid residues selected from the group consisting of D38, K40 and D42 of wild type human TREM-1 and one, two three, four, five, six, seven, eight, nine, ten or all of the amino acid residues selected from the group consisting S74, K75, P79, V80, Q81, V82, G83, Y90, H91, H93 and R97 of wild type human TREM-1 (SEQ ID NO: 3). An antibody according to the invention may have an epitope comprising one, two or all of the amino acid residues selected from the group consisting of D38, K40 and D42 of wild type human TREM-1 and one, two three, four, five, six or all of the amino acid residues selected from the group consisting K75, V80, Q81, Y90, H91, H93 and R97 of wild type human TREM-1 (SEQ ID NO: 3). An antibody according to the invention may have an epitope comprising one, two or all of the amino acid residues selected from the group consisting of D38, K40 and D42 of wild type human TREM-1 and one, two three, four or all of the amino acid residues selected from the group consisting of K75, Y90, H91, H93 and R97 of wild type human TREM-1 (SEQ ID NO: 3). An antibody according to the invention may have an epitope comprising the amino acid residues D38, K40, K75, Y90, H91 and R97 of wild type human TREM-1 (SEQ ID NO: 3). An antibody according to the invention may have an epitope comprising the amino acid residues D38, K40, Y90, H91 and R97 of wild type human TREM-1 (SEQ ID NO: 3).

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in TREM-1.

The epitope and paratope for a given antibody (Ab)/antigen (Ag) pair may be identified by routine methods. For example, the general location of an epitope may be determined by assessing the ability of an antibody to bind to different fragments or variant TREM-1 polypeptides. The specific amino acids within TREM-1 that make contact with an antibody (epitope) and the specific amino acids in an antibody that make contact with TREM-1 (paratope) may also be determined using routine methods. For example, the antibody and target molecule may be combined and the Ab:Ag complex may be crystallised. The crystal structure of the complex may be determined and used to identify specific sites of interaction between the antibody and its target.

Antibody fragments which recognize specific epitopes may be generated by known techniques. For example. Fab and F(ab')2 fragments may be produced by proteolytic cleavage of immunoglobulin molecules, using enzymes such as papain (to produce Fab fragments) or pepsm (to produce F(ab')2 fragments). F(ab')2 fragments contain the complete light chain, and the variable region, the CHI region and the hinge region of the heavy chain. The antibodies of the invention or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook, et a i; supra; and Ausubel, et a i, eds., 1998, Current Protocols in Molecular Biology, John Wiley & Sons, New York, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light chain variable region, both the heavy-chain and light-chain variable regions, an epitope binding fragment of the heavy- and/or light-chain variable region, or one or more complementarity determining regions (CDRs) of an antibody may be cloned into such a vector for expression. An expression vector thus prepared can then be introduced into appropriate host cells for the expression of the antibody. Accordingly, the invention includes host cells containing a polynucleotide encoding an antibody specific for the polypeptides of the invention or fragments thereof.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Nati Acad. Sci., USA 77:2 197). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman, et a i, 1995, J. Immunoi Methods 182:41-50; Ames, et a i, 1995, J. Immunol. Methods 184:177-186; Kettleborough, et a i, 1994, Eur J. Immunoi 24:952-958; Persic, et ai. Gene, 187:9-18, 1997; Burton, et a i, 1994, Advances in Immunology, 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, as described in detail below. For example, techniques to recombinantly produce Fab, Fab' and F(ab')2 fragments can also be employed using methods known in the art such as those disclosed in PCT publication WO 92/22324; Mullinax, et a i, BioTechniques, 12(6):864-869, 1992; and Sawai, et a i, 1995, AJRI 34:26-34; and Better, et a i, 1988, Science 240:1041-1043 (each of which is incorporated by reference in its entirety). Examples of techniques that can be used to produce single-chain Fvs and antibodies include those described in U.S. Pat. Nos. 4,946,778 and 5,258,498; Huston, et ai, \99\, *Methods in Enzymology* 203: 46-88; Shu, et ai, 1993, *Proc Nati Acad. Sei USA* 90:7995-7999; and Skerta, et ai, 1988, *Science* 240:1038-1040.

Once an antibody molecule of the invention has been produced by any methods described above, it may then be purified by any method known in the art for purification of an immunoglobulin molecule, e.g., chromatography (such as ion exchange, affinity, particularly by affinity for the specific antigen after Protein A or Protein G purification, and sizing column chromatography), centrifugation, differential solubility, or by any other standard techniques for the purification of proteins. Furthermore, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See, e.g., Morrison, 1985, Science 229:1202; Oi, et ai, 1986, BioTechniques 4:214; Gillies, et ai, 1989, J. Immunoi Methods 125:191-202; U.S. Pat. Nos. 5,807,715; 4,816,567; and 4,816,397; which are incorporated herein by reference in their entireties'. Humanized antibodies are antibody molecules from non-human species that bind the desired antigen having one or more complementarity determining regions (CDRs) from the non-human species and framework regions from a human immuno globulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g. Queen, et ai, U.S. Pat. No. 5,585,089; Riechmann, et ai, 1988, Nature 332:323, 1988, which are incorporated herein by reference in their entireties. Antibodies can be humanized using a variety of techniques known in the art including, for example, CDR grafting (EP 239,400; PCT publication WO 91/09967; U.S. Pat. Nos. 5,225,539; 5,530,101 and 5,585,089), veneering or resurfacing (EP 592,106; EP 519,596; Padlan, 1991, Molecular Immunology, 28(4/5):489-498; Sttidnicka, et a i, 1994, Protein Engineering, 7(6):805-814; Roguska, et a i, 1994, Proc Nati Acad. Sei USA 91:969-973, and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,1 U; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, 1995, Int. Rev. Immunoi 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; which are incorporated by reference herein m their entireties. In addition, companies such as Abgenix, hic. (Freemont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et a i, 1988, Bio/technology 12:899-903).

Antibodies fused or conjugated to heterologous polypeptides may be used in in vitro immunoassays and in purification methods (e.g., affinity chromatography) well known in the art. See, e.g., PCT publication Number WO 93/21232; EP 439,095; Naramura, et ai, 1994, Immunoi Lett. 39:91-99; U.S. Pat. No. 5,474,981; Gillies, et ai, 1992 Proc. Nati Acad. Sei USA 89:1428-1432; and Fell, et a i, 1991, 7 Immunoi 146:2446-2452, which are incorporated herein by reference in their entireties.

The present invention also encompasses antibodies conjugated to a diagnostic or therapeutic agent. The antibodies can be used diagnostically, for example, to monitor the development or progression of a disease, disorder or infection as part of a clinical testing procedure, such as to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, die h lorotriaziny lamine fluorescein, dansyl chloride or phycoerythrin; an example of a luminescent material includes luminol; examples of bio luminescent materials include luciferase, luciferin, and aequorin; and examples of suitable radioactive material include'^^I, '^I, '"hi or^'"Tc.

An antibody may be conjugated to a therapeutic moiety such as a cytotoxin (e.g., a cytostatic or cytocidal agent), a therapeutic agent or a radioactive element (e.g., alpha emitters, gamma-emitters, etc.). Cytotoxins or cytotoxic agents include any agent that is detrimental to cells. Examples include: paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, I-dehydrotestosterone, glucocorticoids, procaine, tetracaine, lidocaine, propranolol, and puromycin and analogs or homologues thereof. Therapeutic agents include, but are not limited to, anti-inflammatory agents (e.g., anti-TNF-a antibody, REMICADE® (infliximab) (Centocor, Pa.), IL-1 receptor antagonist, anti-MIF antibody, anti-HMG-1 antibody, and methotrexate), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunombicin (formerly daunomycin) and doxombicin), antibiotics (e.g., dactmomycin (formerly actinomycin), bleomycin, mithramycin, and anthramycin (AMC)), and anti-mitotic agents (e.g., vincristine and vinblastine).

Further, an antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity.

In one specific embodiment, an antibody specific for TREM-I (anti-TREM-I antibody) which is coupled with a certain cytotoxin or a drug can be used in a therapy to target leukemia of myeloid origin expressing TREM-1. The anti-TREM-I administered to a subject will deliver the cytotoxin or drug to tumor cells expressing TREM-I, thereby killing specifically the tumor cells.

In another embodiment, an antibody specific for TREM-2 (anti-TREM-2 antibody) can be used for an efficient presentation of an antigen of interest, e.g., by DCs to T cells. As TREM-2 is expressed in DCs in peripheral tissues (e.g., skin and mucosa), an anti-TREM-2 antibody coupled with an antigen of interest may effectively and efficiently deliver the antigen to peripheral DCs, which subsequently process and present the antigen to the T cells at lymph nodes. An antigen of interest can be chemically or genetically conjugated to an anti-TREM-2 antibody or, alternatively, the anti-TREM-2 antibody can be genetically engineered to become bispecific for TREM-2 on one arm and for the antigen of interest on the other. This approach may have a great utility in preparing various vaccines.

Techniques for conjugating such therapeutic moieties to antibodies are well known; see, e.g., Amon, et a i, 1985, Monoclonal Antibodies For Immunotargeting Of Drugs In Cancer Therapy, in Monoclonal Antibodies And Cancer Therapy, Reisfeld, et al. eds., pp. 243-56, Alan R. Liss, Inc.; Hellsttom, et a i, 1987, Antibodies For Drug Delivery, in Controlled Drug Delivery, 2d. ed., Robinson, et ai, eds., pp. 623-53, Marcel Dekker, Inc.; Thorpe, 1985, Antibody Carriers Of Cytotoxic Agents In Cancer Therapy: A Review, in Monoclonal Antibodies '84: Biological And Clinical Applications, Finchera, et a i, eds., pp. 475-506; Analysis, Results, And Future Prospective Of The Therapeutic Use Of Radiolabeled Antibody In Cancer Therapy, 1985, in Monoclonal Antibodies For Cancer Detection And Therapy, Baldwin, et a i, eds., pp. 303-16, Academic Press; and Thorpe, et a i, 1982, Immunoi Rev. 62:119-58.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, Polyacrylamide, nylon, polystyrene, polyvinyl chloride or polypropylene.

5.6 Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, transdermal (topical), transmucosal, intraarticular, intraperitoneal, and intrapleural, as well as oral, inhalation, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy injectability with a syringe exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient, such as starch or lactose; a disintegrating agent, such as alginic acid, Primogel, or com starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act m the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cmikshank, et al., 1997, J. Acquired Immune Deficiency Syndromes and Human Retrovirology 14:193).

Antibodies or antibodies conjugated to therapeutic moieties can be administered to an individual alone or in combination with cytotoxic factor(s), chemotherapeutic drug(s), anti-inflammatory agents, and/or cytokine(s). If the latter, preferably, the antibodies are administered first and the cytotoxic factor(s), chemotherapeutic drug(s), anti-inflammatory agents, and/or cytokine(s) are administered thereafter within 24 hours. The antibodies and cytotoxic factor(s), chemotherapeutic drug(s) and/or cytokine(s) can be administered by multiple cycles depending upon the clinical response of the patient. Further, the antibodies and cytotoxic factor(s), chemotherapeutic drug(s) and/or cytokine(s) can be administered by the same or separate routes, for example, by intravenous, intranasal or intramuscular administration. Cytotoxic factors include, but are not limited to: TNF-a, TNF-β, IL-1, IFN-y and IL-2. Chemotherapeutic drugs include, but are not limited to: 5-fluorouracil (5FU), vinblastine, actinomycin D, etoposide, cisplatin, methotrexate and doxorubicin. Cytokines include, but are not limited to: IL-2, IL-3, IL-4, IL-5, IL-6, IL-7, IL-8, IL-9, IL-10 and IL-12.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5 or 6 weeks, it will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to: peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about I microgram per kilogram to about 500 milligrams per kilogram, about 100 micrograms per kilogram to about 5 milligrams per kilogram, or about 1 microgram per kilogram to about 50 micrograms per kilogram, it is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the tune of administration, the route of administration, the rate of excretion, any drug combination, and the degree of expression or activity to be modulated.

The nucleic acid molecules of the invention can be inserted into vectors and used as gene therapy vectors. Methods of delivering gene therapy vectors to a subject include: intravenous injection, local administration (U.S. Pat. No. 5,328,470) or by stereotactic injection (5ee, e.g., Chen, et a i, 1994, Proe. Nati Acad. Sei USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. With regard to gene therapy, see further discussion in section 5.8.3.

The pharmaceutical compositions can be included in a container, pack, or dispenser together with instructions for administration.

5.7 Utilities and Methods of the Invention

The nucleic acid molecules, proteins, protein homologues, derivatives, variants, and antibodies described herein can be used in one or more of the following non-limiting methods: a) screening assays; b) detection assays (e.g., chromosomal mapping, tissue typing); c) predictive medicine (e.g., diagnostic assays and prognostic assays); and d) methods of treatment (e.g., therapeutic and prophylactic). For example, polypeptides of the invention can be used to: (i) modulate cellular proliferation; (ii) modulate cellular differentiation; and/or (iii) modulate cellular adhesion. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the invention and modulate activity of a protein of the invention. This invention further pertains to novel agents identified by the above-described screening assays and uses thereof for treatments as described herein.

5.7.1 Screening Assays

The invention provides a method for identifying (or screening) modulators, i.e., candidate or test compounds or agents (e.g., peptides, peptidomimetics, small molecules or other drugs) which bind to a polypeptide of the invention or have a stimulatory or inhibitory effect on, for example, expression or activity of a polypeptide of the invention, hi one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt, et al, 1993, Proc. Nati Acad Sei USA 90:6909; Erb, et al., 1994, Proc. Nati Acad Sei aS'-4 91:11422; Zuckermann et al., 1994, 7 Med Chem. 37:2678; Cho, et al., I993, Science 261:1303; Can-ell, et al., 1994, Angew. Chem. Int. Ed Engi 33:2059; Carell, et al., 1994, Angew. Chem. Int. Ed. Engi 33:2061; and Gallop, et al., 1994, 7 Med. C/zem. 37:1233.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull, et al., 1992, Proc. Nati Acad Sei USA 89:1865-1869) or phage (Scott and Smith, 1990, Science 249:386-390; Devlin, 1990, Science 249:404-406; Cwirla, et al., 1990, Proc. Nati Acad. Sei USA 87:6378-6382; and Felici, 1991, 7 Moi Bioi 222:301-310).

In one embodiment, an assay is a cell-based assay in which a cell which expresses a membrane-bound form of a polypeptide of the invention, or a biologically active portion thereof, on the cell surface, is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with i25iˆ 35s, IˆQorˆH, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular Caˆ'", protein tyrosine phosphorylation, phospholipase phosphorylation, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, such as luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound. In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to use a solubilizing agent such that the membrane-bound form of the polypeptide is maintained in solution. Examples of such solubilizing agents include non-ionic detergents, such as: n-octylglucoside, n-dodecylglucoside, n-octylmaltoside, octanoyl-N-methylglucamide, decanoyl-N-methylglucamide, Triton X-IOO, Triton X-114, Thesit, Isottidecypoly(ethylene glycol ether)n, 3-[(3-cholamidopropyl)dimethylamminio]-I-propane sulfonate (CHAPS), 3-[(3-cholamidopropyl)dimethylamminio]-2-hydroxy-I-propane sulfonate (CHAPSO), or N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or a polypeptide of the invention, and the mixture incubated under conditions conducive to complex formation (e.g., at physiological conditions for salt and pFI). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized through conjugation of biotin and streptavidin. Biotinylated polypeptide of the invention or target molecules can be prepared from biotin-NHS(N-hydroxy-succinimide), using techniques well known m the art (e.g., biotinylation kit. Pierce Chemicals; Rockford, Ill.) and immobilized in the wells of streptavidin-coated 96 well plates (Pierce Chemical). Alternatively, antibodies reactive with the polypeptide of the invention or target molecules, but which do not interfere with binding of the polypeptide of the invention to its target molecule, can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three-hybrid assay (see, e.g., U.S. Pat. No. 5,283,317; Zervos, et al., 1993, Ce//72:223-232; Madura, et al., 1993, 7 Bioi Chem. 268:12046-12054; Bartel, et al., 1993, Bio/Techniques 14:920-924; Iwabuchi, et al., 1993, Oncogene 8:1693-1696; and PCT Publication No. WO 94/10300), to identify other proteins, which bind to or interact with the polypeptide of the invention and modulate activity of the polypeptide of the invention. Such binding proteins are also likely to be involved m the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

5.7.2 Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ü) identify an individual from a minute biological sample (tissue typing); and (iii) aid in forensic identification of a biological sample. These applications are described in the subsections below.

A. Chromosome Mapping

Once the sequence (or a portion of the sequence) of a gene has been isolated, this sequence can be used to map the location of the gene on a chromosome. Accordingly, nucleic acid molecules described herein, or fragments thereof, can be used to map the location of the corresponding genes on a chromosome. The mapping of the sequences to chromosomes is an important first step in correlating these sequences with genes associated with disease. The present inventors have mapped the genes encoding TREM-1 and TREM-2 to chromosome 6 in humans where the NKp44 gene is also located.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et ai, 1987, Nature 325:783-787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease.

Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Furthermore, the nucleic acid sequences disclosed herein can be used to perform searches against "mapping databases," e.g., BLAST-type searches, such that the chromosome position of the gene is identified by sequence homology or identity with known sequence fragments which have been mapped to chromosomes.

A polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen, et al., 1988, Cytogenet. Cell Genet. 47:37-41 and Van Keuren, et a i, 1986, Hum. Genet. 74:34-40. Alternatively, the presence of the polypeptide in the somatic cell hybrids can be determined by assaying an activity or property of the polypeptide, for example, enzymatic activity, as described in Bordelon-Riser, et a i, 1979, Somatic Cell Genetics 5:597-613 and Owerbach, et ai, \975, Proc. Nati Acad Sei USA 75:5640-5644.

B. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "dog tags," which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

5.7.3 Diagnostic Assays

One aspect of the present invention relates to diagnostic assays for determining expression of a polypeptide or nucleic acid of the invention and/or activity of a polypeptide of the invention, in the context of a biological sample (e.g., blood, plasma, serum, cells, tissues) to thereby determine whether an individual is afflicted with a disease or disorder, or is at risk of developing a disorder associated with aberrant expression or activity of a polypeptide of the invention, such as a proliferative disorder, e.g., psoriasis or cancer, or an angiogenic disorder. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO: 1 or 2, or a portion thereof, such as an oligonucleotide of at least 15, 20, 25, 30, 50, 100, 250, 500, or more contiguous nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g. Fab or F(ab')2), can be used. See also the detailed descriptions about antibodies in section 5.5.

The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected m the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, in sections above relating to uses of the sequences of the invention. For example, kits can be used to determine if a subject is suffering from or is at increased risk of disorders such as immunological disorders, especially involving inflammatory disorders (e.g., bacterial infection, fungal infection, viral infection, protozoa or other parasitic infection, psoriasis, septicemia, cerebral malaria, inflammatory bowel disease, arthritis, such as rheumatoid arthritis, folliculitis, impetigo, granulomas, lipoid pneumonias, vasculitis, and osteoarthritis), autoimmune disorders (e.g., rheumatoid arthritis, thyroiditis, such as Hashimoto's thyroiditis and Graves' disease, insulin-resistant diabetes, pemicious anemia, Addison's disease, pemphigus, vitiligo, ulcerative colitis, systemic lupus erythematosus (SLE), Sjogren's syndrome, multiple sclerosis, dermatomiositis, mbied connective tissue disease, scleroderma, polymyositis, graft rejection, such as allograft rejection), T cell disorders (e.g., AIDS), allergic inflammatory disorders (e.g., skin and/or mucosal allergies, such as allergic rhinitis, asthma, psoriasis), neurological disorders, eye disorders, embryonic disorders, or any other disorders (e.g., tumors, cancers, leukemia, myeloid diseases, and traumas) which are directly or indirectly associated with aberrant TREM-1 and/or TREM-2 activity and/or expression.

The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) that binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, that hybridizes to a nucleic acid sequence encoding a polypeptide of the invention; or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container, and all of the various containers are within a single package, along with instructions for determining whether the tested subject is suffering from or is at risk of developing a disorder associated with aberrant expression of the polypeptide.

A. Prognostic Assays

The methods described herein can furthermore be used as prognostic assays to identify a subject having, or at risk of developing, a disorder associated with aberrant expression or activity of a polypeptide of the invention, e.g., an immunologic disorder or other disorders as discussed above.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized by aberrant expression or activity of a polypeptide of the invention. In preferred embodiments, the methods include detecting, m a sample of cells from the subject, the presence or absence of a genetic lesion or mutation characterized by an alteration affecting the integrity of a gene encoding the polypeptide of the invention, or the improper expression of the gene encoding the polypeptide of the invention. For example, such genetic lesions or mutations can be detected by ascertaining the existence of at least one of the following: I) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g. Landegran, etai, 1988, 5c/e<<ce 241:1077-1080; and Nakazawa, et al., \994, Proc. Nati Acad. Sei. USA 91:360-364), the latter of which can be particularly useful for detecting point mutations in a gene (see, e.g., Abravaya, etai, \995, Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, etai, 1990, Proc. Nati Acad. Sei USA 87:1874-1878), transcriptional amplification system (Kwoh, etai, 1989, Proc. Nati Acad. Sei USA 86:1173-1177), Q-Beta Replicase (Lizardi, etai, 1988, Bio/Technology 6:\\91), or any other nucleic acid amplification method, followed by the detection of the amplified molecules using techniques well known to those of skill in the art. These detection schemes are especially useful for the detection of nucleic acid molecules if such molecules are present in very low quantities.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high-density arrays containing hundreds or thousands of oligonucleotides probes (Cronin, et a i, 1996, Human Mutation 7:244-255; Kozal, et a i, 1996, Nature Medicine 2:753-759). For example, genetic mutations can be identified in two-dimensional arrays containing light-generated DNA probes as described in Cronin, et a i, supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert, 1977, Proe. Nati Acad Sei USA 74:560; or Sanger, 1977, Proc. Nati Acad. Sei USA 74:5463. It is also contemplated that any of a variety of automated sequencing procedures can be used when performing diagnostic assays (1995, Bio/Techniques, 19:448), including sequencing by mass spectrometry (See, e.g., PCT Publication No. WO 94/16101; Cohen, etai, \996, Adv. Chromatogr. 36:127-162; and Grif™, etai, \993, Appi Biochem. Biotechnoi, 3%:\41-\59).

Other methods for detecting mutations in a selected gene include methods in which protection from cleavage agents is used to detect mismatched bases in RNA/RNA or RNA/DNA heteroduplexes (Myers, et a i, 1985, Science 230:1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex that are generated due to basepair mismatches between the control and sample stands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing Polyacrylamide gels to determine the site of mutation. See, e.g. Cotton, et a i, 1988, Proc. Nati Acad. Sei USA 85:4397; Saleeba, et a i, 1992, Methods Enzymoi 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu, e/a/., 1994, Carcinogenesis 15:1657-1662). In one specific embodiment, a probe based on a selected sequence, e.g., a wild-type sequence, is hybridized to cDNA or other DNA product from a test cell(s). The duplex is treated with a DNA mismatch repair enzyme, and the cleavage products, if any, can be detected from electrophoresis protocols or similar means. See, e.g., U.S. Pat. No. 5,459,039.

In other embodiments, alterations m electrophoretic mobility will be used to identify mutations in genes. For example, single-stand conformation polymorphism (SSCP) may be used to detect differences in electrophoretic mobility between mutant and wild-type nucleic acids (Orita, et a i, 1989, Proc. Nati Acad. Sei USA 86:2766; see also Cotton, 1993, Mutai Res. 285:125-144; Hayashi, 1992, Genet. Anai Tech. Appi 9:73-79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen, et ai, 1991, Trends Genet. 7:5).

In yet another embodiment, the movement of mutant or wild-type fragments in Polyacrylamide gels containing a gradient of denaturant is assayed using denaturing gradient gel electrophoresis (DGGE) (Myers, et al., 1985, A/biure 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, \9%1, Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki, et al., 1986, Nature 324:163; Saiki, etai, 1989, Proc. Nati Acad. Sei USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs, et a i, 1989, Nucleic Acids Res. 17:2437-2448) or at the extreme 3' end of one primer where, under appropriate conditions, mismatch can prevent or reduce polymerase extension (Prossner, 1993, Tibtech 11:238). In addition, it may be desirable to introduce a novel restriction site in the region of the mutation to create cleavage-based detection (Gasparini, et a i, 1992, Mol. Cell Probes 6:1). It is anticipated that in certain embodiments amplification may also be performed using Taq ligase for amplification (Barany, 1991, Proc. Nati Acad. Sei USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by using pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., preferably peripheral blood leukocytes, in which the polypeptide of the invention is expressed may be utilized in the prognostic assays described herein.

5.8 Methods of Treatment 5.8.1 Immunoregulatory Effect of TREMs

Inflammatory disorders are numerous and are highly varied in incidence and severity. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. Inflammatory disorders are generally classified into two types; that is, acute and chronic inflammations. Acute inflammation is triggered by an initiating agent which is often a foreign substance, such as pathogenic organisms (e.g., bacteria, fungi, vims, protozoa and other parasites). The degradation products or toxins released by pathogens may directly cause activation of plasma proteases which leads to a series of inflammatory responses, including vasodilation, increased vascular permeability, recmitment and activation of neutrophils, monocytes, and eosinophils, and production of fever. Furthermore, injured cells can release degradation products which trigger various plasma protease cascades, including complement, kinins, clotting and fibrinolytic proteins, lipid mediators, prostaglandins, leukotrienes, and platelet-activating factor. In addition, expression of proinflammatory cytokines, such as interleukin-1 (IL-1), IL-4, IL-6, IL-8, tumor necrosis factor (TNF) a and β, interferon-y (IFN-y), and IL-12, is upregulated and the inflammatory responses are further augmented. The acute phase inflammatory responses are downregulated once the foreign threat is eliminated. Such downregulation is achieved by cell senescence or apoptosis (programmed cell death) which seems to be promoted by certain cytokines, including T>fF-a, eicosanoids, IL-10, and antioxidants (Cox, etai, 1996, Am J Physiol 27:L566-L571; Gelmd, etai, 1996, Proc. Assoc. Am. Physicians 108:455-456; Gon, et a i, 1996, Microbioi Immunol. 40:463-465; Hebert, etai, 1996, 7 Immunol. 157:3105-3115; Oishi, eia/., \991, Scand. J. Immunoi 45:21-27), and by anti-inflammatory mediators, including IL-4, transforming growth factor-β (TGFβ), IL-10, and IL-13, the latter three being released by macrophages and lymphocytes rather than by granulocytes. However, if the elimination of the foreign substance is incomplete, the inflammatory process persists and chronic inflammation ensues. (5ee e.g., Rosenberg, et ai, 1999, Inflammation, in Fundamental Immunology, 4'*ˆ ed., W. E. Paul, ed., Lippincott-Raven, Philadelphia p. 1051).

As described in examples below, the TREMs trigger cell activation, Ca mobilization and tyrosine phosphorylation via an associated signal transduction molecule, called DAPÍ2 (Lanier, L. L., 1998, Annu. Rev. Immunoi 16:359) (see FIG. 8 and section 6.8 below). Among TREMs, TREM-1 is exclusively expressed on neutrophils and monocytes and upregulated by bacterial and fungal stimuli (see sections 6.5.3 and 6.5.4, and FIGS. 6 and 14). TREM-1 triggers release of proinflammatory cytokines and chemokines, such as tumor necrosis factor-a (TNF-a), interleukin-8 (IL-8) and monocyte chemoattractant protein-1 (MCP-1), and induces degranulation of neutrophils in vitro as described in the section 6.7 below and FIG. 7. In addition, it renders neutrophils and monocytes highly resistant to, spontaneous cell death in culture. These observations strongly indicate that TREM-1 is involved in acute inflammatory reactions and, thus, prompted the present inventors to investigate its role in inflammation in vivo and its potential as a target for treatment of pathogenic hyperinflammatory conditions.

Figure 19D:
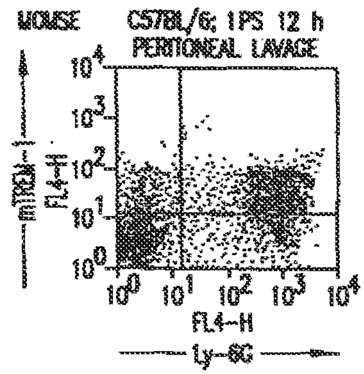

As presented in section 6.5.4 and FIG. 17, TREM-1 is strongly expressed on neutrophils associated with suppurative lesions of the skin caused by *Staphylococcus aureus*, such as folliculitis and hnpetigo, and with suppurative granulomatous lymphadenitis caused by *Bartonella henselae* and *Aspergillus fiimigatus*. Consistent with the role of TREM-I in responses to bacterial infections, TREM-I surface expression was strongly increased on infiltrating neutrophils isolated from the peritoneal cavity of patients with septic shock due to bacterial peritonitis (FIG. 19B) as well as that of the experimental mice having LPS-induced septic shock (FIG. 19D). On the other hand, TREM-1 is poorly expressed in neutrophilic infiltrates found in granulomatous lymphadenitis caused by sarcoid and foreign bodies granulomas and non-bacterial inflammatory reaction, including psoriasis, ulcerative colitis, and vasculitis caused by immune complexes (see FIGS. 18, 19A) and lipoid pneumonia.

Furthermore, administration of soluble TREM-1 before (FIGS. 20, 21 A) or after (FIG. 21C) the injection of LPS protected mice from lethal endotoxemia.

On the other hand, TREM-2 is predominantly expressed on mast cells and immature DCs (FIGS. 25, 26) and is essential for maturation of DCs as well as migration of DCs into lymph nodes to initiate adaptive immune responses (FIGS. 36-37). Furthermore, DAP12-deficient mice, which are also deficient in TREM-2 function, are more resistant to delayed hypersensitivity reaction (e.g., skin contact allergy) and experimental autoimmune encephalomyelitis (i.e., a mouse model for multiple sclerosis) due to reduced T cell stimulation by DCs (Bakker, A. B., et a i, 2000, Immunity 13:345-53; Tomasello, E., et a i, 2000, Immunity 13:355-64). Therefore, blocking TREM-2 with, for example, a soluble TREM-2 should reduce adaptive immune responses and protect the host from various immune disorders including autoimmunity and allergies.

Thus, TREM-I and/or TREM-2 are good targets for preventing and treating various immune and inflammatory disorders. Accordingly, the present invention provides for both prophylactic and therapeutic methods of treating (including treating, ameliorating, and/or reducing the symptoms of) a subject at risk of (or susceptible to) a disorder or having a disorder associated with aberrant expression or activity of a polypeptide of the invention (for example, as discussed in sections above relating to uses of the sequences of the invention). Disorders characterized by aberrant expression or activity of the polypeptides of the invention include: immunological disorders, especially involving inflammatory disorders (e.g., bacterial infection, fungal infection, viral infection, protozoa or other parasitic infection, psoriasis, septicemia, cerebral malaria, inflammatory bowel disease, arthritis, such as rheumatoid arthritis, folliculitis, impetigo, granulomas, lipoid pneumonias, vasculitis, and osteoarthritis), autoimmune disorders (e.g., rheumatoid arthritis, thyroiditis, such as Hashimoto's thyroiditis and Graves' disease, insulin-resistant diabetes, pemicious anemia, Addison's disease, pemphigus, vitiligo, ulcerative colitis, systemic lupus erythematosus (SLE), Sjogren's syndrome, multiple sclerosis, dermatomiositis, mixed connective tissue disease, scleroderma, polymyositis, graft rejection, such as allograft rejection), T cell disorders (e.g., AIDS) and allergic inflammatory disorders (e.g., skin and/or mucosal allergies, such as allergic rhinitis, asthma, psoriasis), neurological disorders, eye disorders and embryonic disorders, or any other disorders (e.g., tumors, cancers, leukemia, myeloid diseases, and traumas) which are directly or indirectly associated with aberrant TREM-1 and/or TREM-2 activity and/or expression. The nucleic acids and polypeptides of the invention, and modulators thereof, can be used to treat these disorders and diseases. Further, the nucleic acids, polypeptides, and modulators thereof of the invention can be coadministered with other therapeutics/prophylactics relevant to the diseases, e.g., anti-inflammatory agents, such as anti-TNF-a antibody, IL-1 receptor antagonist, anti-MIF antibody, and anti-FIMG-I antibody, and chemotherapeutic agents; as such, the nucleic acids, polypeptides, and modulators thereof of the invention are suitable for treatments involving forms of combination therapy.

5.8.2 Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or aggravated by aberrant expression or activity of a polypeptide of the invention can be identified by, for example, any diagnostic or prognostic assays as described herein (or a combination thereof). Administration of a prophylactic agent can occur prior to the manifestation of symptoms characteristic of the aberrancy, such that a disease or disorder is prevented or delayed in its progression. Depending on the type of aberrancy, for example, an agonist or antagonist agent can be used for treating the subject The prophylactic agents described herein, for example, can be used to treat a subject at risk of developing disorders such as those previously discussed.

In a specific embodiment, as described in section 6.10 (5ee also FIGS. 19A-19B), mice were first treated with murine TREM-1-human IgGI fusion protein (mTREM-1-IgGI; 500 jig/animal) intraperitoneally. One (1) hour later, the mice were injected intraperitoneally with a lethal dose of LPS (500 |xg/animal), to induce septic shock. The intraperitoneal injection of LPS at this dosage leads to tissue damage, hemodynamic changes, multiple organ failure and death within 24 hours in control mice which have received control proteins (e.g., IgGI). Surprisingly, eighty (80) percent of the TREM-1 treated mice were protected from a lethal endotoxemia, only showing mild symptoms during the first few hours after LPS injection, and completely recovered within 4 days after LPS injection. It is presumed that the soluble form of TREM-I acted as a decoy receptor for the ligands and prevented the latter from binding to the cell surface TREM-1. Thus, the soluble form of TREM-1 demonstrated its effect as a prophylactic agent against septic shock.

5.8.3 Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable hi situations m which activity or expression is abnormally high or upregulated and/or in which decreased activity is likely to have a beneficial effect.

In a specific embodiment, the modulator is a soluble form of TREM-1 or TREM-2 molecule, for example, a fusion protein such as TREM-1-IgGI or TREM-2-IgM as described m the previous sections. The mTREM-1-IgGI or huTREM-1-IgGI (i.e., a fusion protein between mouse TREM-1 or human TREM-1 and human IgGI) successfully protected the mice from lethal endotoxemia when administered intraperitoneally up to two (2) hours after the LPS injection. Thus, TREM-1 can be used as a therapeutic agent when administered in an early phase of inflammation induced by LPS, presumably reducing the total amount of inflammatory mediators and preventing an irreversible tissue damages (also see section 6.10 and FIG. 21).

hi another specific embodiment, an inhibitory antibody specific for TREM-1 or TREM-2 molecule can be used as a therapeutic agent. Such antibodies would act as an antagonist against TREM-1 or TREM-2 by blocking the ligand-binding sites of TREM-1 and TREM-2 without triggering subsequent signal transduction reactions which lead to inflammatory disorders.

In another embodiment, nucleic acids comprising sequences encoding antibodies or fusion proteins, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available m the art can be used according to the present invention. Exemplary methods are described below.

For general reviews of the methods of gene therapy, see Goldspiel et a i, 1993, Clinical Pharmacy 12:488-505; Wu and Wu, 1991, Biotherapy 3:87-95; Tolstoshev, 1993, Ann. Rev. Pharmacoi Toxicoi 32:573-596; Mulligan, 1993, Science 260:926-932; and Morgan and Anderson, 1993, Ann. Rev. Biochem. 62:191-217; May, 1993, Tibtech 11(5): 155-215. Methods commonly known in the art of recombinant DNA technology which can be used are described in Ausubel, etai, eds., 1993, Current Protocols in Molecular Biology, John Wiley & Sons, N.Y.; and Kriegler, 1990, Ge<<e Transfer and Expression, A Laboratory Manual, Stockton Press, N.Y.

In a preferred aspect, a composition of the invention comprises nucleic acids encoding a polypeptide or an antibody of the invention, or fragments thereof, said nucleic acids being part of an expression vector that expresses the polypeptide or antibody of the invention in a suitable host. In particular, such nucleic acids have promoters, preferably heterologous promoters, operably linked to the coding region of the polypeptide or antibody of the invention, said promoter being inducible or constitutive, and, optionally, tissue specific. In another particular embodiment, nucleic acid molecules of the invention are used in which the desired coding sequences are flanked by regions that promote homologous recombination at a desired site in the genome, thus providing for intrachromosomal expression of the polypeptide of the invention or fragments thereof (KoUer and Smithies, 1989, Proe Nati Acad. Sei USA 86:8932-8935; and Zijlstta, of a i, 1989, Nature 342:435-438).

In another preferred aspect, a composition of the invention comprises nucleic acids encoding a fusion protein, said nucleic acids being a part of an expression vector that expresses the fusion protein in a suitable host. In particular, such nucleic acids have promoters, preferably heterologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein.

Delivery of the nucleic acids into a subject may be either direct, in which case the subject is directly exposed to the nucleic acid or nucleic acid-carrying vectors, or indirect, in which case cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), by direct injection of naked DNA, by use of microparticle bombardment (e.g., a gene gun; Biolistic, Dupont), by coating with lipids or cell-surface receptors or transfecting agents, encapsulation in liposomes, microparticles, or microcapsules, by administering them in linkage to a peptide which is known to enter the nucleus, or by administering it in linkage to a ligand subject to receptor-mediated endocytosis (see, e.g., Wu and Wu, 1987, 7 Biol. Chem. 262:4429-4432) (which can be used to target cell types specifically expressing the receptors). In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; W092/20316; W093/14188; WO 93/20221). Alternatively, the nucleic acid can be introduced intracellularly and incorporated within host cell DNA for expression, by homologous recombination (Koller and Smithies, 1989, Froc. Nati Acad. Sei USA 86:8932-8935; and Zijlstra, et a i, 1989, Nature 342:435-438). In a specific embodiment, viral vectors that contain nucleic acid sequences encoding an antibody or a fusion protein are used. For example, a retroviral vector can be used (see Miller, et a i, 1993, Meth. Enzymoi 217:581-599). These retroviral vectors contain the components necessary for the correct packaging of the viral genome and integration into the host cell DNA. The nucleic acid sequences encoding the polypeptide of the invention, or fragments thereof, or a fusion protein to be used in gene therapy are cloned into one or more vectors, which facilitates delivery of the nucleotide sequence into a subject. Further details about retroviral vectors can be found in Boesen, et a i, 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes, et a i, 1994, 7 Clin. Invest. 93:644-651; Klein, et a i, 1994, Blood 83:1467-1473; Salmons and Gunzberg, 1993, Human Gene Therapy 4:\29-\4\; and Grossman and Wilson, 1993, Curr. Opin. in Genetics and Devei 3:110-114.

Adenoviruses are other viral vectors that can be used in gene therapy. Adenoviruses are especially attractive vehicles for delivering genes to respiratory epithetia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3:499-503) present a review of adenovirus-based gene therapy. Bout, et a i, 1994, Human Gene Therapy, 5:3-10) demonstrated the use of adenovirus vectors to transfer genes to the respiratory epithelia of rhesus monkeys. Other instances of the use of adenoviruses in gene therapy can be found in Rosenfeld, et a i, \99\, Science 252:431-434; Rosenfeld, et a i, 1992, Cell 68:143-155; Mastrangeli, etai, 1993, 7 C/m. Invest 91:225-234; PCT Publication W094/12649; and Wang, etai, 1995, Gene Therapy 2:775-783. In a preferred embodiment, adenovirus vectors are used.

Adeno-associated vims (AAV) has also been proposed for use in gene therapy (see, e.g., Walsh, etai, \993, Proc. Soc. Exp. Bioi Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject. In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymoi 217:599-618; Cohen, eiai, 1993, Meth. Enzymoi 217:618-644; and 1985, Clin. Pharma. Ther 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desfred, available cell type, and include, but are not limited to: epithelial cells, endothelial cells, keratinocytes, fibroblasts, muscle cells, hepatocytes; blood cells, such as T lymphocytes, B lymphocytes, monocytes, macrophages, neutrophils, eosinophils, megakaryocytes, granulocytes; various stem or progenitor cells, m particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding a polypeptide, an antibody or a fusion protein of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598; Stemple and Anderson, 1992, Cell 7 1:973-985; Rheinwald, 1980, Meth. Cell Bio. 21 A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable through control of the presence or absence of the appropriate inducer of transcription.

6. EXAMPLES

The following examples illustrate the cloning, production, isolation, and characterization of TREMs and fusion proteins thereof, and antibodies. These examples should not be construed as limiting.

A. Methods 6.1 Cloning of TREM cDNAs

GenBank expressed sequence tagged database (dbEST) was searched with the amino acid sequences of NKp44 using the tblastn algorithm, and several overlapping cDNAs were found. A continuous sequence assembled from 17 distinct cDNAs (accession nos. D78812, AI337247, AW139572, AW274906, AW139573, A1394041, AI621023, AI186456, AI968134, AI394092, AI681036, AI962750, AA494171, AA099288, AW139363, AW135801, AA101983) contained an open reading frame encoding a protein of 234 amino acids, referred to as TREM-1, with a predicted molecular mass of ~26 kDa (FIG. 1A). Search of the dbEST with the complete TREM-1 open reading frame matched to one related sequence referred to as TREM-2 (accession no. N41388) (FIG. IB). TREM-1 (FIG. 2) and TREM-2 (FIG. 3) sequences have been submitted to GenBank database under accession nos. AF196329 and AF213457, respectively.

6.2 RT-PCR

The ~760-bp TREM-I and ~1000-bp TREM-2 cDNAs were amplified by RT-PCR (reverse transcription PCR), cloned into pCR2.1 (Invitrogen, Carlsbad, Calif.), and sequenced. PCR primers were: TREM-1, 5'-GCTGGTGCA-CAGGAAGGATG (SEQ ID NO:31), 3'-GGCTGGAAGT-CAGAGGACATT (SEQ ID NO: 32); and TREM-2, 5'-TGATCCTCTCTTTTCTGCAG (SEQ ID NO: 33), 3'-GT-GTTTAAAATGTCCAATATT (SEQ ID NO: 34).

6.3 Production of Fusion Proteins and Monoclonal Antibodies (mAb)

6.3.1 Production of huTREM-1-JgGI and anti-TREM-I mAb

To produce soluble huTREM-1-IgG 1, the cDNA fragment encoding the huTREM-1 extracellular region was amplified by PCR and cloned into an expression vector containing the exons for hinge, CH2, and CH3 region of human IgGI. Transfection of the chimeric gene into the mouse myeloma cell line J558L, screening of culture supernatants, and purification of huTREM-1-IgGI were performed as previously described (Traunecker, et a i, 1991, Trends Biotechnoi 9:109). Briefly, the huTREM-1-IgGI plasmid was transfected into J558L mouse myeloma cells by electroporation and cells were cultured in DMEM supplemented with 2 mM L-glutamine, 1% non-essential amino acids, 1% sodium pymvate, 50 mg/ml kanamycm. After two days of culture, selective medium containing 4 mg/ml mycophenolic acid (Calbiochem) and 125 mg/ml xanthine (Sigma) was added and incubation at 37° C. continued until resistant colonies appeared. Clones were screened for production of soluble IgG fusion proteins by enzyme-linked immunosorbent assay (ELISA) using a goat anti-human IgG antibody. Producer clones were expanded, while the FCS content was diminished to 2%. For purification of the fusion protein, culture supernatant was concentrated and adsorbed over a recombinant protein A column (Repligen, Cambridge, Mass.). After washing with PBS-0.02% sodium azide, the bound fusion protein was eluted with O.IM glycine-HCl, pH 2.65. One (1)-ml fractions were collected m test tubes containing 100 ml 2MTris-HCl, pH 8, pooled, and dialyzed against PBS. Purified protein was then concentrated, sterile-filtered and kept frozen. Anti-huTREM-I mAbs were produced by immunizing BALB/c mice with huTREM-1-IgGI and preparing hybridomas using a standard hybridoma technique as reported elsewhere (Celia, etai, 1997, 7 Exp. Med. 185:1743). One of the anti-TREM-I antibodies was designated as 21C7 mAb (IgG I,K).

6.3.2 Production of huILT3-IgGI and mTREM-I-IgCI Fusion Proteins

Human ILT3-IgGI (huILT3-IgGI) was cloned, produced and purified as described for huTREM-1-IgGI above. To produce murine TREM-i (mTREM-1) as a soluble fusion protein, a chimeric gene consisting of the mTREM-1 extracellular domain and human IgGI constant regions was constructed. The cDNA fragment encoding the mTREM-1 extracellular region was amplified by PCR from cloned plasmid DNA. The forward primer contained an EcoKI restriction site and the TREM-I start codon: 5'-TAGTAGGAATTCAGGATGAGG AAGGCTGGG (SEQ ID NO:29). The reverse primer provided a HindIU restriction site, a splice donor sequence, and several mTREM-I codons preceding the transmembrane domain: 3'-TAGTAGAAGCTTATACTTACCGTCAG-CATCTGTCC CATTTAT (SEQ ID NO:30). The ~640-bp PCR product was cut with EcoRI and HináUI, and ligated into an expression vector containing the exons for hinge, CH2 and CH3 regions of human IgGI, the guanosine phosphotransferase gene converting resistance to mycophenolic acid, and the k promoter for the expression in the mouse myeloma cell line J558L. Transfection, screening of culture supernatants and purification of mTREM-1-ígGI were performed as described above. [0302]Anti-mTREM-1 and anti-huILT3 mAbs were prepared using these fusion proteins according to the method described above, and one of the anti-mTREM-1 clones was designated as 50D1 (rat IgGI, ¿) and one of the anti-huILT3 clones as ZM3.8 (murine IgGI, k).

6.3.3 Quantification of Human IgGI Fusion Proteins

Purified human IgGI fusion proteins were assayed for specificity, titer and functionality by ELISA using Protein A as a capturing protein, and either goat anti-human IgGI-HRP-conjugated polyclonal antibody (pAb; SBA), or specific biotinylated mAb against huTREM-I (21C7, murine IgGI,K), mTREM-1 (50D1, rat IgGI,K), or ILT3 (ZM3.8, murine IgG 1,K), followed by streptavidin-HRP. Immunoblot analysis of purified human IgGI fusion proteins revealed only one band of immunore activity.

6.3.4 Production of huTREM-2-IgM and Anti-TREM-2 mAb

To produce TREM-2 as a soluble fusion protein, a chimeric gene encoding the human TREM-2 extracellular domain and human IgGI constant regions was first constructed. The cDNA fragment encoding the TREM-2 extracellular region was amplified by PCR from cloned plasmid DNA. The forward primer 5'-TAGTAGGAATTCACTCTGCTTCTGC-CCTTGGCTGGGG (SEQ ID NO:35) contained an EcoRI restriction site and 25 nucleotides preceding the TREM-2 start codon. The reverse primer 3'-TAGTAGAAGCT-TATACTTACCGGGTGGGAAAGG-GATTTCTCCTTCCAA (SEQ ID NO:36) provided a HindIII restriction site, a splice donor sequence, and several TREM-2 codons preceding the transmembrane domain. The –600-bp PCR product was cut with EcoRS. And HindIII, and ligated into an expression vector containing the exons for hinge, CH2 and CH3 regions of human IgG I. TREM-2 extracellular region together with the splice donor site was re-amplified using the same forward primer (SEQ ID NO:31) and a reverse primer containing a Sail site and the splice donor sequence 3'-ACCTGCAGGCATGCGTCGA-CATACTTACC (SEQ ID NO:37). The ~600-bp PCR product was cut with Sail and ligated into an expression vector containing the exons for hinge, CH2, CH3 and CH4 regions of human IgM, the guanosine phosphotransferase gene conferring resistance to mycophenolic acid, and the k promoter for the expression in the mouse myeloma cell line J558L. Purification of huTREM-2-IgM from culture supernatants was performed using KAPTIV-M-Sepharose according to manufacturers protocols (Tecnogen, Milano). For the production of anti-TREM2 mAb, 6-week-old BALB/c mice (Iffa-Credo, Lárbresle, France) received an initial subcutaneous injection of IOO^g purified huTREM-2-IgM in Freund's complete adjuvant (FCA) behind the neck. The second immunization subcutaneously behind the neck (100 |xg purified huTREM-2-IgM in Freund's huTREM-2-IgM in PBS) were performed in one-week intervals. Three days after the final booster immunization, spleen cells were isolated and fused with the SP2/0 myeloma cells. Hybridoma supernatants were screened by ELISA using huTREM-2-IgM as coating protein and human immunoglobulin-adsorbed goat-anti-mouse IgG labeled with horseradish peroxidase (PharMingen, San Diego, Calif.) as detecting antibody. Supernatants from positive clones were then tested by flow cytometry for their ability to bind to immature DCs and 293 cells that were transiently transfected with flag-tagged TREM-2. One of the anti-TREM-2 antibodies was designated as 29E3 mAb (IgGI,K) (see FIG. 24).

6.3.5 Preparation of Fab/Ffab')2 Fragments

Monoclonal antibodies, 29E3 (anti-TREM-2; IgGI,K:), 21C7 (anti-TREM-I; IgGI,K), and 1B7.U (anti-2,4,6 TNP, American Type Culture Collection; control IgGI,K) were purified using GammaBind-Sepharose (Pharmacia). The purified mAb were either biotinylated (Molecular Probes, Eugene, Oreg.) or labeled with Cy5 (Pharmacia) according to manufacturers protocols. In addition. Fab or F(ab')2 fragments of mAb 29E3 and mAb 21C7 were prepared using the Fab'/F(ab')2 Kit from Pierce Chemical (Rockford, Ill.). Fab and F(ab')2 fragments were subsequently biotinylated thus allowing cross-linking by extravidine (Sigma) or FACS analysis using Streptavidin-APC or -PE (Pharmingen). Functional characterization of Fab and F(ab')2 29E3^'°^" were analyzed by FACS for cell surface expression of TREM-2 (see FIG. 30; grey profile and solid bold profile, respectively). TREM-1 is not detectable on monocyte-derived DCs with Fab or F(ab')2 9E2^'°"" followed by Streptavidine (FIG. 30; dashed profile).

6.4 Transient Transfections

HuTREM-1 and huTREM-2 were subcloned into pCMV-I-FLAG (Kodak) and expressed as amino-terminal FLAG peptide fusion proteins in COS-7 cells or 293 cells. DAP12 was subcloned into pHM6 (Boehringer Mannhehn, Mannheim, Germany) and expressed as amino-terminal hemagglutinin (HA) peptide fusion protein in COS-7 cells. Transient transfections were performed as previously described (Nakajima et a i, 1999, Human myeloid cells express an activating ILT receptor (ILTI) that associates with Fc receptor y-chain, 7 Immunol., 162:5). Cell surface expression of transfected cDNAs was determined by FACS analysis with anti-FLAG (Kodak), anti-HA (Boehringer Mannheim), 21C7 mAb, and 29E3 mAb.

As shown in FIG. 4, mAb 21C7 stained TREM-1-transfected COS-7 cells, as compared with control transfectants (lower right quadrant). In addition, expression of TREM-1 was partially increased by cotransfection of DAP12 cDNA (FIG. 4B), suggesting that cell surface expression of TREM-1 may require association with either DAP12 or a related signaling molecule.

As shown in FIG. 24, 29E3 mAb specifically recognized TREM-2. The 293 cells FLAG c, lif^ expressing TREM-2 (FIGS. 24B, 24D) and those expressing TREM-1^^^^ (FIGS. 24A, 24C) were stained with 29E3 (FIGS. 24C, 24D). 24.1% of TREM-2"^^^ cells and 0.98% of TREM-I^^^*^ cells (upper right quadrant) were stained with 29E3 mAb. Expression of TREM-1^^^^ and TR£M-2^^^^ was confirmed using anti-FLAG mAbs (FIGS. 24A-24B). Staining with isotype-matched control mAbs was set to the indicated lower quadrant.

6.5 Cells 6.5.1 Isolation of Human Monocytes, Neutrophils, and Dendritic Cells

Human blood was mixed with one volume of 3% D extran T-500 (Pharmacia, Uppsala, Sweden) in 0.9% NaCl and left for sedimentation (30 min) to remove erythrocytes. Leukocytes in the supernatant were further separated by gradient density centrifugation on Lymphocyte Separation Medium (ICN Biomedicals/Cappel, Aurora, Ohio) into peripheral blood mononuclear cells (PBMCs) and neutrophils. The pelleted neutrophils were further purified form contaminating erythrocytes by hypotonic treatment with 0.2% NaCl solution for 30 sec. CD14^ monocytes were purified from PBMCs by magnetic cell sorting using CD14 MicroBeads (Miltenyi, Bergisch Gladbach, Germany).

Monocyte-derived dendritic cells (DCs) were prepared from purified monocytes cultured in GM-CSF and TNF-a for 10 days as described by Sallusto, F. and Lanzavecchia, A., \994, J. Exp. Med 179:1109-18.

6.5.2 Surface Biotinylation and Pervanadate Treatment

Monocytes or Monocyte-derived DCs were washed three times in PBS followed by incubation with Sulfo-NHS-Biotin according to the manufacturers protocol (Pierce). For pervanadate treatment, cells were incubated with 200 pM pervanadate and 200 pM H2O2 at 37° C. for 5 min. Biotinylation or Pervanadate stimulation was stopped by washing the cells 3 times or 1 time, respectively, with ice cold PBS.

6.5.3 Human Peritoneal Leukocytes

Human peritoneal leukocytes were obtained from peritoneal lavage of patients diagnosed with aseptic Systemic Inflammatory Response Syndrome or polymicrobial sepsis, as defined by the Consensus Conference of the American College of Chest Physicians and Society of Critical Care Medicine (American College of Chest Physicians/Society of Critical Care Medicine Consensus Conference, 1992, Crit Care. Med. 20:864-74).

6.6 Staining and FACS Analysis 6.6.1 Human Cell Distribution Study of TREM-1

Before staining, all cells were incubated with 20% human semm in PBS for I hour on ice to block Fc receptors. Whole blood leukocytes were incubated with mAbs 21C7 (anti-TREM-I, IgGI), 3C10 (anti-CD14, IgG2b), and L243 (anti-HLA-DR, ígG2a) followed by isotype-specific FITC/PE/biotin-conjugated secondary Abs. After a further incubation step with APC-labeled streptavidin, cells were analyzed by FACS. Monocytes and neutrophils stimulated with LPS (1 pg/ml) for 16 hours were stained with either mAb 21C7 or mAb IB7.11 (control IgGI, anti-2,4,6-trinitrophenyl (TNP); American Type Culture Collection, Manassas, Va.), followed by human immunoglobulinadsorbed PE-conjugated goat anti-mouse IgG (Southern Biotechnology Associates, Birmingham, Ala.). See FIGS. 5 and 6. Monocytes stimulated with proinflammatory cytokines, TNF-a (20 ng/ml), IL-Iβ (20 ng/ml), TGFβ (20 ng/ml), or IL-10 (20 ng/ml) for 24 hours were also stained as described above. 5ee FIG. 15.

6.6.2 Effects of Bacterial Products on Human Cells

Purified monocytes and neutrophils were cultured in the absence or presence of Lipopolysaccharide (100 ng/ml), Lipoteichoic acid (LTA; 100 ng/ml) or mycotic acid (10 ng/ml). Before staining, all cells were preincubated with 20% human semm m PBS for I hour on ice to block Fc receptors. After incubation with either mAb 21C7 (IgGI, anti-TREM-I) or mAb 1B7.11 (control IgGI, anti-2,4,6 TNP, American Type Culture Collection), and a second-step human immunoglobulin-adsorbed phycoerythrin (PE)-conjugated goat anti-mouse IgG, cells were analyzed on a FACSCalibur cytometer using CELLquest software (Beckton Dickinson & Co., Palo Alto, Calif.). See FIGS. 6 and 14B.

6.6.3 Regulation of TREM-1 During Bacterial Infections

To explore how bacterial infections affect the expression of TREM-1 on neutrophils and monocytes, these cells were exposed to various types of bacteria and the degrees of TEM-I expression were compared to that of non-exposed control cells.

*Staphylococcus aureus, Pseudomonas aeruginosa*, and *Bacillus* of Calmette-Guerin (BCG) were cultured to the logarithmic growth phase based on the growth curves. The bacterial cells were then collected and washed twice in PBS. Subsequently, the bacterial cells were incubated at 80^0 for 30 min to be heat-inactivated.

Purified human neutrophils and monocytes were incubated with the heat-inactivated bacteria whose concentration was within the range for the optimal upregulation of TREM-1 (i.e., monocytes/neutrophils:bacteria=1:10-1:100). The resulting cell surface expression of TREM-1 was assessed by flow cytometry with the 21C7 mAb as described in section 6.5.2. 5ee FIG. 14A.

Four-color analysis of human peritoneal leukocytes was performed using anti-TREM-I, anti-CD15 (Immunotech, Marseille), anti-CD14 (hnmunotech) and CD16 (Immunotech) monoclonal antibodies conjugated with Allophycocyanin (APC), CyChrome, Phycoerythrin (PE) and Fluorescein isothiocyanate (FITC), respectively, ^ee FIGS. 19A-19B.

6.6.4 Human Cell Distribution Studies of TREM-2

Before staining, all cells were preincubated with PBS-20% human semm for 1 hour on ice to block Fc receptors (FcR). Monocytes cultured in M-CSF, GM-CSF/TL4, ÍL-4, and GM-CSF were stained with either mAb 29E3 (FIG. 25), mAb 21C7, or mAb IB7.11 (anti-2,4,6 TNP), followed by human immunoglobulin-adsorbed goat anti-mouse IgG conjugated with phycoerythrin (PE). In three-color staining, immature DCs cultured with LPS (100 ng/ml), TNF-a (10 ng/ml), or CD40L-transfected mouse myeloma J558L cells (Lane, P., etai, 1995, Eur 7 Immunoi 6:1788) were incubated with Cy5-labeled 29E3 mAb, Fluoresceine-Isothiocyanate (FITC)-conjugated anti-CD83 mAb (Immunotech, Marseille, France), and PE-conjugated anti-MHC class II mAb (Immunotech). Cells were analyzed on a FACSCalibur cytometer using CELLquest software (Beckton Dickinson & Co., Palo Alto, Calif.). Dead cells were excluded by gating on propidium iodide (PI)-negative cells (i.e., live cells).

Studies to determine in vivo localization of TREM-2 expression were conducted. Normal human tissue samples were collected, including skin, lymph nodes, placenta, lung, bronchi and small gut. Pathological specimens were also collected and included allergic nasal polyps and cutaneous mastocytosis. All tissues were fresh frozen in isopentane that had been previously cooled in liquid nitrogen and stored at −80° C. Immunostaining was performed on frozen sections, applying the anti-TREM-2 antibody at the concentration of ~1 pg/ml, followed by detection of the antibody with the indirect immunoperoxidase technique and use of the Labelled Streptavidin-Biotm (LSAB) procedure (Dako, Denmark), using ethylcarbazole as chromogen (Dako, Denmark), and counter-stained with Meyers haematoxylin. In the nasal polyps, anti-TREM-2 antibody was detected with the indirect-immunoalkaline phosphatase technique. To avoid staining of endogenous peroxidase, some tissue samples, specifically those of allergic nasal polyps and skin mastocytomas, were stained by the LSAB procedure followed by alkaline-phosphatase, using fast red as chromogen (Dako) and counter-stained with Meyers haematoxylin.

6.7 Immunohistochemical Study

Normal tissue samples included two lymph nodes showing non-specific reactive change and three skin biopsies without obvious abnormalities. In addition, two spleens showing extramedullary hematopoiesis were analyzed. Pathological samples included nine cases of infectious epitheloid cell granulomas, three cases of sarcoidosis (lymph node), three cases of lipoid pneumonia, four cases of psoriasis and two skin biopsies affected by *Staphylococcus aureus* infection, with features of impetigo and folliculitis. The infectious granulomas were localized in lymph nodes (eight cases) and mediastinum (one case) and were caused by *Mycobacterium tuberculosis* (three cases), *Bartonella henselae*/cat scratch disease (five cases), and *Aspergillus fumigatus*; the latter belonged to a patient affected by Chronic Granulomatous Disease. Finally, a foreign-body giant-cell reaction associated with a vascular plastic prostheses, which was removed because of thrombosis, was analyzed. Except for sarcoidosis (all cases), tuberculosis (one case) and the foreign-body granuloma, all other granulomas were characterized by variable degrees of suppurative inflammation, which were particularly prominent in the *Bartonella henselae* and *Aspergillus fumigatus* infections. All tissues were freshly frozen in liquid nitrogen-precooled isopentane and stored at −80° C. Immunostaining with 21C7 was performed on frozen sections, applying the antibody at the concentration of ~1 ^ig/ml; an isotype-matched antibody (IgGI) was used as negative control. Anti-CD15 (Dako, Milan, Italy) antibodies were also applied to identify neutrophils. immunostaining followed the streptavidin-biotin hnmunoperoxidase technique (Facchetti, et ai, 1992, Am. J. Surg. Pathol. 16:955-61). Endogenous peroxidase was inhibited by preincubating the sections with 0.001% H2O2 methanol solution; chromogenic reaction was developed with 3-amino-9-ethylcarbazole (AEC), and nuclei were counterstained with Mayer's hematoxylin. See FIGS. 17-18.

6.8 Measurement of Cytokines, Chemokines. Degranulation^ and Cell Surface Activation Markers 6.8.1 Stimulation of TREM-1

To examine whether TREM-1 can trigger acute inflammatory responses, purified monocytes or neutrophils were stimulated for 24 h in 96-well flat-bottom plates coated with F(ab')2 goat anti-mouse IgG (5 pg/ml) followed by either 21C7, IFI 1 (anti-MHC class 0, or 1B7.11 (anti-2,4,6 TNP) mAbs. Cells were plated at a concentration of 5×IO" cells/well in the presence or absence of LPS (1 ng/ml). Supernatants were collected and tested for production of IL-6, IL-8, IL-10, IL-I2p75, monocyte chemoattractant protein-1 (MCP-I), TNF-a, and myeloperoxidase (MPO) by ELISA (PharMmgen, San Diego, Calif.). See FIGS. 7A-7H. To measure the expression of cell surface markers, monocytes and neutrophils were stimulated as described above and, after 48 hours, were stained with PE- or FITC-conjugated anti-CDI Ib, anti-CDI Ic, anti-CD18, anti-CD29, anti-CD32, anti-CD40, anti-CD49d, anti-CD49e, anti-CD54, anti-CD80, anti-CD83, oranti-CD86 (all from Immunotech, Marseille, France) and analyzed by FACS. See Table 1 below.

6.8.2 Stimulation of TREM-2

Immature DCs, 5×10^ cells/well, were stimulated for 36 hours in 24-welt flatbottom plates coated with Fab 29E3 or Fab 21C7 (20 ng/ml). Supernatants were collected and tested for production of IL-6, IL-8, IL-10, IL-I2p75, IL-13, fl.-16, IL-18, IL-Ia, IL-Iβ, TNF-a and MCP-1 by ELISA (PharMingen). See Table II. Type IIFN was measured by evaluating the inhibition of Daudi cell proliferation with reference to a standard IFN-a curve (Nederman, T., Karlsttom, E., and Sjodin, L., 1990, Biologicals 18:29-34). The sensitivity of the assay was 0.2 U/ml. To measure stimulation-dependent changes in the expression of cell surface markers, monocyte-derived DCs were stunulated with F(ab')2 control mAb (anti-TREM-I), F(ab')2 anti-TREM-2 mAb, or LPS. After different time periods (6, 12, 24, and 48 hours), cells were harvested, stained with mouse anti-CCR7 IgM mAb (Pharmingen, San Diego, Calif.) (see FIG. 36), followed by PE-labeled anti-mIgM Ab or PE- or FITC-conjugated anti-MHC class I, -MHC class II, -CD I a, -GDI Ia, CDIIb, GDI Ic, -CD29, -CD31, -CD32, -CD35, -CD40, -CD41, -CD54, -CD61, -CD80, -CD83, -CD86, -CD89, -CD103, -CDI 15, -CDI 16, -CCR5, -CCR6, -CXCR4, (all from hnmunotech) and analyzed by FACS (see Table III below). In experiments where kinase inhibitors (PD98059 (50 pg/ml): Erk inhibitor; or LY294002 (I0|xg/ml): PI 3 kinase inhibitor, both from Calbiochem, San Diego, Calif.) or serine protease inhibitor (TPCK (15 ^g/ml): NFkB-activation inhibitor; Sigma, St. Louis, Mo.) were used, the inhibitors were added 60 min before stimulation.

6.9 Measurement of Cytosolic Ca^^ and Tyrosine-Phosphorylated Proteins Determination of intracellular Ca^"*" mobilization was done according to the previous reports (Nakajima, et a i, 1999, 7 Immunoi 162:5). Briefly, monocytes or monocyte-derived DCs were loaded with hido-1 AM dye (Sigma) for 30 min at 37° C., washed 3 times and resuspended in RPMI-10 mM FIEPES/10% FCS. Cytoplasmic Ca^^ levels were monitored in individual cells by measuring 405/525 spectral emission ratio of loaded Indo-1 dye by flow cytometry (Nakajima, eíí2/..jMpra;Yamashita, ei a/., 1998, 7 Immunoi 161:4042). After obtaining the baseline for at least 30 seconds, for TREM-1 stimulation, anti-TREM-I mAb or anti-MHC class I (isotype-matched control mAb) and a cross-linking Ab (goat anti-mouse IgG) were added to the monocytes, and analysis was allowed to continue (see FIG. 8). For TREM-2 stimulation, either 29E3^"""" (IgGI,K or Fab) or 2107^'°"" (IgGI,K or Fab) was added to a final concentration of 1 pg/ml and analysis was continued up to 512 sec (see FIG. 31). In some experiments, ExtraAvidine (Sigma) was added as cross-linker together with the biotinylated primary antibodies or antibody fragments.

Determination of protein tyrosine phosphorylation, mitogen activated protein kinase activation, phospholipase C-y (PLC-y) phosphorylation, and immunoprecipitations was performed as previously described (Dietrich, et a i, 2000, 7 Immunoi 164:9). Briefly, monocytes were incubated at 37° C. with 27C1 mAb (anti-TREM-I) or control IgGI (anti-MHC class I) mAbs in the presence of a cross-linking Ab for the indicated time periods. After stimulation, an aliquot of the cells was lysed and subjected to anti-phosphotyrosine blotting using PY-20 (Transduction Laboratories, Lexington, Ky.) (see FIG. 9). Likewise, anti-phosphotyrosine blot of cell lysates from monocyte-derived DCs stimulated with F(ab')2 29E3 (anti-TREM-2) or control F(ab')2 9E2 (anti-TREM-I) are shown in FIG. 32.

Another aliquot of stimulated monocytes or monocyte-derived DCs was examined by Western blot analysis using anti-phospho-extracellular signal-regulated kinase 14 (PERKI/2) (FIGS. 10 A and 33A) and anti-ERKI/2 mAbs (FIGS. 10 B and 33B).

Tyrosine phosphorylated proteins were precipitated from the stimulated monocyte lysates and immunoblotted with anti-PLC-y (FIG. IOC) or anti-Hck (FIG. 10 D) Abs. An anti-Hck blotting was performed as a loading control because phosphorylation of Hck is similar in both stimulated and unstimulated monocytes. Phosphorylated proteins are indicated by arrows in all panels. Molecular weight markers are shown.

6.10 Immunoprecipitation

Surface-biotmylated cells were lysed in \% digitonin, 100 mM Tris-HCl pH 7.4, I50 mM NaCl, protease inhibitors (Complete, Roche, Switzerland). After overnight preclearing with normal mouse serum coupled to protein G Sepharose 4B, lysates were subjected to immunoprecipitation with 5^g/ml of 29E3, 21C7, 1 FI 1 (anti-MHC class I mAb), or ÍB7.11 at 4° C. for 3 hours. Immunecomplexes were precipitated by addition of Protein-GSepharose 4B FastFlow (Pharmacia) for 3 hours at 4° C. Precipitates were washed 4 tunes with lysis buffer, followed by a final wash with 0.5% digitonin, 100 mM Tris-HCl pH7.4, 150 mM NaCl. Elution from sepharose occurred under reducing or non-reducing conditions using standard SDS-PAGE sample buffer. After separation by SDS-PAGE, precipitate set up was analyzed by Western Blot with horseradish peroxidase (HRP)-conjugated Streptavidine. In de glycosylation experiments the precipitates were incubated for 18 hours with or without N-Glycanase F (Boehringer Mannheim) according to the manufacturers protocol (see FIGS. 11,27).

In another experiment, pervanadate-treated cells (Lanier, L. L., 1998, Annu. Rev. Immunoi 16:359); which is incorporated herein in its entirety) were subjected to immunoprecipitation with anti-TREM-I (21C7) mAb, anti-TREM-2 (29E3) mAb, antisignal-regulatory protein (SIRP) (Dietrich, et a i, 2000, J. Immunoi, \64:9, which is incorporated herein in its entirety) mAb as a positive control, or control IgGI (anti-MHC class I mAb). The precipitates were analyzed by Western blot, either with antiphosphotyrosine PY20-HRP (Transduction Laboratories, Lexington, Ky.) under reducing and nonreducing conditions (see FIGS. 12,28) or with anti-DAP12 rabbit antisemm followed by Hum an/Mo use-adsorbed anti-Rabbit IgG-HRP (SBA) under reducing condition (see FIGS. 13, 29).

6.11 Chemotaxis Assay

Monocyte-derived DCs were stimulated for 24 hours with LPS (1 pg/ml) or with F(ab)'2 9E2 (anti-TREM-I, IgGI, K) or F(ab)'2 29E3 (20^g/ml) coated on plastic plates. These cells (5×10^ cells/100 ^l/well in IMDM/0.5% BSA) were incubated for 1 hour at 37° C. in new media and subsequently loaded into collagen-coated transwells (Costar, 3 \im pore filter), which were placed to 24-well plates containing 450 ^il medium supplemented with 100 ng/ml ELC or MIP-3β. After an incubation period of 4 hours at 37° C., cells that had migrated to the lower chamber were collected and counted on a FACSCalibur (constant tune acquisition). In blocking experiments, cells were preincubated with ELC (100 ng/ml) or MIP-3β (100 ng/ml) for 1 hour, oranti-CCR7 mAb (I pg/ml) was added to the transwell (see FIG. 37).

6.12 Detection of Apoptosis

As shown in FIG. 34, monocyte-derived DCs were stimulated with GMCSF/IL-4 (closed squares), plastic-bound F(ab')2 (open circles) or control F(ab')2 (closed circles) for the indicated tune periods, and determination of DNA fragmentation was performed as described previously (Nicoletti, I., et a i, 1991, 7 Immunoi Methods 139:271-279). In experiments where kinase inhibitors (PD98059 (50 pg/ml) or LY294002 (10 pg/ml)) or serine protease inhibitor (TPCK (15 ng/ml)) were used, the inhibitors were added 60 min before stimulation (see FIG. 35) and apoptotic cell death was determined after 8 days by measurement of DNA fragmentation. All inhibitors had no effect on cell viability or the rate of constitutive apoptosis at the indicated concentrations.

6.13 Internalization Assays

Monocyte-derived DCs were incubated in RPMI-10% FCS with 2|ig/ml of 29E3 (anti-TREM-2 mAb; whole IgGI, Fab or F(ab')2) or IFI 1 (anti-MHC class I mAb; whole IgGI) for 15, 30, 60 and 120 minutes at 37° C. (5ee FIG. 38). One aliquot was kept at 4° C. for 2 hours in the presence of antibodies to determine the initial levels of TREM-2 expression. Activation was stopped by washing cells twice with ice-cold PBS. Residual surface levels of receptors were measured by FACS after stimulated cells were fixed with 3% paraformaldehyde (PFA) in PBS and staining with PE-conjugated goat anti-mouse IgG antibody (PharMingen) (extracellular receptor levels). Intracellular receptor levels were determined by stripping the cell surface with PBS containing 150 mM β-mercaptoethanol and 5M NaCl for 5 min, followed by fixation, permeabilization with PBS containing 0.1% Saponin and 2% FCS and staining with PE-conjugated goat anti-mouse IgG antibody. To determine total receptor amount and to assess the degree of mAb shedding, stimulated cells were stained for external and internal receptor expression after fixation and permeabilization. When biotinylated Fab or F(ab')2 fragments of 29E3 were used (5\ig/m\), the bound antibody was detected using PE-conjugated Streptavidine (Pharmingen). To prevent the progression of receptor internalization, cells were kept on ice during the whole procedure.

6.14 Antigen Presentation Assay

Irradiated (3000 rad) 2.5×IO^ of DCs were cocultured with 5×10" cells of the VIP 13 T cell clone in 96-well flat-bottom microplates in the presence of serial dilutions of whole IgGI mAbs or F(ab')2 fragments. Monoclonal antibodies used as whole IgGI molecules were: ZM3.8 (anti-ILT3, IgGI, K); 9E2 (anti-TREM-I, IgGI, K); 29E3 (anti-TREM-I, IgGI, K); and ICRF44 (anti-CDI Ib/Mac-I, IgGI, K, Pharmingen). F(ab')2 fragments used in the assay were F(ab')2 9E2 and F(ab')2 29E3. After 72 hours, the cultures were pulsed with [^H]thymidine (1|iCi/well; specific activity: 5 Ci/mmol), and the radioactivity incorporated was measured after an additional 16 hours. The data were plotted against the concentration of mAbs determined by ELISA using a purified mouse IgGI,ic or F(ab')2 IgGI, K as a standard (see FIG. 39).

6.15 Protection of Mice from Endotoxemia 6.15.1 LPS-Induced Endotoxemia

Female C57BL/6 mice (8-10 weeks, 19-22 g) were randomly grouped (5-10 mice per group) and injected intraperitoneally (i.p.) with LPS from *E. coli* 055:B5 (Sigma) (at LDioo, 20 mg per gram body weight, for FIGS. 20, 2IA, 21C;

or different amounts, for FIG. 21B). Purified huTREM-1-IgGI, mTREM-1-IgGI, huIgGI (Sigma), heat-inactivated mTREM-I-IgGI, or ILT3-IgGI (Celia, M., er a/., 1997, J. Exp. Med. 185:1743-51), at 500 [ig/mouse, were administrated, i.p., 1, 2, 4, and 6 hours after (see FIG. 21C) or 1 hour prior (see FIGS. 20, 21A and 2IB) to LPS. Treated mice were monitored 4-6 times a day for at least 10 days.

6.15.2 *E. Coli* Peritonitis Model

*E. coli* peritonitis was induced in mice as described previously (Appelmelk, B. J. et ai, 1986, Antonie Van Leeuwenhoek 52:537-42). Briefly, C57BL/6 mice (female, 8-10 weeks, 19-22 g) were weighed and randomly distributed into groups of 5-15 animals of equal body weight. Mice were injected i.p. with 500 mg of mTREM-1-IgGI or control huIgGI prior to i.p. administration of 500 ^il of a suspension of £". coli 0111:B4 (1.6-2.1×10^CFU per mouse).

6.15.3 Cecal Ligation and Puncture (CLP)

CLP was performed as described previously (Echtenacher, B. et a i, 1990, Requirement of endogenous tumor necrosis factor/cachectin for recovery from experimental peritonitis. 7. Immunoi 145:3762-6; Calandra, T. etai, 2000, Protection from septic shock by neutralization of macrophage migration inhibitory factor. Nat Med. 6:164-70). Briefly, C57BL/6 mice (female, 8-10 weeks, 19-22 g) were anesthetized by intraperitoneal administration of 75 mg/kg Ketanestig) (Parke-Davis & Company, Munich, Germany) and 16 mg/kg Rompun® (Bayer AG, Leverkusen, Germany) in 0.2 ml sterile pyrogen-free saline (B. Braun Melsungen AG, Melsungen, Germany). The caecum was exposed through a 1.0-1.5 cm abdominal midline incision and subjected to a 50-80% ligation of the distal half followed by a single puncture with a G23 needle. A small amount of stool was expelled from the punctures to ensure patency. The caecum was replaced into the peritoneal cavity and the abdominal incision closed in layers with 5/0 Prolene thread (Ethicon, Norderstedt, Germany). Five-hundred (500) pi sterile saline containing 500 mg of mTREM-1-IgGI, 500 mg of huIgGI,K (Sigma) or 100 pg TNF-RI-IgGI (Pharmingen) (together with 400 |ig huIgGI,K (Sigma) was injected intraperitoneally immediately after CLP. The CLP was performed blinded to the identity of the treatment group. Survival after CLP was assessed 4-6 times a day for at least 7 days.

6.16 Analysis of Blood and Lavage Fluids

Blood (250 pi) was collected from the tail vein of mice into a Serum Separator Tube (Becton Dickinson) at different time points after induction of LPS-induced endotoxemia in the presence of TREM-1-IgG 1 or control IgG 1. Quantification of murine TNF-a and IL-1 β in the semm was determined using cytokine-specific ELISAs according to the manufacturers protocol (R&D Systems, Minneapolis, Minn.). Peritoneal lavage (PL) cells were harvested at different time points after LPS administration in the presence of TREM-1-IgGI or control IgGI. Total cell numbers were determined on a Coulter counter and differential counts were performed according to standard morphological criteria on cytospin preparations stained with Giemsa & May-Gmenwald solution (Sigma). A minimum of 200 cells were counted per field, with 3 fields per sample for PL. See FIGS. 22C-22D.

Four-color analysis of peritoneal leukocytes from LPS-treated C57BL/6 mice (FIG. 19D) compared to control animals (FIG. 19C) was conducted using anti-TREM-1, anti-LY-6G (PharMingen) and anti-Mac-I (PharMmgen) monoclonal antibodies conjugated with Cy5, Phycoerythrin (PE) and Fluorescein isothiocyanate (FITC), respectively, and biotinylated anti-F4/80 followed by streptavidine-CyChrome (Pharmingen).

B. RESULTS

TREMs are Novel Transmembrane Proteins of the Ig-SF

As shown in FIG. IA, the amino acid sequence of TREM-1 begins with a hydrophobic signal peptide followed by an extracellular region composed of a single Ig-SF domain containing three potential A'^glycosylation sites. The length of the Ig-type fold and the characteristic pattern in the region leading to the β-strand F indicate that the Ig-type fold is of the V-type. The putative transmembrane domain contains a charged lysine residue and is followed by a cytoplasmic tail of 5 amino acids with no signaling motifs. Similar transmembrane and cytoplasmic domains are present in activating NK cell receptors which pair with the transmembrane adapter protein DAP 12 (Lanier, L. L., 1998, Annu. Rev. Immunoi 16:359). A cDNA containing the entire open reading frame was amplified by RTPCR from monocytes and neutrophils, but not from lymphocytes or other cell types (data not shown). Therefore, this molecule was designated as TREM-1. The GenBank EST database was then searched with TREM-1 polypeptide, and a novel cDNA encoding a TREM-1 homologue was identified and designated as TREM-2 (FIG. IB), which has very similar structure to that of TREM-1. The alignment of TREM-1, TREM-2, and NKp44 extracellular domains revealed ~20% o identity (data not shown). Analysis of somatic cell hybrids containing different human chromosomes demonstrated that the genes encoding TREMs map on human chromosome 6, as does the NKp44 gene (data not shown).

TREM-1

Figure 5D:
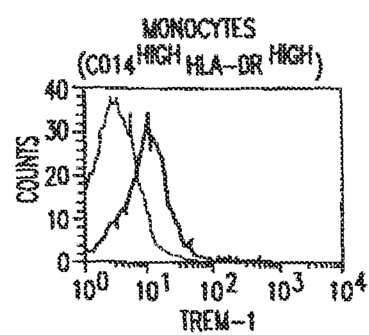
Figure 5E:
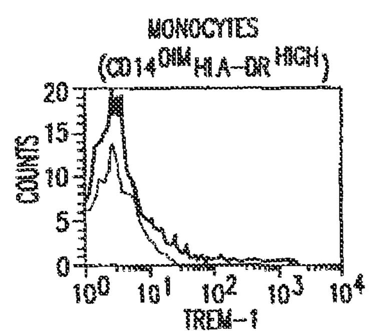
Figure 5F:
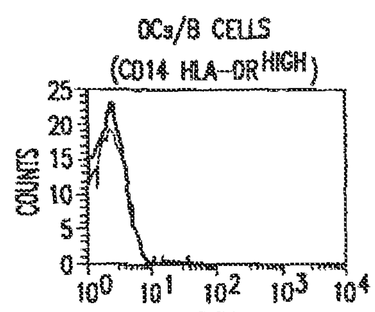
Figure 5G:
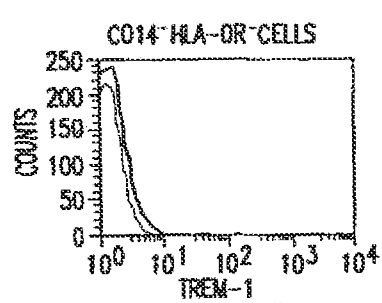

TREM-1 is Selectively Expressed on Blood Neutrophils and Monocytes and is Up-Regulated by Bacterial and Fungal Stimuli In three-color FACS analysis of whole blood leukocytes, high side scatter cells correspond to TREM-1^ neutrophils. Low side scatter cells include CD14'^'^"/HLA-DR^ cells (monocytes), CD14'^™/HLA-DR-(monocytes), CD14'/HLA-DR^ cells (which include B cells and dendritic cells or DCs), and CD14'/HLA-DR' cells (mostly lymphocytes). In peripheral blood of different donors, 21C7 mAb stained neutrophils and, to a less extent, CDM*"^ monocytes (FIGS. 5C-5D). CDM""™ monocytes, DCs or lymphocytes were TREM-1 negative (FIGS. 5E-5G). The expression of TREM-1 was further investigated during differentiation of CD 14^ monocytes into either DCs or macrophages in the presence of GMCSF/IL-4 or M-CSF, respectively. TREM-1 was completely down-regulated on these cells after 3 days of culture (data not shown). Stimulation of DCs with LPS, heat-inactivated Gram-positive bacteria. Gram-negative bacteria, or fungi did not induce TREM-1 expression (data not shown). In striking contrast, these stimuli induced strong up-regulation of TREM-1 on neutrophils and monocytes (for LPS stimulation, see FIG. 6; for other stimulants, data not shown). This selective expression of TREM-1 on neutrophils (FIG. 6B) and monocytes (FIG. 6A), coupled with its induction by pathogens indicate its role in acute inflammatory responses.

TREM-1 is a -JO-kDa Glycoprotein Associated with DAP12

Biochemical analysis of TREM-1 immunoprecipitated from surface-biotinylated monocytes revealed that TREM-1 is a glycoprotein of –30 kDa, which is reduced to 26 kDa after AT-deglycosylation, in agreement with the predicted molecular mass of TREM-1 (FIG. 11). Because TREM-1 lacks known signaling motifs in the cytoplasmic domain, it should associate with a separate signal transduction subunit to mediate activating signals. Adapter molecules, such as DAP 12, are tyrosine phosphorylated upon cell treatment with the phosphatase-inhibitor pervanadate (Lanier, L. L., 1998, Annu. Rev. Immunoi 16:359). Indeed, anti-phosphotyrosine blotting of TREM-1 immunoprecipitates from pervanadate stimulated monocytes revealed a phosphorylated protein of −12 kDa and ~24 kDa under reducing and nonreducing conditions, respectively (FIG. 12). An identical pattern was observed after immunoprecipitation of SIRPβI, which is associated with DAP12 (Diettich, et ai, 2000, 7 Immunol. 164:9; which is incorporated herein in its entirety). Indeed, immunoblotting of TREM-1 immunoprecipitates with anti-DAP12 demonstrated that TREM-1 associates with DAP 12 (FIG. 13).

Figure 7A:
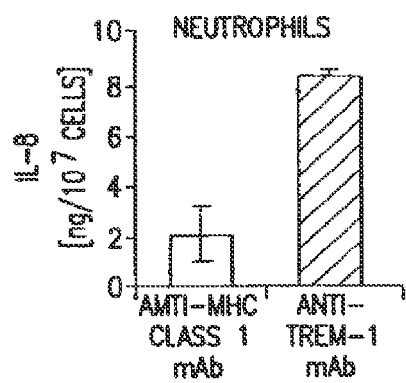
Figure 7B:
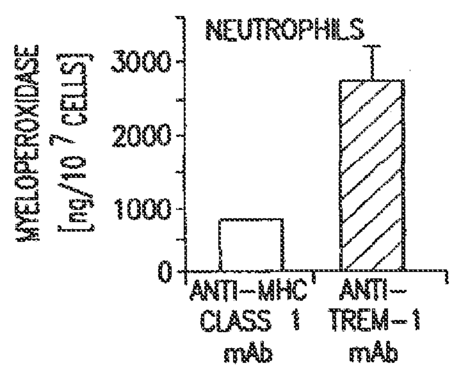
Figure 7C:
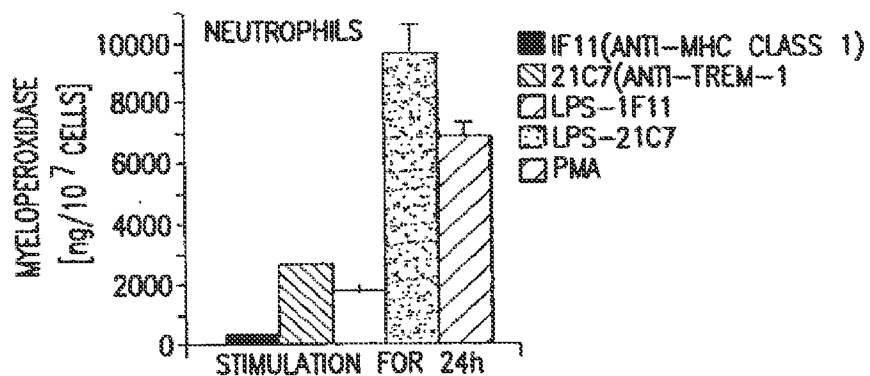
Figure 7D:
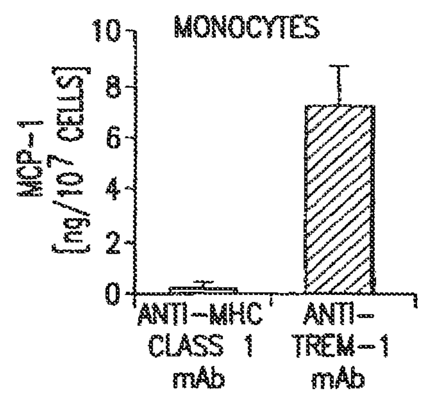
Figure 7E:
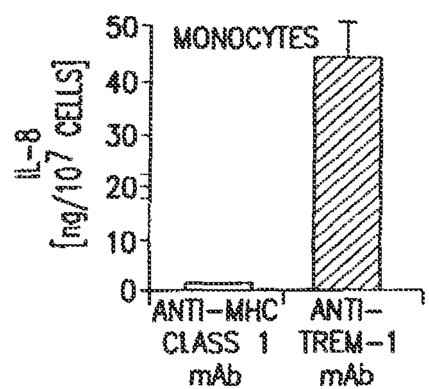
Figure 7F:
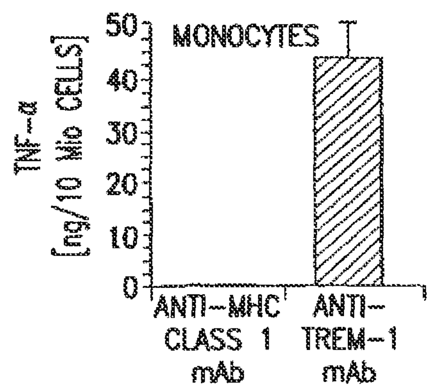
Figure 7G:
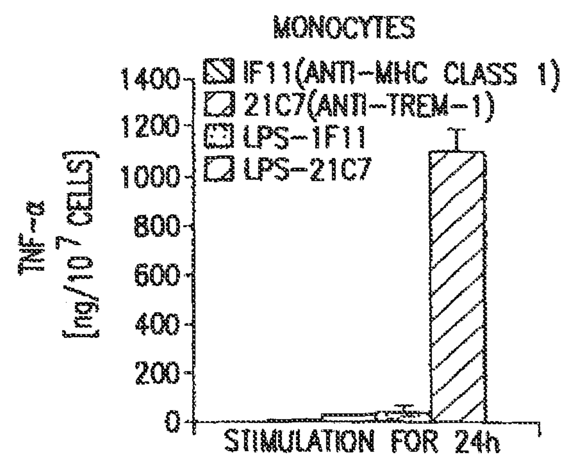
Figure 7H:
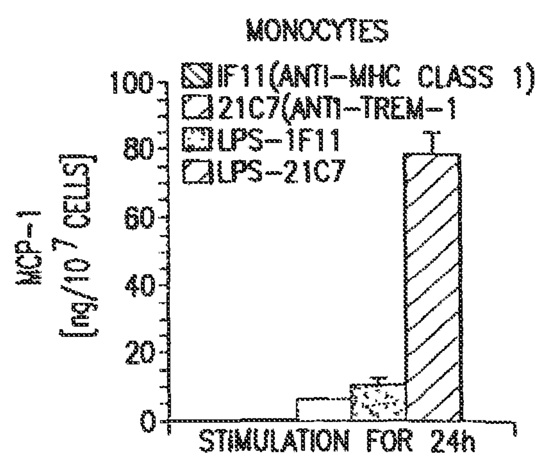

TREM-1 Triggers Release of Pro-Inflammatory Chemokines and Cytokines, as Well as Increased Surface Egression of Cell Activation Markers In neutrophils, cross-linking of TREM-1 induced secretion of IL-8 and release of MPO (FIGS. 7A-7B). This latter release was strongly potentiated following priming of neutrophils with LPS (FIG. 7C). In monocytes, cross-linking of TREM-I generated release of large amounts of IL-S as well as MCP-1 and TNF-a (FIGS. 7D-7F). TNF-a and MCP-1 secretion was strongly up-regulated by LPS-mediated priming (FIG. 7G-7H), further demonstrating the importance of bacterial costimuli for TREM-I-mediated activation. In control experiments, neutrophils and monocytes were stimulated with isotype-matched Abs which either bind (such as anti-MHC class I mAbs) or do not bind (such as an anti-TNP mAb) cells. In both cases, secretion of cytokines, chemokines, and MPO was 5- to 50-fold lower than that induced via TREM-1 (FIG. 7 and data not shown). Thus, activation of neutrophils and monocytes triggered by anti-TREM-I mAb is not due to engagement of Fc receptors. Secretion of cytokines important for the adaptive immune response, such as IL-6, IL-10, IL-12, or for surveillance against viral infections, such as type I IFN, were not significantly increased by engagement of TREM-I (data not shown).

The rapid migration of neutrophils and monocytes from the blood steam to the inflammatory site requires adhesion to endothelium and extracellular matrix proteins (Springer, T. A., 1994, Cell 76:301). Therefore, whether engagement of TREM-1 stimulates upregulation of adhesion molecules was tested. As shown in Table 1, cell surface expression of CD29, CDI Ic, and CD49e, and to a lesser extent, CDI Ib, CD49d, and CD 18, were increased on both neutrophils and monocytes. Thus, TREM-1 may increase cellular adhesion to fibronectin, fibrinogen, and VCAM by upregulating CD 11 b/CD 18 (Mac-1), CD29/CD49d, and CD29/CD49e heterodimers, respectively. In addition, TREM-1 stimulation led to a strong upregulation of the costimulatory molecules CD40, CD86 (B7.2), and CD54 (ICAM-1), as well as of CD83 and CD32 (FcRII) on monocytes. Thus, TREM-I is not only capable of increasing adhesion of myeloid cells to endothelium and extracellular matrix molecules but also can prepare monocytes for costimulation of other cells recmited to the inflammatory lesions.

TABLE I

TREM-I-dependent regulation of cell surface activation markers

| | Stimulation for 24 h | | | |
|---|---|---|---|---|
| | Neutrophils | | Monocytes | |
| Surface Marker | Anti-MHC class 1 | Anti-TREM-1 | Anti-MHC class 1 | Anti-TREM-1 |
| CD40 | | | 23.9 | 254.1 |
| CD80/B7.I | | | 0.6 | 0.1 |
| CD86/B7.2 | | | 32.6 | 521.5 |
| CD54/ICAM1 | 10.9 | 35.6 | 27 | 97.5 |
| CDIIb | 0.4 | 27.9 | 234.9 | 256.8 |
| CDIIc | 75.3 | 85.7 | 175.6 | 385.5 |
| CD18 | 54.8 | 76.9 | 198.8 | 211.9 |
| CD49d | 21.8 | 30.2 | 0.1 | 4.8 |
| CD49e | 76.1 | 91.9 | 14.9 | 46.5 |
| CD29 | 2.7 | 14.7 | 23.2 | 76.9 |
| CD32/FcRII | 86.2 | 100.2 | 72.1 | 114 |
| CD83 | | | 0.9 | 44.6 |

Monocytes or neutrophils cultured for 24 h in plates either coated with anti-TREM-I or control IgGI (anti-MHC class 1 mAb). Cells were then analyzed by FACS for the indicated cell surface molecules. Numerical values indicate specific mean fluorescence intensity (MFI) after subtraction of the fluorescence detected with an isotype-matched control. The shown data are representative for seven experiments.

Stimulation of TREM-1 Induces Calcium Mobilization and Tyrosine Phosphorylation

Activation of neutrophils and monocytes is often accompanied by a number of intracellular changes. Indeed, ligation of TREM-1 with the mAb 21C7 elicited a rapid rise in intracellular Ca^^ concentration (FIGS. 8B-8C). Ca^^ mobilization occurred even in the absence of a cross-linking Ah (FIG. 8B). In addition, cross-linking of TREM-I stimulated tyrosine phosphorylation of several proteins with apparent molecular masses of −40, −60, −70, and −100 kDa (as indicated with arrows in FIG. 9). The observed −40-kDa tyrosine phosphorylated proteins correspond to mitogen activated protein kinases, as demonstrated by anti-phospho-ERKI/2 immunoblotting (FIG. I OA). Precipitation of tyrosine phosphorylated proteins and immunoblotting with an anti-PLC-y Ab revealed that the observed −100-kDa phosphoprotein corresponds to PLC-y (FIG. 10 B), thus explaining the observed Ca^" influx.

Human TREM-1 Expression on Neutrophils and Monocytes is Strongly Upregulated by Bacterial and Fungal Stimuli As shown in FIG. 14A, TREM-1 expression was strongly upregulated by grampositive and gram-negative bacteria, such as *Staphylococcus aureus* and *Pseudomonas aeruginosa*, respectively, but not by mycobacteria, such as *Bacillus* of Calmette-Guerin (BCG). TREM-1 expression was also increased by incubating monocytes and granulocytes with gram-positive and gram-negative bacterial cell wall components, such as lipoteichoic acid (LTA) and lipopolysaccharide (LPS), whereas incubation with mycobacterial mycolic acid had no effect (FIG. 14B). Proinflammatory cytokines, such as TNF-a and IL-Iβ, produced a moderate increase of TREM-1 expression, while IL-10, TGF-β (FIG. 15) and dexamethasone (data not shown) which mediate anti-inflammatory responses, completely abolished TREM-1 expression. These results suggested that TREM-I is upregulated under inflammatory conditions, especially those caused by gram-positive and gram-negative bacteria. TREM-1 upregulation was paralleled with an increased capacity of triggering inflammatory responses in vitro. As shown in FIG. 16, secretion of TNF-a and IL-Iβ induced by cross-linking of TREM-1 on monocytes was strongly potentiated by priming of monocytes with LPS.

Human TREM-1 is Selectively Expressed in Bacterial Infections

Figure 17G:
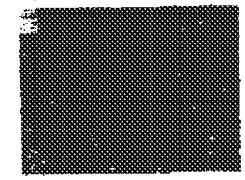
Figure 17H:
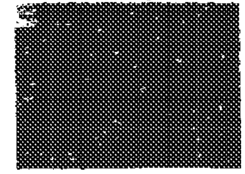

TREM-1-expression in vivo was determined in tissue spechnens derived from acute or granulomatous inflammatory lesions caused by either bacterial, fungal or non-microbial agents. As shown in FIG. 17, TREM-1 expression level was extremely strong in neutrophils associated with suppurative lesions of the skin, such as folliculitis and impetigo, caused by *Staphylococcus aureus* (FIGS. 17A and 17C, respectively). Obvious TREM-I expression was also observed in suppurative granulomatous lymphadenitis caused by *Bartonella henselae* and *Aspergillus fumigatus* (FIGS. 17E and 17G, respectively), hi the latter, TREMI was expressed not only in neutrophils, but also in epitheloid and multinucleated giant cells surrounding the suppurative granulomas (FIG. 17G). In contrast, TREM-1 positivity was either weak and focal or totally absent in granulomatous lymphadenitis caused by *Mycobacterium tuberculosis* as well as in sarcoid and foreign bodies granulomas (data not shown). In all cases showing TREM-I positive inflammatory infiltrates, the reactivity was mostly confined to the cells within the inflammation, and was absent from the surrounding tissues.

Infections by gram-positive and gram-negative bacteria and by certain fungi are characterized by the recmitment of large numbers of neutrophils, which collect in the inflammatory site to form an exudate known as pus. Thus, one could argue that the strong expression of TREM-I in bacterial and fungal infections is simply due to the massive infiltration of neutrophils. However, TREM-1 was poorly expressed in neutrophilic infiltrates found in non-bacterial inflammatory reactions. As shown in FIG. 18A, psoriasis is characterized by a prominent infiltration of neutrophils which form microabscesses within the hyperproliferative epidermis. However, TREM-1 was weakly expressed in psoriasis (FIG. 18B). Similarly, ulcerative colitis, vasculitis caused by immune complexes and lipoid pneumonias expressed very low levels of TREM-1 despite a considerable infiltration of neutrophils and monocytes (FIGS. 18C-18F and data not shown). Together, these results are consistent with a predominant role of TREM-I in acute and granulomatous inflammations caused by bacterial and fungal products.

Soluble TREM-1 Protects Mice from LPS-Induced Lethal Endotoxemia

Mouse TREM-1, which is 90% similar to human TREM-1, is expressed on murine granulocytes and monocytes/macrophages isolated from blood. Importantly, mouse TREM-1 expression is upregulated in peritoneal granulocytes and macrophages after intraperitoneal injection of LPS. See FIG. 19D. Thus, human and murine TREM-1 have similar cell surface expression pattern and regulation. If TREM-1 promotes host inflammatory responses to bacterial and iimgal products in vivo, inhibition of TREM-1 using soluble TREM-1 as a receptor decoy would be predicted to reduce such responses. To test this hypothesis, LPS induced septic shock in mice was chosen as a model of acute inflammation. In this model, intraperitoneal injection of LPS leads to tissue damage, hemodynamic changes, multiple organ failure and death. This process is caused by the massive release of proinflammatory mediators, such as TNF-a, IL-Iβ, macrophage migration inhibitory factor (MIF) and high mobility group-1 (HMG-1) protein (Wang, H., etai, 1999, Science 285:248-51). A murine TREM-1-human IgGI fusion protein (mTREM-1-IgGI) was injected in the peritoneal cavity (500 \i.g fusion protein per animal) 1 hour before the induction of endotoxemia by LPS. Lethality was monitored over time by comparing to animals which had received control injections of heat-inactivated mTREM-1-IgGI (500 pg/animal), human IgGI (500 ^g/animal) or control-IgGI fusion protein (500 pg/animal) prior to LPS administration. As shown in FIG. 21 A, 76% of the mice treated with mTREM-1-IgGI (open cueles) were protected from a lethal dose of LPS (400 pg/mouse) as compared to 7% i of mice that received control proteins (IgGI, ILT3-IgGI, or heat-inactivated mTREM-1-IgGI). The heat-inactivated mTREM-1-IgGI was included as a control to exclude a possibility that the mTREM-1-IgGI preparation was contaminated by LPS which could allow the mice to tolerate the subsequent injection of LPS, thus possibly explaining the observed protective effect. Heat inactivation of the mTREM-I-IgGI. denatures the soluble protein without affecting potential contaminating endotoxins. As shown in FIG. 21A (closed triangles), the heat-inactivated preparation lost completely its protective capacity against LPS-induced endotoxemia, demonstrating lack of LPS-induced tolerance by mTREM-I-igGI. All susceptible mice succumbed to LPS within the first 24 hours, showing severe signs of endotoxemia, such as shivering and lethargy. In contrast, TREM-1-IgG I-treated mice showed mild symptoms during the first few hours after LPS injection, recovered completely within day 4 after LPS injection and survived showing no signs of sickness or physical limitations.

To precisely quantify the protection provided by mTREM-1-IgGI, groups of mice pretreated with mTREM-1-IgGI or huIgGI were challenged with various doses of LPS. The LD50 of LPS in animals treated with mTREM-1-IgGI (LD50=621 pg) was significantly higher than the LD50 in control animals (LD50=467 pg) (FIG. 2IB).

Since clinical diagnosis and treatment of septic shock usually occurs hours after the onset of an infection, it was important to determine whether mTREM-1-IgGI could protect mice from LPS-induced lethal shock when injected after administration of LPS. Accordingly, 500 pg of mTREM-1-ïgGI was injected into mice at 1 hour, 2 hours, 4 hours and 6 hours after LPS injection and monitored lethality as compared to animals treated with control proteins. See FIG. 21C. Remarkably, mTREM-1-IgGI conferred %0% protection against endotoxic shock when applied 1 hour after LPS injection. Partial protection was also observed after 2 and 4 hours, whereas no protection occurred after 6 hours. Thus, soluble TREM-1 is effective even when injected after the outbreak of endotoxemia.

To explore the serological and cellular mechanisms by which TREM-1-IgGI conferred protection to the mice, blood samples from mice pretreated with TREM-1-IgGI and control animals were tested at different time points after LPS administration to determine TN F-a and IL-Iβ semm levels by ELISA. In both groups, TNF-a levels peaked at 1-2 hours after LPS injection, while IL-Iβ levels peaked at approximately 6 hours after LPS injection. The survival benefit obtained with TREM-1-IgGI was associated with a significant reduction of the plasma concentrations of both TNF-a and IL-Iβ (FIGS. 22A and 22B, respectively). The cellular composition of the peritoneal lavage at various time points after injection of LPS in mTREM-1-IgGI-pretreated animals and controls was also studied. A significant reduction in the total cell number of neutrophils and monocytes/macrophages infiltrating the peritoneum 6-8 hours after LPS injection was observed in mTREM-I-IgGI pretreated animals as compared to controls (see FIGS. 22C and 22D). Injection of mTREMI-IgGI in normal mice did not affect the levels of circulating leukocytes. Furthermore, mTREM-1-IgGI was effective against endotoxemia even when the IgGI-Fc portion of the fusion protein was mutated to inhibit Fc receptor binding and complement fixation (data not shown). Thus, inhibition of TREM-1-mediated responses is sufficient to lower systemic levels of TNF-a and ÍL-1β and reduce cellular infiltrates at the site of inflammation below levels that are lethal for the host, without causing leukopenia. Remarkably, human TREM-1-IgGI fusion protein also provided protection against LPS-induced endotoxemia in mice suggesting a substantial functional identity of TREM-I s between mouse and human (FIG. 20).

mTREM-1 is Protective in Bacterial Peritonitis

Experimental endotoxic shock reproduces human sepsis only in part, since it does not involve the replication and dissemination of bacteria. In these conditions, a complete block of TREM-1 signalling could be deleterious by impairing the capacity of the immune system to fight infections, as previously observed for anti-TNF-a treatments (Echtenacher, B., etai, 1990, 7 Immunoi 145:3762-6; Echtenacher, B., etai, \996, Nature 381:75-7; Malaviya, R, etai, 1996, Nature 381: 77-80; Rothe, J., etai, 1993, Nature 364:798-802; Pfeffer, K., e/a/., 1993, Ce//73:457-67; Peschon, J. J., eí a/., \99S, J. Immunoi 160:943-52; Eskandari, M. K., et a i, 1992, 7 Immunoi 148:2724-30). Accordingly, two models of microbial peritonitis and sepsis caused by intraperitoneal administration of *Escherichia coli* or by cecal ligation and puncture (CLP) were studied to see whether mTREM-1-IgGI protects against septic shock. As shown in FIGS. 23A-23B, injection of mTREM-1-IgGI converted significant protection against lethal *E. coli* peritonitis (FIG. 23A) and CLP-induced septic shock (FIG. 23B) compared to control huIgGI. In contrast, in the CLP model, treatment with TNF-a receptor 1-IgGI (TNF-RI-IgGI) caused accelerated and complete death of all animals (FIG. 23B). Thus, mTREM-1-IgGI reduces inflammatory responses but still allows sufficient control of the bacterial infection.

TREM-2

TREM-2 is Selectively Expressed on Mast Cells, Immature DCs and IL-4-Stimulated Monocytes Results from studies conducted to determine in vivo expression of TREM-2 reveal TREM-2 expression in mast cells of normal tissues and allergic nasal polyps. In FIGS. 40A-40H, mast cell expression of TREM-2 is evident in samples from: skin (FIG. 40A); lymph node (FIG. 40B); lung (FIG. 40C); placenta (FIG. 40D); normal bronchi (FIG. 40E, and at higher magnification, FIG. 40F); small intestine (FIG. 40G); as well as in a nasal polyp caused by allergy (FIG. 40H). Furthermore, FIGS. 41A-41F demonstrates that TREM-2 expression in tissues largely overlaps with the expression of c-Kit, which is specifically expressed on mast cells. Serial sections of intestinal mucosa, stained for TREM-2 (FIG. 41 A) and Toluidin blu (FIG. 41B), indicate and show the co-localization TREM-2" cells and metachromatic cells, respectively. Two-color immunofluorescence analysis of nasal mucosa for TREM-2 (FIG. 41C, red)) and c-Kit (FIG. 41D, green)) show that TREM-2 and c-Kit co-localize, albeit that TREM-2 is found on a subset of c-Kit positive mast cells. A section of intestinal mucosa was initially stained for TREM-2 (FIG. 4IE), then bleached using 50%) ethanol and finally stained with the Giemsa technique (FIG. 41F); results show clear evidence that TREM-2^ and Giemsa metachromatic cells (mast cells) co-localize. In FIG. 42A, cutaneous mastocytoma is stained with TREM-2, revealing TREM-2 expression as clearly indicated in comparison with cutaneous mastocytoma stained with a negative control antibody (FIG. 42B).

As shown in FIG. 25, three-color FACS analysis for TREM-2 expression on monocytes was conducted using 29E3 mAb which is specific for TREM-2 (see FIGS. 24A-24D). Monocytes were stimulated with M-CSF (FIG. 24A), GM-CSF (FIG. 24C), IL-4 (FIG. 24D) or GM-CSF+IL-4 (FIG. 24B) for 36 hours. TREM-2 expression was strongly upregulated after stimulation of monocytes with either IL-4 alone or GM-CSF+IL-4. Furthermore, in three-color FACS analysis for TREM-2 and CD83 (DC surface marker) expression on monocyte-derived DCs that are stimulated with LPS, CD40L, TNF-a, or medium for 36 hours (FIG. 26), TREM-2 was rapidly downregulated upon maturation of DCs, demonstrating that TREM-2 is selectively expressed on immature DCs. Also see FIG. 30. TREM-2 is a ~40-kDa glycoprotein associated with the adaptor protein DAP12 TREM-2 immunoprecipitated from surface-biotinylated monocyte-derived DCs showed that TREM-2 is a glycoprotein of −40 kDa, which is reduced to −26 kDa after A^-deglycosylation (FIG. 27). Similar to TREM-I, TREM-2 also lacks signaling motifs in the cytoplasmic domain and requires a separate signal transduction subunit to mediate activating signals. As shown m FIG. 28, when the immunoprecipitates of pervanadate-treated monocyte-derived DCs by anti-TREM-2 mAb were subjected to Western blot analysis using anti-phosphotyrosine blot under reducing and non-reducing conditions, tyrosine phosphorylated protein was observed. This protein was also detected by anti-DAPI2 blot analysis (FIG. 29), demonstrating that TREM-2 also associates with DAP12 adaptor molecule.

TREM-2 does not Trigger Secretion of Cytokines and Chemokines by DCs but Upregulates Certain Cell Surface Activation Markers To study whether stimulation of TREM-2 on DCs triggers the secretion of proinflammatory cytokines and chemokines, DCs were stimulated by culturing for 48 hours in the plates coated with either F(ab')2 control mAb (anti-TREM-I), F(ab')2 anti-TREM-2 mAb, or LPS, and culture supernatant was analyzed by ELISA for secretion of various mediators. As shown in Table II below, TREM-2 stimulation did not trigger secretion of cytokines and chemokines by DCs. The data are representative of 5 independent experiments.

TABLE II

Secretion of cytokines and chemokines by stimulation of TREM-2 on DCs

| Cytokines/ Chemokines (pg/ml) | F(ab')2 anti-TREM-1 | F(ab')2 anti-TREM-2 | LPS |
|---|---|---|---|
| IL-1alpha | N.D.* | N.D. | 0.135 ± 0.026 |
| IL-1beta | 0.027 ± 0.012 | N.D. | 0.162 ± 0.09 |
| TNF-alpha | 0.042 ± 0.005 | N.D. | 4.015 ± 0.078 |
| IL-18 | N.D. | N.D. | 2.56 ± 1.31 |
| IL-6 | N.D. | N.D. | 16.7 ± 5.43 |
| IL-10 | N.D. | N.D. | 2.03 ± 0.45 |
| TGF-beta1 | N.D. | N.D. | N.D. |
| IL-12p40 | N.D. | N.D. | 3.48 ± 1.25 |
| IL-12p70 | N.D. | N.D. | 1.45 ± 0.09 |
| IL-13 | N.D. | N.D. | N.D. |
| IL-15 | N.D. | N.D. | N.D. |
| MCP-1 | 2.018 ± 0.875 | 0.449 ± 0.067 | 98.18 ± 35.86 |
| IL-8 | 1.23 ± 0.451 | 0.023 ± 0.01 | 124.76 ± 23.91 |

*Not detectable

TREM-2-dependent regulation of cell surface activation markers was also studied. DCs were stimulated as described above and analyzed by FACS for various cell surface molecules. See Table III below. Numerical values indicate specific mean fluorescence intensity (MFI) after subtraction of the fluorescence detected with an isotype-matched control. The data are representative of 5 independent experiments. The surface markers which are especially upregulated by TREM-2 stimulation compared to controls (treated with anti-TREM-I mAb F(ab')2), are indicated in bold face.

TABLE III

TREM-2-dependent regulation of cell surface activation markers

| Surface marker | F(ab')2 anti-TREM-1 | F(ab')2 anti-TREM-2 | LPS |
|---|---|---|---|
| MHC Class I | 67.8 | 65.3 | 107.1 |
| MHC Class II | 89.12 | 168.65 | 214.67 |
| CD40 | 171.35 | 398.6 | 435.89 |
| CD86/B7.2 | 14.04 | 287.91 | 683.56 |
| CD83 | 3.34 | 3.23 | 26.7 |
| CDIa | 106.76 | 134.9 | 87.54 |
| CCR5 | 12.95 | 13.56 | 3.12 |
| CCR6 | 3.68 | 3.45 | 4.01 |
| CCR7 | 6.82 | 19.98 | 5.45 |
| CXCR4 | 5.13 | 4.56 | 17.8 |
| CDUa/aL | 10.92 | 6.78 | 13.72 |
| CDIIb/aM | 53.9 | 65.7 | 23.1 |
| CDUc/aX | 91.1 | 65.7 | 123.5 |
| CD29/βI | 38.22 | 37.56 | 37.5 |
| CD31/PECAM-1 | 3.52 | 16.92 | 3.21 |
| CD4I/aIIβ | 4.54 | 4.67 | 4.39 |
| CD54/ICAM-1 | 56.87 | 54.78 | 271.45 |
| CD61/β3 | 4.95 | 5.03 | 4.21 |
| CD103/aE | 3.63 | 3.96 | 3.26 |
| Mannose-R | 81.8 | 82.9 | 30.9 |
| CD32 | 17.21 | 16.78 | 2.34 |
| CD89/FcaR | 4.54 | 4.75 | 4.96 |
| CD35/CR1 | 3.94 | 4.23 | 3.67 |
| M-CSF-R | 14.6 | 4.23 | 5.21 |
| GM-CSF-R | 15.6 | 13.7 | 13.5 |

TREM-2 Ligation on Monocyte-Derived DCs Induces Calcium Mobilization and Tyrosine Phosphorylation and Prolongs DC Survival by an Erk-Dependent Pathway As shown in FIG. 31, cross-linking of TREM-2 induced intracellular Ca^"-mobilization in monocyte-derived DCs. Monovalent engagement of TREM-2 by Fab 29E3^'°^" was sufficient for induction of Ca^^-flux only in the presence of cross-linking Streptavidine (data not shown). Furthermore, cross-linking of TREM-2 stimulated tyrosine phosphorylation of several proteins as indicated with arrows in FIG. 32. Again, –40-kDa tyrosine phosphorylated proteins correspond to mitogen activated protein kinases, as demonstrated by anti-phospho-ERKI/2 immunoblotting (FIG. 33). Monocyte-derived DCs stimulated with GM-CSF±IL-4 or F(ab')2 29E3 for various time periods showed resistance to apoptosis (FIG. 34) and the prolonged survival of these cells seem to be mediated by an Erk-dependent pathway (FIG. 35).

Stimulation of TREM-2 Induces CCR 7 Expression and DC Chemotaxis to ECL and MIP-3β

FACS analysis of DCs stimulated with anti-TREM-2 mAb F(ab')2 showed that TREM-2 stimulation induced rapid upregulation of CCR7 expression by DCs (FIG. 36). Furthermore, Chemotaxis assays showed that DCs stimulated with anti-TREM-2 mAb F(ab')2 exhibited strong Chemotaxis towards ELC and MIP-3β and this Chemotaxis occurred via a CCR7-dependent pathway because the presence of anti-CCR7 mAb inhibited the migration of DCs towards ELC and MIP-3β (FIG. 37).

TREM-2 is Internalized Upon Ligation and Functions as an Antigen-Capturing Molecule In Vitro Monocyte-derived DCs were stimulated with anti-TREM-2 mAb, its F(ab')2 or Fab fragments and the amount of total, extracellular and intracellular TREM-2 were measured by FACS analysis using goat anti-mouse IgG-PE as a second antibody. As shown in FIG. 38, antibody-bound TREM-2 was quickly internalized and the degree of internalization was higher with divalent antibodies (i.e., whole anti-TREM-2 mAb and its F(ab')2 fragments) than monovalent antibody (Fab fragments). Presentation of anti-TREM-2 mAb to a T cell clone specific for mouse IgGI by irradiated DCs was also studied based on the [3H]thymidine uptake by the T cells (FIG. 39) cocultured with DCs in the presence of serially diluted mAbs or their F(ab')2 fragments. Anti-TREM-2 mAb and its F(ab')2 were presented –100-fold more efficiently than F(ab')2 of control mAb.

Example 7.1

Determination of the Interaction Interface Between TREM-1 and 9E2

The 9E2 epitopes were mapped on recombinant human TREM-1 (rhTREM-1) residues 1-134 with six histidine residues added to the C-terminus (cat. no. PRO-457, ProSpec-Tany TechnoGene Ltd., Rehovot, Israel).

Solutions of TREM-1, alone or in the presence of 9E2, were diluted 25-fold in 97% deuterated hepes buffer (20 mM hepes, 150 mM sodium chloride, pH 7.4). Non-deuterated controls were prepared by diluting into protiated hepes buffer. The hydrogen exchange experiments were performed on a waters HDX nanoAcquity ultra-high performance liquid chromatography (UPLC) system (Waters Corporation, Milford, Mass., USA) which included the HD-x PAL auto sampler (LEAP Technologies Inc., Carrboro, N.C., USA) for automated sample preparation. The LC tubing, pre- and analytical columns and switching valves were located in a chamber cooled to 0.3° C. The trypsin digestion column was stored at 15° C. Hydrogen exchange reactions were performed at 20° C. Mass analysis was performed online using a Waters SYNAPT G2 HDMS mass spectrometer.

A volume containing 100 pmol of human TREM-1 (1.54-1.98 μl) with or without 120 pmol mAb 9E2 was diluted into deuterated hepes buffer to a final volume of 50 μl. At the appropriate time intervals the entire volume was transferred to and quenched in 50 μl 1.35 mM Tris(2-carboxyethyl)phosphine adjusted to pH 2.4 and held at 3° C. 99 μl of the quenched solution was immediately injected and passed over a Porozyme immobilised pepsin column (2.1 mm×30 mm) (Applied Biosystems, Life Technologies Corporation, Carlsbad, Calif., USA) and trapped on a Waters VanGuard BEH C18 1.7 μm (2.1 mm×5 mm) column at 100 μl/min flowrate using a 5% (vol/vol) methanol and 0.1% formic acid mobile fase. The peptides were separated on a Waters UPLC BEH C18 1.7 μm (1.0 mm×100 mm) column using a 10-40% acetonitrile gradient containing 0.1% formic acid at a 40 μl/min flow-rate.

The mass spectrometer was operated in positive ion mode with ion mobility separation enabled. The electrospray conditions were 3.2 kV capillary, 25 V sample cone, and 4 V extraction cone offsets, 850 ml/min flow of nitrogen desolvation gas heated to 350° C. and 50 ml/min cone gas flow. The source block was heated to 120° C. Lock-mass correction data was acquired using the 1+ ion of Leucine-enkephalin (m/z 556.2771) as reference compound and applied during data analysis. For peptide identification $MS^E$-type experiments using trap collision offsets of 6 V (low-energy) and 50 V (elevated energy) were performed. Deuterated samples were analysed using the 6 V low energy trap collision offset only. For further details see Andersen, M. D., Faber, J. H., *Int. J. Mass Spectrom.* (2011), 302, 139-148. Experiments using ETD to obtain high-resolution hydrogen exchange information was performed using 1,4-dicyano benzene as ETD reagent administered into the instrument by a 35 ml/min gas flow and a 90 V discharge current.

The $MS^E$-data was analysed using Waters Protein Lynx Global Server 2.5 and peptides of TREM-1 were identified that covered 80% of the protein sequence (Table IV). The HX-MS data files were analysed using Waters DynamX 1.0 that automatically applies lock-mass correction and determines the degree of deuterium incorporation in each peptide. In addition, all data was manually inspected to ensure correct peak assignment and calculation of deuterium incorporation.

TABLE IV

| Peptide | 9E2 |
|---|---|
| A21-L37 | N |
| A21-D38 | N |
| A21-V39 | N |
| A21-C69 | EX |
| T22-D38 | N |
| D38-Q56 | EX |
| D38-M63 | EX |
| D38-L67 | EX |
| D38-A68 | EX |
| D38-C69 | EX |
| V39-A68 | EX |
| V39-C69 | EX |
| D42-C69 | EX |
| T44-C69 | EX |
| K47-A68 | N |
| A49-C69 | N |
| I57-A68 | N |
| I57-C69 | N |
| I57-L87 | EX |
| L67-L87 | EX |
| A68-E88 | EX |
| A68-L96 | EX |
| C69-L87 | EX |
| C69-L96 | EX |
| T70-L87 | EX |
| T70-E88 | EX |
| T70-L96 | EX |
| R84-L96 | EX/LE |
| E88-L96 | LE |
| Q104-L110 | N |
| Y111-M124 | N |
| Y111-F126 | N |
| Y111-D127 | N |
| C113-F126 | N |
| V114-F126 | N |
| V114-D127 | N |
| I115-F126 | N |
| I115-D127 | N |

EX: Epitope region indicated by hydrogen exchange protection upon antibody binding. (Exchange difference (EX) > 0.6)
N: No protection from exchange upon antibody binding. (EX < 0.3)
LE: Low intrinsic exchange 9E2 Epitope on hTREM-1

When 9E2 bound hTREM-1, protection from exchange was observed in peptides covering the sequence from A21 to L96 and the epitope was consequently determined to be within this region. When taking into account peptides that showed no protection from exchange upon binding of 9E2, the epitope could be narrowed to the regions D38-F48 and T70-L96. The region from R88-L96 showed little to no exchange in either the presence or the absence of 9E2 and it was not possible to conclude whether it was part of the 9E2 binding epitope. The peptide covering the sequence R84-L96 also showed low intrinsic exchange, but a consistent protection upon binding of 9E2 was observed at incubation times of 105 seconds or longer. The first two residues of a peptide back-exchanges quickly and exchange information for those residues was lost. Hence, at least one of the residues I86, L87, E88 and D89 was found to be important for the binding of the 9E2 antibody. The peptide K47-A68 did not show protection from exchange upon binding of 9E2, but the peptide T44-C69 was protected when 9E2 was bound. Hence, at least one of the residues E46, K47, and F48 was determined to be important for the binding of the 9E2 antibody.

To identify specific residues involved in antibody binding, the peptide 70-87 was selected for ETD fragmentation. The observed fragments are listed in Table V, below. The protection was calculated by subtracting the mass of the deuterated fragment with 9E2 bound from that of the fragment without mAb present. The C-fragments going from the N-terminal towards the C-terminal in the ETD data revealed that residues T70, E71, R72, and S74 were not protected from exchange when 9E2 was bound. At position K75 there was protection from exchange when 9E2 was bound and this residue was determined to contribute to the binding epitope. No further protection was observed for residues N76, S77, and H78. At position Q81 the protection increased, meaning that at least one of the residues V80, or Q81 was protected and contributed to the binding epitope. No further protection was observed for residues V82, G83, and I85. Likewise for the Z-ions going from the C-terminal towards the N-terminal revealed that R84-L87 were not protected from exchange, but at position P79 there was protection from exchange upon 9E2 binding and at least one of the residues V80, Q81, V82, or G83 contributed to the binding epitope. No further protection was observed at S77 and N76, thus, there was no protection in the region N76-H78. At position P73 there was further protection meaning that at least one of the residues S74, or K75 was protected and contributed to the binding epitope. In conclusion, ETD experiments showed that residue K75 as well as V80 and/or Q81 contribute to the 9E2 binding epitope on hTREM-1.

TABLE V

| ETD fragmentation | | |
|---|---|---|
| Fragment | Fragment sequence | Protection |
| C2 | T70-R72 | 0.02 |
| C4 | T70-S74 | 0.00 |
| C5 | T70-K75 | 0.13 |
| C6 | T70-N76 | 0.10 |
| C7 | T70-S77 | 0.13 |
| C8 | T70-H78 | 0.07 |
| C11 | T70-Q81 | 0.27 |
| C12 | T70-V82 | 0.29 |
| C13 | T70-G83 | 0.26 |
| C15 | T70-I85 | 0.19 |
| Z5 | R84-L87 | 0.04 |
| Z10 | P79-L87 | 0.38 |
| Z12 | S77-L87 | 0.32 |
| Z13 | N76-L87 | 0.35 |
| Z16 | P73-L87 | 0.48 |

Example 7.2

Competition Binding Studies of Anti-Human TREM-1 Monoclonal Antibodies by Surface Plasmon Resonance SPR binding competition studies were performed with monoclonal mouse or recombinantly expressed anti-hTREM-1 antibodies in order to discriminate between different binding sites (epitopes). Commercially available antibodies included were Biolegend #314907 (Biolegend, USA) and SC98Z12 (Santa Cruz Biotechnology, USA). Anti hTREM-1 monoclonal antibodies that compete for the same or an overlapping binding site (epitope) on the antigen are not able to bind simultaneously to the antigen and are therefore assigned to the same bin. Anti-TREM-1 monoclonal antibodies that do not compete for the same or overlapping binding site on the antigen are able to bind simultaneously and are thus assigned to different bins. Experiments were performed using soluble, human TREM-1 extracellular domain as antigen (amino acid residues 21-200 of SEQ ID NO: 3).

All studies were run at 25° C., and the samples were stored at 15° C. in the sample compartment. Individual anti-TREM-1 monoclonal antibodies and a unrelated control monoclonal antibody were immobilized onto separate flow cells of a GLC sensor chip using a 1:1 mixture of 0.4 M EDAC [1-ethyl-3-(3-dimethylaminopropyl)carbodiimide hydrochloride] and 0.1 M Sulfo-NHS [N-hydroxysulfosuccinimide]. Each antibody was diluted in 10 mM sodium acetate pH 5.0 to a concentration of 25 or 10 (SC98Z12 (80394)) μg/ml, and was immobilized to an individual flow cell at 30 μl/min for 240 s. The antibodies were immobilized to flow cells L1-L6 (including control). After immobilization of the antibody, the active sites on the flow cell were blocked with 1 M ethanolamine. Immobilizations were performed with activation and deactivation in horizontal direction creating interspot reference points without immobilized protein. The final immobilization level of test antibodies ranged from approximately 1100 to 1300 RU in one experiment, except for one antibody (SC98Z12) where only 390 RU was immobilized. Recombinant human TREM-1 was diluted to 100 nM into running buffer (10 mM Hepes 0.15 M NaCl, 5 mM EDTA, 0.05% surfactant P20, pH 7.4).

The antigen was injected over immobilized antibodies in horizontal direction at 30 μl/min for 300 s, allowing control of potential unspecific binding both to interspot references and immobilized control antibodies resulting in 150-600 RU captured TREM-1, except for one antibody (SC98Z12) with low immobilization level where only 4 RU was captured.

Each antibody (the same ones that had been immobilized) was injected over parallel flow cells in horizontal direction to allow for comparative analysis of binding to hTREM-1 captured by the primary antibodies relative to binding to both the interspot references and the immobilized control antibodies. Each competing antibody was diluted to 100 nM and injected at 100 μl/min for 250 s. The GLC chip was regenerated after each injection cycle of analyte via two 18 s injections of 1M Formic acid pH 3.5, 3M MgCl2 and 50 mM NaOH at 100 μl/min. This regeneration step removed the TREM-1 antigen and any bound secondary antibody from the immobilized antibody surface, and allowed for the subsequent binding of the next test sample. The regeneration procedure did not remove the directly immobilized anti-TREM-1 test antibody (primary antibody) from the chip surface. Data analysis was performed with the ProteOn Manager™ 3.1.0.6 Software. Capture levels were assessed to ensure that the regeneration step provided a consistent binding surface throughout the sequence of injections. No significant non-specific binding of human TREM-1 neither to the interspot control surfaces nor to immobilized control antibody was observed. Binding curves were processed by subtraction of interspot control surface signals. This allowed correction for instrument noise and bulk shift during sample injections.

The competition results were reported as either positive or negative binding (Table IV). Positive (+) binding indicates that the competing antibody was capable of binding the hTREM-1 simultaneously with the primary antibody (i.e. they do not compete), and the primary and competing antibodies were consequently assigned to different epitope bins. Negative binding indicates that the competing antibody was unable to bind the hTREM-1 simultaneously with the primary antibody (i.e. they do compete), and the primary and competing antibodies were thus assigned to the same epitope bin. The response values in these experiments were significant and allowed for an unambiguous determination of epitope bins of the anti-TREM-1 monoclonal antibodies.

TABLE IV

Ability to bind (+) or to compete (−) for antibodies tested in SPR competition assay. SC98Z12 did not give high enough capture of TREM-1 to evaluate as primary antibody (*).

| | Primary | | |
|---|---|---|---|
| Secondary | Biolegend #314907 | SC98Z12 | mAb 9E2 |
| Biolegend #314907 | − | * | + |
| SC98Z12 | − | * | + |
| mAb 9E2 | + | * | − |

Biolegend #314907 and SC98Z12 did not compete with 9E2 for binding to human TREM-1 but competed with each other.

Example 7.3

Study of Interaction Kinetics for Anti TREM-1 Antibodies to hTREM-1 by Surface Plasmon Resonance (SPR). Comparison Between mAb 9E2 and Commercially Available Anti TREM-1 Antibodies Binding studies were performed on a ProteOn Analyzer (BioRad) that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in six parallel flow cells. Commercially available antibodies included were Biolegend #314907, Biolegend #316102 (Biolegend, USA), Hycult Biotech HM2252 (Hycult Biotech, Netherlands), R&D #MAB1278 (R&D systems, United Kingdom), SC98Z12 (Santa Cruz Biotechnology, USA), Sigma #WH0054210 m4, Sigma #SAB1405121 (Sigma-Aldrich Danmark A/S)

Anti-murine Fc polyclonal antibody from Biacore mouse Fc capture kit was immobilized in horizontal direction onto flow cells of a GLM sensor chip according to the manufacturer's instructions. The final immobilization level of capture antibody was approximately 2600-6000 RU in different experiments. Capture of purified monoclonal mouse antibodies was conducted by diluting the antibodies to 5-10 nM into running buffer (10 mM Hepes 0.15 M NaCl, 5 mM EDTA, 0.05% surfactant P20, pH 7.4) and injected in vertical direction at 30 μl/min for 60 s, creating reference interspots adjacent to all flow cells with only anti-Fc antibody immobilized. This typically resulted in final capture levels of test antibodies of approximately 100-300 RU and Rmax values of analyte of 30-90 RU. Binding of the TREM-1 (amino acids 21-200 of SEQ ID NO: 3) protein was conducted by injecting analyte over all flow cells in horizontal direction to allow for comparative analyses of binding to different captured anti-TREM-1 antibodies relative to binding to the reference interspot. TREM-1 protein was diluted serially 1:3 to 1.2-100 nM or into running buffer, injected at 100 μl/min for 210 s and allowed to dissociate for 600 s. The GLM surface was regenerated after each injection cycle of analyte via two injections of 10 mM Glycine, pH 1.7 and 50 mM NaOH at 100 μl/min. This regeneration step removed the anti-TREM-1 antibody and any bound TREM-1 protein from the immobilized capture antibody surface, and allowed for the subsequent binding of the next interaction sample pair. The regeneration procedure did not remove the directly immobilized anti-Fc capture antibody from the chip surface.

Binding affinity between antibodies and the antigen was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by fitting data to 1:1 Langmuir model using the ProteOn evaluation software 3.1.0.6 for data analysis. $K_D$ is related to $k_a$ and $k_d$ through the equation $K_D=k_d/k_a$.

Binding curves were processed by double referencing (subtraction of reference surface signals as well as blank buffer injections over captured anti-TREM-1 antibodies) prior to data analysis. This allowed correction for instrument noise, bulk shift and drift during sample injections.

TABLE VII

Results from measurements of KD (equilibrium dissociation constant) for the interaction of TREM-1 to different TREM-1 monoclonal antibodies.

| Antibody | human TREM-1 KD (M) |
|---|---|
| mAb 9E2 | 3E−09 |
| Biolegend #314907 | 9E−10 |
| Biolegend #316102 | 8E−10 |
| Hycult Biotech HM2252 | 3E−09 |
| R&D #MAB1278 | 8E−09 |
| SC98Z12 | 3E−08 |
| Sigma #WH0054210m4 | 2E−08 |
| Sigma #SAB1405121 | No binding |

Example 7.4

Kinetic Analysis of 9E2 Fab Binding to Mutated Versions of TREM-1

Interaction studies were performed by SPR to define the epitope of the 9E2 TREM-1 antibody on human TREM-1. By comparing binding kinetics to human TREM-1 variants with introduced alanine mutations in epitope regions defined in Example 7.1, amino acid residues responsible for 9E2 binding were identified.

TREM-1 extracellular domain alanine mutant constructs are summarised in Table VII, below. All constructs used were alanine mutants of amino acids 21-200 of SEQ ID NO: 3, including a C-terminal-cmyc$^2$-His$^6$ tag for capture in SPR binding kinetics assay.

TABLE VII constructs used

| TREM-1 variant | Protein | Mutations |
|---|---|---|
| 0221 | human TREM-1 Ala mut 1 | D38A |
| 0222 | human TREM-1 Ala mut 2 | K40A |
| 0223 | human TREM-1 Ala mut 3 | D42A |
| 0224 | human TREM-1 Ala mut 4 | T44A |
| 0226 | human TREM-1 Ala mut 6 | K47A |
| 0227 | human TREM-1 Ala mut 7 | S50A |
| 0228 | human TREM-1 Ala mut 8 | R84A |
| 0229 | human TREM-1 Ala mut 9 | Y90A |
| 0230 | human TREM-1 Ala mut 10 | H91A |
| 0232 | human TREM-1 Ala mut 12 | H93A |
| 0233 | human TREM-1 Ala mut 13 | R97A |
| 0234 | human TREM-1 Ala mut 14 | R99A |
| 0235 | human TREM-1 Ala mut 15 | D127A |
| 0236 | human TREM-1 Ala mut 16 | R128A |
| 0237 | human TREM-1 Ala mut 17 | R130A |

Binding studies were performed on a ProteOn Analyzer that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in six parallel flow cells. Anti-His monoclonal antibody was immobilized onto 6 parallel flow cells of a GLM sensor chip using a 1:1 mixture of 0.4 M EDAC [1-ethyl-3-(3-dimethylaminopropyl)carbodiimide hydrochloride] and 0.1 M Sulfo-NHS [N-hydroxysulfosuccinimide]. Antibody was diluted in 10 mM sodium acetate pH 5.0 to a concentration of 25 μg/ml, and was immobilized onto individual flow cells at 30 μl/min for 240 s. After immobilization of the antibody, the active sites on the flow cells were blocked with 1 M ethanolamine. Immobilization was performed with all steps in horizontal direction. The final immobilization level of capture antibody was approximately 8000 RU in one experiment.

Cell culture medium from HEK 293 cells expressing wild type or different mutated variants of TREM-1 ECD was diluted 40-60 times in running buffer (10 mM HEPES, 150 mM NaCl, 3 mM EDTA, 0.05% surfactant P20, pH 7.4). TREM-1 proteins were injected over immobilized anti-His capture antibody in vertical direction at 30 μl/min for 60 s. This resulted in 50-250 RU captured TREM-1 and created interspot references with only immobilized capture antibodies but no captured TREM-1 in horizontal direction. Each Fab was injected over parallel flow cells in horizontal direction to allow for kinetic analysis of binding to TREM-1 variants captured by anti-His antibody. Prior to injection each Fab was diluted to 0, 5.5 (in one experiment), 16.7 and 50 nM in running buffer, and injected at 100 μl/min for 250 s (association time). The dissociation time following these injections was monitored for 10 minutes. The GLM chip was regenerated after each interaction cycle of TREM-1 and Fab via two 18 s injections of 10 mM Glycine and 50 mM NaOH at 100 μl/min. This regeneration step removed the TREM-1 variants and any bound Fab from the anti-His antibody surface, and allowed for the subsequent binding of the next interaction pair. The regeneration procedure did not remove the directly immobilized anti-His capture antibody from the chip surface.

In order to obtain kinetic data, such as ka (association rate), kd (dissociation rate) and KD (equilibrium dissociation constant), data analysis was performed using the ProteOn Manager™ 3.1.0.6 Software. Capture and binding levels of samples run in duplicates or triplicates were assessed to ensure that the regeneration step provided a consistent binding surface throughout the sequence of injections. No significant unspecific binding to interspot references with only immobilized capture antibody was observed. Binding curves were processed by subtraction of interspot control surface signals as well as injection of running buffer. This allowed correction for instrument noise and bulk shift during sample injections.

The affinity of Fab 9E2 to different TREM-1 ECD variants were compared to the affinity to wild type human TREM-1 ECD.

The level of binding 10 s after end of injection of Fab, normalized to level of captured TREM-1 variant, was also assessed in order to identify mutated versions with abrogated or very low binding. A decrease in affinity combined with significantly lower normalized binding level can indicate a disrupted folding due to introduced mutations. It should however be noted that changes in kinetics will also affect this value. Each binding curve was therefore visually inspected for conclusion.

The results for human TREM-1 with alanine single mutations (table VIII) show that 9E2 binding was strongly affected by mutating five positions (D38, K40, Y90, H91, R97) where binding was decreased more than two-fold.

TABLE VIII

Affinity of the control Fab and 9E2 Fab to human TREM-1 with alanine mutations relative to human TREM-1 wt. Binding level of the control Fab and 9E2 Fab 10 s after end of association, expressed as degree of theoretical maximum binding level.

| | | KD relative to wild type TREM-1 | | Normalized binding (% Rmax theor) | |
|---|---|---|---|---|---|
| NNCD | Mut | control Fab | 9E2 Fab | control Fab | 9E2 Fab |
| 0247 | — | 1 | 1 | 44 | 41 |
| 0221 | D38A | 0.7 | 15.0 | 29 | 5 |
| 0222 | K40A | 0.9 | No binding | 43 | 1 |
| 0223 | D42A | 132.9 | 26.9 | 13 | 3 |
| 0224 | T44A | 1.2 | 1.8 | 46 | 40 |
| 0226 | K47A | 1.0 | 1.1 | 40 | 38 |
| 0227 | S50A | 0.7 | 0.9 | 45 | 41 |
| 0228 | R84A | 0.5 | 1.3 | 15 | 8 |
| 0229 | Y90A | 0.5 | 2.9 | 40 | 31 |
| 0230 | H91A | 0.9 | 2.5 | 41 | 33 |
| 0232 | H93A | 36.4 | 5.2 | 22 | 29 |
| 0233 | R97A | 1.1 | 6.2 | 36 | 22 |
| 0234 | R99A | 0.8 | 1.0 | 15 | 11 |
| 0235 | D127A | 1.1 | 0.8 | 43 | 41 |
| 0236 | R128A | 0.9 | 1.2 | 39 | 35 |
| 0237 | R130A | 1.0 | 0.8 | 35 | 34 |

C. SUMMARY

These results presented here demonstrate that TREM-1 mediates a novel proinflammatory pathway in granulocytes and monocytes. Such a pathway is particularly important in regulating inflammatory responses to bacterial and fungal infections. Namely, human TREM-1 is upregulated in the presence of heat-inactivated bacteria or bacterial cell wall components in vitro and, most importantly, in bacterial infections of the skin and lymph nodes in vivo. In addition, mouse TREM-I significantly contributes to the pathogenesis of LPS-induced shock, as demonstrated by prevention of clinical, cellular and serological manifestations of endotoxemia in the presence of an inhibitor of TREM-1. Thus, the present inventors propose a role of TREM-1 as an amplifier of inflammatory responses triggered by pattern recognition receptors (PRRs). In an early phase of a bacterial infection, neutrophils and monocytes are rapidly alerted through the engagement of PRRs by bacterial products. This leads to an initial release of proinflammatory cytokines which is required to launch an inflammatory response. At the same time, bacterial products induce upregulation of TREM-1, which, upon engagement, activates DAPI2-signaling pathways (Lanier, L. L., etai, 1998, Nature 391:703-7), which amplify inflammatory responses. The present inventors have shown that ligation of TREM-I leads to sustained secretion of proinflammatory cytokines (TNF-a and IL-Iβ) and chemokines (IL-8 and MCP-1), and may also result in prolonged survival of neutrophils and monocytes at the inflammatory site. Upon clearance of the pathogenic stimuli, TREM-1 is downregulated, contributing to the reduction of the inflammation and the enhancement of tissue repair. It will be important to define the ligand that engages TREM-1 during inflammatory responses. TREM-1 ligand could be a soluble mediator released by cells following recognition of bacterial products by PRRs and intracellular signaling. Alternatively, TREM-I ligand could be a cell surface molecule that is upregulated during bacterial infections to alert granulocytes and monocytes to elicit a strong inflammatory response. Cell surface molecules with an hypothetical "alert" function have been recently identified on epithelial cells (Bauer S, etai, 1999, Science 285:727-9; Katsuura M, et a i, 1998, Acta Paediatr Jpn. 40:580-5). These molecules, called MIC and CD48, are over-expressed during heat shock, stress and viral infections and detected by the natural killer (NK) cell activating receptors NKG2D and 2B4, which trigger NK cell responses (Bauer, S., et a i, supra; Nakajima H. and Colonna M., 2000, Hum Immunoi 61:39-43; Bakker A B, Wu J, Phillips J H, and Lanier L L., 2000, Hum Immunoi 61:18-27). Remarkably, inhibition of TREM-I-mediated functions in LPS-induced shock is sufficient to reduce serum TNF-a and IL-Iβ to sublethal levels, preventing shock and death. In addition, mTREM-1-IgG I protects against bacterial peritonitis, in contrast to prophylactic treatment with anti-TNF-a antibodies (Beutler, B., Milsark, 1. W. & Cerami, A. C., 1985, Science 229:869-71) or IL-1R antagonists, which increase lethality (Ohlsson, K., et ai, 1990, Nature 348:550-2; Alexander, H. R., et a i, 1991, 7 Exp. Med. 173:1029-32; McNamara, M. J., et ai, 1993, J. Surg Res. 54:316-21). Most likely, the residual levels of TNF-a and IL-Iβ after mTREM-I treatment are sufficient for clearance of bacterial infections (Echtenacher, B., etai, 1990, supra; Echtenacher, B., etai, 1996, supra; Malaviya, R., et. a i, 1996, supra; Rothe, J., et a i, 1993, supra; Pfeffer, K., et a i, 1993, supra; Peschon, J. J. et a i, 1998, supra; Eskandari, M. K., etai, 1992, supra), importantly, mTREM-I-IgGI was even protective after injection of LPS, an effect that was previously only reported for inhibition of MIF and HMG-1 (Wang, H., et a i, 1999, supra; Calandra, T., et a i, 2000, supra). Thus, post-infection administration of soluble TREM-1 might be a suitable therapeutic tool for the treatment of septic shock as well as other microbial-mediated diseases. The results of these studies demonstrate a central role of TREM-1 in the amplification of inflammatory responses to bacteria and fungi and provide a promising new strategy for the management of patients with acute inflammations and sepsis.

On the other hand, the studies have demonstrated that TREM-2 is significantly involved in mast cell function and particularly DC functions, including DC maturation, migration to lymph nodes, presentation of antigens to T cells, and, thus, overall initiation of adaptive immune responses. Accordingly, interference with TREM-2's functions or its expression on mast cells and DCs should be able to modulate the immune responses of the host, thus controlling various immune disorders, including autoimmune diseases (e.g., systemic lupus erythematosus, multiple sclerosis, dermatomiositis, rheumatoid arthritis, and allergies) and allergic disorders.

The contents of all references, patents and published patent applications cited throughout this application are hereby incorporated by reference in their entireties.

D. EQUIVALENTS

Those skilled in the art will recognize, or be able to ascertain many equivalents to the specific embodiments of the invention described herein using no more than routine experimentation. Such equivalents are intended to be encompassed by the following claims.

What is claimed is:

1. An isolated antibody that specifically binds to a wild type human TREM-1 having a sequence as set forth in SEQ ID NO:3, wherein the antibody binds to an epitope comprising amino acid residues D38, K40, K75, Y90, H91 and R97.

2. An isolated antibody that specifically binds to a wild type human TREM-1 having a sequence as set forth in SEQ ID NO:3, wherein the antibody binds to an epitope comprising the amino acid residues D38, K40, Y90, H91 and R97.

* * * * *